United States Patent
McKeown et al.

(10) Patent No.: US 11,322,253 B2
(45) Date of Patent: May 3, 2022

(54) WIRELESS SENSOR CONNECTIVITY

(71) Applicant: MODO MEDICAL DESIGN LLC, Kailua, HI (US)

(72) Inventors: Morgan Taylor McKeown, Kailua, HI (US); Douglas M. Patton, Irvine, CA (US)

(73) Assignee: MODO Medical Design LLC, Kailua, HI (US)

( * ) Notice: Subject to any disclaimer, the term of this patent is extended or adjusted under 35 U.S.C. 154(b) by 0 days.

(21) Appl. No.: 17/115,309

(22) Filed: Dec. 8, 2020

(65) Prior Publication Data
US 2021/0174953 A1 Jun. 10, 2021

Related U.S. Application Data

(60) Provisional application No. 62/945,192, filed on Dec. 8, 2019.

(51) Int. Cl.
*G16H 40/67* (2018.01)
*G16H 40/63* (2018.01)
*H04W 4/38* (2018.01)
*G16H 10/60* (2018.01)

(52) U.S. Cl.
CPC ............. *G16H 40/63* (2018.01); *G16H 10/60* (2018.01); *G16H 40/67* (2018.01); *H04W 4/38* (2018.02)

(58) Field of Classification Search
CPC ..... A61B 5/0015; A61B 5/002; A61B 5/0022; A61B 5/0024; A61B 5/0205; H04W 4/38; H04W 4/80
USPC ................................................ 600/300, 301
See application file for complete search history.

(56) References Cited

U.S. PATENT DOCUMENTS

| | | | | |
|---|---|---|---|---|
| 6,850,788 B2* | 2/2005 | Al-Ali | ..................... | A61B 5/742 600/323 |
| 7,149,474 B1* | 12/2006 | Mikhak | ................. | H04M 1/738 455/41.2 |
| 7,722,358 B2* | 5/2010 | Chatterjee | ............... | H02J 50/10 439/38 |
| 7,979,136 B2* | 7/2011 | Young | .................... | G16H 40/67 607/60 |
| 9,026,053 B2* | 5/2015 | Molettiere | ........... | A61B 5/0022 455/41.2 |
| 9,467,222 B1* | 10/2016 | Pollmann | ................. | H04B 7/24 |
| 9,516,335 B2* | 12/2016 | Chernyshev | ......... | H04N 19/164 |

(Continued)

FOREIGN PATENT DOCUMENTS

WO    WO-2020198169 A1 *  10/2020   ........... A61B 5/0015

OTHER PUBLICATIONS

International Search Report dated Apr. 2, 2021 for PCT/US20/63680.
Written Opinion dated Apr. 2, 2021 for PCT/US20/63680.

*Primary Examiner* — John R Downey
(74) *Attorney, Agent, or Firm* — Chang & Hale LLP

(57) ABSTRACT

A wireless-connectivity system includes a sensor dongle configured to be electrically connected to a sensor device, a monitor dongle configured to be electrically connected to a medical monitor system, and a dongle-connectivity management hub configured to cause a wireless coupling to be established between the sensor dongle and the monitor dongle. The sensor dongle is configured to receive sensor data from the sensor and wirelessly transmit data to the monitor dongle via the wireless coupling, the data being based at least in part on the sensor data.

20 Claims, 45 Drawing Sheets

(56) References Cited

U.S. PATENT DOCUMENTS

| | | | | |
|---|---|---|---|---|
| 9,838,868 | B1* | 12/2017 | Nelson | H04W 12/033 |
| 2009/0231124 | A1 | 9/2009 | Klabunde et al. | |
| 2011/0021140 | A1* | 1/2011 | Binier | H04B 5/0043 |
| | | | | 455/41.1 |
| 2011/0317021 | A1* | 12/2011 | Takahashi | H04N 7/181 |
| | | | | 348/207.1 |
| 2012/0136223 | A1* | 5/2012 | Hodge | A61B 5/0024 |
| | | | | 600/301 |
| 2013/0210346 | A1* | 8/2013 | Ling | H04B 5/0037 |
| | | | | 455/41.1 |
| 2014/0199893 | A1* | 7/2014 | Lisogurski | H01R 13/64 |
| | | | | 439/660 |
| 2014/0278260 | A1 | 9/2014 | Gettings et al. | |
| 2015/0265903 | A1* | 9/2015 | Kolen | G16H 20/30 |
| | | | | 700/91 |
| 2015/0365507 | A1* | 12/2015 | Vasapollo | H04W 4/80 |
| | | | | 455/556.1 |
| 2017/0064755 | A1* | 3/2017 | Ha | H04W 76/11 |
| 2017/0172478 | A1* | 6/2017 | Lisogurski | A61B 5/7225 |
| 2018/0049671 | A1* | 2/2018 | Markison | A61B 5/1036 |
| 2018/0192122 | A1* | 7/2018 | Rajapakse | H04N 21/43615 |
| 2018/0247712 | A1* | 8/2018 | Muhsin | G08B 21/02 |
| 2019/0102521 | A1* | 4/2019 | Biewer | G16H 40/67 |
| 2019/0341146 | A1* | 11/2019 | Kamen | G16H 40/60 |
| 2020/0044735 | A1* | 2/2020 | Wang | H01L 33/48 |
| 2020/0092221 | A1* | 3/2020 | Sukoff | H04L 47/70 |

* cited by examiner

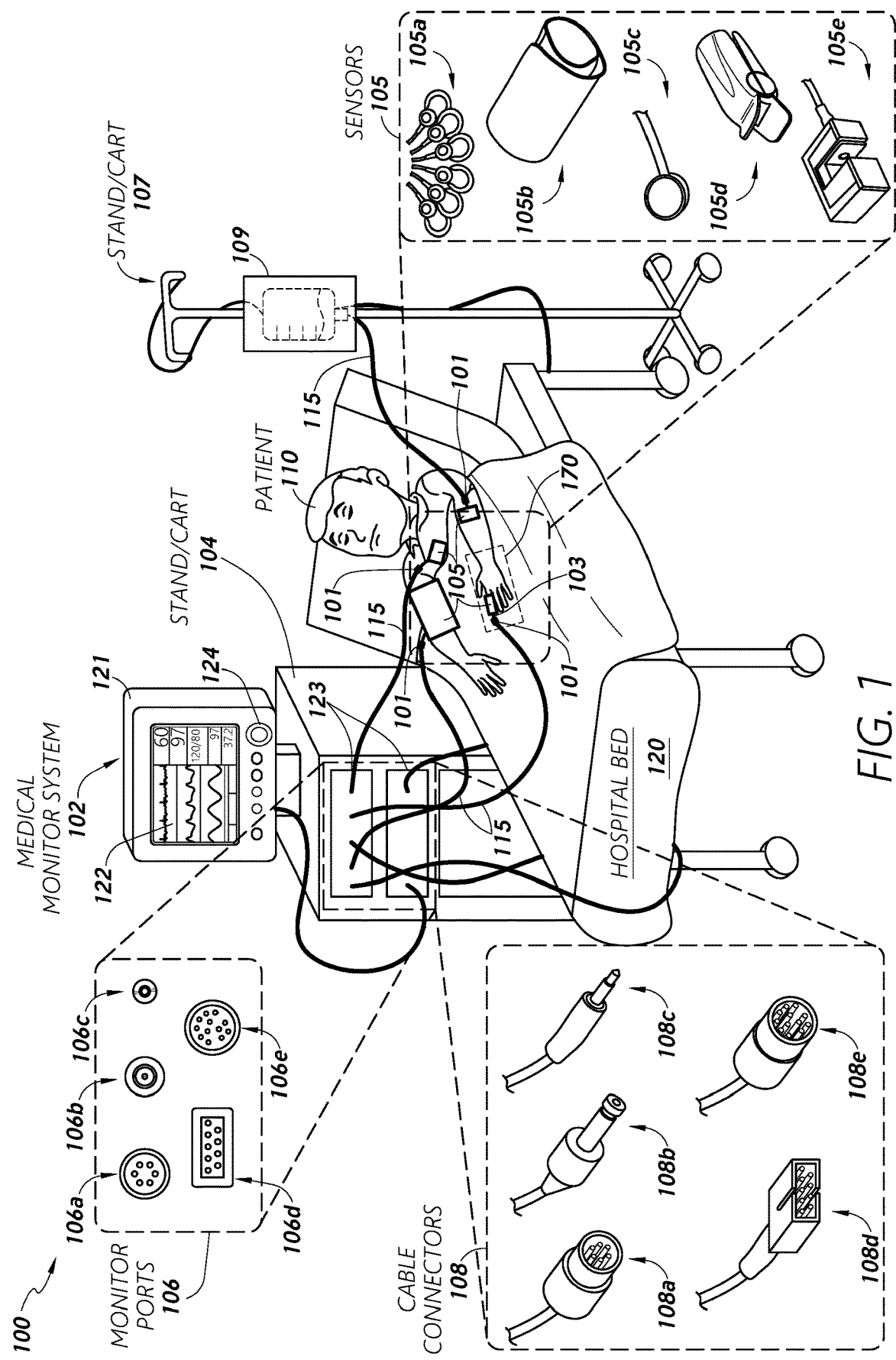

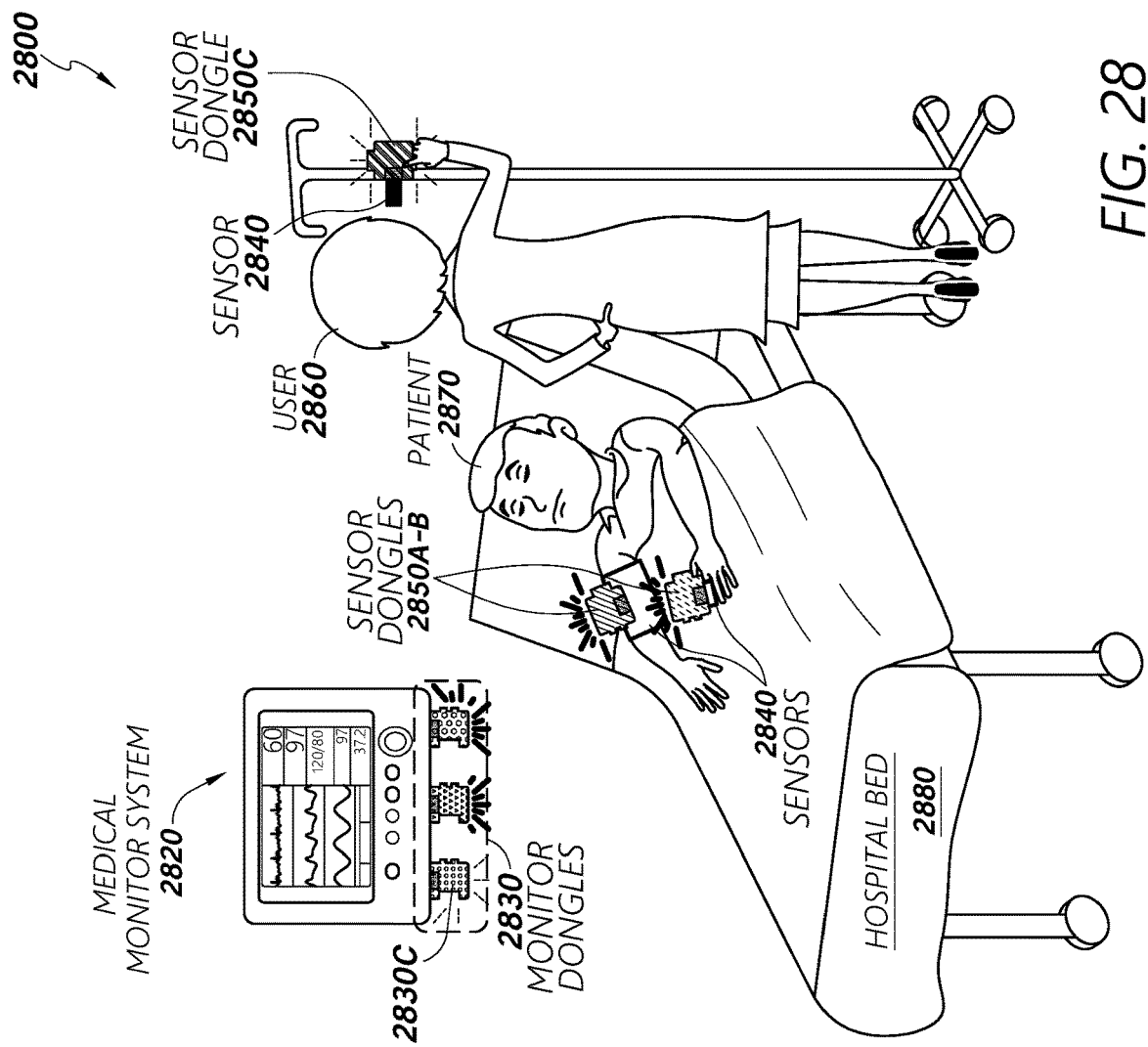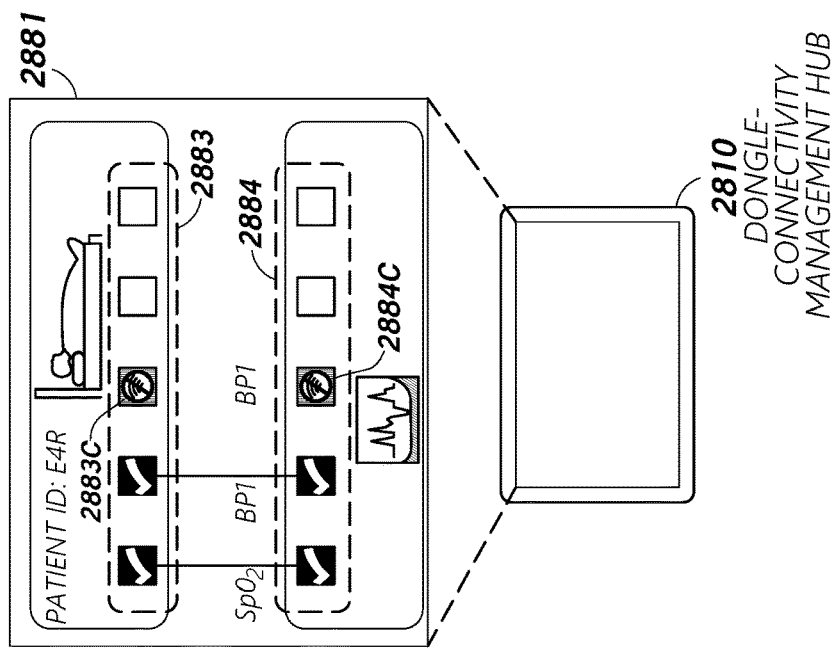
FIG. 28

WIRELESS SENSOR CONNECTIVITY

RELATED APPLICATION

This application claims priority to U.S. Provisional Application No. 62/945,192, filed Dec. 8, 2019, and entitled WIRELESS SENSOR CONNECTIVITY SYSTEM, the disclosure of which is hereby incorporated by reference in its entirety.

BACKGROUND

Field

The present disclosure relates to the field of medical sensors.

Description of the Related Art

Healthcare providers often use medical devices in providing care to patients. These devices include medical monitors and a variety of different types of sensors for monitoring patient health, such as heart function, brain function, vascular/fluid conditions, and the like. Such sensors can include cables of various forms that connect the sensors to medical monitors located in proximity to the patients.

SUMMARY

Described herein are one or more systems, devices, and methods for implementing and/or managing wireless connectivity with respect to certain sensor and/or dongle devices, such as in the context of medical sensing and/or medical care applications.

In some implementations, the present disclosure relates to a wireless-connectivity system comprising a sensor dongle configured to be electrically connected to a sensor device, a monitor dongle configured to be electrically connected to a medical monitor system, and a dongle-connectivity management hub configured to cause a wireless coupling to be established between the sensor dongle and the monitor dongle. The sensor dongle can be configured to receive sensor data from the sensor device and wirelessly transmit data to the monitor dongle via the wireless coupling, the data being based at least in part on the sensor data. In some embodiments, the sensor device is configured to measure one or more physiological parameters of a patient. In some embodiments, causing the wireless coupling to be established includes sending a signal to one or more of the sensor dongle and the monitor dongle, the signal instructing the one or more of the sensor dongle and the monitor dongle to establish the wireless coupling.

In some implementations, the present disclosure relates to a sensor dongle comprising a sensor connector configured to be electrically connected to a corresponding connector of a sensor device, one or more wireless network interfaces, and control circuitry. The control circuitry is configured to establish, at least partly using the one or more wireless network interfaces, a wireless coupling with a monitor dongle, receive, via the sensor connector, sensor data from the sensor, and wirelessly transmit, via the wireless coupling and using the one or more wireless network interfaces, data to the monitor dongle, the data being based at least in part on the sensor data.

In some implementations, the present disclosure relates to a monitor dongle comprising a monitor connector configured to be electrically connected to a corresponding connector of a medical monitor system, one or more wireless network interfaces, and control circuitry. The control circuitry is configured to establish, at least partly using the one or more wireless network interfaces, a wireless coupling with a sensor dongle, receive, via the wireless coupling and using the one or more wireless network interfaces, first data from the sensor dongle, and sending, via the monitor connector, second data to the medical monitor system, the second data being based at least in part on the first data.

In some implementations, the present disclosure relates to a wireless-connectivity system comprising a sensor dongle including a sensor connector configured to be physically and electrically connected to a connector of a sensor device, a monitor dongle including a monitor connector configured to be physically and electrically coupled to a monitor port of a medical monitor system, and a dongle-connectivity management hub circuitry configured to cause a wireless coupling to be established between the sensor dongle and the monitor dongle. The sensor dongle is configured to receive sensor data from the sensor device and wirelessly transmit data to the monitor dongle via the wireless coupling, the data being based at least in part on the sensor data.

The sensor device can be configured to measure one or more physiological parameters of a patient. Causing the wireless coupling to be established can include sending a signal to one or more of the sensor dongle and the monitor dongle, the signal instructing the one or more of the sensor dongle and the monitor dongle to establish the wireless coupling. In some embodiments, the connector of the sensor device is associated with a distal end of a cable coupled to a sensor housing of the sensor device. The connector of the sensor device can have a form that is configured to mate with the monitor port of the medical monitor system. In some embodiments, the sensor connector of the sensor dongle has a similar form to the monitor port of the medical monitor system. The monitor connector of the monitor dongle can have a similar form to the connector of the sensor device. In some embodiments, the dongle-connectivity management hub circuitry is a component of the medical monitor system. In some embodiments, the connector of the sensor device and the monitor connector of the monitor dongle are male connectors and the sensor connector of the sensor dongle and the monitor port of the medical monitor system are female connectors.

The system can further comprise an electronic display communicatively coupled to the dongle-connectivity management hub circuitry, wherein the dongle-connectivity management hub circuitry is further configured to generate user interface data representing the wireless coupling between the sensor dongle and the monitor dongle. For example, the dongle-connectivity management hub circuitry can be further configured to receive user input using the electronic display, wherein said causing the wireless coupling to be established is performed in response to the user input. In some embodiments, the user interface data includes representations of the sensor dongle and the monitor dongle and the representations of the sensor dongle and the monitor dongle have shape characteristics that indicate respective types of dongles for the sensor dongle and the monitor dongle. The dongle-connectivity management hub circuitry can be further configured to determine that the sensor dongle has moved outside a connection range of the monitor dongle and in response to said determination, receive sensor-based data from the sensor dongle over a wireless connection with the sensor dongle.

In some implementations, the present disclosure relates to a sensor dongle comprising a housing, a sensor connector configured to be physically and electrically coupled to a corresponding connector of a sensor device, and control circuitry including wireless network interface circuitry. The control circuitry is disposed at least partially within the housing and configured to receive, via the sensor connector, sensor data from the sensor device and wirelessly transmit, via a first wireless connection and using the wireless network interface circuitry, first data that is based at least in part on the sensor data.

In some embodiments, the control circuitry is further configured to establish, at least partly using the wireless network interface circuitry, a wireless coupling with a monitor dongle and wirelessly transmitting the first data involves wirelessly transmitting the first data to the monitor dongle. Wirelessly transmitting the first data can involve wirelessly transmitting the first data to a medical monitor system. In some embodiments, wirelessly transmitting the first data involves wirelessly transmitting the first data to a mobile computing device.

The sensor connector can be a female physical connector structure. In some embodiments, the sensor dongle further comprises an electronic display configured to display at least one of a patient identifier, a monitor dongle identifier associated with a monitor dongle wirelessly coupled to the sensor dongle, or a status indicator indicating a connection status of the sensor dongle.

In some embodiments, the first wireless connection is between the sensor dongle and a monitor dongle, wirelessly transmitting the first data involves transmitting the first data to the monitor dongle over the first wireless connection, and the control circuitry is further configured to determine that the first wireless connection has been lost. The control circuitry can be further configured to, in response to said determining that the wireless connection has been lost, buffer second data that is based at least in part on the sensor data in data storage of the control circuitry. For example, the control circuitry can be further configured to, in response to said determining that the first wireless connection has been lost, wirelessly transmit, via a second wireless connection between the sensor dongle and a dongle-connectivity management hub system, second data that is based at least in part on at least a portion of the sensor data that is received from the sensor subsequent to the loss of the first wireless connection.

The control circuitry can be further configured to receive, via a second wireless connection between the sensor dongle and another sensor dongle that is physically and electrically coupled to another sensor device, second data from the other sensor dongle, the second data is based at least in part on sensor data received by the other sensor dongle and transmit the second data over the first wireless connection. The sensor dongle can further comprise a physical monitor dongle connector configured to physically mate with a corresponding connector of a monitor dongle. For example, the sensor dongle can be configured to transmit electrical power between the sensor dongle and the monitor dongle over the monitor dongle connector.

In some implementations, the present disclosure relates to a monitor dongle comprising a housing, a monitor connector configured to be physically and electrically connected to a sensor port associated with a medical monitor system, one or more wireless network interfaces, and control circuitry including wireless network interface circuitry, the control circuitry disposed at least partially within the housing. The control circuitry is configured to establish a first wireless connection with a sensor dongle, receive, via the first wireless connection, first sensor data from the sensor dongle, and transmitting, via the monitor connector and the sensor port, second sensor data to the medical monitor system, the second sensor data being based at least in part on the first sensor data.

In some embodiments, the first sensor data and the second sensor data comprise the same data. In some embodiments, the monitor connector has a male connector form and the sensor port has a female connector form. The monitor dongle can further comprise a monitor adapter configured to be physically and electrically coupled to a connector associated with the housing, wherein the monitor connector is part of the monitor adapter.

In some implementations, the present disclosure relates to a method of monitoring a physiological parameter of a patient. The method comprises connecting a sensor connector of a sensor dongle to a connector of a sensor device, connecting a monitor connector of a monitor dongle to a sensor port of a monitor system, and causing a wireless connection to be established between the sensor dongle and the monitor dongle.

The method can further comprise associating a patient identifier with the sensor dongle and the monitor dongle. In some embodiments, causing the wireless connection to be established involves pressing a button associated with at least one of the sensor dongle or the monitor dongle. In some embodiments, causing the wireless connection to be established involves providing input using an electronic display that associates a first icon representing the sensor dongle with a second icon representing the monitor dongle. The method can further comprise, prior to said causing the wireless connection to be established, identifying a plurality of dongles within a wireless connectivity range.

The method can further comprise manipulating a user control associated with one of the sensor dongle and the monitor dongle to indicate a visual identifier associated with another of the sensor dongle and the monitor dongle, wherein said causing the wireless connection to be established is based at least in part on said manipulating the user control. For example, manipulating the user control can involve rotating a color wheel feature. In some embodiments, causing the wireless connection is performed automatically at least partially in response to said manipulating the user control

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIGS. 13-1 through 13-3 illustrate various electrical dongle-to-dongle connections in accordance with one or more embodiments.

FIGS. 24-1 through 24-9 illustrate aspects of certain example processes of connecting various dongles in accordance with one or more embodiments.

FIGS. 26-1 through 26-3 illustrate aspects of example processes of attempting to reestablish one or more wireless couplings that have been lost between dongles in accordance with one or more embodiments.

FIG. 28 illustrates aspects relating certain example processes of decoupling one or more dongles based on input accordance with one or more embodiments.

FIGS. 29-1 through 29-3 illustrate aspects of certain example processes for decoupling one or more dongles in accordance with one or more embodiments.

FIGS. 31-1 through 31-3 illustrate aspects of example patient-transport connectivity systems and processes in accordance with one or more embodiments.

DETAILED DESCRIPTION

The headings provided herein are for convenience only and do not necessarily affect the scope or meaning of the claimed inventive subject matter. The present disclosure relates to systems, devices, and methods for facilitating wireless connection of various medical devices to provide and/or facilitate reduced cumbersomeness, increased monitoring range, improved ease of use, efficient operation on the patient, and/or other improvement(s) compared to certain other patient-monitoring/treatment solutions.

Although certain preferred embodiments and examples are disclosed below, inventive subject matter extends beyond the specifically disclosed embodiments to other alternative embodiments and/or uses, and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Figures 1, 13:
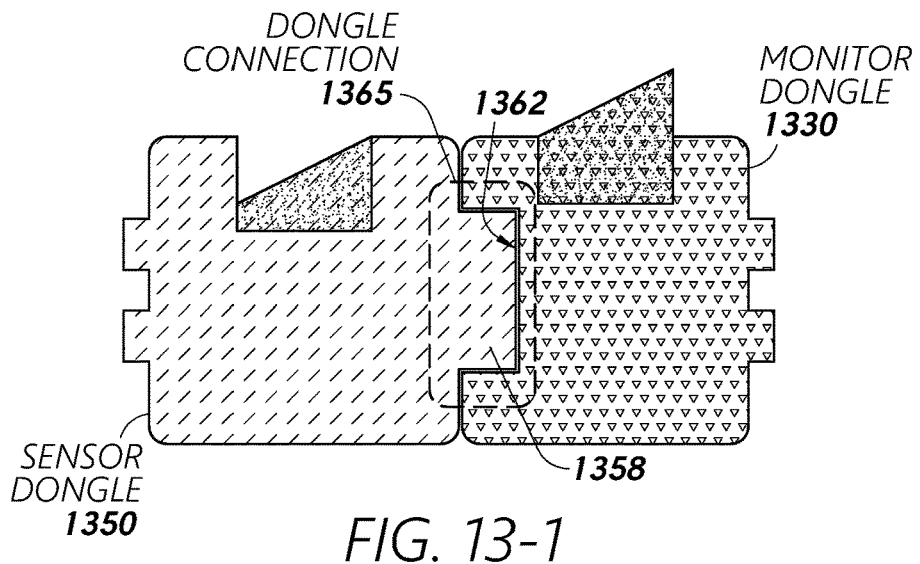
Figures 2, 13:
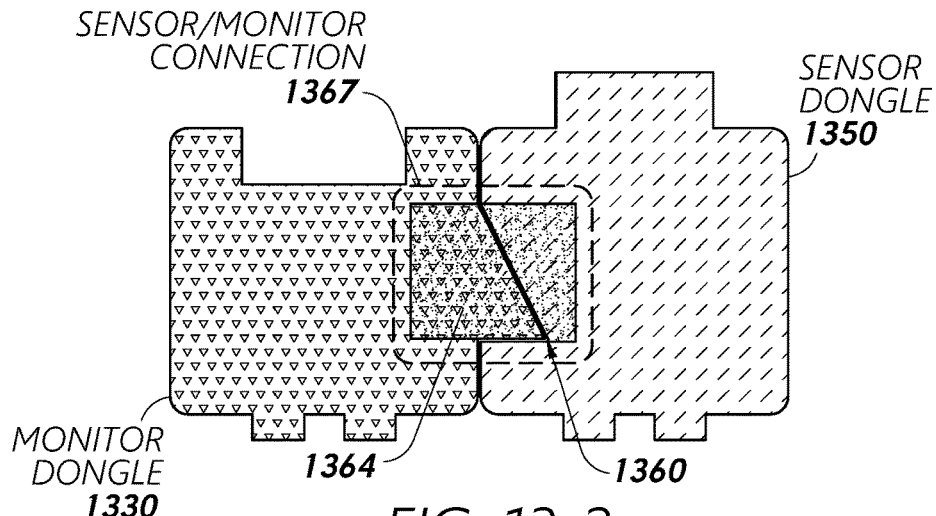
Figures 3, 13:
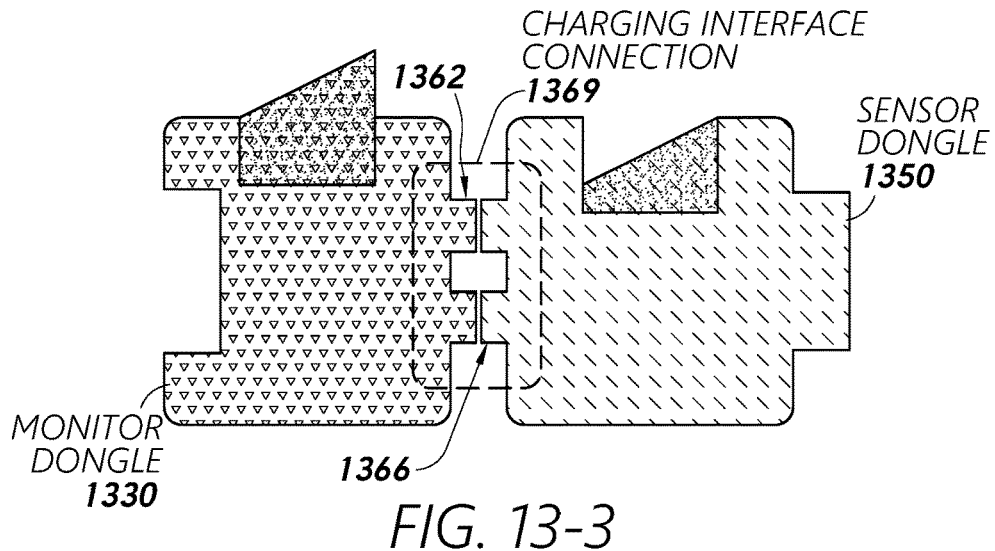

FIG. 1 illustrates an example patient care (e.g., hospital) environment 100 according to certain embodiments to provide care to a patient 110. The healthcare environment 100 may also include a hospital bed 120 to support the patient 110 and one or more chairs and/or other furniture to assist healthcare provider(s). In some example scenarios, a healthcare provider (not illustrated) or other individual (e.g., the patient 110) connects and/or configures one or more cable-connected sensors 105 to the patient 110 and to a medical monitor system 102 for the purpose of monitoring various parameters related to the health of the patient 110. The medical monitor system 102 is physically and/or electrically coupled to the sensors 105 via various monitor ports 106. For example, the sensors 105 may have respective cables 115 and connectors 108 associated therewith, wherein the cable connectors 108 are configured to mate or otherwise engage with respective ones of the monitor ports 106.

The monitor system 102 can include a display unit or device 121 including an electronic display 122 and/or one or more user-input features (e.g., button(s), knob(s), and/or the like). The monitor ports 106 provide a physical and electrical interface for coupling to the monitor system 102. In some embodiments, one or more of the monitor connectors 106 are integrated at least in part with the display unit or device 121. Additionally or alternatively, one or more of the monitor ports 106 may be associated with one or more units 123 electrically coupled to the display unit 121 via one or more wired and/or wireless connections. For example, the input-unit(s) 123 can be at least partially housed and/or maintained/disposed on or in a stand or cart structure 104 associated with the medical monitor system 102. In some embodiments, the stand 104 comprises mobility/ambulatory features (not shown; e.g., wheels or the like) that facilitate movement of the stand 104 from place to place. The terms "coupled" and "coupling" are used herein according to their broad and ordinary meanings. For example, where a first feature, element, component, device, or member, is described as being "coupled" with or to a second feature, element, component, device, or member, such description may be understood as indicating that the first feature, element, component, device, or member, or portion thereof, is physically/mechanically attached, fixed, fastened, mounted, connected, linked, or joined to, or united, associated together, or integrated with, or embedded at least partially within, or otherwise physically related to, the second feature, element, component, device, or member, or portion thereof, whether directly or indirectly. A "coupling" can refer to any device, structure, form, tool, mechanism, means, position, apparatus, or portion, component, or position thereof that at least partially facilitates and/or effects/achieves the coupling of two or more features, elements, components, devices, or members, and/or portions thereof.

The medical sensor(s) 105 can include one or more devices that are configured to detect or determine one or more physical, physiological, chemical, and/or biological signals, parameters, properties, states and/or conditions (referred to herein individually and/or collectively as "parameters") associated with the patient 110 and/or environment in which the patient 110 is disposed. The sensor(s) 105 are advantageously configured to provide and/or generate signals representative and/or indicative of the parameter(s) they are designed/configured to sense/measure. Signals generated and/or provided by sensors 105 in accordance with embodiments of the present disclosure may be any suitable, practical, or desirable types of signals, whether analog, digital, electrical, pneumatic, acoustic/sonic, hydraulic, tactile, and/or combinations thereof. Furthermore, the sensor(s) 105 may be configured to determine/detect any type of physical properties, including temperature, pressure, vibration, haptic/tactile features, sound, optical levels or characteristics, load or weight, flow rate (e.g., of target gases and/or liquid), amplitude, phase, and/or orientation of magnetic and electronic fields, constituent concentrations relating to substances in gaseous, liquid, or solid form, and/or the like. In some embodiments, medical sensors in accordance with the present disclosure comprise microelectromechanical systems/devices. Sensor devices in accordance with embodiments of the present disclosure can be configured on/for a patient by applying the sensor to the skin of the patient, implanting at least partially within the patient (e.g., subcutaneous sensors), and/or disposed in proximity to the patient in a position to allow for sensor readings to be generated.

Example sensors that can be implemented in connection with embodiments of the present disclosure include non-invasive blood pressure (NIBP) sensors or other sphygmomanometer sensors. It should be understood that references herein to blood pressure sensors may refer to any type of sensor device that can be used to measure blood pressure. For reference, FIG. 1 shows a blood pressure sensor 105b, which may be similar to certain blood pressure sensor(s) that may be implemented in connection with any of the embodiments disclosed herein. Blood pressure sensors relating to embodiments of the present disclosure can include, for example, an inflatable cuff that can selectively, sporadically, and/or intermittently be inflated or otherwise tightened and deflated/collapsed or otherwise loosened. Such tightening and loosening may be implemented in a controlled manner to determine pressure levels. The pressure sensor 105b may further include one or more manometer (e.g., mercury-based or mechanical/aneroid) configured to generate signals indicative of pressure levels. The blood pressure sensor can further include a means or mechanism for inflation/tightening the cuff, which may be a manually operated bulb and valve or a pump operated electrically.

Pressure measurement may advantageously be implemented digitally at least in part. For example, oscillometric measurements and/or electronic calculations can be employed to determine pressure, whether manual or automatic inflation/tightening is implemented. Systolic and diastolic pressures may be measured based on deformable membrane(s) that are measured using differential capacitance, or differential piezoresistance. Blood pressure sensors in accordance with the present disclosure can include one or more microprocessors or other control circuitry for determining pressure signals and/or measurements. In addition to pressure, the blood pressure sensor 105b may provide information indicative of heart rate, arterial stiffness, and/or other physiological parameter(s).

Example sensors that can be implemented in connection with embodiments of the present disclosure further include electrocardiographic (ECG) sensors, or other sensors of electrical signals. ECG measurements can provide readings of electrical activity in the heart. ECG readings may be obtained through the placement of ECG leads 105a, which are often affixed to the external chest wall of the patient in proximity to the heart. The leads placed on the surface of the chest may pick up electrical signals generated in the heart and provide a reading reflective thereof, which may be analyzed or used for various purposes.

The ECG sensor leads 105a can include electrodes in the form of conductive pads that are configured to be disposed on the body surface. Generally, pairs of electrodes can be utilized to measure the electrical potential difference between the two corresponding locations of attachment. The term "lead" is used herein according to its broad and ordinary meaning and may refer to a single electrode and/or associated pad and/or cable, or to an electrode pair and/or associated components. Although FIG. 1 shows an ECG sensor 105a including six electrodes/leads, ECG sensors may be implemented with 8, 10, or 12 electrodes or leads, or any other number.

The electrodes of the ECG sensor 105a can be secured to the patient 110 using respective pads, as shown detached from the respective electrodes in FIG. 1. For example, the pads may comprise relatively flat and/or thin stickers and/or other adhesive (e.g., self-adhesive) distal surface(s). In some implementations, ECG leads are used with electrically-conductive electrolyte gel and/or a conductor (e.g., silver, silver chloride, and/or the like). Such gel may comprise potassium chloride, silver chloride, or the like, to permit electron conduction from the skin to the electrode.

Example sensors that can be implemented in connection with embodiments of the present disclosure further include pulse oximeters 105d, or other optical sensors. Pulse oximetry is a noninvasive method for monitoring a person's oxygen saturation ($SO_2$). Generally, pulse oximeters in accordance with embodiments of the present disclosure may be configured to read peripheral oxygen saturation ($SpO_2$), as opposed to arterial oxygen saturation ($SaO_2$), although it should be understood that $SaO_2$ sensors are within the scope of certain embodiments disclosed herein.

The pulse oximeter 105d may be placed on a relatively thin part of the patient's body, such as a fingertip or earlobe, or in the case of an infant, across a foot. In some embodiments, the pulse oximeter 105d is configured to transmit wavelengths of light through the body part to a photodetector. The changing absorbance at each of the wavelengths can be measured to determine the absorbances due to the pulsing arterial blood alone, excluding venous blood, skin, bone, muscle, fat, and/or other intervening matter/tissue. Although transmissive pulse oximeters are described herein in connection with various embodiments, it should be understood that reflectance pulse oximeters (e.g., cerebral pulse oximeter) also may be utilized in some embodiments. For example, such devices may be disposed on a patient's feet, forehead, chest, or other anatomy.

Example sensors that can be implemented in connection with embodiments of the present disclosure further include temperature sensors 105c. Such sensors may be disposed on the skin of the patient 110 at a desired location or may be inserted into a chamber or vessel of the patient's anatomy. Temperature sensors in accordance with aspects of the present disclosure can comprise, for example, one or more thermistors or other temperature-sensing devices. In some embodiments, a temperature sensor includes a metal housing and is coupled to a cable 101.

The sensor(s) 105 may further include any other type(s) of medical sensors, such as sensors configured to be used to sense end tidal $CO_2$ levels ($EtCO_2$), or other capnographic sensor(s), as represented by the sensor 105e in FIG. 1. Such sensor 105e may be configured to provide signals indicative of the maximum expired carbon dioxide concentration during a respiratory cycle. Such information may be used to determine parameters of pulmonary function and/or indirect indications of cardiac function, ventilator function, and/or perfusion.

The sensors 105 can include sensors of various types, such as sensors that detect different types of information, sensors that are manufactured by different entities (e.g., companies), sensors that are designed for different protocols or standards, and so on. Each type of sensor can include a specific type of connector 108 for connection to another device, such as to one of the ports 106 of the medical monitor system 102. To allow multiple sensors to be connected to the medical monitor system 102, the monitor ports 106 can advantageously include a variety of connectors. For example, in some embodiments, the monitor ports 106 include a port 106c for a temperature sensor connector 108c, a port 106d for a pulse oximeter connector 108d, a port 106a for an ECG sensor connector 108a, a port 106b for a blood pressure sensor connector 108b, a port 106e for an $EtCO_2$ sensor connector 108e, and so on.

Although the various ports 106 have been described as corresponding to certain types of cable connectors, it should be understood that such ports may be used and/or correspond to respective cable connectors associated with other types of sensors. In some implementations, one or more of the ports 106 may be a substantially generic or configured to receive or mate with cable connectors that may be associated with a variety of types of sensors or other devices.

Each of the cable connectors 108 can comprise an electromechanical device used to join electrical termination(s) of the respective connector and/or cable to corresponding termination(s) of the respective monitor ports 106. In some embodiments, certain of the cable connectors 108 and/or corresponding monitor ports 106 have a gender, such as a male component, (i.e., a plug) or a female component (i.e., a socket). The connectors 108 are advantageously removable from the ports 106 in some embodiments and may or may not require a tool for assembly and/or removal. In some embodiments, the cable connectors 108 are permanent electrical interfaces. In some embodiments, adapters can be used to join dissimilar connectors and ports.

The cable connectors 108 and/or ports 106 can be configured for power, data, and/or audiovisual communication. Furthermore, the cables connectors 108 and/or ports 106 can be chassis or panel connectors, as described in detail herein, or may be inline connectors, PCB-mount connectors, splice or butt connectors, or any other type of connectors/connections. In addition, the connectors 108 may have any configuration and/or arrangement of pins/pinout, method of connection, materials, size, contact resistance, insulation, mechanical durability, ingress protection, lifetime (e.g., number of cycles), and/or ease of use. In some embodiments, the connectors 108 are designed to be relatively easily-identifiable, to facilitate ease of use and assembly. The cable connectors 108 and/or monitor ports 106 advantageously may comprise one or more conductors and one or more insulators configured to provide electrical and/or thermal isolation for the conductor(s). Example materials for conductors can include copper, copper alloys, brass, phosphor bronze, beryllium copper, and other metals and at least partially conductive materials. The connectors 108 and/or ports 106 can also include contact carrier structures configured to hold the parts of the connector/port together. Such structures can comprise plastic or other at least partially insulating material(s).

The connectors 108 and/or ports 106 can be configured for and/or adaptable to any type of physical layer communication standard or protocol, including but not limited to any serial or parallel transmission standard, ethernet, FireWire, coaxial connection, universal serial bus (USB), video graphics array (VGA), digital visual interface (DVI), high-definition multimedia interface (HDMI), and so on. In some embodiments, a connector and/or associated port is associated with a particular standard or protocol and/or a particular type of health monitoring (e.g., ECG, $SpO_2$, pulse rate, respiratory monitoring, NIBP, etc.). Further, in some embodiments, a connector can include a leadwire port such as a 3-, 5-, 6-, or 12-leadwire port.

In some implementations, medical sensors may be coupled to medical monitor systems via an intermediate cable connection 101, as shown in FIG. 1. For example, in some implementations, a medical sensor 105 has an abbreviated cord portion 103 coupled to a sensor connector 101. The sensor connector 101 may include mated connectors associated with each of the abbreviated cord portion 103 and primary cord 115, which is in turn coupled to the medical monitor system 102 via a cable connector 108 and monitor port 106. Such configurations may be particularly applicable to systems incorporating disposable sensor devices. For example, a disposable sensor device may comprise the sensor itself 105, as well as the abbreviated cord portion 103 and associated cable connector. The disposable portion 170 can be coupled to the primary cable 115 at the inter-cable connection to facilitate monitoring using the sensor 105. In such arrangement, the cable 115 and medical monitor system 102 may be reusable for multiple patients and/or multiple iterations or periods with the same patient, whereas only the disposable portion 170 is replaced between sensing iterations. Use of disposable sensor assemblies, such as the disposable sensor assembly 170 in FIG. 1 may advantageously provide improved sanitary conditions and/or efficiency of use for the monitoring system 100. Although FIG. 1 shows intermediate inter-sensor connections 101, such features are illustrated for example and clarity only, and it should be understood that the system 100 may not include such intermediate inter-cable connections.

FIG. 1 illustrates many challenges that can be associated with certain patient-monitoring solutions that implement various types of sensors. For example, as shown, when the patient 110 is connected to a plurality of sensors 105 via a plurality of respective cables 115, the cables 115 can obstruct the healthcare environment 100, which can affect the safety of individuals within the healthcare environment 100. That is, a healthcare provider can be required to maneuver around the cables 115 to administer medication, evaluate the patient, view information on the medical monitor system 102, attach the cables 115 to the patient 110, and so on. Further, in instances where the patient 110 is transported from one room or facility to another room or facility, a healthcare provider may be required to perform a time-consuming process of unplugging the cables 115 from the medical monitor system 102 in one room or facility and reconnecting the cables 115 into a medical monitor in the other room or facility once the patient 110 is transported to the other room or facility. Moreover, certain patient-transport processes may require a separate transport monitor to be used while the patient 110 is being transported between rooms or facilities. Furthermore, to ensure interoperability of medical devices, a facility may wish to implement devices of the same type and/or having the same types of connectors/ports. For example, a hospital may purchase a medical monitor system and sensors from the same company to ensure that the sensors can connect to the medical monitor system. This can restrict the ability of the hospital to implement medical devices from other companies, which may be advantageous in some cases. Further, since medical monitor systems are often implemented/maintained within a facility for many years (e.g., due to cost and other factors), the facility can be tied to specific sensors that are compatible with the type of medical monitor system employed. This can further restrict the ability of the facility to implement other devices that are more advantageous, such as devices with different/more functionality and different types of connectors, newer devices with different types of connectors, and so on. Furthermore, in some instances, users inadvertently connect the cables 115 to the wrong ports of the medical monitor 102, which can prevent a connection from being made between the cables 115 and the medical monitor 102 and/or cause unexpected or inaccurate data to be displayed on the medical monitor 102.

Wireless Connectivity Systems

Figure 2:
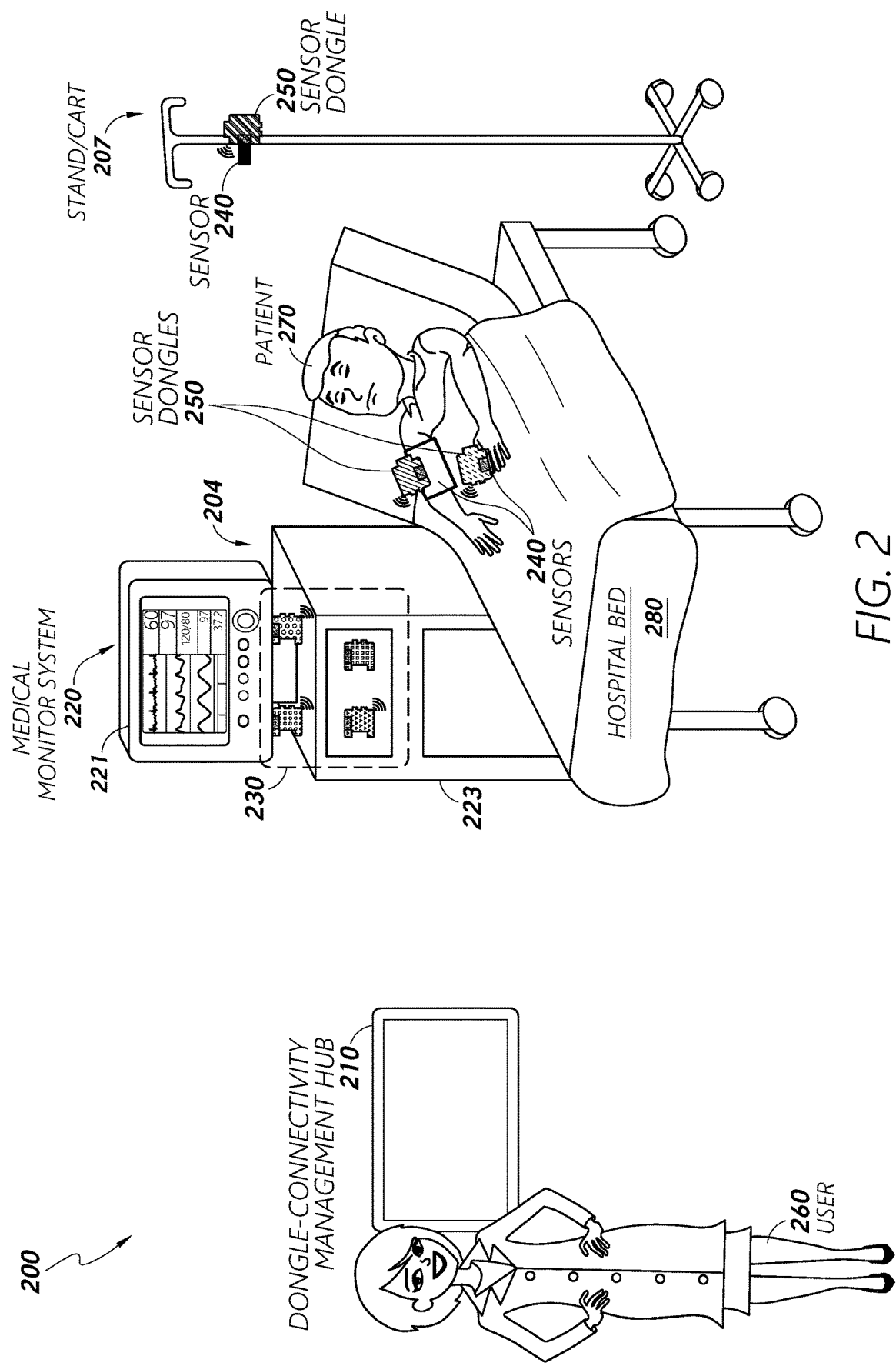
FIG. 2 illustrates an example wireless sensor-monitor connectivity system implemented within a healthcare environment in accordance with one or more embodiments.

In some implementations, embodiments of the present disclosure advantageously provide a solution for data coupling between medical sensors and monitoring systems that are at least partially less cumbersome that solutions relying exclusively on wired/cable-coupled sensor-monitor connections. For example, FIG. 2 illustrates an example wireless sensor-monitor connectivity system 200 implemented within a healthcare environment in accordance with one or more embodiments. The healthcare environment can include a hospital room, an operating room, or any other room or facility where a patient can receive medical care/treatment. For example, the healthcare environment can include an operating room where many medical sensors 240 are implemented to monitor aspect(s) of the health of a patient 270, such as during surgery. In this example, the patient 270 is located on a hospital bed 280. The hospital bed 280 can include special features to assist in providing care to the patient 270, such as side rails, a mattress, components to adjust a height/incline of the hospital bed 280, buttons to operate nearby electronic devices and/or the hospital bed 280, wheels to move the hospital bed 280, and so on.

The monitor-sensor connectivity system 200 includes one or more monitor dongles 230, one or more sensor dongles 250, and a dongle-connectivity management hub 210 configured to facilitate connectivity between the monitor dongles 230 and the sensor dongles 250. In some implementations, each of the sensor dongles 240 and the monitor dongles 250 comprises certain control circuitry configured to facilitate wireless data communication between the sensors 240 and the medical monitor system 220.

Figure 5:
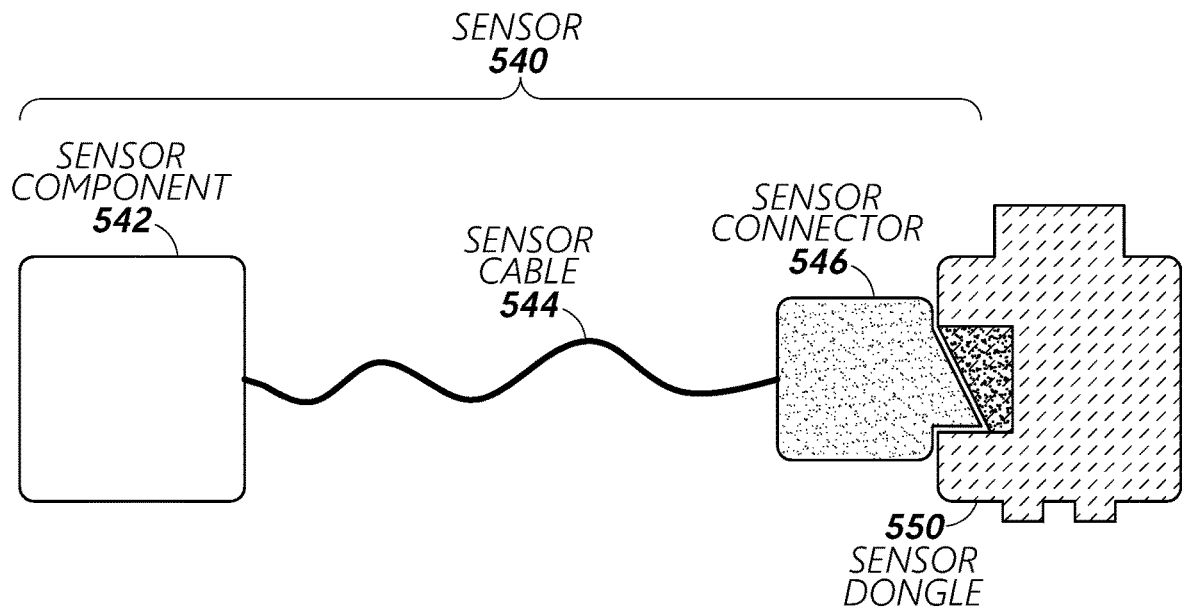
FIG. 5 illustrates an example sensor-dongle physical connectivity configuration in accordance with one or more embodiments.

As an alternative to wired/cable connections between the sensors 240 and the medical monitor system 220, the system 200 includes sensors 240 that are electrically coupled to the sensor dongles 250, respectively, rather than to a cable that is physically connected to the medical monitor system 220. The sensor dongles 250 may advantageously have physical connector features that are configured and/or designed to mate with corresponding connector features associated with the sensors 240. For example, such connectors of the sensors 240 may be associated with the sensor unit itself, or with an abbreviated cable that is in turn electrically coupled to the sensor units. That is, the sensors 240 shown in FIG. 2 may represent sensors having a direct coupling to the respective sensor dongles 250, or may be sensors including an abbreviated cable and associated distal connector (e.g., as with certain disposable sensor devices/units) as illustrated in FIG. 5 and discussed in detail below.

The sensor dongles 250 can advantageously comprise certain control circuitry configured to enable and/or implement a wireless communication between the sensor dongles 250 and certain wireless communication control circuitry associated with the medical monitor system 220. For example, in some embodiments, certain monitor dongles 230 may be physically and/or electrically coupled to the medical monitor system 220, wherein such monitor dongles 230 comprise control circuitry configured to implement a wireless connectivity/communication between the sensor dongles 250 and the monitor dongles 230. That is, the monitor dongles 230 may be configured to receive wireless signal transmissions from the sensor dongles 250 and/or transmit wireless signals (e.g., operational commands, parameters, and the like) that the sensor dongles 250 are configured to receive and/or process. The sensor dongles 250 and/or monitor dongles 230 may comprise certain physical and/or wireless coupling/connector features for coupling to one another and/or to power sources and/or other devices or systems not shown in FIG. 2.

The medical monitor system 220 may have any suitable or desirable designer configuration. For example, the medical monitor system 220 may include a monitor display unit 221, which may comprise an electronic display configured to visually represent certain information related to the operation of the sensors 240. The monitor dongles 230 may be physically connected/coupled to the monitor display unit 221 and/or to one or more other sensor input units 223. For example, one or more sensor input units 223 may be communicatively coupled to the monitor display unit 221 via one or more wired and/or wireless connections. In some implementations, the sensor input units 223 are disposed on/in and/or secured to the monitor stand/cart 204, which may have mobility features (e.g., wheels). Additionally or alternatively, one or more monitor dongles 230 may be directly coupled to the monitor display unit 221, as shown in the diagram of FIG. 2. In some embodiments, the medical monitor system 220 comprises the monitor display unit 221, which may be disposed and/or mounted in any suitable or desirable location and/or configuration, wherein the medical monitor system 220 is not associated with a bedside cart or stand. The dongle-connectivity management hub 210, the medical monitor system 220, the monitor dongles 230, the sensor dongles 250, and/or the sensors 240 can include various corresponding components/devices discussed in greater detail below.

In the example of FIG. 2, the medical monitor system 220 is implemented on a stand 204 positioned adjacent to or nearby the patient 270 and/or bed 280 (e.g., within a desirable distance to the patient 270). The dongle-connectivity management hub 210 may be employed by a user 260 within the healthcare environment in which the connectivity system 200 is implemented. In some implementations, at least a portion of the medical monitor system 220 (e.g., a display unit 221 thereof), the dongle-connectivity management hub 210, and/or the monitor dongle(s) 230 may be configured/disposed in a wall-mount assembly/display and/or other local or remote location within or external to the healthcare environment. Such flexibility in location of such components can be due at least in part to the wireless functionality that is facilitated and/or executed by the dongle-connectivity management hub 210, the monitor dongles 230, and/or the sensor dongles 250. The wireless functionality can provide improved safety and/or access to the patient 270 than other solutions that implement cables to connect devices within a healthcare environment. The dongle-connectivity management hub 210 can be implemented or embodied in a mobile computing device, such as a smartphone, tablet computer, or laptop computer.

Although sensor dongles are illustrated in many embodiments as individual devices, in some embodiments a sensor dongle can be integrated into a device. For example, one or more of the sensor dongles 250 can be integrated into the bed 280 and one or more of the sensors 240 can be configured to be connected to one or more of the integrated sensor dongles 250, such as via a cable that connects to a port on the bed 280 and one or more of the sensors 240.

Figure 3:
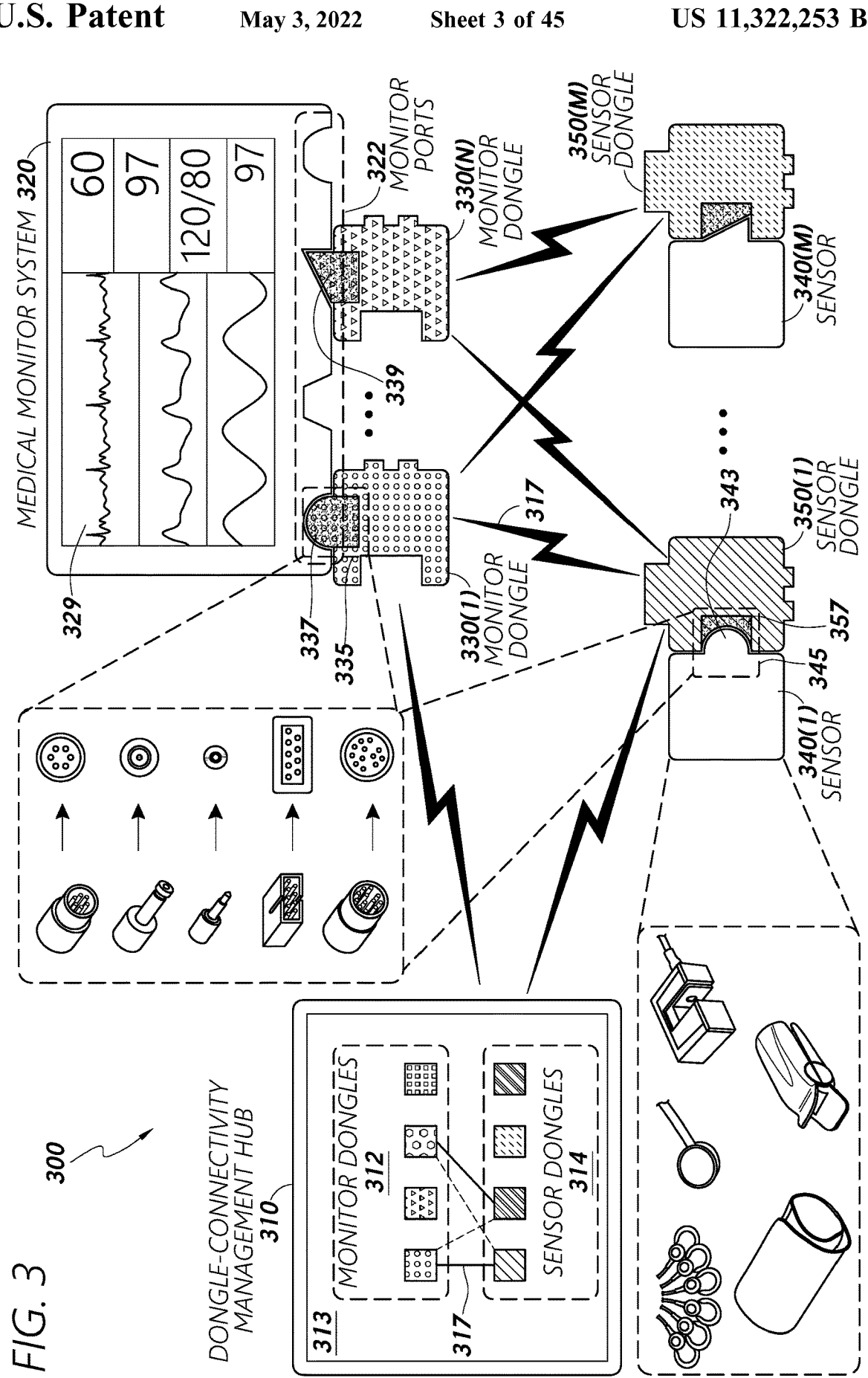
FIG. 3 illustrates an example wireless connectivity system in accordance with one or more embodiments.

FIG. 3 illustrates an example wireless connectivity system 300 that provides wireless connectivity for various types of medical devices, such as for the purpose of monitoring health-related parameters/information about a patient (not shown) in accordance with one or more embodiments. For example, the system 300 may be configured to communicatively couple various types of sensors (e.g., medical sensors) wirelessly to a medical monitor system and/or one or more other devices to facilitate patient monitoring and/or other functionality. Such wireless connectivity can help reduce or avoid obstructions within an environment in which the system 300 is implemented that may otherwise result from cables and/or other wired-connectivity components that may be implemented in certain wired-connectivity solutions to communicatively couple sensors to a medical monitor system.

The system 300 may also advantageously include features configured to provide wireless connectivity management functionality with respect to certain components/devices of the system 300 in a relatively convenient manner. In some implementations, such management functionality may be implemented with certain features configured/designed to provide desirable ease-of-use for corresponding to various skill levels to help ensure wireless connectivity. Furthermore, the system 300 may include certain features that provide relative flexibility in communicatively coupling various types of devices, as well as features that allow a patient to be monitored without a dedicated medical monitor unit separate from the connectivity management system 210 and/or as a patient is being transported between rooms, facilities, and/or areas thereof. The terms "communicatively coupled" and variations thereof are used according to their broad and ordinary meanings and may refer to any state or configuration of connection between devices, components, entities, persons, systems, or the like, whether physical or otherwise, over which signal(s) may be transmitted or otherwise communicated, whether such signal(s) are digital, analog, discrete, continuous, wired, wireless, electrical, mechanical, pneumatic, hydraulic, optical, electromagnetic, audible, or any other type of signal.

As shown, the system 300 includes one or more sensors 340(1)-340(M) that are configured to be attached to otherwise configured for one or more patients (not illustrated) to provide information relating to and/or indicative of one or more physiological parameters of the one or more patients. The term "configured for," with respect to a sensor or associated device, component, or feature thereof being "configured for" a patient or other individual or group of individuals/patients, is used herein according to its broad and ordinary meaning and may refer to a sensor, and/or any component, feature, device, or member thereof or associated therewith or otherwise related thereto, being at least partially physically coupled to, attached to, connected to, adhered to, or otherwise disposed adjacent to and/or in proximity to, the patient. Furthermore, where a sensor is described as being configured for a patient, such description may additionally or alternatively refer to particular positioning, orienting, aligning, and/or the like, of the sensor with respect to the patient and/or one or more other features/components of a patient monitoring system/environment.

The diagram of the system 300 further shows one or more sensor dongles 350(1)-350(M) that are configured to be electrically and/or physically connected to respective ones of the sensors 340. The system 300 further includes one or more monitor dongles 330(1)-330(N) that are configured to be electrically and/or physically connected to the medical monitor system 320 via one or more respective monitor ports 322. In the example of FIG. 3, the monitor ports 322, connectors on the sensors 340, and connectors on the sensor dongles 350 are illustrated with different types of male and female forms/shapes, such as a semi-circle, triangle, trapezoid, and the like, to represent different types of connectors. However, it should be understood that such forms/shapes are used merely for the purpose of identifying like and/or corresponding connectors, and the particular forms/shapes illustrated are not intended to represent any specific or particular types of connectors. For example, an illustrated semicircular projection and/or corresponding recess/concavity may refer to connector component(s) associated with a blood pressure sensor, pulse oximeter sensor, or any other type of sensor. Furthermore, although male and female forms/shapes are illustrated, it should be understood that the connector components represented thereby may or may not have similar male and/or female attributes. That is, in some embodiments, a male-type projection form/shape may represent a male, female, and/or other type of connector component. In addition, any connector illustrated or described herein can be a wireless near-field coupling or other wireless coupling. Further, in FIG. 3, "N" and "M" each represent an arbitrary integer that is greater than one and can be the same or different integers.

The sensor dongles 350 and the monitor dongles 330 can be configured to wirelessly couple with one another and to communicate data between the sensors 340 and/or the medical monitor system 320 over such coupling, such as to provide data obtained/generated by the sensors 340 that relates at least in part to one or more physiological and/or environmental parameters to the medical monitor system 320. For example, according to one example use case, a medical sensor device 340(1) may be physically and/or electrically connected to a sensor dongle 350(1), wherein such connection facilitates data-communicative coupling between the sensor device 340(1) and the sensor dongle 350(1). The sensor 340(1) may advantageously be configured to generate, determine, or otherwise obtain signals and/or data indicative of the presence and/or attributes/characteristics of one or more physiological and/or environmental parameters, such as one or more parameters relating to the health of a patient for whom the sensor 340(1) is configured (e.g., attached or otherwise secured to the patient).

The sensor dongle 350(1) may be configured to receive signals/data from the sensor over connection 345, wherein the sensor dongle 350(1) is configured to wirelessly transmit signals based at least in part on the signals/data received from the sensor 340(1). For example, the sensor dongle 350(1) may be paired or coupled wirelessly to a respective one of the monitor dongles 330, such as to the monitor dongle 330(1), as shown in FIG. 3. The wireless coupling between the sensor dongle 350(1) and the monitor dongle 330(1) may allow for the monitor dongle 330(1) to receive the transmitted signals/data from the sensor dongle 350(1). The wireless coupling between the sensor dongle 350(1) and the monitor dongle (1) may be any type of wireless coupling, such as Wi-Fi, Bluetooth, cellular, and so on, and may be pure-to-peer or a network connection. The monitor dongle 330(1) may advantageously be physically and/or electrically coupled to the medical monitor system 320 as illustrated by the connection 335. Having received the signal source/data over the wireless connection/coupling with the sensor dongle 350(1), the monitor dongle 330(1) may be configured to transmit or otherwise communicate such data/signals to the medical monitor system 320. The medical monitor system 320, in turn, may display and/or otherwise output information, such as on the electronic display 322.

The dongle-connectivity management hub 310 can be configured to manage connectivity of the monitor dongles 330 and/or the sensor dongles 350 in an efficient and/or user-friendly manner. For example, the dongle-connectivity management hub 310 can provide/comprise a user interface via, such as an electronic display screen or the like to assist a user (not shown) in connecting the sensor dongles 350 to the monitor dongles 330. In some embodiments, the dongle-connectivity management hub 310 can also communicate with the sensor dongles 350 and/or the monitor dongles 330 to provide audible and/or visual notifications regarding connectivity of the dongles.

The term "dongle" is used herein in connection with embodiments according to its broad and ordinary meaning, and may refer to a hardware device that can connect to a connector or port on another device to provide additional functionality to the other device and/or facilitate data and/or power input and/or output to/from the other device. "Dongles," as described herein, include certain control circuitry for facilitating wireless connectivity and/or adapter functionality; The various functionalities of dongles disclosed herein can be performed in whole or in part by control circuitry of the respective dongle. the control circuitry can include wireless interface circuitry for receiving and/or transmitting wireless data/signals. In some embodiments, a dongle can be an adapter configured to connect to a device via one type of connection and connect to another device via another type of connection. For example, the sensor dongles 350 can advantageously be configured to be physically connected to respective connectors associated with the sensors 340 over a physical interface and wirelessly connect to respective ones of the monitor dongles 330 over a wireless communication interface. As such, in some embodiments, a dongle refers to a wireless adapter. However, a dongle can connect to a device to provide another type of functionality relating to the device, such as data processing, data storage, and so on. According to some embodiments, a dongle can include a housing, one or more physical and electrical connectors, and control circuitry disposed at least partially within the housing and configured to perform processing on signals received over an electrical and/or physical connector, and/or received over a wireless interface of the control circuitry.

The sensor dongles 350 and/or the monitor dongles 330 can include hardware devices that provide wireless connectivity functionality for the sensors 340 and/or the medical monitor system 320, which may not include wireless communication capabilities in some embodiments. For example, the sensor dongles 350 can include multiple types of dongles, with each type of dongle being configured to connect to a specific type of connector, or group of types of connectors, associated with certain medical sensor(s). Similarly, the monitor dongles 330 can include multiple types of dongles configured to connect to different types of port connectors associated with the medical monitor system 320, such as the monitor ports 322. In some embodiments, the sensor dongles 350 and the monitor dongles 330 can be configured so that specific types of dongles are able to wirelessly couple (e.g., dongles having a same type of connector).

In some embodiments, the sensor dongles 350 and/or the monitor dongles 330 can be configured to provide audible and/or visual output relating to operation of the dongles. For example, in some embodiments, the sensor dongles 350 and/or the monitor dongles 330 can output different audible sounds, light, colors, and so on, to indicate a connectivity state or status of the dongles. In some embodiments, the sensor dongles 350 and/or the monitor dongles 330 can provide output in a particular manner to assist a user in verifying that one or more of the sensor dongles 350 and one or more of the monitor dongles 330 are wirelessly coupled in the desired manner (e.g., to ensure that the medical monitor system 320 receives the appropriate signal(s) through one or more monitor port(s)).

In some embodiments, the sensor dongles 350 and/or the monitor dongles 330 include control circuitry and/or components configured to allow the dongle(s) to operate at least partially independently of the medical monitor system 320 and/or the dongle-connectivity management hub 310. For example, the sensor dongles 350 and/or the monitor dongles 330 may be configured to communicate with each other to exchange and/or process data received from the sensors 340. In some embodiments, the sensor dongles 350 and/or the monitor dongles 330 can be configured to perform functionality similar to functionality that may be performed by the medical monitor system 320 and/or the dongle-connectively management hub 310. Such functional configuration of the sensor dongle(s) 350 and/or monitor dongle(s) 330 can advantageously allow for connectivity between the sensor dongle(s) 350 and the monitor dongle(s) 330 to be managed in cases where the medical monitor system 320 and/or the dongle-connectivity management hub 310 are not implemented and/or are experiencing operational issues or otherwise absent/omitted. For instance, in some implementations, if a patient is being transported from one room or facility to another room or facility, the sensor dongles 350 can enter a transport mode and collect and/or process data from the sensors 340 so that the data is not lost. One or more of the sensor dongles 350 and/or monitor dongles 330 may comprise certain data storage and/or data processing components for buffering sensor-related data and/or managing dongle connectivity during a patient-transport period or during any other period in which one or more of a separate dongle-connectivity hub and/or medical monitor device/system are not communicatively coupled to the dongle(s).

In some embodiments, the sensor dongles 350 and/or the monitor dongles 330 can be configured to be physically connect to each other, such as through an electrical connector, non-electrical connector (e.g., one or more attachment mechanisms, structures, or other features associated with the housing(s) of the dongles), and so on. The sensor dongles 350 and/or the monitor dongles 330 can be connected for storage, charging, organization, or other purposes, as discussed in further detail herein.

The dongle-connectivity management hub 310 can comprise control circuitry and/or other software and/or hardware components configured to manage connections (e.g., communicative couplings) between the sensor dongles 350 and the monitor dongles 330 to allow wireless communication between the sensors 340 and the medical monitor 320. In some embodiments, the dongle-connectivity management hub 310 is configured to automatically associate the sensor dongles 350 with respective ones of the monitor dongles 330. For example, the dongle-connectivity management hub 310 can be configured to detect and/or identify sensor dongles and monitor dongles that have a same type of electrical connectors (e.g., corresponding male and female connectors for a type of connector) and associate such sensor dongles with such monitor dongles in some data-organizational and/or visual manner. According to an example use case, the dongle-connectivity management hub 310 may associate a sensor dongle, such as the sensor dongle 350(1), which has an electrical sensor connector (e.g., a female-type sensor connector; illustrated for clarity as a semi-circular recesses) of a type of connector (e.g., ECG, $SpO_2$, or other specialized or at least partially generic connector) with a monitor dongle, such as the monitor dongle 330(1), which has an electrical monitor connector 337 (e.g., a male-type monitor connector; illustrated for clarity as a semi-circular projection) of a connector that has features and/or dimensions configured to mate with connectors like the connector 357 of the sensor dongle 350(1). The association 317 between the sensor dongle 350(1) and the monitor dongle 330(1) may advantageously be displayed or otherwise represented by the dongle-connectivity management hub 310, as shown by the line 317 in accordance with one or more implementations.

Additionally or alternatively, the dongle-connectivity management hub 310 can facilitate associations of dongles of different types of connectors in some implementations. For example, the dongle-connectivity management hub 310 can be configured to initiate and/or enable a sensor dongle of a first type of connector, such as the sensor dongle 350(1) having a first type of connector 357 (i.e., sensor connector; illustrated as the example symbolic representation of a semi-circular female-type recess), to be associated with a monitor dongle of a second type of connector, such as the monitor dongle 330(N) having a second type of connector (illustrated as the example symbolic representation of a triangular projection 339).

With respect to dongle-connectivity management hubs and/or functionality described herein as relating to dongle-connectivity management, the terms "associate" and "associated" are used to refer to the maintenance, processing, and/or management of data indicative of or relating to, and or the display, notification, and/or other manner of indication of, actual or potential wireless communicative coupling/connection between dongles, and/or the absence thereof. Furthermore, with respect to description herein of dongle-management functionality relating to the association of one dongle with another, such description of the "association" may refer to a passive indication, maintenance, display, notification, or the like, of a wireless coupling between the dongles, or may refer to the active initiation, facilitation, enablement, causing, and/or effecting of the wireless communicative coupling between the dongles. That is, the dongle-connectivity management hub 310 may serve to provide data, display, and/or notification of wireless communicative couplings, and/or may serve to cause or trigger the formation of wireless communicative couplings/connections. As an example, "associating" a first dongle with another dongle may involve initiating, or causing the initiation of, a wireless connectivity handshake or other wireless connection initiation process between the dongles. For example, such associating may involve sending a signal to one or both of the associated (or to be associated) dongles to initiate and/or cause the dongle(s) to initiate the wireless connection/handshake.

As shown in some embodiments, the dongle-connectivity management hub 310 comprises an electronic display that can be used and/or configured to display a user interface 313 that facilitates user management of dongle connectivity and/or patient monitoring by healthcare personnel. For example, the dongle-connectivity management hub 310 can display visual representations 312 of monitor dongles and visual representations 314 of sensor dongles to allow a user to identify and/or create associations between respective ones of the sensor dongles 312/350 and the monitor dongles 314/330.

In some embodiments, the dongle-connectivity management hub 310 can be configured to manage data obtained/generated by the sensors 340. For example, the dongle-connectivity management hub 310 can be configured to receive data from the sensor dongles 350 that is generated/provided by the sensors 340. In some embodiments, control circuitry of the dongle-connectivity management hub 310 can process the sensor data, display the sensor data, provide the sensor data to another device or system (e.g., the medical monitor system 320, or otherwise perform operations based on the data using certain hardware and/or software components. In some embodiments, the dongle-connectivity management hub 310 may be configured to perform similar processing to that performed by the medical monitor system 320 according to certain implementations of the medical monitor system 320. For example, if a patient is being transported from one room or facility to another room or facility, the dongle-connectivity management hub 310 can be configured to at least temporarily monitor data from the sensors 340 and/or sensor dongle(s) 350, such as by displaying the data (e.g., data that is based at least in part on the data from the sensors 340), providing notifications regarding the data, or otherwise processing the data. The term "data" is used herein according to its broad and ordinary meaning. With respect to transmission of and/or operation on sensor data, it should be understood that references to the relevant "data," or "sensor data," may refer to the particular embodiment of the data/signal(s) generated, obtained, and/or provided by the relevant sensor device, or may refer to any data that is based at least in part on and/or indicative of the data/signal(s) generated, obtained, and/or provided by the relevant sensor device.

Although the dongle-connectivity management hub 310 and the medical monitor system 320 are illustrated as separate units (e.g., devices and/or systems) in the example of FIG. 3, in some embodiments the dongle-connectivity management hub 310 and the medical monitor system 320 can be implemented as, and/or embodied in, a singular device or system. In some embodiments, the dongle-connectivity management hub 310 can be configured to manage other aspects of the sensor dongles 350, the monitor dongles 330, the sensors 340, and/or the medical monitor system 320 in addition, or alternative, to dongle-connectivity-related aspects/functionality. For example, the dongle-connectivity management hub 310 can be configured to monitor general performance of the sensors 340 and/or dongle devices (e.g., sensor dongles 350 and/or monitor dongles 330), such as battery life, operating status (e.g., powered-off, powered-on, experiencing an error, etc.), and so on, and/or provide notifications regarding such performance to other devices, systems, and/or users.

The sensors 340 can include various types of medical and/or non-medical sensors that can be configured for (e.g., attached and/or oriented to) one or more patients to obtain/generate information relating to a patient. For example, the sensors 340 can include one or more blood oxygenation ($SpO_2$) determination devices (e.g., pulse oximeters), electrocardiography (ECG) devices, temperature sensors (e.g., an external surface sensor to detect a body temperature of a patient, a catheter-based temperature sensor to be inserted into a patient's body, an ambient temperature sensor to detect an environmental temperature, etc.), pressure transducers (e.g., radial arterial pressure devices, central venous pressure devices, pulmonary artery pressure devices, etc.), cerebral oximetry devices, hemodynamic monitoring devices, blood pressure cuff devices, catheter devices, and/or other sensor(s), whether configured external or internal to the patient. Each of the sensors 340 can advantageously generally detect or determine presence, concentration(s), and/or condition(s) associated with one or more biological, chemical, physiological/physical, or other process(es), elements, and/or compounds of a human body, such as a heart rate (ECG and/or HRV), brainwave (EEG), muscle bio-signals (EMG), etc. The sensors 340 may be further configured to generate data relating to and/or indicative of such detection/determination. When connected to one of the sensor dongles 350, a sensor 340 may provide sensor data to the sensor dongle 350 so that the sensor dongle 350 can provide the sensor data (and/or data/signal(s) representative or indicative thereof) wirelessly to an associated (e.g., wirelessly communicatively coupled) monitor dongle 330. However, each of the sensors 340 can also be configured to provide the data directly to one or more of the monitor dongles 330 and/or to the medical monitor system 320, such as when the sensor 340 is electrically connected to the medical monitor 320 via a cable.

Each of the sensors 340 can include a physical and/or electrical connector (e.g., connector 343 of the sensor 340(1)) for physically and/or electrically connecting/coupling to another device. For example, each of the sensors 340 can include a connector that is configured to electrically connect to the medical monitor system 320 and/or to a cable (not shown) that may be connected between the sensor and the monitor system to provide wired coupling between the sensor and the monitor system 320. In various embodiments, the sensors 340 each include a specific type of connector (e.g., a male-type physical/electrical connector structure/form) that comprises features appropriate for and/or based at least in part on or directed by the particular detection mechanism employed by the sensor (e.g., electrical current/signal detection using conductive contact electrode(s), photodetection, pressure transducing, etc.), the type of data generated by the sensor, the entity that manufactured or designed the sensor, the protocol(s) or standard(s) to which the sensor conforms or according to which the sensor operates, and so on. In some embodiments, each of the sensors 340 includes an abbreviated cable with an end having a connector for connection to another device or cable. Additionally or alternatively, one or more of the sensors 340 may not include a cable, but rather may comprise a connector (i.e., "stub connector") attached directly to a main body, housing, or other portion of the respective sensor 340. As used herein, the term "sensor" can refer to a detection component or a cable and/or a connector associated with the sensor, or combination thereof. Example sensor and cable configurations/embodiments are discussed below in reference to FIGS. 5 and 6.

The medical monitor system 320 (also referred to as the "patient monitor system 320") can generally serve to monitor information regarding the health of one or more patients. The medical monitor system 320 can receive data from the sensors 340 via one or more sensor dongles and/or monitor dongles, convert the data into a displayable format or otherwise process the data, and/or display the data via an electronic display screen 322. For example, the medical monitor system 320 can display information about a heart rate (e.g., ECG, HRV, etc.), brainwave (e.g., EEG), muscle bio-signals (e.g., EMG), blood pressure/rate, body temperature, environmental temperature, oxygen saturation (e.g., $SpO_2$), $CO_2$, and so on.

The medical monitor system 320 can include certain monitor ports 322 configured to enable physical/electrical connection to various types of medical devices, such as physical/electrical connection to any of the types of sensors noted above. The monitor ports 322 and/or connectors on the sensors 340 can include any serial or parallel transmission standard, ethernet, FireWire, coaxial connection, universal serial bus (USB), video graphics array (VGA), digital visual interface (DVI), high-definition multimedia interface (HDMI), and so on. In some embodiments, a connector and/or associated port is associated with a particular standard or protocol and/or a particular type of health monitoring (e.g., ECG, SpO$_2$, pulse rate, respiratory monitoring, NIBP, etc.). To illustrate, the monitor ports 322 can include a port for a temperature sensor connector, a port for a pulse oximeter connector, a port for an ECG sensor connector, a port for a blood pressure sensor connector, a port for an EtCO$_2$ sensor connector, and so on. Further, in some embodiments, a port/connector can include a leadwire port such as a 3-, 5-, 6-, or 12-leadwire port. In some embodiments, the sensors 340 and/or monitor dongles 330 include male connectors (or female connectors, in some cases) and the monitor ports 322 include corresponding female connectors (or male connectors, in some cases).

A port/connector can be configured for power, data, and/or audiovisual communication. Furthermore, a port/connector can be chassis or panel connectors, as described in detail herein, or may be inline connectors, PCB-mount connectors, splice or butt connectors, or any other type of connectors/connections. In addition, a port/connector may have any configuration and/or arrangement of pins/pinout, method of connection, materials, size, contact resistance, insulation, mechanical durability, ingress protection, lifetime (e.g., number of cycles), and/or ease of use. In some embodiments, a port/connector is designed to be relatively easily-identifiable, to facilitate ease of use and assembly. A port/connector may comprise one or more conductors and one or more insulators configured to provide electrical and/or thermal isolation for the conductor(s). Example materials for conductors can include copper, copper alloys, brass, phosphor bronze, beryllium copper, and other metals and at least partially conductive materials. A port/connector can also include contact carrier structures configured to hold the parts of the connector/port together. Such structures can comprise plastic or other at least partially insulating material(s).

As noted above, the system 300 provides various advantages over certain other solutions. For example, the system 300 can advantageously enable the sensors 340 to wirelessly connect/couple to the medical monitor system 320 and/or the dongle-connectivity management hub 310. Therefore, embodiments of the present disclosure can advantageously provide relatively less cumbersome healthcare environments by reducing obstructions within such environments that are caused by the presence of various sensor-to-monitor cables or other components implemented to connect sensors to a medical monitor.

Further, the dongle-connectivity management hub 310, the sensor dongles 350, and/or the monitor dongles 330 can provide various notifications (e.g., visual representations on a user interface, audible and/or light alerts on a dongle, etc.) in a user-friendly manner to assist an individual in connecting or otherwise managing the various devices.

Moreover, in embodiments in which the sensor dongles 350 are configured to connect to various types of monitor dongles, even if the physical connectors are not compatible (e.g., a sensor and/or associated sensor dongle do not have the same type of connector as an available monitor dongle), the system 300 can allows various types of sensors to be connected to the medical monitor system 320 or other devices that would not be connectable using a sensor-to-monitor cable. That is, the sensor and/or monitor dongles can advantageously provide adapter functionality in addition to wireless connectivity functionality for medical sensor devices, which can provide improved flexibility in connecting various types of sensors to the system 300.

Moreover, the dongle-connectivity management hub 310, the sensor dongles 350, and/or the monitor dongles 330 can be configured to operate at least partially independently or in cooperation with the medical monitor 320 to monitor a patient while the patient is being transported, when the medical monitor 320 is experiencing operation issues, or at other times. Furthermore, interoperability of the sensor dongles 350 and the monitor dongles 330 can provide backwards compatibility with previous (e.g., outdated or obsolete) sensors and/or medical monitors, as well as forward compatibility, such as by implementing new sensor dongles for new sensors and/or new monitor dongles for new monitors. Further, since multiple sensor/monitor dongles can be designed to be compatible with various types of connectors (in a relatively inexpensive manner, in some cases), the system 300 can be implemented with various types of sensors and/or medical monitors (in a relatively inexpensive manner, in some cases).

Figure 4:
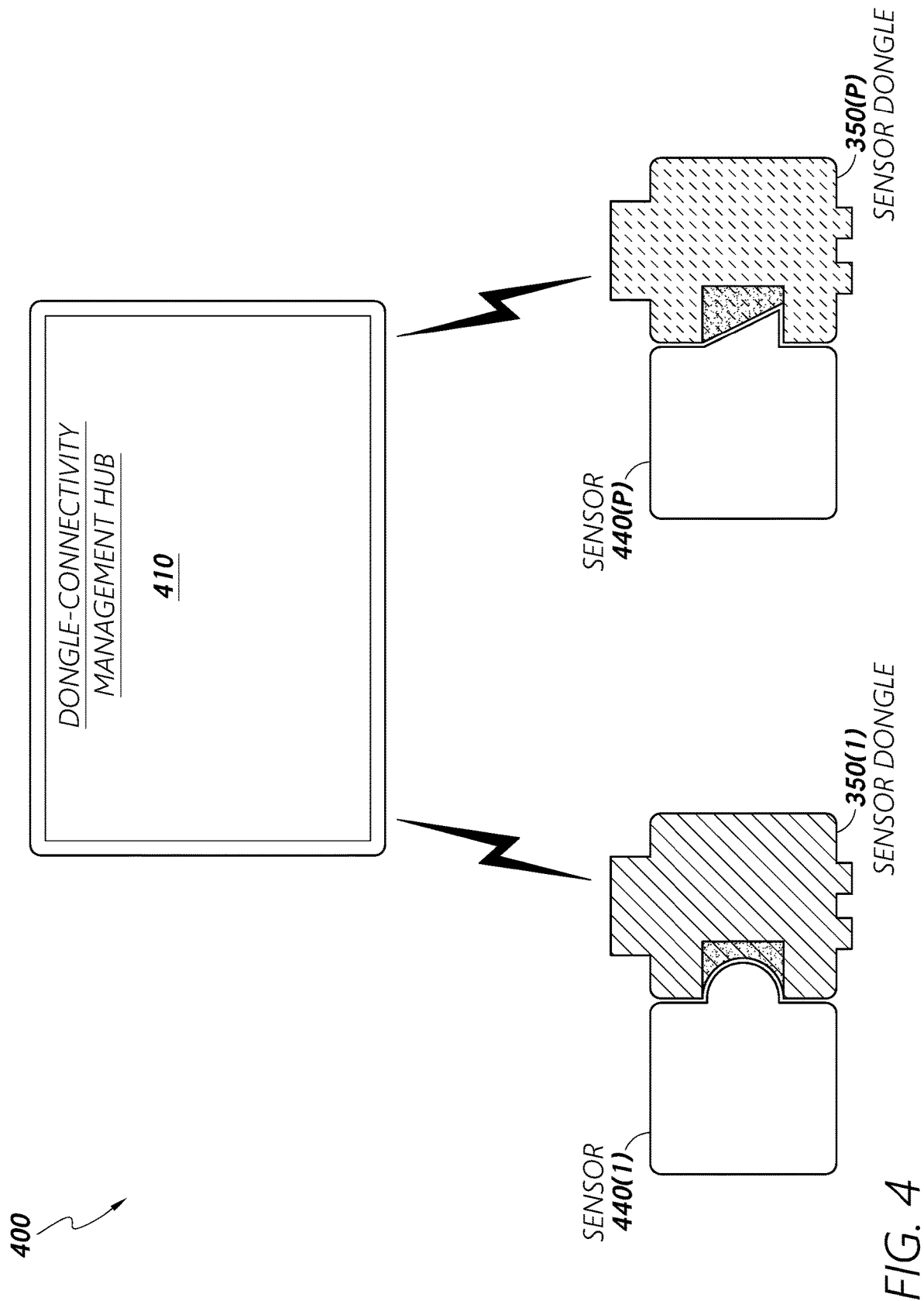
FIG. 4 illustrates an example wireless connectivity system in accordance with one or more embodiments.

FIG. 4 illustrates an example wireless connectivity system 400 that facilitates wireless connectivity for various sensors 440 in accordance with one or more embodiments of the present disclosure. The system 400 may be configured to advantageously facilitate monitoring of a patient (not shown) without a traditional medical monitor system. As an example, the system 400 includes a dongle-connectivity management hub 410 configured to wirelessly connect/couple to at least one of one or more sensor dongles 450(1)-450(P), where "P" represents an integer greater than one. The wireless connectivity functionality may be facilitated at least in part by sensor dongles 450(1)-450(P), which are configured to physically and/or electrically connect to respective ones of the sensors 440(1)-440(P), such as through connectors on the sensors 440 and corresponding ports/connectors of the respective sensor dongles 450. Although the dongle-connectivity management hub 410 is shown without physical connectors to connect to monitor dongles, the dongle-connectivity management of 410 can be implemented with such connectors in some embodiments.

The sensor dongles 450 can include dongles having various types of sensor ports/connectors discussed herein, respectively, and the sensors 440 can include various types of sensors and/or associated connectors discussed herein, respectively. Although embodiments of the present disclosure are described in which sensors are associated with male-type connectors and physically coupled sensor dongles comprise corresponding female-type connection ports, it should be understood that sensor devices may include female-type connectors and sensor dongles can include male-type connectors. In connection with certain embodiments disclosed herein, the term "port" may refer to a connector having a generally female-type form and/or structure.

In some implementations, the dongle-connectivity management hub 410 can perform processing and/or functionality that may be similar in one or more respects to certain processing and/or functionality described herein in connection with medical monitor systems. For example, the dongle-connectivity management hub 410 may be configured to display certain information/data relating to and/or indicative of one or more physiological parameters associated with a monitored patient. Additionally or alternatively, the dongle-connectivity management of 410 may be configured to perform additional functionality not generally performed by medical monitor systems, namely monitoring wireless connectivity between the sensor dongles 450 and the dongle-connectivity management hub 410. For example, the dongle-connectivity management hub 410 can be configured to wirelessly connect to the sensor dongles 450 and/or receive sensor data from the sensors 440 via the sensor dongles 450. That is, the sensor dongles 450 can serve as middlemen to facilitate wireless communication of data that is based at least in part on signals provided and/or generated by sensor devices 440.

In some embodiments, the dongle-connectivity management hub 410 is configured to process and/or perform certain operations on the data received wirelessly from the sensor dongles 450 and/or display data related to the same on an electronic display associated with the dongle-connectivity management of 410. For example, the dongle-connectivity management hub 410 may display certain health-related data in a waveform representation via an electronic display of the dongle-connectivity management of 410, similar to how a medical monitor may display information regarding health of a patient according to certain solutions. In some embodiments, the dongle-connectivity management hub 410 can also provide connectivity to one or more devices or systems not illustrated in FIG. 4, such as one or more remote devices or systems implemented within a cloud environment, one or more devices or systems associated with an administrator individual and/or entity of the system 400, one or more devices or systems associated with a nurse station or other healthcare provider, and so on.

Figure 6:
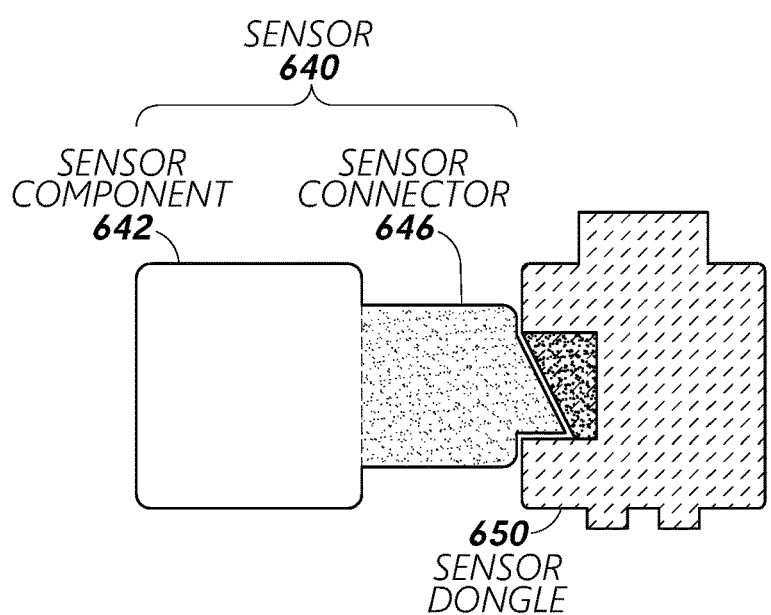
FIG. 6 illustrates an example sensor-dongle physical connectivity configuration in accordance with one or more embodiments.

Certain types of physical/electrical connections between sensor devices and sensor dongles are illustrated and described in the present disclosure. However, it should be understood that sensors may be physically/electrically coupled to sensor dongles in any suitable or desirable manner. That is, any description herein of a sensor device, component, and/or element being electrically connected to a sensor dongle may be interpreted to apply to any type of wired or wireless electrical and/or physical connection/coupling between such components/devices. FIGS. 5 and 6, for example, illustrate two types of connections between sensors and sensor dongles. In particular, FIGS. 5 and 6 show two types of embodiments/configurations of sensor connectors vis-á-vis associated sensor devices/elements. Although FIGS. 5 and 6 show certain embodiments of wired connections between sensors (e.g., sensor assemblies) and sensor dongles, it should be understood that in some implementations, data coupling between a sensor device/assembly and a sensor dongle may be at least partially wireless in nature. For example, near-field data transmission may be implemented, and/or other types of relatively short-range or long-range wireless data communication.

Sensor Connectivity Configurations

FIG. 5 illustrates an example sensor 540 that includes a sensor component 542, a sensor cable 544, and a sensor connector 546 electrically and physically connected to the sensor component 542 via the sensor cable 544 in accordance with one or more embodiments. As described herein, the sensor cable 544 may be considered an "abbreviated" cable, in that the cable 544 may represent a relatively short length of cable not intended for coupling directly to a medical monitor. That is, abbreviated cables in accordance with embodiments of the present disclosure may have a cable length of less than or equal to about 3 feet. For example, in some embodiments, abbreviated sensor cables in accordance with the present disclosure may be about 18 inches in length, or less. In some embodiments, abbreviated sensor cables in accordance with the present disclosure may be between about 18 inches and 3 feet in length. Therefore, "abbreviated" sensor cables may be understood according to the broad and ordinary meanings of such term(s).

The sensor 540 can include one or more of the various types of sensors discussed herein. The sensor connector 546 is generally configured to electrically connect to a medical monitor, a cable, or another device. In some embodiments, in a wired configuration (not illustrated in FIG. 5), the sensor 540 is implemented with an additional cable (not illustrated) that connects the sensor 542 to a medical monitor port. For example, the sensor 540 can be implemented in a daisy-chained manner with the sensor cable 544 and an additional cable that connects to the sensor connector 546 and a medical monitor. Such additional monitor cable may comprise, for example, a length of flexible electrical cable with a connector/plug at a distal end thereof and one or more port/socket connectors at a proximal end thereof. The distal connector(s)/plug(s) may generally be of the same/corresponding type as the proximal port(s)/socket(s). Additional cabling for electrically coupling abbreviated sensor cables with monitor devices/systems may further provide adaptor functionality for adapting one type of proximal port/socket to another type of distal connector/plug. Although the sensor cable 544 can have any length, in some examples, the sensor cable 544 can be shorter in length than typical monitor cables. In some embodiments, the sensor 540 is implemented as a disposable sensor that is configured to connect directly to a medical monitor system and/or to a medical monitor system via an additional monitor cable.

In the example of FIG. 5, the sensor 540 is connected to a sensor dongle 550 to facilitate wireless connectivity/coupling to a medical monitor system or another device/system. That is, although the sensor 540 is able to electrically connect directly to a medical monitor system or another device (e.g., monitor cable), the sensor 540 is electrically connected to the sensor dongle 550 to facilitate a wireless connection instead of a physical electrical connection. As illustrated, the sensor connector 546 is physically and/or electrically connected to the sensor dongle 550 to allow data from the sensor component 542 to be communicated to another device wirelessly through a wireless coupling that is facilitated and/or implemented by the sensor dongle 550. The sensor component 542 can include any type of detector that is configured to detect a biological, chemical, physiological/physical, and/or other process/parameter associated with a human body. Further, the sensor cable 544 and/or any other cables discussed herein can include any type of conductive material to facilitate an electrical connection between two components. For example, a cable can include one or more wires, one or more conductive traces, and the like.

FIG. 6 illustrates an example sensor 640 that includes a sensor component 642 and a sensor connector 646 connected directly to the sensor component 642, or otherwise connected to the sensor component 642 without a cable connection therebetween, in accordance with one or more embodiments of the present disclosure. Implementation of the sensor 640 without a cable connecting the sensor component 642 to the sensor connector 646 can provide a relatively reduced length, size, and/or profile for the sensor 640. In some embodiments, the sensor 640 can be integrated at least in part with a housing or another enclosure or structure of the sensor 640, wherein the sensor connector 646 is at least partially exposed through the housing or other structure so that an electrical connection can be made to the sensor connector 646. The sensor 640 can include any of the various sensors discussed herein. In some implementations, although the sensor connector 646 may be generally configured to electrically connect to a medical monitor device/system or other device/system, the sensor 640 can be alternatively electrically connected to a sensor dongle 650 to facilitate wireless connectivity to a medical monitor device/system or other device/system.

Sensor and Monitor Dongles

Figure 7:
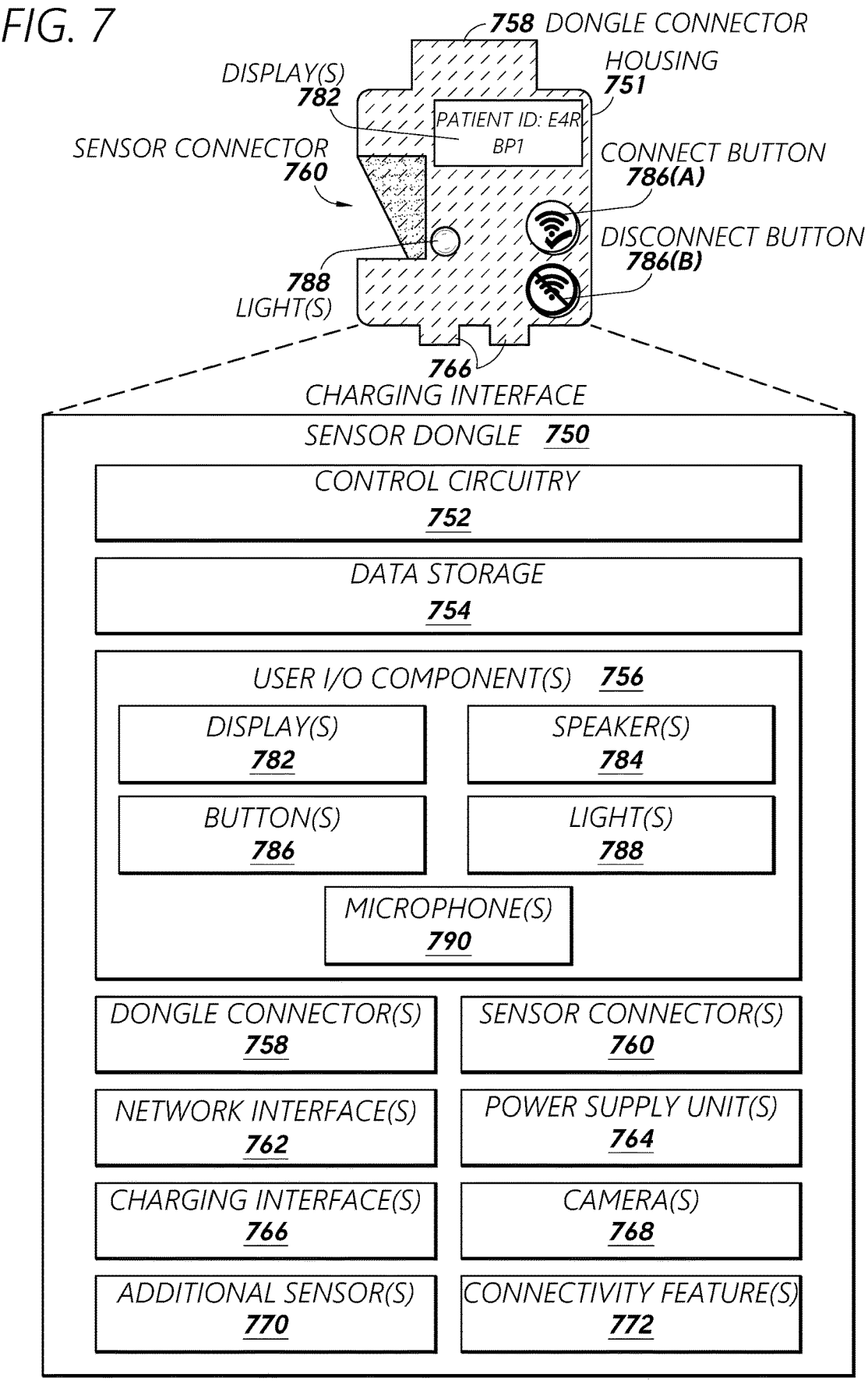
FIG. 7 illustrates a block diagram of an example sensor dongle in accordance with one or more embodiments.

FIG. 7 illustrates a block diagram of an example sensor dongle 750 in accordance with one or more embodiments of the present disclosure. As illustrated, the sensor dongle 750 can include one or more of the following components, devices, modules, and/or units (referred to herein as "components"), either separately/individually and/or in combination/collectively: control circuitry 752, data storage/memory 754, user input/output (I/O) component(s) 756, dongle connector(s) 758, sensor connector(s) 760, network interface(s) 762, power supply unit(s) 764, charging interface(s) 766, camera(s) 768, and/or additional sensor(s) 770. As used herein, the terms "data storage" refers to one or more data storage devices and/or systems (e.g., hardware devices). Although certain components of the sensor dongle 750 are illustrated in FIG. 7, it should be understood that additional components not shown may be included in embodiments of sensor dongles in accordance with the present disclosure. Furthermore, certain of the illustrated components may be omitted in some embodiments. Although the control circuitry 752 is illustrated as a separate component in the diagram of FIG. 7, it should be understood that any or all of the remaining components of the sensor dongle 750 may be embodied at least in part in the control circuitry 752. That is, the control circuitry 752 may include various devices (active and/or passive) semiconductor materials and or areas, layers, regions, and/or portions thereof, conductors, leads, vias, connections, and/or the like, wherein one or more of the other components of the sensor dongle 750 and/or portion(s) thereof can be formed and or embodied at least in part in/by such circuitry components/devices.

The various components of the sensor dongle 750 may be electrically and/or communicatively coupled using certain connectivity circuitry/devices/features 772, which may or may not be part of the control circuitry 752. For example, the connectivity feature(s) 772 may include one or more printed circuit boards configured to facilitate mounting and/or interconnectivity of at least some of the various components/circuitry of the sensor dongle 750. In some embodiments, two or more of the control circuitry 752, the data storage 754, the user input/output (I/O) component(s) 756, the dongle connector 758, the sensor connector 760, the network interface(s) 762, the power supply unit 764, the charging interface 766, the camera(s) 768, and/or the additional sensors 770 can be electrically and/or communicatively coupled to each other. The sensor dongle 750 can comprise a housing/enclosure 751 configured and/or dimensioned to house or contain at least part of one or more of the components of the sensor dongle 750. The housing/enclosure 751 can include various types of materials that can be configured according to medical standards or practices. In some embodiments, the housing/enclosure 751 can be configured to be subjected to sterilization processes, as discussed in further detail below. The housing/enclosure 751 may advantageously comprise relatively hard/rigid material, which may serve to protect components disposed at least partially therein from physical damage and/or contamination. For example, the housing/enclosure 751 may advantageously be air- and/or fluid-tight (e.g., hermetically sealed).

The control circuitry 752 can include one or more processors, such as one or more central processing units (CPUs), one or more microprocessors, one or more graphics processing units (GPUs), one or more digital signal processors (DSPs), and/or other processing circuitry. Alternatively or additionally, the control circuitry 752 can include one or more application specific integrated circuits (ASIC), one or more field-programmable gate arrays (FPGAs), one or more program-specific standard products (ASSPs), one or more complex programmable logic devices (CPLDs), and/or the like. The control circuitry 752 can advantageously be configured to execute one or more instructions stored in the data storage 754 to thereby perform one or more operations to implement various functionality discussed herein. The control circuitry 752 can operate in cooperation with any of the components of the sensor dongle 750 to facilitate such functionality.

The data storage 754 can include any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data. Computer readable media that may be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media. The data storage 754 can store one or more instructions that are executable by the control circuitry 752 to facilitate various functionality discussed herein. Additionally or alternatively, the data storage 754 can store data regarding the sensor dongle 750, a sensor, and/or other device. For example, the data storage 754 can store sensor data received from a connected sensor and/or sensor data received from another sensor dongle.

The one or more user I/O components 756 can include one or more electronic displays 782 configured to display data associated with certain aspects of the present disclosure. The one or more displays 782 can include one or more liquid-crystal displays (LCD), light-emitting diode (LED) displays, organic LED displays, plasma displays, electronic paper displays, and/or any other type(s) of technology. In some embodiments, the one or more displays 782 include one or more touchscreens configured to receive input and/or display data. The one or more user I/O components 756 can also include one or more speakers 784 configured to output an audio signal, one or more buttons 786 configured to be engaged and/or actuated in some manner by a user, wherein such engagement/actuation can generate or otherwise result in provision/receipt of certain input signal(s) that may be used/interpreted by the sensor dongle 750 and/or control circuitry 752 thereof. The one or more buttons 786 can include one or more mechanical push-buttons configured to be depressed or pushed, one or more touch buttons configured to receive touch input, or any other type of buttons. As illustrated in FIG. 7, the one or more buttons 786 can include a connect button 786(A) and/or a disconnect button 786(B). The user I/O component(s) 756 may further comprise one or more lights 788 (e.g., LED device(s)) configured to output light. The one or more lights 788 can include one or more LEDs, one or more incandescent lights, and the like. The user I/O component(s) 756 may also include one or more microphones 790 configured to detect sound and convert the sound into an electrical signal. Although the one or more user I/O components 756 are illustrated as separate components, any of the components can be implemented together. For example, the one or more buttons 786 can include one or more lights, and so on.

Although described primarily as an electronic display(s) 782, the display(s) 782 may comprise a nonelectronic display/notification area. For example, certain patient-related labels and/or other information may be adhered or otherwise attached or disposed on an area of the housing 751 to provide relevant information relating to the patient, sensor, and/or one or more other aspects associated with the sensor dongle 750. In some implementations, the area of the display(s) 782 may be at least partially available for writing (e.g. using markers or the like) and/or otherwise labeling or marking the sensor dongle 750.

The one or more user I/O components 756 can be configured to provide or present information relating to the sensor dongle 750. For example, the one or more displays 782 can display one or more of the following types of data/information: a patient identifier for a patient associated with the sensor dongle 750 (e.g., a patient that is attached to a sensor (not illustrated) that is communicatively coupled/connected to the sensor dongle 750); information indicating sensor type(s) to which the sensor dongle 750 is configured to connect; a number of sensors to which the sensor dongle 750 is connected; a status of the sensor dongle 750 (as discussed in further detail below); and/or any other information associated with the sensor dongle 750.

As one example, FIG. 7 illustrates the one or more displays 782 presenting a patient identifier ("E4R") and an identifier ("BP1") of a sensor/another dongle to which the sensor dongle 750 is communicatively coupled/connected. Further, the one or more displays 782, the speaker 784, the one or more buttons 786, and/or the one or more lights 788 can provide output regarding a status of the sensor dongle 750, such as, for example, a status indicating that the sensor dongle 750 is searching for another dongle to wirelessly couple to, currently wirelessly coupling to another dongle (e.g., engaging in a hand-shake or other coupling initiation process), currently wirelessly coupled to another dongle, currently wirelessly decoupling from another dongle, and so on.

To illustrate, according to an example use case, the one or more lights 788 can output a green light when the sensor dongle 750 is wirelessly coupled to a monitor dongle, a yellow light when the sensor dongle 750 is searching for a monitor dongle, a red light when the sensor dongle 750 is not coupled to (e.g., decoupled from) a monitor dongle, and so on. Additionally or alternatively, the speaker 784 can output a predetermined audio signal when the sensor dongle 750 enters a particular status, such as outputting a first audio signal when the sensor dongle 750 wirelessly couples with a monitor dongle, outputting a second audio signal when the sensor dongle 750 wirelessly decouples from another device, and so on. In some embodiments, the speaker 784 can output a speech signal indicating a status of the sensor dongle 750, such as by outputting "connected" when the sensor dongle 750 wirelessly couples to another dongle, outputting "disconnected" when the sensor dongle 750 decouples, and so on. As such, the one or more user I/O components 756 can provide a variety of types of output to inform a user about a status of the sensor dongle 750 or otherwise assist a user in managing the sensor dongle 750.

Additionally or alternatively, the one or more user I/O components 756 can be configured to receive input to control the sensor dongle 750. For example, the one or more displays 782 can be configured to present a graphical user interface (GUI) to facilitate operation of the sensor dongle 750, such as to wirelessly connect/disconnect the sensor dongle 750. In some embodiments, the display(s) 782 have touch-screen functionality that may be employed by a user to input commands or other input. Further, a user can provide input via the one or more buttons 786 to request that the sensor dongle 750 perform an operation associated with a connection to another device. To illustrate, according to particular embodiments that are compatible with aspects of the illustrated sensor dongle 750 in FIG. 7, in response to receiving an input via the connect button 786(A), the sensor dongle 750 can be configured to search for another device within communication range (e.g., a monitor dongle, medical monitor system, etc.) and/or wirelessly couple to such device. As another example, in response to receiving an input via the disconnect button 786(B), the sensor dongle 750 may be configured to decouple from a wireless connection with a presently-coupled-to device. Moreover, in some embodiment, the microphone 760 can receive speech input from a user, which can be processed locally at the sensor dongle 750 and/or sent to another (e.g., remote) device for processing. The processing can include natural language processing, speech recognition, or other types of processing to interpret the speech input. If the processing determines that the user is requesting an operation, the sensor dongle 750 can perform such operation in response thereto, such as coupling/decoupling with/from another device or performing another connectivity management operation.

The dongle connector 758 can be configured to physically and/or electrically connect to another dongle, such as a monitor dongle or another sensor dongle. In some embodiments, the sensor dongle 750 can be electrically connected to a monitor dongle via the dongle connector 758 to receive power from the other dongle. For example, the sensor dongle 750 can be electrically connected to a monitor dongle and the monitor dongle can be electrically connected to a medical monitor system, wherein the sensor dongle 750 can be charged by the medical monitor system via the dongle connector 758. Further, in some embodiments, the sensor dongle 750 can provide power to another dongle via the dongle connector 758. As such, the dongle connector 758 can be electrically coupled to the power supply unit 764 to facilitate power transfer to and/or from the power supply unit 764. Moreover, in some embodiments the dongle connector 758 can provide a physical connection to another device (e.g., dongle) without necessarily providing an electrical connection to the other dongle/device. For example, the sensor dongle 750 can be physically connected to a monitor dongle or other device for storage and/or organization of the sensor dongle 750 and/or to maintain a particular association of dongles.

The sensor connector 760 can be configured to physically and/or electrically connect to a sensor device (e.g., medical sensor device as described in detail herein). The sensor connector 760 can include a specific type of connector that is configured to connect to a specific type of sensor, such as a sensor that is configured for a particular detection method, a sensor that is configured to generate a particular type of data, a sensor that is manufactured or designed by a particular entity, a sensor that generates or provides data according to a particular protocol or standard, and so on. Furthermore, the sensor connector 760 can include any suitable or desirable arrangement and/or number of electrical contacts and/or associated structural components, such as electrical contacts and/or associated structural components providing one or more serial ports, parallel ports, non-invasive blood pressure (NIBP) ports, ethernet ports, FireWire ports, coaxial ports, Universal serial bus (USB) ports, video graphics array (VGA) ports, digital visual interface (DVI) ports, high-definition multimedia interface (HDMI) ports, plug-/jack-type connectors (e.g., 2.5 mm mono (TS), 3.5 mm mono (TS), 3.5 mm stereo (TRS), 6.35 mm (TRS)), and so on. In some embodiments, the sensor connector 760 is associated with a particular standard or protocol and/or a particular type of health monitoring (e.g., ECG, $SpO_2$, pulse rate, respiratory monitoring, NIBP, etc.). Further, in some embodiments, the sensor connector 760 can include a leadwire port such as a 3-, 5-, 6-, or 12-leadwire port. As discussed in further detail below in reference to FIG. 8, in some embodiments the sensor connector 760 can include multiple types of connectors configured to connect to multiple types of sensors, respectively.

The one or more network interfaces 762 can be configured to communicate with one or more devices over a communication network. For example, the one or more network interfaces 762 can send/receive data in a wireless or wired manner over a network. A communication network can include a local area network (LAN), a wide area network (WAN) (e.g., the Internet), a personal area network (PAN), a body area network (BAN), etc. In some embodiments, the one or more network interfaces 762 can implement a wireless technology such as Bluetooth, Wi-Fi, near field communication (NFC), or the like. In some embodiments, the one or more network interfaces 762 can include a transceiver (e.g., transceiver circuitry embodied in one or more devices) configured to transmit/receive signals wirelessly. For example, the sensor dongle 750 can use the transceiver to communicate with a monitor dongle, a medical monitor system, a dongle-connectivity management hub, and/or another sensor dongle to establish a wireless connection, provide sensor data regarding a sensor reading, and so on. The network interface(s) 762 can comprise one or more wireless transceiver circuits or circuitry. For example, the network interface(s) can comprise one or more front end modules, amplifiers, antennas, filters, and/or other signal/processing circuitry configured to facilitate reception and/or transmission of wireless signals/data. As with other modules of the sensor dongle 750, the network interface(s) 762 can be embodied in whole or in part in the control circuitry 752.

The power supply unit 764 can be configured to manage power for the sensor dongle 750, such as power provided to and/or received from one or more components of the sensor dongle 750. In some embodiments, the power supply unit 768 includes one or more batteries, such as a lithium-based battery, a lead-acid battery, an alkaline battery, and/or another type of battery. That is, the power supply unit 764 may comprise one or more devices and/or circuitry configured to provide a source of power and/or provide power management functionality. Further, in some embodiments the power supply unit 764 operates in cooperation with the dongle connector 758, the sensor connector 760, and/or the charging interface 766 to receive and/or provide power. For example, the power supply unit 764 can charge a battery thereof using power received via the dongle connector 758, the sensor connector 760, and/or the charging interface 766. Moreover, in some embodiments the power supply unit 764 (and/or the charging interface 766) includes a mains power connector that is configured to couple to an alternating current (AC) or direct current (DC) mains power source.

The charging interface 766 can include various types of interfaces to facilitate charging of the sensor dongle 750. For example, the charging interface 766 can operate in cooperation with the power supply unit 764 to charge one or more batteries of the sensor dongle 750 (e.g., power supply unit 764). In some embodiments, the charging interface 766 can facilitate wireless power transfer to charge one or more batteries of the sensor dongle 750 (e.g., the power supply unit 764). In one example, the charging interface 766 can include an inductance coil configured to couple to an inductive pad/coil of another device to provide power to the sensor dongle 750. In some embodiments, the charging interface 766 can include an element configured to receive light from an external light source and convert the light into energy that is storable and/or usable by the sensor dongle 750. In some embodiments, the charging interface 766 includes a connector to electrically connect to another device to receive power. Although the charging interface 766 is illustrated as a separate component of the sensor dongle 750, as noted above, in some instances the dongle connector 758 and/or the sensor connector 760 can facilitate power transfer to charge one or more batteries of the sensor dongle 750 (e.g., power supply unit 764) without using a separate charging interface.

As referenced above, the sensor dongle can include one or more cameras 768 in some embodiments. The camera(s) 768 can be configured to capture an image. For example, the camera(s) 768 can be configured to capture an image of a patient associated with the sensor dongle 750. In some embodiments, the sensor dongle 750 can capture an image using the camera(s) 768 and provide the image to another device for analysis, such as to identify a patient associated with the sensor dongle 750, or other individual or item present in the environment of the sensor dongle 750. In some embodiments, the control circuitry 752 and/or camera(s) 768 may be utilized to identify and/or capture images of certain labels, markers, codes, icons and or the like, which may be used to identify/label certain patients and/or items associated there with. For example, in some implementations, the sensor dongle 750 may be configured to read a barcode, QR code, or the like, which may provide an identifier for a patient (e.g., on a bracelet or other wearable device/item). Additionally or alternatively, the sensor dongle 750 (e.g., control circuitry 752) may be configured to implement electromagnetic radiation/fields to read/interrogate passive radio-frequency identification (RFID) tags, wherein such tags may provide identification information relating to patients, sensors, dongles, and/or other items or individuals.

Further, in some embodiments, the sensor dongle 750 (e.g., the control circuitry 752) can be configured to analyze/process an image locally to identify a patient or other individual(s)/item(s). Such functionality may be useful to determine if a dongle is associated with the correct patient. In some embodiments, the camera(s) 768 can be adjustable by a user or otherwise to configure the camera(s) 768 in a particular orientation and/or capture a particular point of view. Although FIG. 7 and certain other embodiments disclosed herein are described in the context of camera devices being implemented as part of a sensor dongle or another dongle device, in some implementations, a dongle-connectivity management hub may be configured to communicate with a camera device that is not connected to our otherwise associated with a particular dongle or sensor.

The additional sensor(s) 770 can include one or more accelerometers configured to detect acceleration, magnetometers configured to detect magnetism, gyroscopes configured to detect orientation and/or angular velocity, and/or a satellite-based navigation (e.g., Global Positioning System (GPS)) sensors configured to determine a geographical location of the sensor dongle 750. In some embodiments, data from the additional sensor(s) 770 can be analyzed to detect if the sensor dongle 750 and/or an associated sensor is moving, has moved outside of a particular geofence/radius of interest, is positioned appropriately on a patient, and so on. In some embodiments, data from the additional sensor(s) 770 can be analyzed to determine if a patient is being transported, such as by determining if a patient has moved beyond a predetermined radius/distance associated with a room.

In some embodiments, the sensor dongle 750 can at least partly manage wireless connectivity for a system. For example, the sensor dongle 750 can act as a connectivity management hub that is configured to communicate with other dongles to facilitate connectivity, facilitate sensor data communication, and so on, similar to functionality that can be performed by a dongle-connectivity management hub in some implementations. In some embodiments, the sensor dongle 750 can perform such functionality when the sensor dongle 750 enters a transport mode associated with transporting a patient from one room, area, or facility to another room, area, or facility. While transporting the patient, the sensor dongle 750 can be configured to at least temporarily store data from a sensor connected to the sensor dongle 750 (e.g., buffer data locally) and/or receive/store data from other sensors connected to other sensor dongles, as discussed in further detail below.

Although not illustrated in FIG. 7, in some embodiments, the sensor dongle 750 can include a transport button, similar to the button(s) 786, to enable/disable a transport mode for the sensor dongle 750 or otherwise facilitate patient-transport functionality. In some embodiments, selecting a transport button on the sensor dongle 750 can cause the sensor dongle 750 and/or other sensor dongles attached or otherwise associated with a patient to enter a transport mode or perform other patient-transport functionality, as discussed in further detail below.

Figure 8:
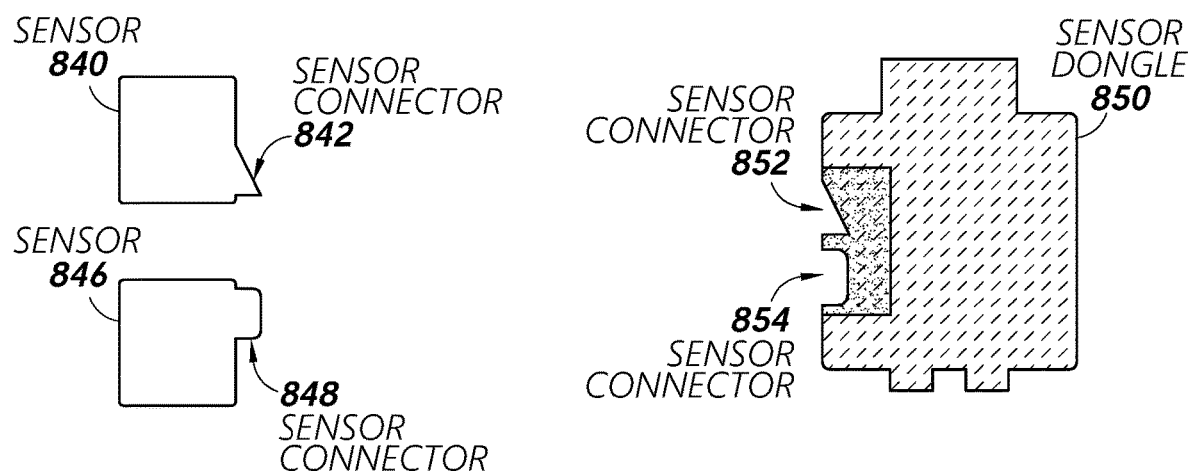
FIG. 8 illustrates an example sensor dongle including a plurality of sensor connectors in accordance with one or more embodiments.

FIG. 8 illustrates an example sensor dongle 850 that includes two sensor connectors configured to connect to two different types of sensors in accordance with one or more embodiments. As illustrated, the sensor dongle 850 includes a sensor connector 852 configured to connect to a first type of sensor (represented by a female version of a triangle-shaped connector recess/void) and a sensor connector 854 configured to connect to a second type of sensor (represented by a female version of a curved-rectangular-shaped connector recess/void). For example, a sensor 840 having a sensor connector 842 (represented by a male version of a triangle-shaped connector projection/extension) is configured to connect to the sensor connector 852. Further, a sensor 846 having a sensor connector 848 (represented by a male version of a curved-rectangular-shaped connector projection/extension) is configured to connect to the sensor connector 854.

Although two connectors are illustrated for the sensor dongle 850 in the example of FIG. 8, the sensor dongle 850 can be implemented with any number of connectors. Furthermore, although various sensors are illustrated herein with male connectors and various sensor dongles are illustrated with female connectors, the sensors and sensor dongles can include male or female connectors. In addition, although FIG. 8 and the accompanying description relate to a sensor dongle having two or more sensor connectors of different types, it should be understood that in embodiments of the present disclosure, the sensor dongle may have a plurality of sensor connectors of the same or similar type. Furthermore, as with any of the illustrated and/or described embodiments of the present disclosure, connections between the sensor dongle 850 and one or more sensors (e.g., sensor 840 and/or sensor 846) may involve a physical and/or electrical connection/coupling between one or more components of the sensor dongle and one or more components of the respective sensor(s). In some embodiments, once connected, a sensor dongle and connected sensor may be locked or otherwise secured in an engaged physical connection using one or more engagement features of either or both of the devices and/or friction-fit engagement.

Figure 9:
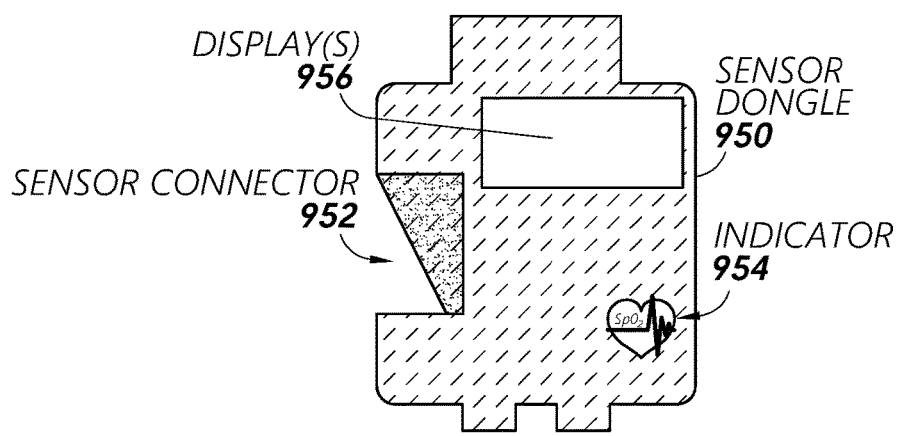
FIG. 9 illustrates an example sensor dongle that includes a sensor-type indicator in accordance with one or more embodiments.

FIG. 9 illustrates an example sensor dongle 950 that includes an indicator 954 to provide information about a type of sensor with which the sensor dongle 950 is configured to connect. For example, the indicator 954 can provide information about a sensor connector 952 for the sensor dongle 950, such as a type of the sensor connector 952. In the example of FIG. 9, the indicator 954 is provided as a sticker, engraving, label, or other marking on an enclosure of the sensor dongle 950. However, the indicator 954 can be provided in other manners, such as through a display screen 956. In some embodiments, the indicator 954 includes a symbol, trademark, icon, or other marking associated with a type of sensor (and/or monitor dongle) with which the sensor dongle 950 is configured to associate. In some embodiments, information about a type of sensor with which the sensor dongle 950 is configured to connect can be provided to another device, such as a dongle-connectivity management hub, to assist a user and/or the dongle-connectivity management hub in establishing appropriate connections between sensor dongles and monitor dongles (e.g., matching sensor dongles to monitor dongles).

Although various features are illustrated in FIGS. 8 and 9 with respect to a sensor dongle, any of such features can similarly be implemented for a monitor dongle. For example, a monitor dongle can include multiple monitor connectors to connect to different types of ports on a medical monitor system. Additionally or alternatively, a monitor dongle can include an indicator, similar to the indicator 954 of FIG. 9, to provide information about a type of sensor/connector/port/dongle with which the monitor dongle is configure to connect or associate.

Although the dongle 950 is shown and described as a sensor dongle, it should be understood that FIG. 9 and the related description can describe a monitor dongle. The feature 956 in FIG. 9 can represent, or portion thereof, in some embodiments, can represent a color wheel feature, which may comprise a physical and/or digital dial or other user input device. Such dial/user input feature can be engaged/actuated to a desired color or other visual feature (e.g., shape, text) associated with the dial/input device that is associated with a desired sensor/monitor dongle to which the dongle 950 is to be connected. For example, in a wireless dongle connectivity system, color wheels located on each sensor dongle and monitor dongle can be toggled to multiple colors/positions. The color wheel can be a button, switch, or other user input/engagement feature. the visual features of the color wheel can be color, or may alternatively or additionally comprise shape- or word-identifier features.

The use of a color wheel or other visual-feature-based user input mechanism can be used when connecting multiple sensor dongles of a first type (e.g., blood pressure sensor dongles) with multiple monitor dongles of a compatible type (e.g., blood pressure sensor monitor dongles). In order to associate respective ones of the sensor dongles with respective ones of the monitor dongles, the visual-feature-based user input mechanism(s) associated with either or both of a matched pair of dongles. For example, distinguishing sensor dongle to monitor dongle matching using visual user input features (e.g., color-, symbol-, or shape-alignment/matching) that are physically engaged/actuated by the user, such as by turn a wheel actuator/control until a certain color, shape, or text/symbol is displayed or aligned, or by pushing a certain button input feature. In some implementations, turning a wheel on a sensor dongle to a certain color (or other visual identifier) and turning a corresponding wheel on a monitor dongle to a matching color (or other visual identifier) can cause the sensor and monitor dongles to automatically connect/couple to one another as part of a dongle connection process as disclosed herein. Such features/embodiments can be helpful with respect to certain sensor types that are often implemented in multiple such sensors in a treatment environment. For example, a treatment environment may include a plurality of blood pressure sensor devices that are identified as either arterial, central venous, pulmonary artery, or other blood pressure sensor. The connectivity of such sensors can be based on user input through color wheel actuation or the like.

Figure 10:
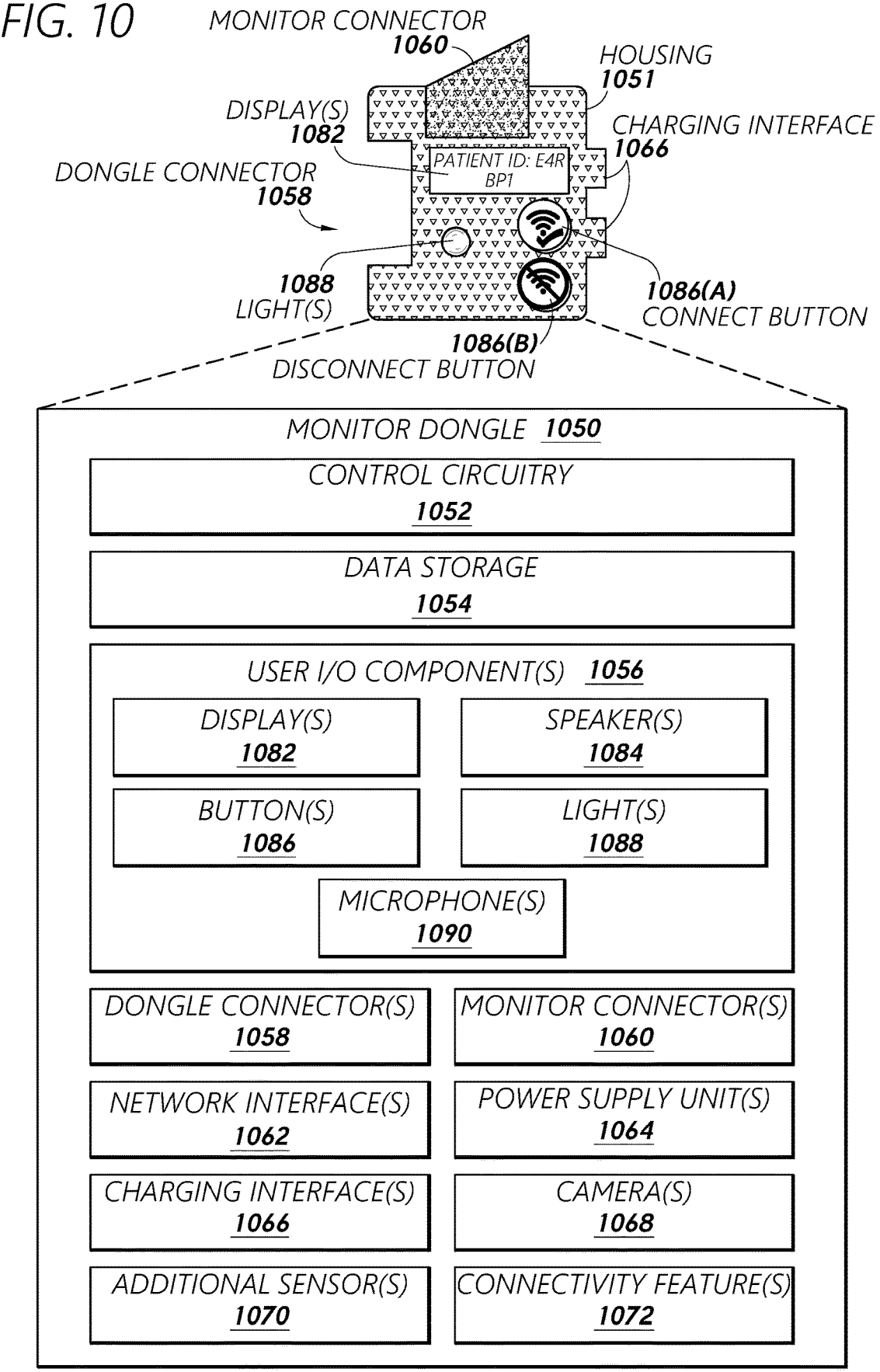
FIG. 10 illustrates a block diagram of an example monitor dongle in accordance with one or more embodiments.

FIG. 10 illustrates a block diagram of an example monitor dongle 1050 in accordance with one or more embodiments of the present disclosure. As illustrated, the monitor dongle 1050 can include one or more of the following components, devices, modules, and/or units (referred to herein as "components"), either separately/individually and/or in combination/collectively: control circuitry 1052, data storage/memory 1054, user input/output (I/O) component(s) 1056, dongle connector(s) 1058, monitor connector(s) 1060, network interface(s) 1062, power supply unit(s) 1064, charging interface(s) 1066, camera(s) 1068, and/or additional sensor(s) 1070.

Although certain components of the monitor dongle 1050 are illustrated in FIG. 10, it should be understood that additional components not shown may be included in embodiments of monitor dongles in accordance with the present disclosure. Furthermore, certain of the illustrated components may be omitted in some embodiments. Although the control circuitry 1052 is illustrated as a separate component in the diagram of FIG. 10, it should be understood that any or all of the remaining components of the monitor dongle 1050 may be embodied at least in part in the control circuitry 1052. That is, the control circuitry 1052 may include various devices (active and/or passive) semiconductor materials and or areas, layers, regions, and/or portions thereof, conductors, leads, vias, connections, and/or the like, wherein one or more of the other components of the monitor dongle 1050 and/or portion(s) thereof can be formed and or embodied at least in part in/by such circuitry components/devices.

The various components of the monitor dongle 1050 may be electrically and/or communicatively coupled using certain connectivity circuitry/devices/features 1072, which may or may not be part of the control circuitry 1052. For example, the connectivity feature(s) 1072 may include one or more printed circuit boards configured to facilitate mounting and/or interconnectivity of at least some of the various components/circuitry of the monitor dongle 1050. In some embodiments, two or more of the control circuitry 1052, the data storage 1054, the user input/output (I/O) component(s) 1056, the dongle connector 1058, the monitor connector(s) 1060, the network interface(s) 1062, the power supply unit 1064, the charging interface(s) 1066, the camera(s) 1068, and/or the additional sensors 1070 can be electrically and/or communicatively coupled to each other.

The monitor dongle 1050 can comprise a housing/enclosure 1051 configured and/or dimensioned to house or contain at least part of one or more of the components of the monitor dongle 1050. The housing/enclosure 1051 can include various types of materials that can be configured according to medical standards or practices. In some embodiments, the housing/enclosure 1051 can be configured to be subjected to sterilization processes, as discussed in further detail below. The housing/enclosure 1051 may advantageously comprise relatively hard/rigid material, which may serve to protect components disposed at least partially therein from physical damage and/or contamination. For example, the housing/enclosure 1051 may advantageously be air- and/or fluid-tight (e.g., hermetically sealed).

The control circuitry 1052 can include one or more processors, such as one or more central processing units (CPUs), one or more microprocessors, one or more graphics processing units (GPUs), one or more digital signal processors (DSPs), and/or other processing circuitry. Alternatively or additionally, the control circuitry 1052 can include one or more application specific integrated circuits (ASIC), one or more field-programmable gate arrays (FPGAs), one or more program-specific standard products (ASSPs), one or more complex programmable logic devices (CPLDs), and/or the like. The control circuitry 1052 can advantageously be configured to execute one or more instructions stored in the data storage 1054 to thereby perform one or more operations to implement various functionality discussed herein. The control circuitry 1052 can operate in cooperation with any of the components of the monitor dongle 1050 to facilitate such functionality.

The data storage 1054 can include any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer readable media that may be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media. The data storage 1054 can store one or more instructions that are executable by the control circuitry 1052 to facilitate various functionality discussed herein. Additionally or alternatively, the data storage 1054 can store data regarding the monitor dongle 1050, a sensor dongle, a sensor, and/or another device. For example, the data storage 1054 can store sensor data received from a sensor dongle.

The one or more user I/O components 1056 can include one or more electronic displays 1082 configured to display data associated with certain aspects of the present disclosure. The one or more displays 1082 can include one or more liquid-crystal displays (LCD), light-emitting diode (LED) displays, organic LED displays, plasma displays, electronic paper displays, and/or any other type(s) of technology. In some embodiments, the one or more displays 1082 include one or more touchscreens configured to receive input and/or display data.

The one or more user I/O components 1056 can also include one or more speakers 1084 configured to output an audio signal, one or more buttons 1086 configured to be engaged and/or actuated in some manner by a user, wherein such engagement/actuation can generate or otherwise result in provision/receipt of certain input signal(s) that may be used/interpreted by the monitor dongle 1050 and/or control circuitry 1052 thereof. The one or more buttons 1086 can include one or more mechanical push-buttons configured to be depressed or pushed, one or more touch buttons configured to receive touch input, or any other type of buttons. As illustrated in FIG. 10, the one or more buttons 1086 can include a connect button 1086(A) and/or a disconnect button 1086(B). The user I/O component(s) 1056 may further comprise one or more lights 1088 (e.g., LED device(s)) configured to output light. The one or more lights 1088 can include one or more LEDs, one or more incandescent lights, and the like. The user I/O component(s) 1056 may also include one or more microphones 1090 configured to detect sound and convert the sound into an electrical signal. Although the one or more user I/O components 1056 are illustrated as separate components, any of the components can be implemented together. For example, the one or more buttons 1086 can include one or more lights, and so on.

Although described primarily as an electronic display(s) 1082, the display(s) 1082 may comprise a nonelectronic display/notification area. For example, certain patient-related labels and/or other information may be adhered or otherwise attached or disposed on an area of the housing 1051 to provide relevant information relating to the patient, sensor, sensor dongle, and/or one or more other aspects associated with the monitor dongle 1050. In some implementations, the area of the display(s) 1082 may be at least partially available for writing (e.g. using markers or the like) and/or otherwise labeling or marking the monitor dongle 1050.

The one or more user I/O components 1056 can be configured to provide or present information relating to the monitor dongle 1050. For example, the one or more displays 1082 can display one or more of the following types of data/information: a patient identifier for a patient associated with the monitor dongle 1050; information indicating sensor type(s) to which the monitor dongle 1050 is configured to connect; a number of sensor dongles/sensors to which the monitor dongle 1050 is connected; a status of the monitor dongle 1050 (as discussed in further detail below); and/or any other information associated with the monitor dongle 1050.

As one example, FIG. 10 illustrates the one or more displays 1082 presenting a patient identifier ("E4R") and an identifier ("BP1") of a sensor/another dongle associated with the monitor dongle 1050 (e.g., a blood pressure sensor that provides data to the monitor dongle 1050 via a sensor dongle). Further, the one or more displays 1082, the speaker 1084, the one or more buttons 1086, and/or the one or more lights 1088 can provide output regarding a status of the monitor dongle 1050, such as, for example, a status indicating that the monitor dongle 1050 is searching for another dongle to wirelessly couple to, currently wirelessly coupling to another dongle (e.g., engaging in a hand-shake or other coupling initiation process), currently wirelessly coupled to another dongle, currently wirelessly decoupling from another dongle, and so on.

To illustrate, according to an example use case, the one or more lights 1088 can output a green light when the monitor dongle 1050 is wirelessly coupled to a sensor dongle, a yellow light when the monitor dongle 1050 is searching for a sensor dongle, a red light when the monitor dongle 1050 is not coupled to (e.g., decoupled from) a sensor dongle, and so on. Additionally or alternatively, the speaker 1084 can output a predetermined audio signal when the monitor dongle 1050 enters a particular status, such as outputting a first audio signal when the monitor dongle 1050 wirelessly couples with a sensor dongle, outputting a second audio signal when the monitor dongle 1050 wirelessly decouples from another device, and so on. In some embodiments, the speaker 1084 can output a speech signal indicating a status of the monitor dongle 1050, such as by outputting "connected" when the monitor dongle 1050 wirelessly couples to another dongle, outputting "disconnected" when the monitor dongle 1050 decouples, and so on. As such, the one or more user I/O components 1056 can provide a variety of types of output to inform a user about a status of the monitor dongle 1050 or otherwise assist a user in managing the monitor dongle 1050.

Additionally or alternatively, the one or more user I/O components 1056 can be configured to receive input to control the monitor dongle 1050. For example, the one or more displays 1082 can be configured to present a graphical user interface (GUI) to facilitate operation of the monitor dongle 1050, such as to wirelessly connect/disconnect the monitor dongle 1050. In some embodiments, the display(s) 1082 have touch-screen functionality that may be employed by a user to input commands or other input. Further, a user can provide input via the one or more buttons 1086 to request that the monitor dongle 1050 perform an operation associated with a connection to another device. To illustrate, according to particular embodiments that are compatible with aspects of the illustrated monitor dongle 1050 in FIG. 10, in response to receiving an input via the connect button 1086(A), the monitor dongle 1050 can be configured to search for another device within communication range (e.g., a sensor dongle, medical monitor system, etc.) and/or wirelessly couple to such device. As another example, in response to receiving an input via the disconnect button 1086(B), the monitor dongle 1050 may be configured to decouple from a wireless connection with a presently-coupled-to device. Moreover, in some embodiment, the microphone 1060 can receive speech input from a user, which can be processed locally at the monitor dongle 1050 and/or sent to another (e.g., remote) device for processing. The processing can include natural language processing, speech recognition, or other types of processing to interpret the speech input. If the processing determines that the user is requesting an operation, the monitor dongle 1050 can perform such operation in response thereto, such as coupling/decoupling with/from another device or performing another connectivity management operation.

The dongle connector 1058 can be configured to physically and/or electrically connect to another dongle, such as a sensor dongle or another monitor dongle. In some embodiments, the monitor dongle 1050 can be electrically connected to a sensor dongle via the dongle connector 1058 to provide or receive power. For example, the monitor dongle 1050 can be electrically connected to a sensor dongle via the dongle connector 1058 and electrically connected to a medical monitor system via the monitor connector 1060, wherein the monitor dongle 1050 can receive power from the medical monitor system and provide such power to the sensor dongle. As such, the dongle connector 1058 can be electrically coupled to the power supply unit 1064 to facilitate power transfer to and/or from the power supply unit 1064. Moreover, in some embodiments the dongle connector 1058 can provide a physical connection to another device (e.g., dongle) without necessarily providing an electrical connection to the other dongle/device. For example, the monitor dongle 1050 can be physically connected to a sensor dongle or other device for storage and/or organization of the monitor dongle 1050 and/or to maintain a particular association of dongles.

The monitor connector(s) 1060 can be configured to physically and/or electrically connect to a medical monitor system. The monitor connector(s) 1060 can include a specific type of connector that is configured for a specific type of sensor/cable, such as a sensor that is configured for a particular detection method, a sensor that is configured to generate a particular type of data, a sensor that is manufactured or designed by a particular entity, a sensor that generates or provides data according to a particular protocol or standard, and so on. Furthermore, the monitor connector(s) 1060 can include any suitable or desirable arrangement and/or number of electrical contacts and/or associated structural components, such as electrical contacts and/or associated structural components providing one or more serial ports, parallel ports, non-invasive blood pressure (NIBP) ports, ethernet ports, FireWire ports, coaxial ports, Universal serial bus (USB) ports, video graphics array (VGA) ports, digital visual interface (DVI) ports, high-definition multimedia interface (HDMI) ports, plug-/jack-type connectors (e.g., 2.5 mm mono (TS), 3.5 mm mono (TS), 3.5 mm stereo (TRS), 6.35 mm (TRS)), and so on. In some embodiments, the monitor connector(s) 1060 is associated with a particular standard or protocol and/or a particular type of health monitoring (e.g., ECG, SpO$_2$, pulse rate, respiratory monitoring, NIBP, etc.). Further, in some embodiments, the monitor connector(s) 1060 can include a leadwire port such as a 3-, 5-, 6-, or 12-leadwire port. In some embodiments, the monitor dongle 1050 can receive power via the monitor connector 1060, such as from a connected medical monitor system.

The one or more network interfaces 1062 can be configured to communicate with one or more devices over a communication network. For example, the one or more network interfaces 1062 can send/receive data in a wireless or wired manner over a network. A communication network can include a local area network (LAN), a wide area network (WAN) (e.g., the Internet), a personal area network (PAN), a body area network (BAN), etc. In some embodiments, the one or more network interfaces 1062 can implement a wireless technology such as Bluetooth, Wi-Fi, near field communication (NFC), or the like. In some embodiments, the one or more network interfaces 1062 can include a transceiver (e.g., transceiver circuitry embodied in one or more devices) configured to transmit/receive signals wirelessly. For example, the monitor dongle 1050 can use the transceiver to communicate with a sensor dongle, a medical monitor system, a dongle-connectivity management hub, and/or another monitor dongle to establish a wireless connection, receive/provide sensor data regarding a sensor reading, and so on. The network interface(s) 1062 can comprise one or more wireless transceiver circuits or circuitry. For example, the network interface(s) can comprise one or more front end modules, amplifiers, antennas, filters, and/or other signal/processing circuitry configured to facilitate reception and/or transmission of wireless signals/data. As with other modules of the monitor dongle 1050, the network interface(s) 1062 can be embodied in whole or in part in the control circuitry 1052.

The power supply unit 1064 can be configured to manage power for the monitor dongle 1050, such as power provided to and/or received from one or more components of the monitor dongle 1050. In some embodiments, the power supply unit 1068 includes one or more batteries, such as a lithium-based battery, a lead-acid battery, an alkaline battery, and/or another type of battery. That is, the power supply unit 1064 may comprise one or more devices and/or circuitry configured to provide a source of power and/or provide power management functionality. Further, in some embodiments the power supply unit 1064 operates in cooperation with the dongle connector 1058, the monitor connector(s) 1060, and/or the charging interface 1066 to receive and/or provide power. For example, the power supply unit 1064 can receive power via the dongle connector 1058, the monitor connector(s) 1060, and/or the charging interface 1066. Moreover, in some embodiments the power supply unit 1064 (and/or the charging interface 1066) includes a mains power connector that is configured to couple to an alternating current (AC) or direct current (DC) mains power source.

The charging interface 1066 can include various types of interfaces to facilitate charging of the monitor dongle 1050. For example, the charging interface 1066 can operate in cooperation with the power supply unit 1064 to charge one or more batteries of the monitor dongle 1050 (e.g., power supply unit 1064). In some embodiments, the charging interface 1066 can facilitate wireless power transfer to charge one or more batteries of the monitor dongle 1050 (e.g., the power supply unit 1064). In one example, the charging interface 1066 can include an inductance coil configured to couple to an inductive pad/coil of another device to provide power to the monitor dongle 1050. In some embodiments, the charging interface 1066 can include an element configured to receive light from an external light source and convert the light into energy that is storable and/or usable by the monitor dongle 1050. In some embodiments, the charging interface 1066 includes a connector to electrically connect to another device to receive power. Although the charging interface 1066 is illustrated as a separate component of the monitor dongle 1050, as noted above, in some instances the dongle connector 1058 and/or the monitor connector(s) 1060 can facilitate power transfer to charge one or more batteries of the monitor dongle 1050 (e.g., power supply unit 1064) without using a separate charging interface.

As referenced above, the sensor dongle can include one or more cameras 1068 in some embodiments. The camera(s) 1068 can be configured to capture an image. For example, the camera(s) 1068 can be configured to capture an image of a patient associated with the monitor dongle 1050. In some embodiments, the monitor dongle 1050 can capture an image using the camera(s) 1068 and provide the image to another device for analysis, such as to identify a patient associated with the monitor dongle 1050, or other individual or item present in the environment of the monitor dongle 1050. In some embodiments, the control circuitry 1052 and/or camera(s) 1068 may be utilized to identify and/or capture images of certain labels, markers, codes, icons and or the like, which may be used to identify/label certain patients and/or items associated there with. For example, in some implementations, the monitor dongle 1050 may be configured to read a barcode, QR code, or the like, which may provide an identifier for a patient (e.g., on a bracelet or other wearable device/item).

Additionally or alternatively, the monitor dongle 1050 (e.g., control circuitry 1052) may be configured to implement electromagnetic radiation/fields to read/interrogate passive radio-frequency identification (RFID) tags, wherein such tags may provide identification information relating to patients, sensors, dongles, and/or other items or individuals. Further, in some embodiments, the monitor dongle 1050 (e.g., the control circuitry 1052) can be configured to analyze/process an image locally to identify a patient or other individual(s)/item(s). Such functionality may be useful to determine if a dongle is associated with the correct patient. In some embodiments, the camera(s) 1068 can be adjustable by a user or otherwise to configure the camera(s) 1068 in a particular orientation and/or capture a particular point of view. Although FIG. 10 and certain other embodiments disclosed herein are described in the context of camera devices being implemented as part of a monitor dongle or another dongle device, in some implementations, a dongle-connectivity management hub may be configured to communicate with a camera device that is not connected to our otherwise associated with a particular dongle or sensor.

The additional sensor(s) 1070 can include one or more accelerometers configured to detect acceleration, magnetometers configured to detect magnetism, gyroscopes configured to detect orientation and/or angular velocity, and/or a satellite-based navigation (e.g., Global Positioning System (GPS)) sensors configured to determine a geographical location of the monitor dongle 1050. In some embodiments, data from the additional sensor(s) 1070 (and/or the camera 1068) can be analyzed to detect if the monitor dongle 1050, an associated patient, and/or a monitor stand/cart is moving, has moved outside of a particular geofence/radius of interest, and so on. In some embodiments, data from the additional sensor(s) 1070 (and/or the camera 1068) can be analyzed to determine if a patient is being transported, such as by determining if a patient has moved beyond a predetermined radius/distance associated with a room.

In some embodiments, the monitor dongle 1050 can at least partly manage wireless connectivity for a system. For example, the monitor dongle 1050 can act as a connectivity management hub that is configured to communicate with other dongles to facilitate connectivity, facilitate sensor data communication, and so on, similar to functionality that can be performed by a dongle-connectivity management hub in some implementations. In some embodiments, the monitor dongle 1050 can perform such functionality when the monitor dongle 1050 enters a transport mode associated with transporting a patient from one room, area, or facility to another room, area, or facility. While transporting the patient, and/or while the monitor dongle 1050 is disconnected (e.g., unplugged for a medical monitor system) for the transport, the monitor dongle 1050 can be configured to at least temporarily store data from a sensor (e.g., buffer data locally) and/or receive/store data from other dongles.

Although not illustrated in FIG. 10, in some embodiments, the monitor dongle 1050 can include a transport button, similar to the button(s) 1086, to enable/disable a transport mode for the monitor dongle 1050 or otherwise facilitate patient-transport functionality. In some embodiments, selecting a transport button on the monitor dongle 1050 can cause the monitor dongle 1050 and/or other dongles associated with a patient to enter a transport mode or perform other patient-transport functionality, as discussed in further detail below.

Connectivity with Medical Monitor Systems

Figure 11:
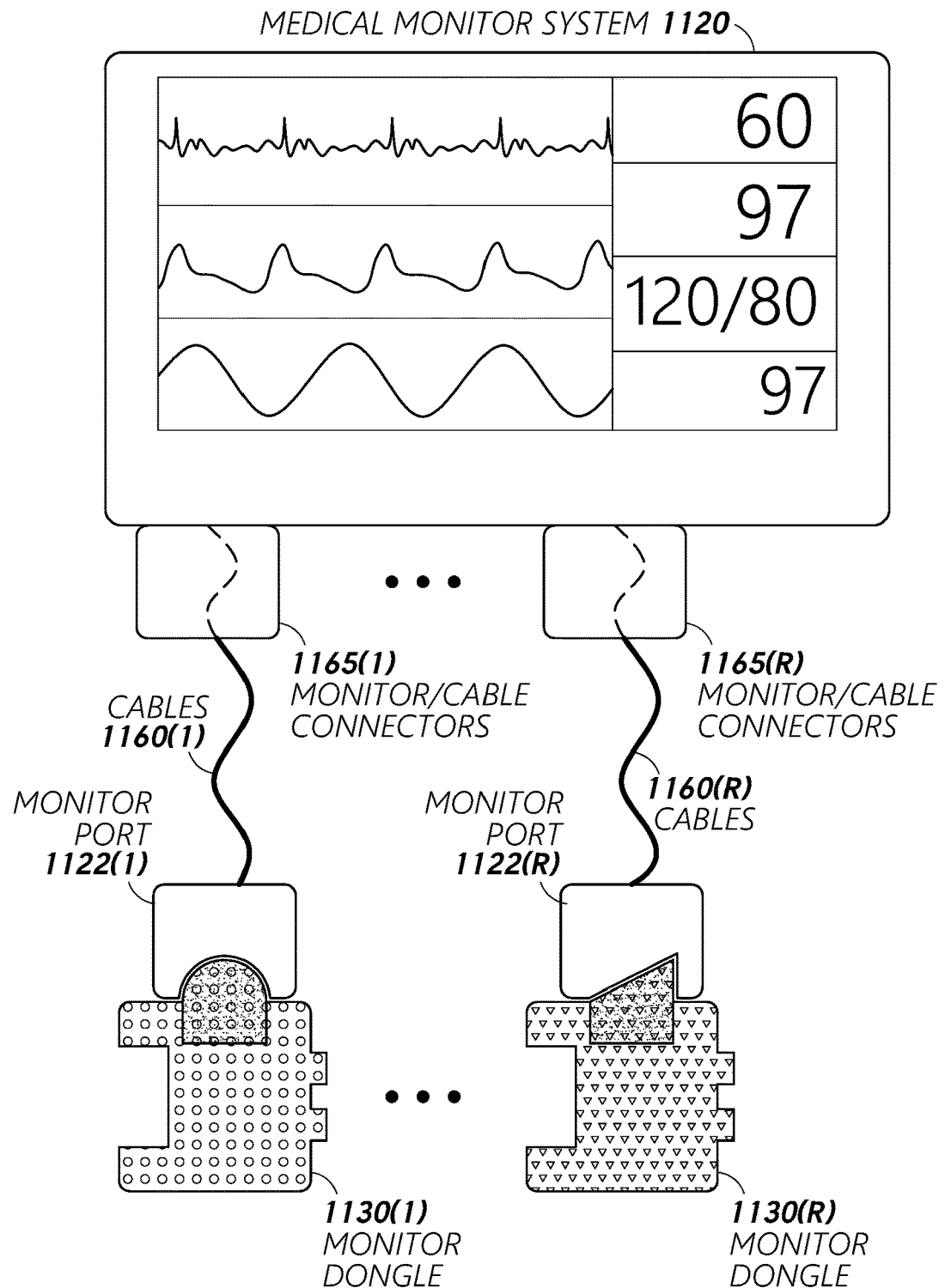
FIG. 11 illustrates a medical monitor system showing example monitor dongle physical connectors in accordance with one or more embodiments.

FIG. 11 illustrates an example medical monitor system 1120 with cables 1160(1)-1160(R) and monitor ports 1122(1)-1122(R) at ends of the cables 1160 to electrically connect to respective monitor dongles 1130(1)-(R) in accordance with one or more embodiments of the present disclosure. The letter "R" represents an integer greater than one. In some embodiments, the cables 1160 can advantageously provide flexibility in connecting the monitor dongles 1130 to the medical monitor system 1120, such as by enabling the monitor ports 1122 to be positioned at locations that are convenient for facilitating connections to the monitor dongles 1130. In some embodiments, the cables 1160, the monitor ports 1122, and/or the monitor dongles 1130 can be at least partly hidden within an environment from a user's view, such as within a drawer of a cart, behind the medical monitor system 1120, or any other location.

In some embodiments, the cables 1160 can be permanently connected to the medical monitor system 1120, while in other embodiments, the cables 1160 are connected to the medical monitor system 1120 via monitor-to-cable connectors 1165, which may have similar or different types of connector/port features to the monitor ports 1122 and/or monitor dongles 1130, or may adapt such monitor dongle and/or monitor port connectors/ports to different type(s) of monitor connectors/ports. The monitor ports 1122 can include various types of connectors configured to connect to various types of monitor dongles, as illustrated in FIG. 11 by the connector representations having different shapes representing different types of connectors/ports.

Figure 12:
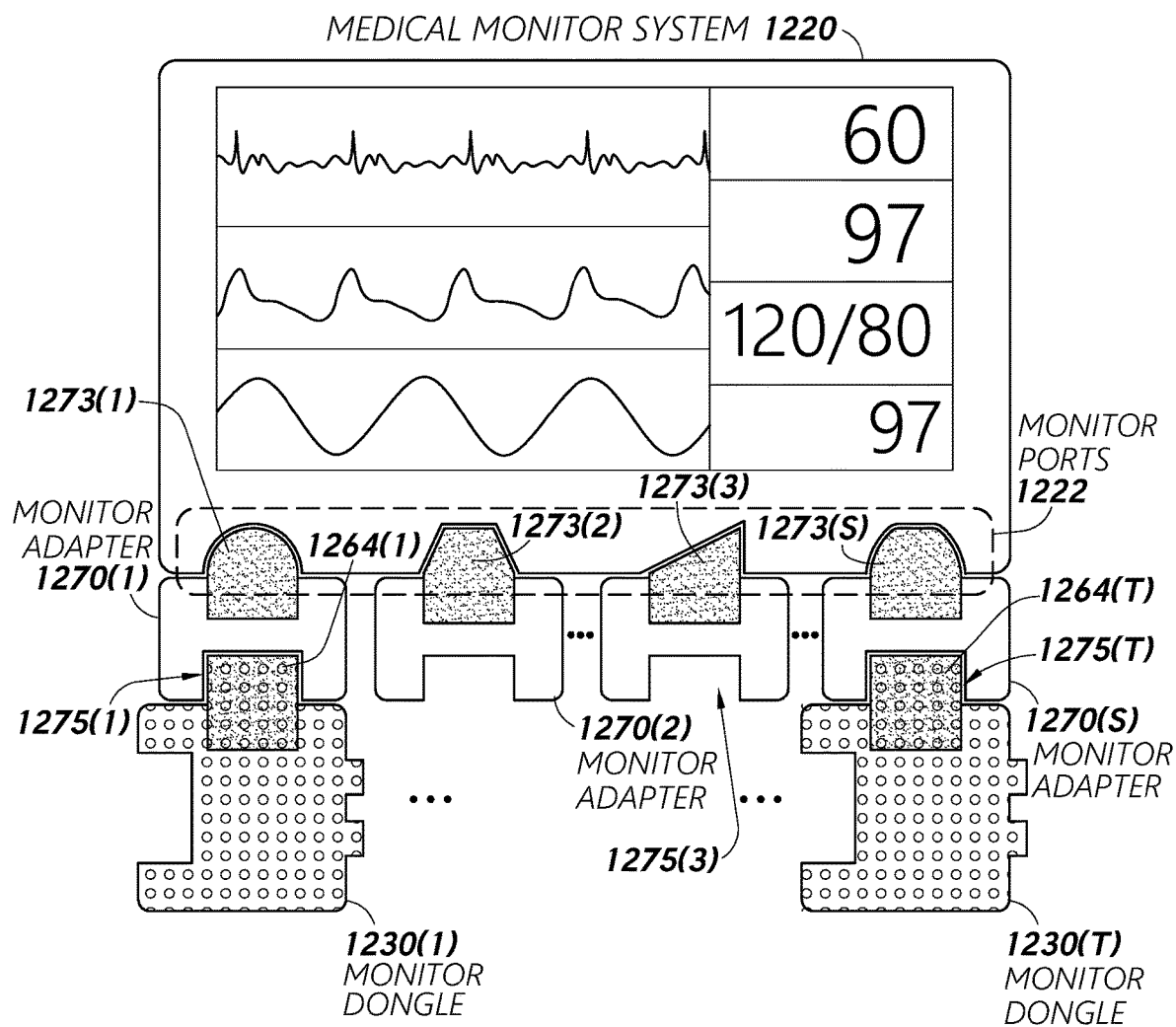
FIG. 12 illustrates a medical monitor system electrically connected to monitor adapters in accordance with one or more embodiments.

FIG. 12 illustrates an example medical monitor system 1220 electrically connected to monitor adapters 1270(1)-1270(S) that are configured to provide uniform connectors for monitor dongles 1230(1)-1230(T) in accordance with one or more embodiments. The letters "S" and "T" each represent integers greater than one. The monitor adapters 1270 are sometimes referred to as "stub connectors." As shown, the monitor adapters 1270 can advantageously include first connectors 1273 that are configured to electrically connect to monitor ports 1222 of the medical monitor system 1220 and second connectors/ports 1275 that are configured to electrically connect to (e.g., receive) connectors 1264 of the respective monitor dongles 1230, with the first connector connectors 1273 potentially facilitating different types of connections and the second connectors 1275 facilitating a common type of connection (i.e., a uniform connection type) across a plurality of the monitor adapters 1270. The monitor adapters 1270 can allow various monitor dongles having a common type of connector to be electrically connected through different types of ports of the medical monitor system 1220. In some embodiments, the monitor adapters 1270 are implemented so that various monitor dongles can be used that all have a common type of connector, such as in the case where backwards compatibility is needed or desirable for a medical monitor system that includes, for example, one or more outdated connectors/ports.

Dongle-to-Dongle Connections

FIGS. 13-1 through 13-3 illustrate various electrical connections that can be made between an example sensor dongle 1350 and an example monitor dongle 1330 in accordance with one or more embodiments of the present disclosure. It should be understood that the monitor dongle 1330 and the sensor dongle 1350 each may be configured for connection according to any one or more of the types of connections shown in FIGS. 13-1, 13-2, and 13-3, respectively. That is, the sensor dongle 1350 and monitor dongle 1330, in accordance with various embodiments of the present disclosure, may be configured to connect according to the connection shown in FIG. 13-1, the connection shown in FIG. 13-2, and/or the connection shown in FIG. 13-3, or may not be configured for connection in accordance with any of the connections shown in FIGS. 13-13 13-3.

The sensor dongle 1350 and the monitor dongle 1330 can be connected for a variety of purposes, such as to facilitate charging of one or more of the dongles, to physically associate the dongles for storage, to maintain an association between same or similar types of dongles, and so on. In some embodiments, the sensor dongle 1350 is configured to be connected to the monitor dongle 1330 when one or more of the dongles are connected to another device, such as when the sensor dongle 1350 is connected to a sensor, the monitor dongle is connected to a medical monitor system, and so on. In some examples, such configuration can facilitate charging of the sensor dongle 1350 and/or the monitor dongle 1330, such as through the transfer of power from the monitor dongle 1330 to the sensor dongle 1350 or vice versa. FIG. 13-1 illustrates the sensor dongle 1350 electrically and/or physically coupled/connected to the monitor dongle 1330 via a dongle connection 1365 that is facilitated by a male dongle connector 1358 on the sensor dongle 1350 and a female dongle connector 1362 on the monitor dongle 1330. In some embodiments, the monitor dongle 1330 and the sensor dongle 1350 may be connected, wherein the dongle connector 1362 is a male-type connector, whereas the dongle connector 1358 is a female-type connector/port.

FIG. 13-2 illustrates the sensor dongle 1350 electrically and/or physically coupled/connected to the monitor dongle 1330 via a sensor/monitor connection 1367 that is facilitated by a male monitor connector 1364 of the monitor dongle 1330 and a female sensor connector 1360 of the sensor dongle 1350. The connection 1367 may be used to transfer data and/or power between the monitor dongle 1330 and the sensor dongle 1350. In some embodiments, the monitor dongle 1330 and the sensor dongle 1350 may be connected, wherein the monitor connector 1364 of the monitor dongle 1330 is a female-type connector/port, whereas the sensor connector 1360 of the sensor dongle 1350 is a male-type connector.

FIG. 13-3 illustrates the sensor dongle 1350 electrically and/or physically coupled/connected to the monitor dongle 1330 via a charging interface connection 1367 that is facilitated by a charging interface 1366 on the sensor dongle 1350 and a charging interface 1362 on the monitor dongle 1330, which may be joined/engaged with each other in some manner or otherwise connected or brought into proximity with one another in order to facilitate the transfer of power and/or data between the dongles 1330, 1350. Although various male and female connections are illustrated in FIGS. 13-1 through 13-3, such connector representations are provided as examples, and it should be understood that such connectors may be male, female, or other types of connectors.

Figure 14:
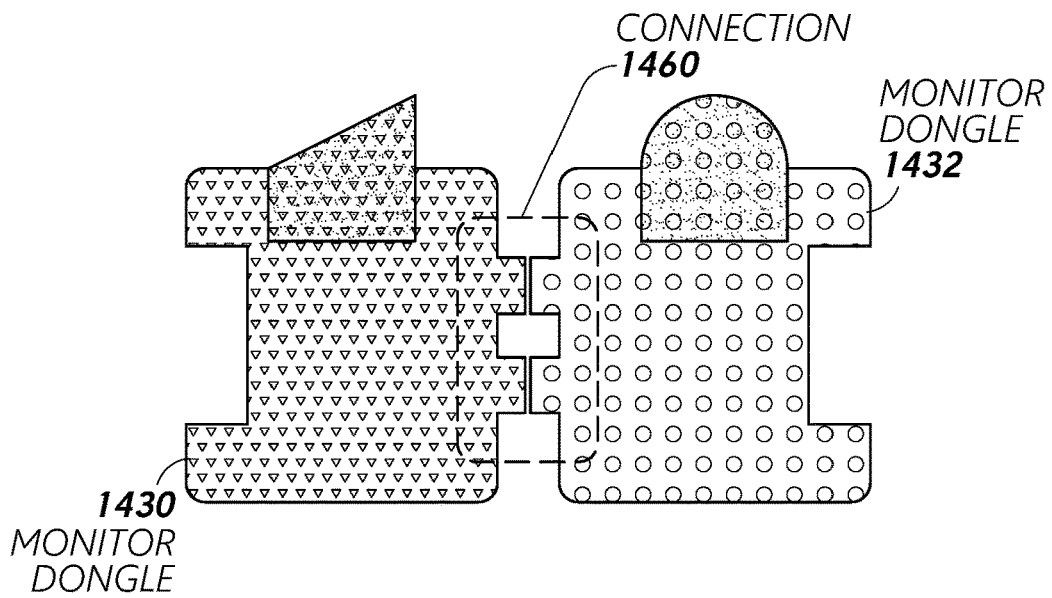
FIG. 14 illustrates an example connection between monitor dongles in accordance with one or more embodiments.

FIG. 14 illustrates an example connection that can be made between monitor dongles 1430 and 1432 in accordance with one or more embodiments. As an example, the electrical and/or physical connection 1460 between the monitor dongle 1430 and the monitor dongle 1432 can be a charging interface connection, which may be facilitated by a charging interface on the monitor dongle 1430 and/or a charging interface on the monitor dongle 1432, wherein power is transferred over the connection 1460 from the monitor dongle 1430 to the monitor dongle 1432 and/or vice versa. In some embodiments, the connection 1460 may be used for data transfer between the monitor dongles 1430, 1432. With respect to embodiments in which the connection 1460 is representative of and/or associated with a charging interface, the connection 1460 can be used to charge one or more of the dongles 1430 and 1432 (e.g., transfer power from the monitor dongle 1430 to the monitor dongle 1432 to charge the monitor dongle 1432 and/or transfer power from the monitor dongle 1432 to the monitor dongle 1430 to charge the monitor dongle 1430). However, the charging interface connection 1460 can be used for a variety of purposes, such as to physically associate the monitor dongles 1430 and 1432 for storage, maintain an association between the monitor dongles 1430 and 1432 (e.g., between dongles that have a common type of connector), and so on.

Figure 15:
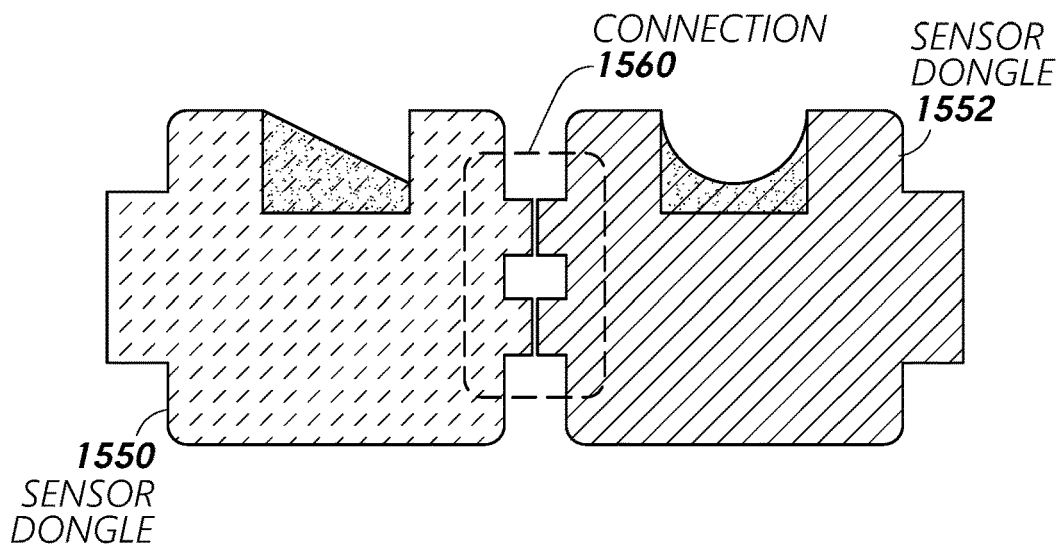
FIG. 15 illustrates an example connection between sensor dongles in accordance with one or more embodiments.

FIG. 15 illustrates an example connection that can be made between sensor dongles 1550 and 1552 in accordance with one or more embodiments. As an example, the electrical and/or physical connection 1560 between the sensor dongle 1550 and the sensor dongle 1552 can be a charging interface connection, which may be facilitated by a charging interface on the sensor dongle 1550 and a charging interface on the sensor dongle 1552, wherein power is transferred over the connection 1560 from the sensor dongle 1550 to the sensor dongle 1552 and/or vice versa. In some embodiments, the connection 1560 may be used for data transfer between the sensor dongles 1550, 1552, such as for the purpose of sharing connectivity-related data and/or other data related to the operation of one or more of the sensor dongles 1550, 1552. With respect to embodiments in which the connection 1560 is representative of and/or associated with a charging interface, the connection 1560 can be used to charge one or more of the sensor dongles 1550 and 1552 (e.g., transfer power from the sensor dongle 1550 to the sensor dongle 1552 to charge the sensor dongle 1552 and/or transfer power from the sensor dongle 1552 to the sensor dongle 1550 to charge the sensor dongle 1550). However, the charging interface connection 1560 can be used for a variety of purposes, such as to physically associate the sensor dongles 1550 and 1552 for storage, maintain an association between the sensor dongles 1550 and 1552 (e.g., between dongles that have a common type of connector), and so on.

Dongle-Connectivity Management Hubs

Figure 16:
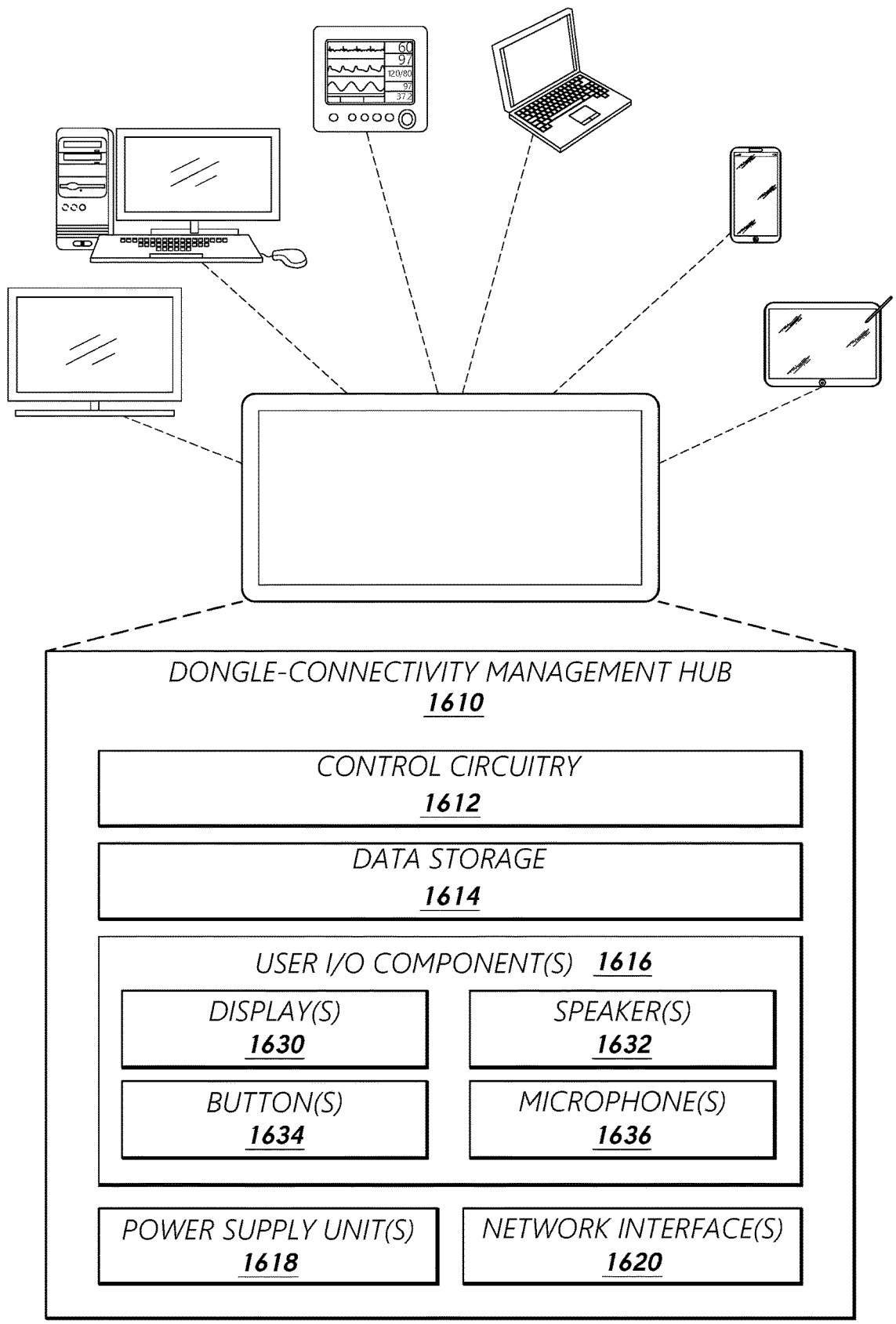
FIG. 16 illustrates an example block diagram of a dongle-connectivity management hub in accordance with one or more embodiments.

FIG. 16 illustrates an example block diagram of a dongle-connectivity management hub 1610 in accordance with one or more embodiments. The dongle-connectivity management hub 1610 can comprise and/or be communicatively coupled to any type of computing device, such as a laptop computer, a desktop, a server, a medical monitor system, a laptop computer, a smartphone, a tablet computer, an electronic reader device, a mobile handset, a portable navigation device, a wearable device (e.g., a watch, an optical head-mounted display, etc.), a portable media player, a television, a set-top box, a navigation system, an appliance, a camera, a security system, a projector, an automated teller machine (ATM), and the like. In some embodiments, the dongle-connectivity management hub 1610 comprises a computing device that is designed or designated specifically for a dongle-connectivity system in accordance with various embodiments discussed herein, while in other embodiments the dongle-connectivity management hub 1610 comprises a computing device that is designed or designated for various other types of operations/functions.

As illustrated, the dongle-connectivity management hub 1610 can include one or more of the following components, devices, modules, and/or units (referred to herein as "components"), either separately/individually and/or in combination/collectively: control circuitry 1612, data storage 1614, user input/output (I/O) component(s) 1616, a power supply unit(s) 1618, and/or network interface(s) 1620. The various components of the dongle-connectivity management hub 1610 may be electrically and/or communicatively coupled using certain connectivity circuitry and/or devices, which may or may not be part of the control circuitry 1612. For example, the connectivity feature(s) may include one or more printed circuit boards configured to facilitate mounting and/or interconnectivity of at least some of the various components/circuitry of the dongle-connectivity management hub 1610. In some embodiments, two or more of the control circuitry 1612, data storage 1614, the one or more user input/output (I/O) components 1616, the power supply unit(s) 1618, and/or the one or more network interfaces 1620 can be communicatively coupled to each other.

Although certain components of the dongle-connectivity management hub 1610 are illustrated in FIG. 16, it should be understood that additional components not shown may be included in embodiments of dongle-connectivity management hubs in accordance with the present disclosure. Furthermore, certain of the illustrated components may be omitted in some embodiments. Although the control circuitry 1612 is illustrated as a separate component in the diagram of FIG. 16, it should be understood that any or all of the remaining components of the dongle-connectivity management hub 1610 may be embodied at least in part in the control circuitry 1612. That is, the control circuitry 1612 may include various devices (active and/or passive) semiconductor materials and or areas, layers, regions, and/or portions thereof, conductors, leads, vias, connections, and/or the like, wherein one or more of the other components of the dongle-connectivity management hub 1612 and/or portion(s) thereof can be formed and or embodied at least in part in/by such circuitry components/devices.

The control circuitry 1612 can include one or more processors, such as one or more central processing units (CPUs), one or more microprocessors, one or more graphics processing units (GPUs), one or more digital signal processors (DSPs), and/or other processing circuitry. Alternatively or additionally, the control circuitry 752 can include one or more application specific integrated circuits (ASIC), one or more field-programmable gate arrays (FPGAs), one or more program-specific standard products (ASSPs), one or more complex programmable logic devices (CPLDs), and/or the like. In many embodiments, the control circuitry 1612 can advantageously be configured to execute one or more instructions stored in the data storage 1614 to perform one or more operations to implement various functionality discussed herein. The control circuitry 1612 can operate in cooperation with any of the components of the dongle-connectivity management hub 1610 to facilitate such functionality.

The data storage 1614 can include any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other data types. Computer readable media that may be implemented in accordance with embodiments of the present disclosure includes, but is not limited to, phase change data storage, static random-access data storage (SRAM), dynamic random-access data storage (DRAM), other types of random access data storage (RAM), read-only data storage (ROM), electrically erasable programmable read-only data storage (EEPROM), flash data storage or other data storage technology, compact disk read-only data storage (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

The data storage 1614 can store one or more instructions that are executable by the control circuitry 1612 to facilitate various functionality discussed herein. Additionally or alternatively, the data storage 1614 can store data regarding a dongle, a sensor, and/or another device. For example, the data storage 1614 can store sensor data received from a dongle and/or sensor.

The one or more user I/O components 1616 can include one or more electronic displays 1630 configured to display data, one or more speakers 1632 configured to output an audio signal, one or more buttons 1634 configured to receive input, and/or one or more microphones 1636 configured to detect sound and convert the sound into an electrical signal. The one or more displays 1630 can include one or more liquid-crystal (LCD) displays, light-emitting diode (LED) displays, organic LED displays, plasma displays, electronic paper displays, and/or any other type of technology. In some embodiments, the one or more displays 1630 include one or more touchscreens configured to receive input and/or display data. The one or more buttons 1634 can include one or more mechanical push-buttons configured to be depressed or pushed, one or more touch buttons configured to receive touch input, or any other type of button. Although the one or more user I/O components 1616 are illustrated as separate components, any of the components can be implemented together.

The one or more user I/O components 1616 can be configured to receive input from a user and/or provide output to the user. In one example, the one or more user I/O components 1616 provide a user interface via the one or more displays 1630 with information regarding the dongle-connectivity management hub 1610, one or more sensor and/or monitor dongles, a medical monitor system, and/or other device(s), and a user can provide input via the user interface to control one or more of the devices. In some embodiments, a user can provide speech input via the microphone(s) 1636 and the dongle-connectivity management 1610 can perform operations requested by the speech input. In some embodiments, a user can provide input via the one or more buttons 1634 and the dongle-connectivity management hub 1610 can perform an operation based on the input. In some embodiments, one or more of the user I/O components 1616 or other components can operate to receive gesture input (e.g., a camera(s) on the dongle-connectivity management hub 1610 can capture an image(s) of a user making a gesture(s) and the gesture(s) can be processed using gesture recognition to identify an operation being requested).

The power supply unit(s) 1618 can be configured to manage power for the dongle-connectivity management hub 1610, such as power provided to and/or received from one or more components of the dongle-connectivity management hub 1610. In some embodiments, the power supply unit(s) 1618 includes one or more batteries, such as a lithium-based battery, a lead-acid battery, an alkaline battery, and/or another type of battery. That is, the power supply unit(s) 1618 may comprise one or more devices and/or circuitry configured to provide a source of power and/or provide power management functionality. Further, in some embodiments the power supply unit(s) 1618 includes a mains power connector that is configured to couple to an alternating current (AC) or direct current (DC) mains power source. Moreover, in some embodiments the dongle-connectivity management hub 1610 includes a charging interface (not illustrated) configured to connect to a dongle and operate in cooperation with the power supply unit(s) 1618 to charge the dongle. In some embodiments, the dongle-connectivity management hub 1618 can be powered-on for a period of time to establish connections between dongles and then power down or enter a sleep state associated with less power consumption than the power-on state.

The one or more network interfaces 1620 can be configured to communicate with one or more devices over a communication network. For example, the one or more network interfaces 1620 can send/receive data in a wireless or wired manner over a network. A communication network can include a local area network (LAN), a wide area network (WAN) (e.g., the Internet), a personal area network (PAN), a body area network (BAN), etc. In some embodiments, the one or more network interfaces 1620 can implement a wireless technology such as Bluetooth, Wi-Fi, near field communication (NFC), or the like. In some embodiments, the one or more network interfaces 1620 can include a transceiver configured to transmit/receive signals wirelessly. For example, the dongle-connectivity management hub 1610 can use the transceiver to communicate with a monitor dongle and a sensor dongle to establish a wireless connection between the sensor dongle and the monitor dongle.

The dongle-connectivity management hub 1610 can be configured to manage wireless connectivity between a variety of devices, such as sensor dongles, monitor dongles, and/or medical monitor systems. In some embodiments, the dongle-connectivity management hub 1610 can generate, display, and/or provide a user interface (e.g., user interface data) via the one or more displays 1630 to assist a user in managing dongles. The user interface can enable a user to establish wireless connections between dongles, view information about the dongles (e.g., status information regarding connectivity, battery life, etc.), and so on.

In some embodiments, a user interface can provide an additional layer of information to inform a user of operations being performed by the dongle-connectivity management hub 1610, dongles, and/or a medical monitor system. Such information can be implemented to assist a user in confirming that the appropriate connections are/have being/been made. For example, when a wireless connection is established between a sensor dongle and a monitor dongle, lighting features or other 110 components of one or both of the dongles may light up in particular manner or provide other notifications (e.g., audio) to inform/notify a user that the dongles are connecting to each other. In addition, the dongle-connectivity management hub 1610 can be configured to generate and/or display user interface data (e.g., using a user interface) representing the connected dongles. For example, representative icons, text, and/or other imagery relating to the dongles can be presented and/or represented by graphical interface data to indicate the status of dongles that are connected/connecting to each other. Therefore, in some implementations, a user can view or receive two or more types of notifications regarding communicative couplings of two or more dongles.

In some embodiments, the dongle-connectivity management hub 1610 is configured to detect or otherwise determine the presence of sensor dongles and/or monitor dongles that are located within a certain range of the dongle-connectivity management hub 1610 and/or each other (e.g., a range corresponding to a particular wireless technology implemented by the hub 1610 and/or dongle(s)), wherein the dongle-connectivity management hub 1610 and/or dongle(s) is/are configured to initiate communicative coupling of the dongle(s) with each other and/or with the hub 1610 in response to detection/determination of the presence of the dongle(s). For example, detection/determination of the presence of the dongle(s) can trigger communicative coupling (e.g., automatically) of sensor dongles and monitor dongles of a specific and/or common type (e.g., dongles configured for a specific type of sensor, sensor port, etc.) and/or sensor dongles and monitor dongles that have been previously coupled/connected, as determined by the hub 1610 and/or dongle(s). In some implementations, dongles can be configured to transmit data to the dongle-connectivity management hub 1610 indicating a dongle type, and the dongle-connectivity management hub 1610 can be configured to communicatively couple, or initiate coupling of, dongles and/or generate graphical interface data relating to the dongles based at least in part on the transmitted data. Moreover, in some embodiments, the dongle-connectivity management hub 1610 can be configured to perform/provide troubleshooting functionality, allocate network resources for wireless connectivity (e.g., allocate bandwidth/channels, monitor/control data throughput or other network parameters, and so on) and/or perform a variety of other functions.

Charging/Sterilization Systems

Figure 17:
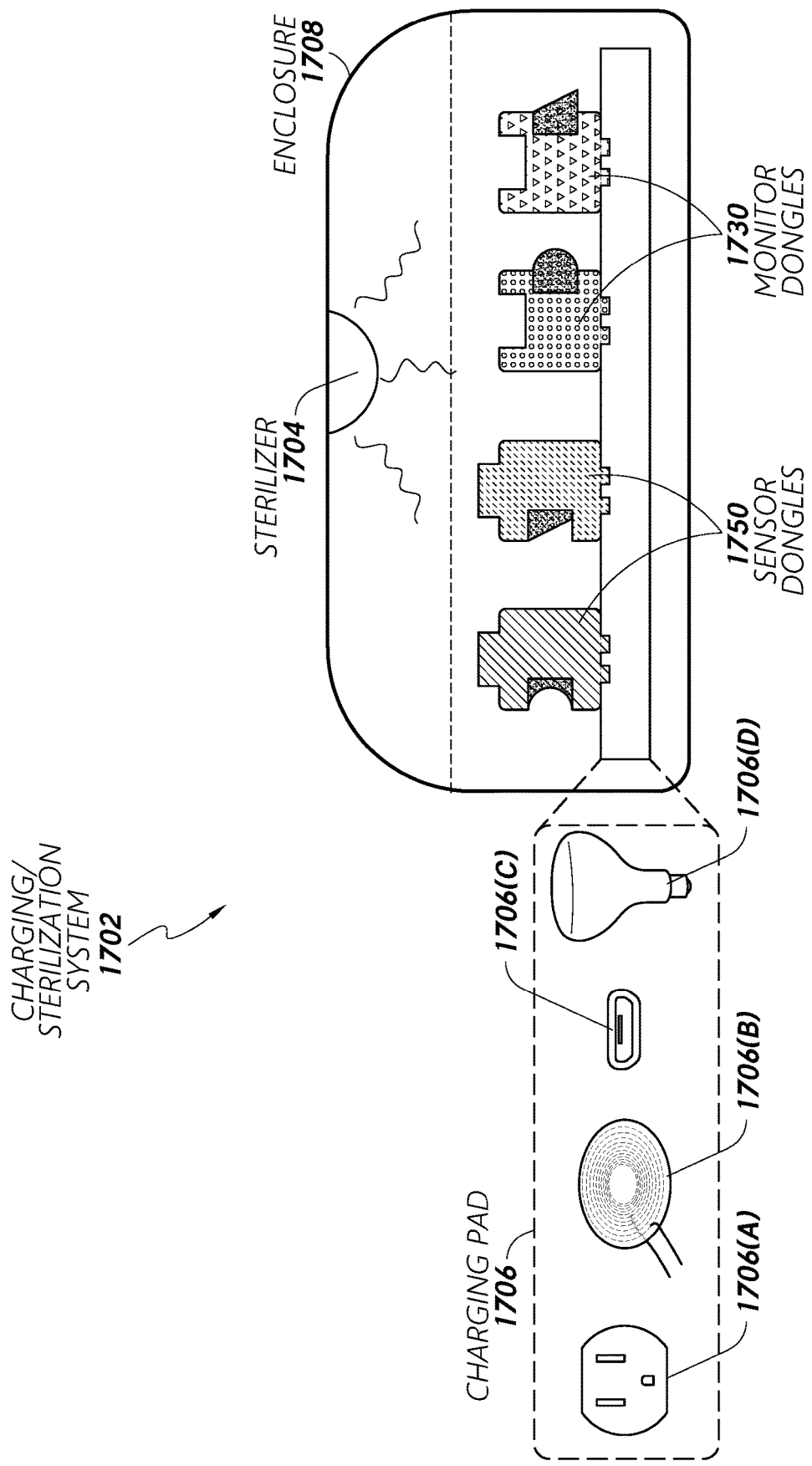
FIG. 17 illustrates an example charging/sterilization system in accordance with one or more embodiments.

FIG. 17 illustrates an example charging/sterilization system 1702 configured to charge and/or sterilize one or more dongles in accordance with one or more embodiments. The charging/sterilization system 1702 can include an enclosure 1708 to at least partially house a sterilization element/device (also referred to as "sterilizer" for convenience) 1704, a charging pad 1706, and/or one or more dongles, such as one or more sensor dongles 1750 and/or one or more monitor dongles 1730. The sterilizer 1704 can be configured to sterilize one or more of the sensor dongles 1750 and the monitor dongles 1730 (or any other type of device disposed win the enclosure 1708). Although some description of sterilization systems/devices herein refers to sterilization of device(s) disposed within an enclosure, it should be understood that such embodiments may rather be implemented such that one or more devices are sterilized without being disposed within an enclosure. That is, the system 1702 may be configured and/or comprise component(s) such that no enclosure is necessary. For example, the sterilizer 1704 (e.g., lamp) may be configured and/or arranged to direct sterilization radiation (or other sterilization mechanism/element) at the target device(s) in an at least partially open target area.

In some embodiments, the enclosure 1708 is configured to seal the sensor dongle 1750 and/or the monitor dongle 1730 within an enclosed chamber for sterilization and/or charging. The enclosure 1708 may be at least partially open/unsealed in some implementations. Therefore, description of enclosures herein should be understood to refer to an enclosure structure configured to completely envelope and/or seal-off a chamber in which device(s) may be placed, or to a structure that in configured to hold or secure one or more of the sterilizer 1704, the dongle(s) 1730, 1750, and the charging pad 1706. In some embodiments, the sensor dongles 1750 and/or the monitor dongles 1730 are placed within the charging/sterilization system 1702 for simultaneous charging and sterilization. Although the sterilizer 1704 and the charging bad 1706 are shown in FIG. 17, it should be understood that embodiments may include only one of such components/devices.

The sensor dongle 1750 and/or the monitor dongle 1730 can be positioned/arranged in the enclosure 1708 in a variety of manners, such as placed on a surface within the enclosure 1708, connected to a port or other connection mechanism within the enclosure, and so on. In some embodiments, the dongle(s) 1730, 1750 may be placed at least partially within, or otherwise exposed at least partially to, a sterilizing fluid solution (e.g., gas and/or liquid), or other sterilization matter. Although two sensor dongles and two monitor dongles are illustrated in FIG. 17, any number of sensor dongles and/or monitor dongles can be implemented. Furthermore, although one charging/sterilization system is illustrated in FIG. 17, any number of charging/sterilization systems can be implemented, such as a first charging/sterilization system for sensor dongles and a second charging/sterilization system for monitor dongles.

The sterilizer 1704 can implement a process/mechanism to sterilize a device, which can include removing, eliminating, deactivating, or destroying a biological constituent, such as bacteria, viruses, fungi, and so on. The sterilizer 1704 can implement heat sterilization (e.g., exposing an object to heat with an autoclave, dry heat sterilizer, incinerator, etc.), irradiation sterilization (e.g., exposing an object to radiation, such as gamma rays, electron-beam, x-rays, or other frequency/band of electromagnetic radiation, including possibly visible light spectrum), chemical sterilization (e.g., exposing an object to a chemical in a liquid or gas form), pressure sterilization (e.g., exposing an object to pressure), filtration sterilization (e.g., filtering a constituent from another constituent), and so on. In the example of FIG. 17, the sterilizer 1704 is positioned at a top portion of the enclosure 1708 and is configured to project a sterilization agent (e.g., sterilizing radiation, liquid or gas medium, or the like) at or near the target device(s) 1730, 1750 to thereby at least partially sterilize the target device(s). However, the sterilizer 1704 can be positioned at other locations and/or implement other techniques to sterilize the target sensor dongles 1750 and/or the monitor dongles 1730.

The charging pad 1706 can include one or more components that are configured to provide power to one or more of the sensor dongles 1750 and the monitor dongles 1730. The charging pad 1706 can include a relatively flat surface dimensioned to hold one or more of the sensor dongles 1750 and the monitor dongles 1730, such that the dongle(s) can be placed on the surface for wireless power transfer and/or sterilization. In some embodiments, the charging pad 1706 includes an induction coil 1706(B) configured to transfer power to corresponding coils or other conductive element(s) in one or more of the sensor dongles 1750 and the monitor dongles 1730 through wireless charging. For example, the charging pad can be configured to implement electromagnetic fields to induce electrical current in the target device(s) 1730, 1750 from which charging power can be derived (also known as inductive charging). In certain wireless charging embodiments, one or more of the sensor dongles 1750 and monitor dongles 1730 can include induction coils to receive the wirelessly-transferred power induced by the induction coil 1706(B) of the charging/sterilization system 1702.

In some embodiments, the charging pad 1706 includes an electrical connector 1706(A) or 1706(C), such as a port, plug, socket, jack, or the like, configured to be electrically and/or physically connected to corresponding connector(s) of one or more of the sensor dongles 1750 and monitor dongles 1732 to thereby allow for the transfer of power between the system 1702 and the dongle(s) 1730, 1750 via a physical/electrical connection. For example, the electrical connector 1706(A) or 1706(C) can be configured to connect to a charging interface/connector on a dongle, or to another type of connector, such as a sensor connector, dongle connector, or monitor connector according to one or more embodiments disclosed herein. In some instances, the electrical connector 1706(A) or 1706(C) can include any serial or parallel transmission standard, ethernet, FireWire, coaxial connection, universal serial bus (USB), video graphics array (VGA), digital visual interface (DVI), high-definition multimedia interface (HDMI), and so on. Moreover, in some embodiments, the charging pad 1706 can include a heat/light element 1706(D) configured to produce heat or light to transfer power to one or more of the sensor dongles 1750 and dongles 1730. As such, the charging pad 1706 can provide power to one or more of the sensor dongles 1750 and the monitor dongles 1730 through a wireless connection and/or an electrical connection.

In the example of FIG. 17, the charging interfaces of the sensor dongle 1750 and the monitor dongles 1730 can advantageously be placed within proximity to the charging pad 1706 to facilitate power transfer/generation. However, the sensor dongles 1750 and/or monitor dongles 1730 can be positioned in a variety of manners relative to the charging pad 1706. In some embodiments, a sensor dongle and a monitor dongle can be electrically connected, such as through a dongle connector (e.g., using a cable or stub connection), and one of the dongles can be placed on the charging pad 1706 to transfer power to both the sensor dongle and the monitor dongle. That is, in some implementations, one of the dongles can receive power in an indirect manner through the other dongle, which is powered using the charging pad 1706. In some embodiments, the charging/sterilization system 1702 can include an indicator on an exterior portion of the enclosure 1708 to inform a user of a charging status and/or sterilization status of one or more of the target sensor dongles 1750 and/or monitor dongles 1730, such as charging, charge, sterilizing, sterilized, etc. In some embodiments, the charging/sterilization system 1702 receives mains power (e.g., AC or DC power) from a mains power outlet, such as a power outlet on a wall. Alternatively or additionally, the charging/sterilization system 1702 can include a battery or other power source to charge one or more of the sensor dongle 1750 and the monitor dongles 1730.

Figure 18:
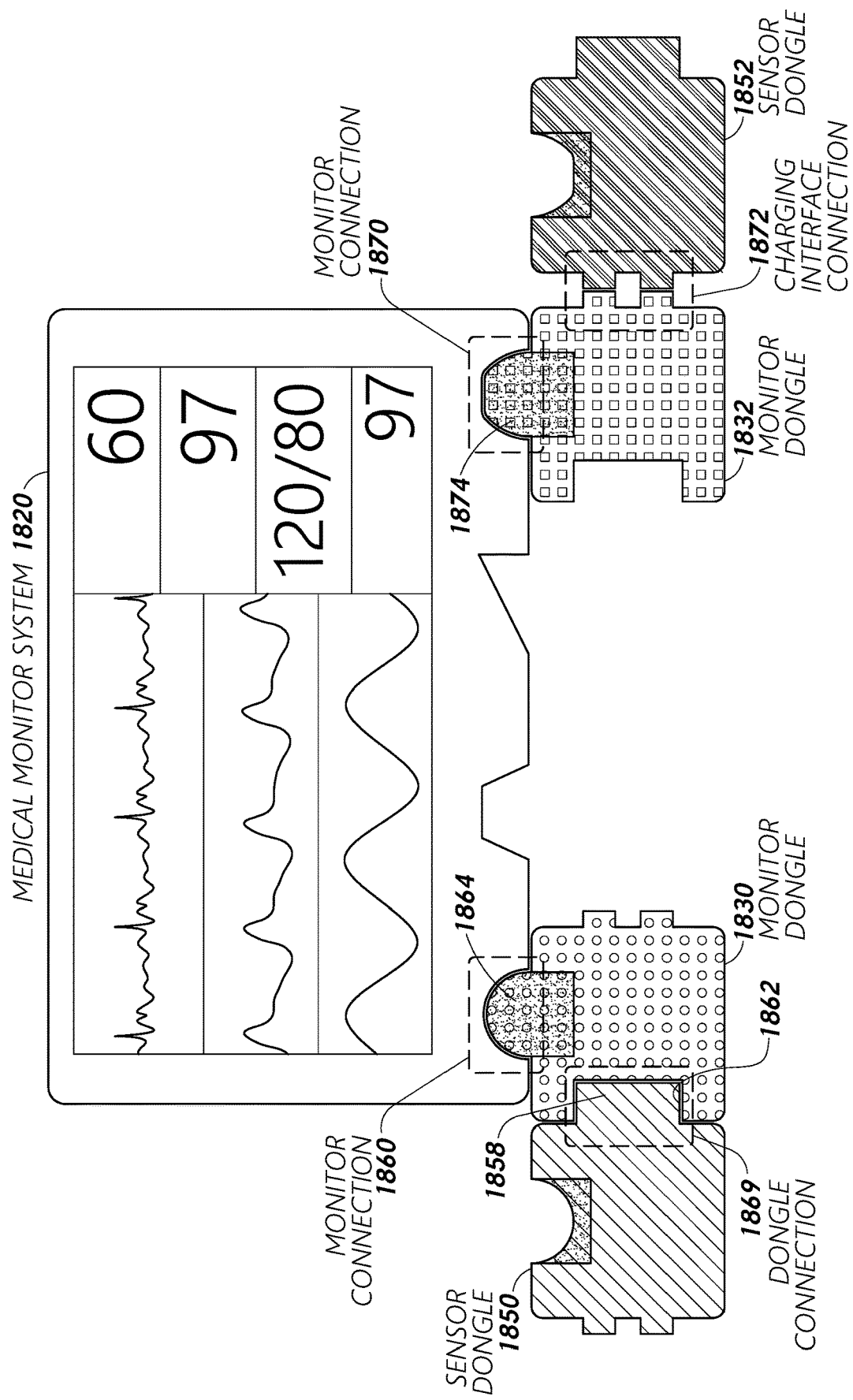
FIG. 18 illustrates example charging configurations that utilize a medical monitor system or other charging device to charge dongles in accordance with one or more embodiments.

FIG. 18 illustrates example charging configurations that use a medical monitor system 1820, or other charging device, to charge dongles in accordance with one or more embodiments of the present disclosure. In some embodiments, a sensor dongle 1850 can be charged or otherwise powered via a dongle-to-dongle connection 1869 with a monitor dongle 1830 that is connected to the medical monitor system 1820 (or other charging device/system). In particular, the sensor dongle 1850 can be electrically connected to the monitor dongle 1830 through the dongle-to-dongle connection 1869 that is facilitated by a dongle connector 1858 on the sensor dongle 1850 and a corresponding dongle connector 1862 on the monitor dongle 1830. Further, the monitor dongle 1830 can be connected to the medical monitor system 1820 (or other charging-enabled device/system) through a monitor connection 1860 that is facilitated by a monitor connector 1864 associated with the monitor dongle 1830 and a corresponding connector/port associated with the medical monitor system 1820. For example, the monitor dongle 1830 can be configured to receive power from the medical monitor system 1820 and use such power to charge or otherwise operate the monitor dongle 1830 and/or to provide power to the sensor dongle 1850. That is, the sensor dongle 1850 can be configured to receive power from the monitor dongle 1830 over the dongle-to-dongle connection 1869. The sensor dongle 1850 can use the power to charge a battery or otherwise power various devices/components of the sensor dongle 1850.

Further, in some embodiments, a sensor dongle 1852 can be charged or otherwise powered via a charging interface connection 1872 with a monitor dongle 1832 that is connected to the medical monitor system 1820 (or other charging-enabled device/system). In particular, the sensor dongle 1852 can be electrically connected to the monitor dongle 1832 through a charging interface connection 1872 that is facilitated by a charging interface on the sensor dongle 1852 and a charging interface on the monitor dongle 1832. For example, the monitor dongle 1832 can be configured to be connected to the medical monitor system 1820 through a monitor connection 1870 that is facilitated by a monitor connector 1874 of the monitor dongle 1832 and a corresponding connector/port of the medical monitor system 1820. In some embodiments, the monitor dongle 1832 is configured to receive power from the medical monitor system 1820 (or other charging-enabled device/system) and use such power to charge or otherwise operate the monitor dongle 1832 and/or to provide power to the sensor dongle 1852. That is, the sensor dongle 1852 can be configured to receive power from the monitor dongle 1832 over the dongle-to-dongle connection 1872. The sensor dongle 1852 can use the power to charge a battery or otherwise power various devices/components of the sensor dongle 1852.

Additional Connectivity Features

Figure 19:
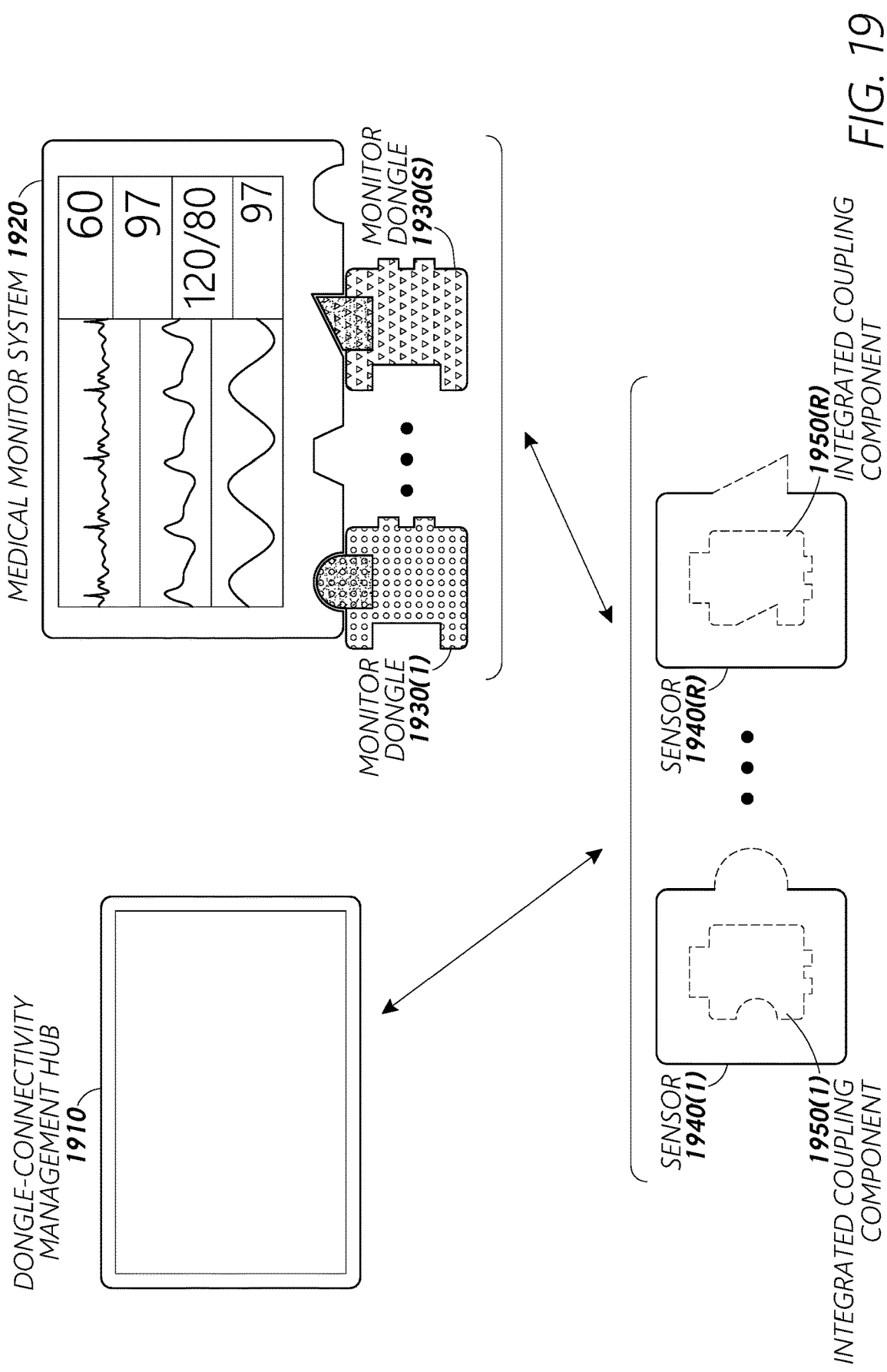
FIG. 19 illustrate example sensors configured to implement and/or facilitate wireless connectivity in accordance with one or more embodiments.

FIG. 19 illustrate example sensors 1940(1)-1940(R) that include integrated coupling components 1950(1)-1950(R) configured to implement and/or facilitate wireless connectivity in accordance with one or more embodiments of the present disclosure. In particular, one or more (e.g., each) of the sensors 1940 includes an integrated coupling component 1950 that enables the sensor 1940 to wirelessly communicate with a dongle-connectivity management hub 1910 and/or monitor dongle(s) 1930(1)-1930(S). The integrated coupling component 1950 can be embodied in any type of hardware and/or software device(s)/system(s) associated with the sensor 1940. For example, the sensor 1940 may comprise certain control circuitry configured to perform operations and/or functionality relating to wireless connectivity between the sensor 1940 and one or more other devices and/or systems (e.g., sensor and/or monitor dongle(s), dongle-connectivity management hub(s) 1910, medical monitor system(s) 1920, or the like). The integrated coupling component 1950 may further be embodied at least in part in computer-readable media in the form of executable instructions and/or other data that, when executed by control circuitry of the sensor 1940, directs the sensor 1940 to perform certain operations/functionality relating to wireless connectivity in accordance with aspects of the present disclosure. Such control circuitry may comprise one or more active and/or passive electronic devices (e.g., transistors, pastors, resistors, inductors, diodes, and or the like). Furthermore, such control circuitry may comprise one or more chips/dies and/or certain connectivity components (e.g., conductive traces, layers, vias, wires, and/or the like) configured to facilitate certain aspects of the wireless functionality implemented and/or enabled by the integrated coupling component 1950.

In some embodiments, the sensors 1940 are manufactured with the integrated coupling components 1950 included therein at one or more stages of a manufacturing process associated with the sensors 1940. The integrated coupling components 1950 can each include similar components and/or implement similar functionality as certain of the sensor dongles discussed herein, except that the integrated coupling components 1950 may not include some features of the sensor dongles, such as external physical sensor connector(s), which generally may not be required due to the integration of the integrated coupling component 1950 with and/or within the sensor 1940. In some embodiments, the integrated coupling components 1950 are configured to communicate wirelessly with the dongle-connectivity management hub 1910 to establish a wireless coupling with one or more of the monitor dongles 1930. In some embodiments, the integrated coupling components 1950 are configured to communicate directly with respective ones of the monitor dongles 1930 in a peer-to-peer pairing. That is, in some embodiments, connectivity between the sensors 1940 and respective ones of the monitor dongles 1930 may not require implementation of a dongle-connectivity management hub.

As shown, the monitor dongles 1930 can be physical and/or electrically connected to a medical monitor system 1920. As such, the sensors 1940 with the integrated coupling components 1950 can advantageously wirelessly couple to the monitor dongles 1930 in order to communicate with the medical monitor system 1920. Although the monitor dongles 1930 are illustrated in FIG. 19, in some embodiments, the monitor dongles 1930 can be eliminated/omitted and/or integrated with/within the medical monitor system 1920, such that the sensors 1940 can communicate directly with the medical monitor system 1920 over a wireless connection without the necessity of separate wireless connectivity dongle(s).

Figure 20:
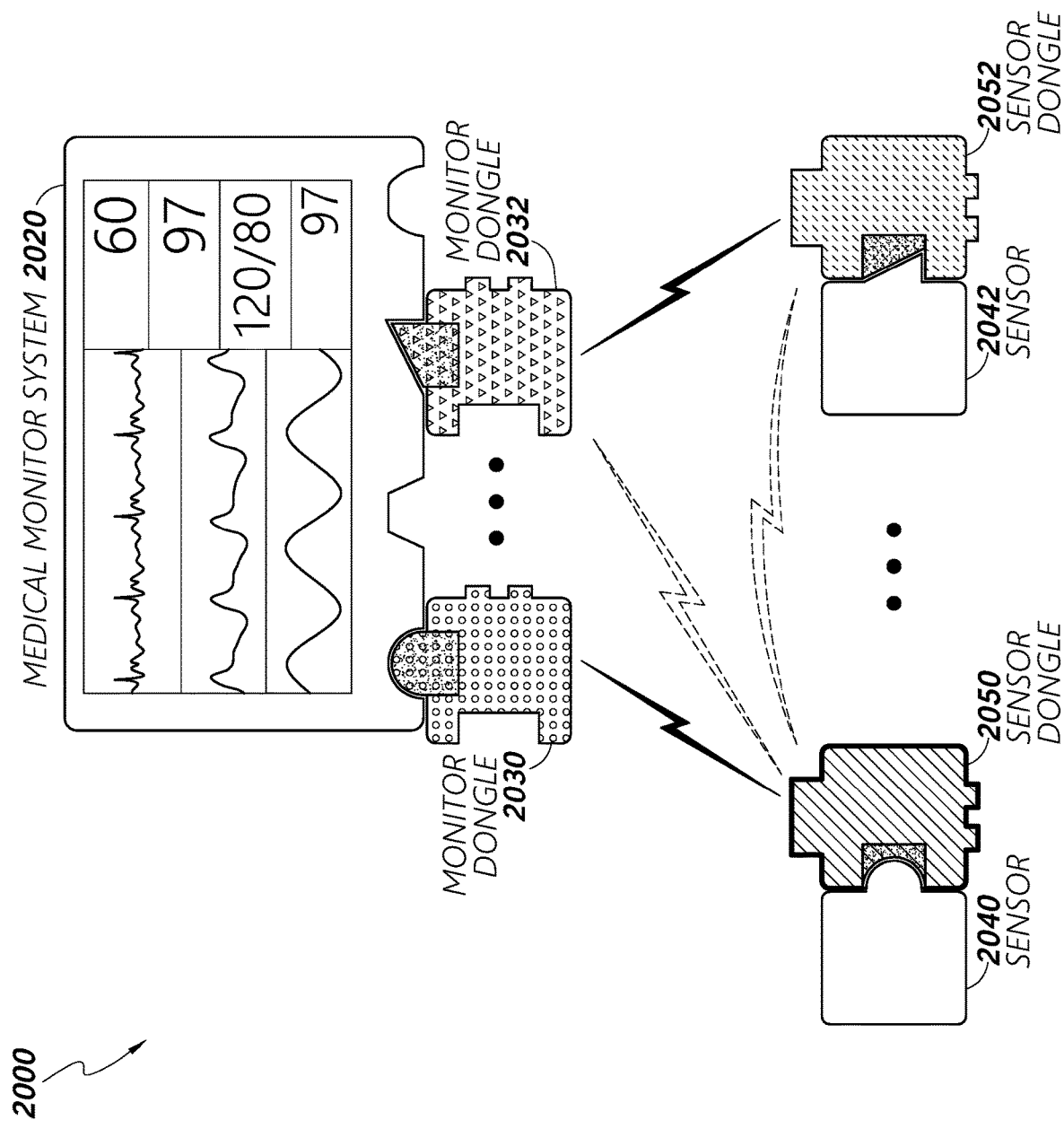
FIG. 20 illustrates a distributed wireless connectivity management system in accordance with one or more embodiments.

FIG. 20 illustrates an example distributed wireless connectivity management system 2000 in which a sensor dongle 2050 implements wireless connectivity management functionality in accordance with one or more embodiments of the present disclosure. For example, the sensor dongle 2050 can be configured to implement functionality that is generally or otherwise performed by a dongle-connectivity management hub with respect to certain other embodiments disclosed herein. For example, the sensor dongle 2050 can be configured to communicate with any number of monitor dongles and/or sensor dongles to establish wireless couplings between sensor dongles and respective ones of the monitor dongles. In the example of FIG. 20, the sensor dongle 2050 is configured to communicate with the monitor dongle 2030, the monitor dongle 2032, and/or the sensor dongle 2052. In some cases, the sensor dongle 2050 is referred to as a main or primary dongle (e.g., primary sensor dongle) and the sensor dongle 2052 is referred to as an auxiliary or secondary dongle (e.g., secondary sensor dongle). In some embodiments, the sensor dongle 2050 is configured to implement wireless connectivity management functionality in cases when a patient is being transported and/or when a dongle-connectivity management hub is not implemented or available, experiencing operational issues (e.g., not functioning properly, at least in part), and/or outside of wireless range to one or more dongles and/or a medical monitor system. Furthermore, in some embodiments, the particular device/system (e.g., management hub, dongle, etc.) that is in charge of wireless connectivity management can switch in response to occurrence of certain event(s).

As one example use case, wireless connectivity management functionality may be initially implemented at a dongle-connectivity management hub, wherein such management functionality may be transferred over to a sensor or monitor dongle when the dongle-connectivity management hub is experiencing operational issues and/or outside of wireless range to a sensor dongle (e.g., when a patient is being transported without the dongle-connectivity management hub and/or one or more sensor dongles or monitor dongles enter a transport mode).

In some embodiments of wireless connectivity management devices, processes, and/or systems, a main sensor dongle 2050 can search for dongles within wireless communication range of the main sensor dongle 2050. For example, as shown in the example of FIG. 20, the main sensor dongle 2050 can be configured to detect a monitor dongle 2030 that is electrically connected to a medical monitor system 2020. The main sensor dongle 2050 can further be configured to detect the monitor dongle 2032 electrically connected to the medical monitor system 2020, and/or the secondary sensor dongle 2052 electrically connected to a sensor 2042. The monitor dongle 2030 may be a common type of dongle with respect to the main sensor dongle 2050 (e.g., is implemented for a same type of sensor), while the monitor dongle 2032 may be a common type of dongle with respect to the secondary sensor dongle 2052. As such, the main sensor dongle 2050 can be configured to establish a wireless coupling between the monitor dongle 2030 and the main sensor dongle 2050 and establish a wireless coupling between the auxiliary sensor dongle 2052 and the monitor dongle 2032.

Upon establishing the relevant wireless couplings, the main sensor dongle 2050 can be configured to communicate data associated with sensor readings of a sensor 2040 to the medical monitor system 2020 over the wireless coupling with the monitor dongle 2030, whereas the secondary sensor dongle 2052 can communicate data associated with sensor readings of a sensor 2042 to the medical monitor system 2020 over the wireless coupling with monitor dongle 2032. For example, the main sensor dongle 2050 can be configured to send sensor data from the sensor 2040 (or other data based at least in part on sensor data generated by the sensor 2040) to the monitor dongle 2030 for display and/or storage at/by the medical monitor system 2020. Similarly, the secondary sensor dongle 2052 can be configured to send sensor data from the sensor 2042 (or other data based at least in part on sensor data generated by the sensor 2042) to the monitor dongle 2032 for display and/or storage at/by the medical monitor system 2020. In FIG. 20, the solid communication lines can be interpreted to represent established wireless couplings between sensor dongles and/or monitor dongles, while the dashed communication lines can be interpreted to represent wireless connections used by the main sensor dongle 2050 to establish the wireless couplings between sensor dongles and/or monitor dongles (e.g., wireless connections used for different types of dongles in some examples).

Further, in some embodiments of wireless connectivity management devices, processes, and/or systems, a main sensor dongle 2050 can reestablish, and/or otherwise resolve issues with, wireless couplings between dongles. For example, if a wireless coupling between the monitor dongle 2032 and the sensor dongle 2052 is disrupted or disconnected, the main sensor dongle 2050 can be configured to communicate with the monitor dongle 2032 and/or the sensor dongle 2052 to determine a cause of the disruption or disconnection and/or reestablish a wireless coupling between the monitor dongle 2032 and the sensor dongle 2052. Moreover, the main sensor dongle 2050 can perform other operations/functionality to manage wireless connectivity of one or more devices within the system 2000.

For ease of illustration, FIG. 20 is discussed in the context of a main sensor dongle 2050 that is configured to manage wireless coupling(s) between another sensor dongle and a monitor dongle. However, the main sensor dongle 2050 can be configured to communicate with any number of sensor dongles and/or monitor dongles to manage any number of wireless couplings between dongles (e.g., establish wireless couplings for any number of sensor dongles and respective monitor dongles). Furthermore, although the example of FIG. 20 is discussed with respect to a sensor dongle implementing wireless connectivity management functionality, a monitor dongle can similarly (e.g., alternatively) implement such functionality. For example, the monitor dongle 2030 can act as a main dongle to perform wireless connectivity management functionality according to aspects of the present disclosure.

Figure 21:
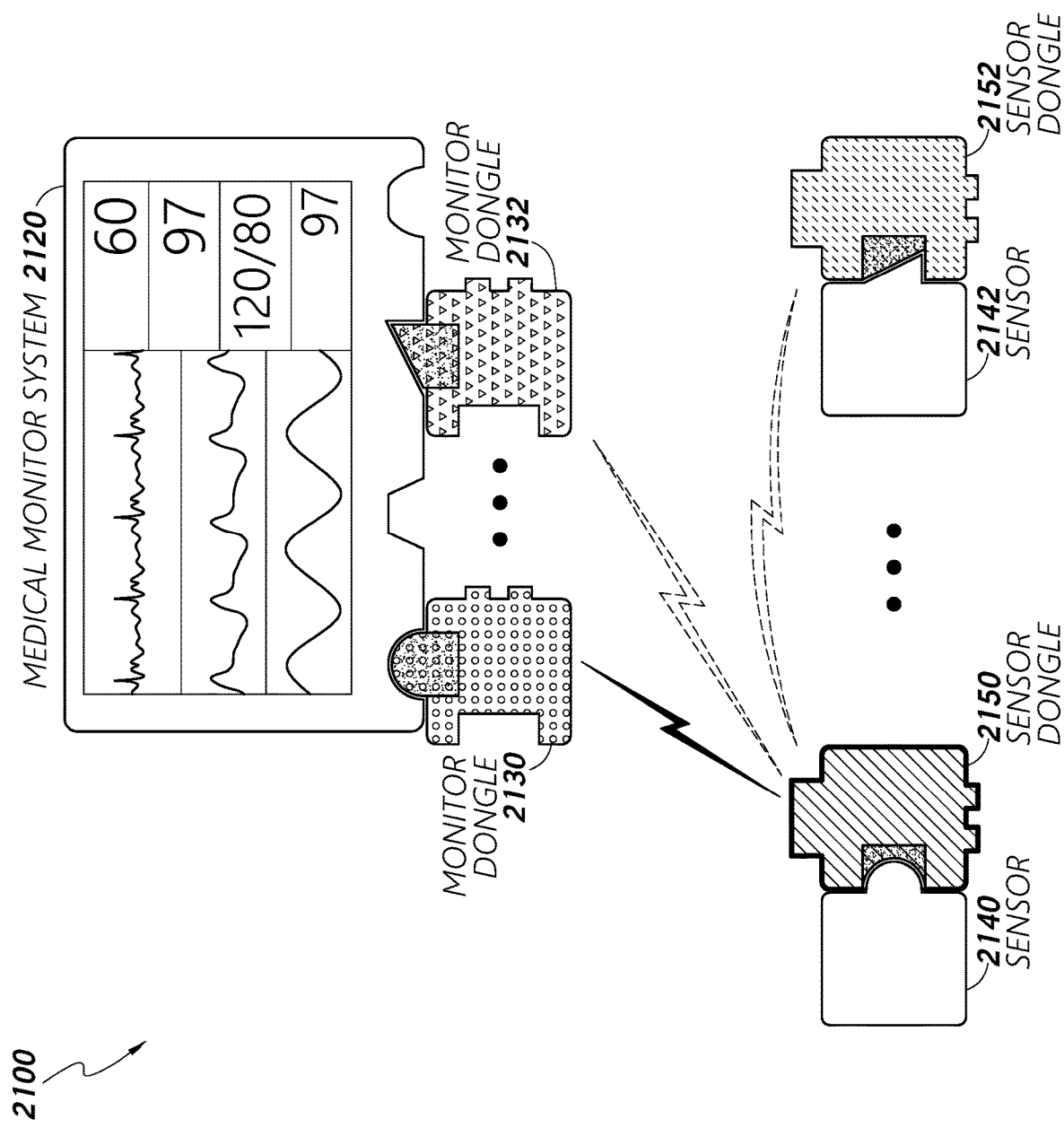
FIG. 21 illustrates a wireless connectivity relay management system in accordance with one or more embodiments.

FIG. 21 illustrates an example relay system 2100 in which a sensor dongle 2150 acts as a relay for another sensor dongle 2152 in accordance with one or more embodiments of the present disclosure. In some cases, the sensor dongle 2150 is referred to as a main or primary dongle and the sensor dongle 2152 is referred to as an auxiliary or secondary dongle. As shown, the primary sensor dongle 2150 is electrically coupled to a sensor 2140, whereas the secondary sensor dongle 2152 is electrically coupled to a sensor 2142, and the monitor dongles 2130 and 2132 are electrically coupled to a medical monitor system 2120. The monitor dongle 2130 may be a common type of dongle with respect to the primary sensor dongle 2150 (e.g., is implemented for a same type of sensor), while the monitor dongle 2132 may be a common type of dongle with respect to the secondary sensor dongle 2152. In some embodiments, the sensor dongle 2150 acts as a relay for the sensor dongle 2152 when the sensor dongle 2152 and/or the monitor dongle 2132 are experiencing communication issues (e.g., unable to establish a wireless coupling for communication, out of wireless range of each other, experiencing interference, etc.), when the sensor dongle 2150 is associated with better wireless connectivity to the monitor dongle 2132 than the sensor dongle 2152 (e.g., when a signal strength between the sensor dongle 2150 and the monitor dongle 2132 is greater than a signal strength between the sensor dongle 2152 and the monitor dongle 2132), and so on. Although FIG. 21 is illustrated with the primary/main sensor dongle 2150 relaying data for a single sensor dongle and monitor dongle, the main sensor dongle 2150 can relay data for any number of sensor dongles and/or respective monitor dongles.

In some embodiments of relaying data in connection with FIG. 21, the main sensor dongle 2150 can be configured to use a wireless coupling between the sensor dongle 2152 and the sensor dongle 2150, as well as a wireless coupling between the sensor dongle 2150 and the monitor dongle 2132. For example, sensor data generated by the sensor 2142 can be received at the sensor dongle 2152, wherein the data (or other data based at least in part thereon) can be relayed from the sensor dongle 2152 to the sensor dongle 2150 via a wireless coupling between the sensor dongle 2152 and the sensor dongle 2150, and then relayed from the sensor dongle 2150 to the monitor dongle 2132 via a wireless coupling between the sensor dongle 2150 and the monitor dongle 2132. As such, the main sensor dongle 2150 can act as an intermediary device to relay data for the sensor dongle 2152, which may not have a direct wireless coupling with the monitor dongle 2132. Furthermore, in some embodiments, the main sensor dongle 2150 can also communicate with the monitor dongle 2130 on behalf of the sensor 2140. In FIG. 21, the solid communication line can be interpreted to represent a wireless coupling between dongles of a common type (e.g., a primary wireless coupling), while the dashed communication lines can be interpreted to represent wireless couplings that are used to relay data (e.g., secondary wireless couplings).

Figure 22:
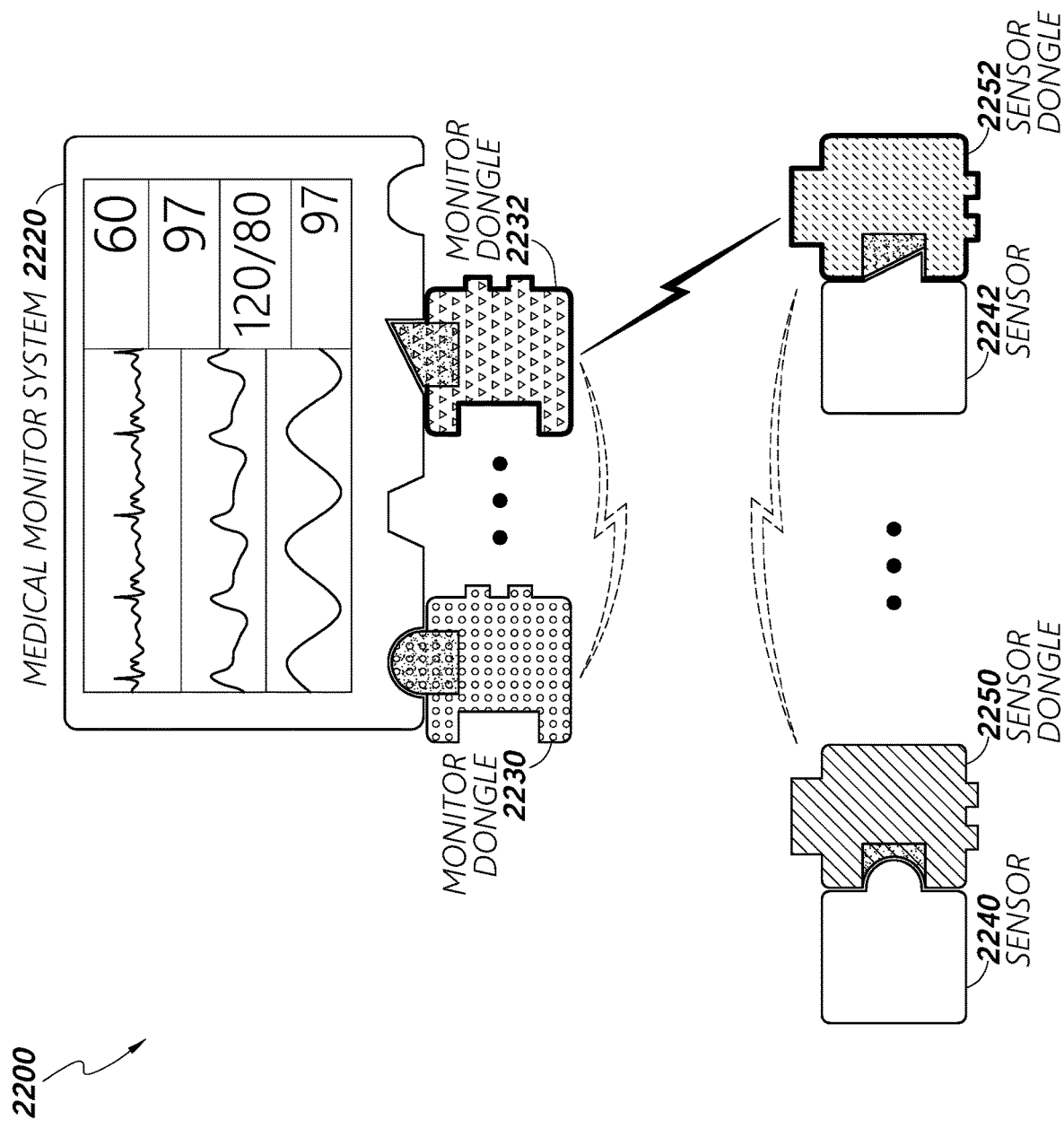
FIG. 22 illustrates a wireless connectivity relay management system in accordance with one or more embodiments.

FIG. 22 illustrates an example relay system 2200 in which a sensor dongle 2252 acts as a relay for another sensor dongle 2250 and/or a monitor dongle 2232 acts as a relay for another monitor dongle 2230 in accordance with one or more embodiments. In some cases, the sensor dongle 2252 and the monitor dongle 2232 are each referred to as a main or primary dongle, and the sensor dongle 2250 and the monitor dongle 2230 are each referred to as an auxiliary or secondary dongle. As shown, the auxiliary sensor dongle 2250 can be electrically coupled to the sensor 2240. In addition, the main sensor dongle 2252 can be electrically coupled to a sensor 2242 and monitor dongles 2230 and 2232 can be electrically coupled to a medical monitor system 2220.

The auxiliary monitor dongle 2230 can be the same type of dongle as the auxiliary sensor dongle 2250 (e.g., is implemented for a same type of sensor), whereas the main monitor dongle 2232 can be the same type of dongle as the main sensor dongle 2252. In some embodiments, the sensor dongle 2152 acts as a relay and/or the monitor dongle 2232 acts as a relay when the sensor dongle 2250 and/or the monitor dongle 2230 are experiencing communication issues (e.g., unable to establish a wireless coupling for communication, out of wireless range of each other, experiencing interference, etc.), when the sensor dongle 2252 is associated with better wireless connectivity to the monitor dongle 2232 than the sensor dongle 2250 is to the monitor dongle 2230 (e.g., when a signal strength between the sensor dongle 2252 and the monitor dongle 2232 is greater than a signal strength between the sensor dongle 2250 and the monitor dongle 2230), and so on. Although FIG. 22 is illustrated with the main sensor dongle 2252 relaying data for a single sensor dongle and the main monitor dongle 2232 relaying data for a single monitor dongle, the main sensor dongle 2252 can relay data for any number of sensor dongles and/or the main monitor dongle 2232 can relay data for any number of monitor dongles.

In some embodiments of relaying data in the context of FIG. 22, the main sensor dongle 2252 uses a wireless coupling with the secondary sensor dongle 2250 and a wireless coupling with the main monitor dongle 2232, and the main monitor dongle 2232 uses a wireless coupling with the secondary monitor dongle 2230. For example, sensor data generated by the sensor 2240 can be received at the secondary sensor dongle 2250, relayed from the secondary sensor dongle 2250 to the main sensor dongle 2252 via a wireless coupling between the secondary sensor dongle 2250 and the main sensor dongle 2252, relayed from the main sensor dongle 2252 to the main monitor dongle 2232 via a wireless coupling between the main sensor dongle 2252 and the main monitor dongle 2232, and then relayed from the main monitor dongle 2232 to the secondary monitor dongle 2230 via a wireless coupling between the main monitor dongle 2232 and the secondary monitor dongle 2230. Further, the main sensor dongle 2252 can also communicate with the main monitor dongle 2232 on behalf of the sensor 2242. In FIG. 22, the solid communication line can be interpreted to represent a wireless coupling between dongles of the same type (e.g., a primary wireless coupling) that is used for communication between dongles of the same type, for example, and used to relay data, while dashed communication lines can be interpreted to represent wireless couplings that are used to relay data (e.g., secondary wireless couplings).

Establishing Wireless Dongle Couplings/Associations

Figure 23:
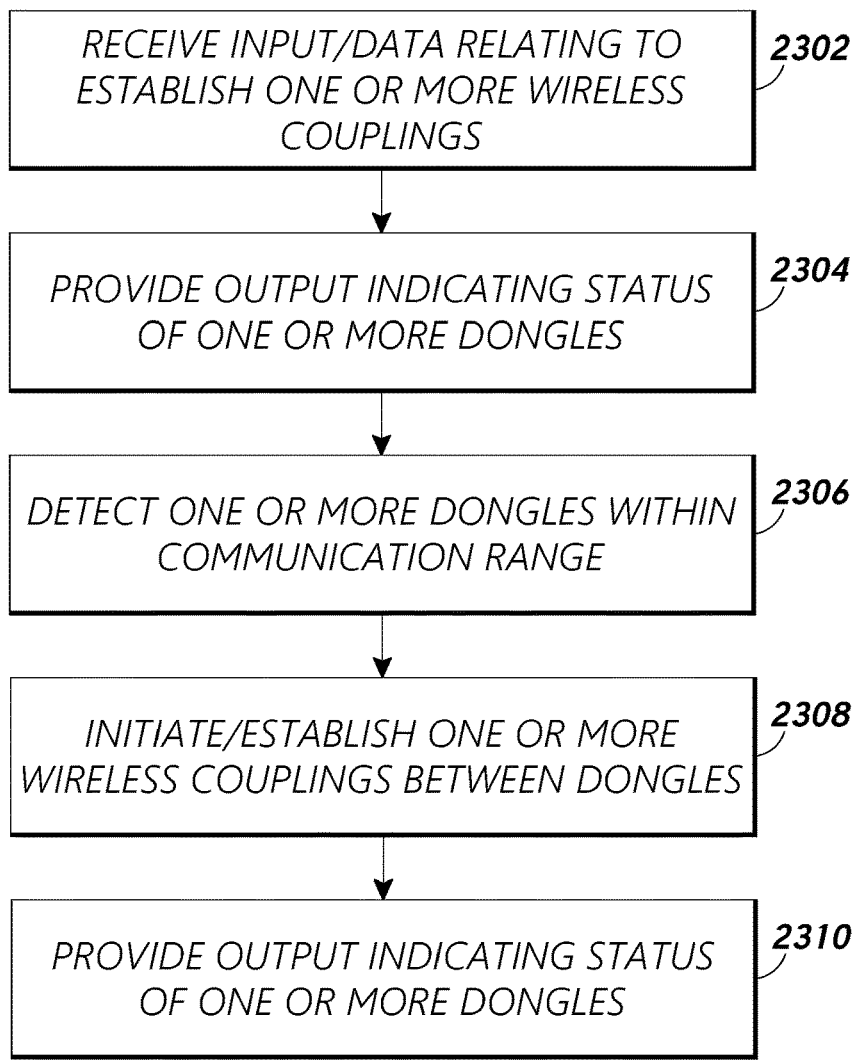
FIG. 23 is a flow diagram illustrating a process for establishing one or more wireless couplings between dongles in accordance with one or more embodiments.

FIG. 23 illustrates an example flow diagram of a process 2300 for establishing one or more wireless couplings between dongles in accordance with one or more embodiments. The various operations associated with the process 2300 can be performed by any of the devices discussed herein, or a combination thereof, such as a dongle-connectivity management hub, one or more sensor dongles, one or more monitor dongles, and/or one or more medical monitor systems.

At block 2302, the process 2300 can involve receiving input/data relating to one or more wireless couplings. For example, such input can indicate or direct the initiation/ establishment of such wireless coupling(s). According to certain use cases, a dongle-connectivity management hub can receive user input via one or more user I/O components on the dongle-connectivity management hub (e.g., a user interface on a display), wherein the user input indicates a request that one or more wireless couplings be established between one or more dongles and/or medical monitor systems. Additionally or alternatively, a sensor dongle and/or a monitor dongle can receive user input via one or more user I/O components on the sensor dongle and/or the monitor dongle (e.g., a connect button), wherein the user input requests that one or more wireless couplings be established between one or more sensor dongles and one or more monitor dongles.

At block 2304, the process 2300 can involve providing output of any suitable or desirable type/form that indicates a status of one or more dongles. For example, according to certain use cases, a sensor dongle and/or a monitor dongle can output light, audio, or other indicator via one or more user I/O components to provide an indication of a status of the sensor dongle and/or the monitor dongle. The status can indicate that the sensor dongle and/or the monitor dongle are in a connecting/pairing mode in which the sensor dongle and/or the monitor dongle attempt to connect to another device and/or be detected (e.g., initiate a handshake process). Additionally or alternatively, a dongle-connectivity management hub can provide output via one or more user I/O components (e.g., an icon or other visual representation on a display) to indicate a status (e.g., wireless connectivity/ coupling status) of a sensor dongle and/or a monitor dongle. In some embodiments, output can be provided in response to and/or based at least in part on the input received in connection with the operation(s) associated with block 2302.

At block 2306, the process 2300 can involve detecting one or more dongles within a relevant communication range associated with one or more dongles and/or a dongle-connectivity management hub. For example, in accordance with certain use cases, a dongle-connectivity management hub can be configured detect one or more dongles within communication range of the dongle-connectivity management hub and/or each other. The dongle-connectivity management hub can be configured to communicate with one or more sensor dongles and/or monitor dongles to determine that the one or more sensor dongles and/or monitor dongles are within communication range of the dongle-connectivity management hub and/or each other. In some embodiments, the dongle-connectivity management hub can be configured to analyze data associated with certain wireless connectivity functionality, such as a signal strength and/or other parameter(s) associated with a communication. In some implementations, the dongle-connectivity management hub can be configured to determine a location and/or proximity of one or more sensor dongles and/or monitor dongles. Further, in some embodiments, a dongle can be configured to communicate with another dongle and/or the dongle-connectivity management hub to determine that/whether the other dongle and/or the dongle connectivity management hub is within communication range of the/a dongle of interest. In some embodiments, detection of one or more dongles can be performed based at least in part on the input received in connection with the operation(s) associated with block 2302.

At block 2308, the process 2300 can involve initiating/establishing one or more wireless couplings between dongles. For example, in accordance with certain use cases, a dongle-connectivity management hub can be configured to cause a wireless coupling to be initiated/established between a sensor dongle and a monitor dongle that are within wireless communication range of each other. In some implementations, the dongle-connectivity management hub can be configured to send signal(s) to the sensor dongle and/or the monitor dongle directing such dongle(s) to initiate/establish a wireless coupling (e.g., pairing). Additionally or alternatively, a sensor dongle can be configured to establish a wireless coupling with a monitor dongle by communicating with the monitor dongle directly (e.g., over a peer-to-peer wireless connection).

In some embodiments, a wireless coupling can be established automatically, at least in part, between a sensor dongle and a monitor dongle based at least in part on the sensor dongle and the monitor dongle being associated with a same type of sensor and/or connector, the sensor dongle and the monitor dongle having previously established a coupling, and so on. That is, the dongle-connectivity hub, monitor dongle, and/or sensor dongle may be configured to automatically implement certain wireless connectivity functionality based on type(s) of monitor and/or sensor dongle(s). Further, in some embodiments, a wireless coupling can be established between a sensor dongle and a monitor dongle based at least in part on user input that indicates a desired wireless coupling between the sensor dongle with the monitor dongle, such as a linking of the sensor dongle to the monitor dongle via a user interface on a dongle-connectivity management hub, as described in greater detail below in connection with certain other figures and/or embodiments.

At block 2310, the process 2300 can include providing output indicating a status (e.g., wireless connectivity status, power level, signal strength, and/or other parameter(s)) of one or more dongles. For example, in accordance with certain use cases, a sensor dongle and/or a monitor dongle can be configured to output one or more light, audio, and/or other indicator(s) via one or more user I/O components to provide an indication of a status of the sensor dongle and/or the monitor dongle. The status can indicate that the sensor dongle and the monitor dongle are wirelessly coupled, that the sensor dongle and the monitor dongle failed to establish a wireless coupling, and so on. Additionally or alternatively, a dongle-connectivity management hub can be configured to provide output via one or more user I/O components (e.g., an icon or other visual representation on a display) to indicate a status of a sensor dongle and/or a monitor dongle. In some embodiments, output can be provided in response to, and/or based at least in part on, the establishment of one or more wireless couplings between dongles in connection with the operation(s) associated with block 2308.

Figure 24:
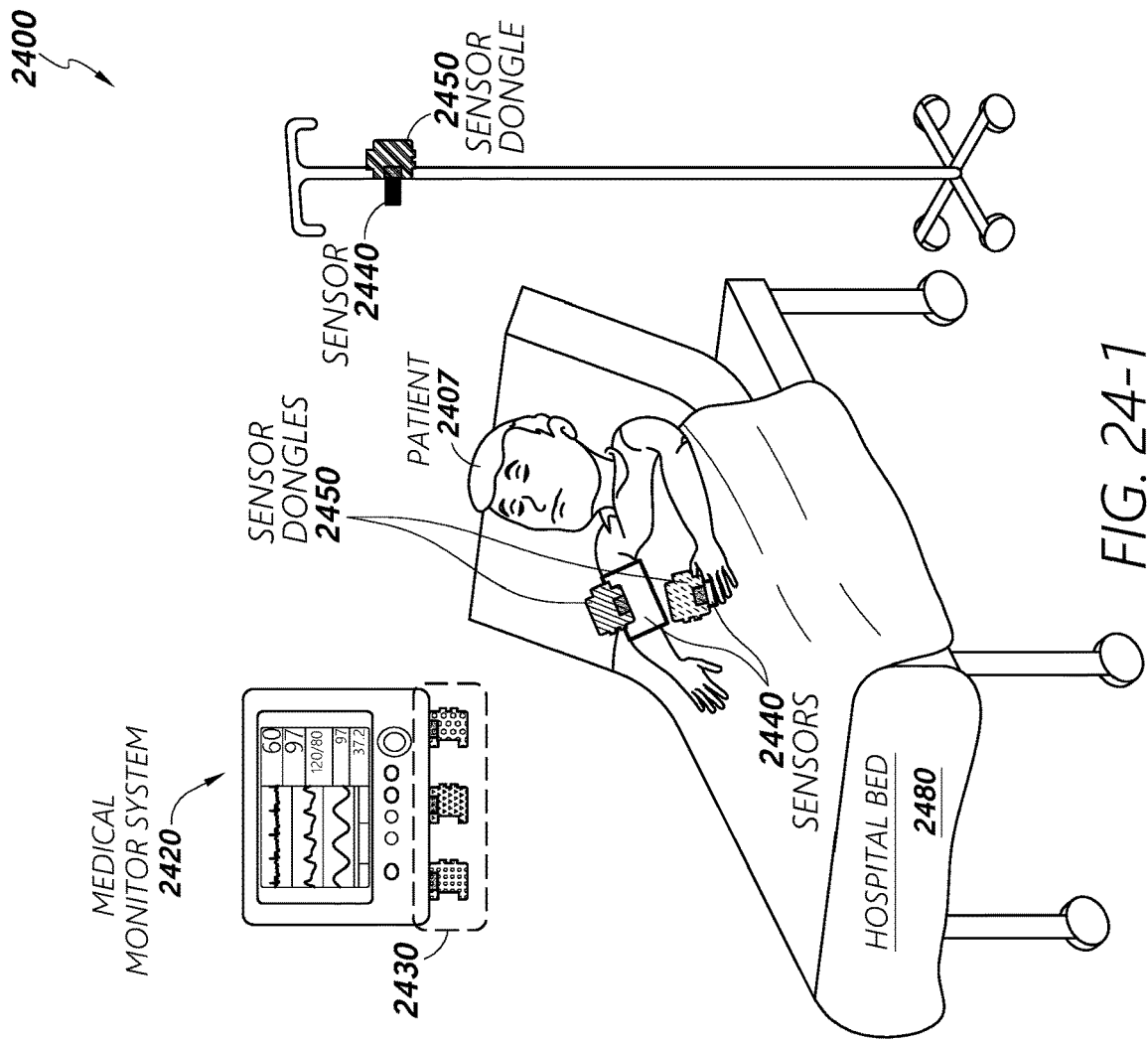
Figure 1:
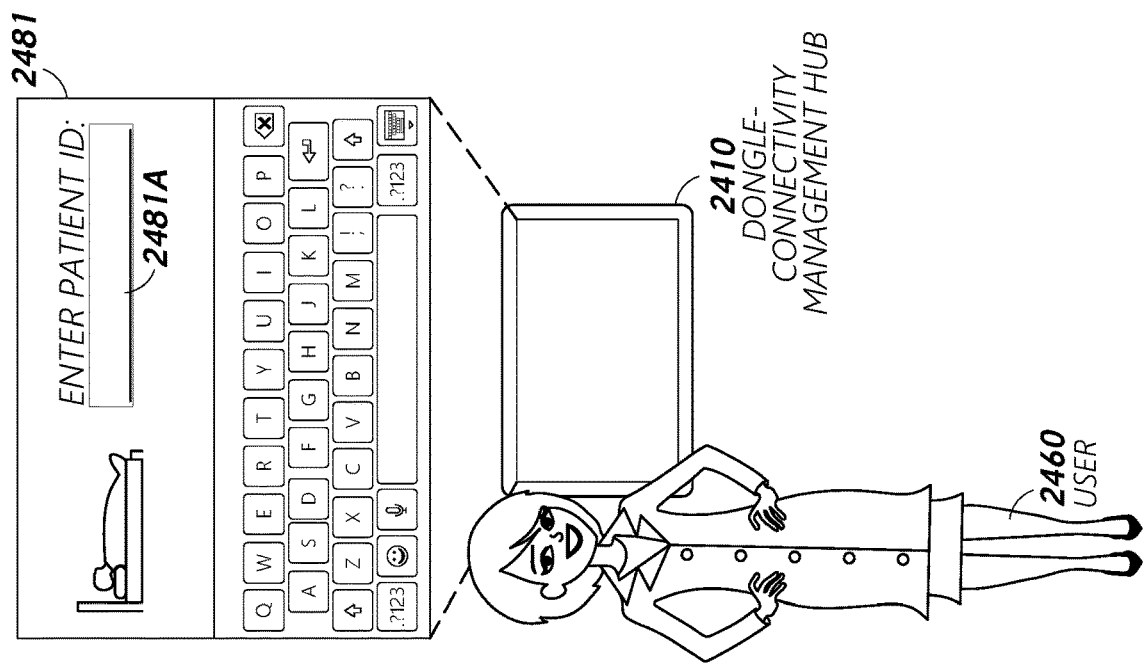
FIG. 1 illustrates an example patient care environment according to one or more embodiments.
Figure 24:
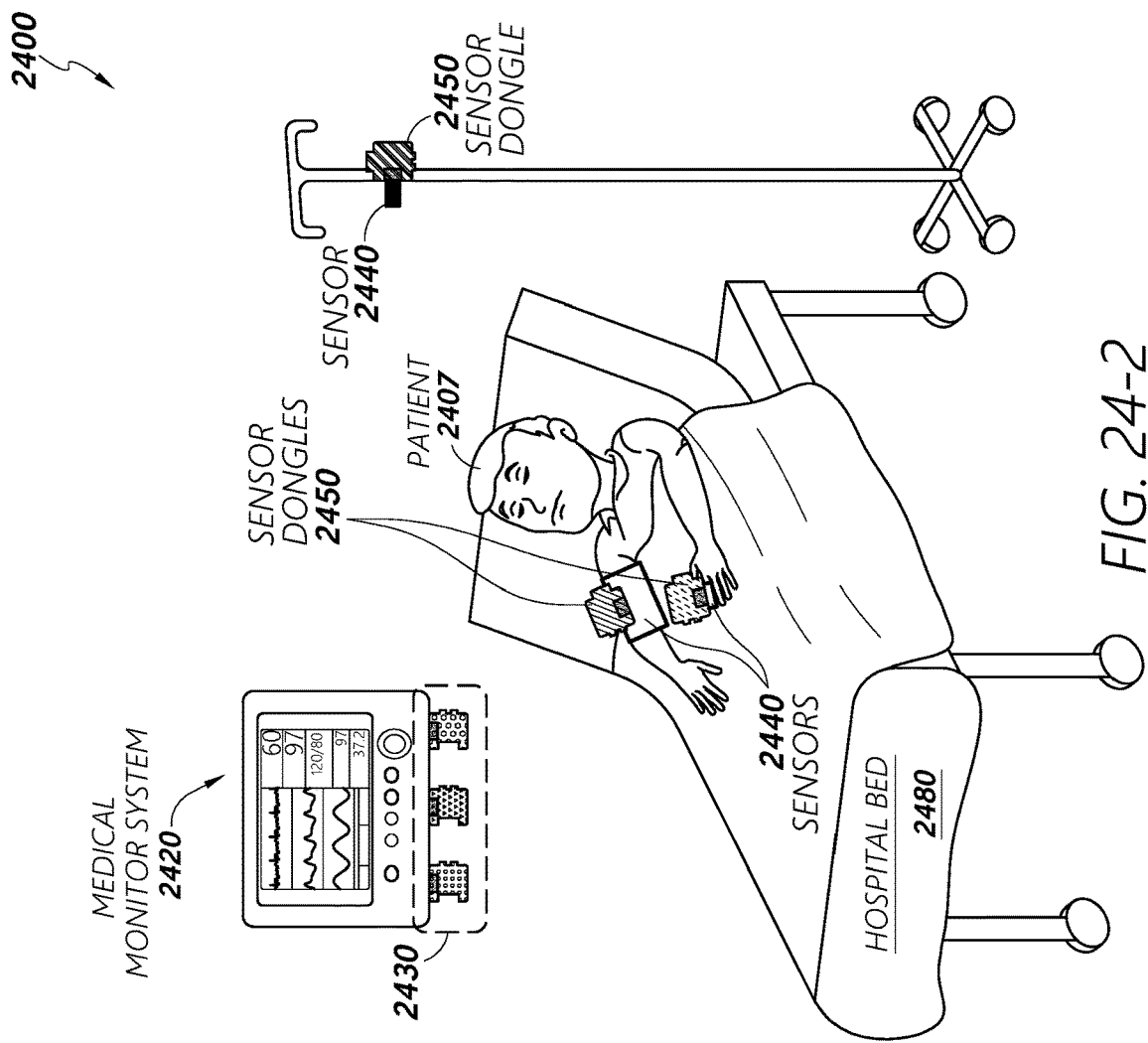
Figure 2:
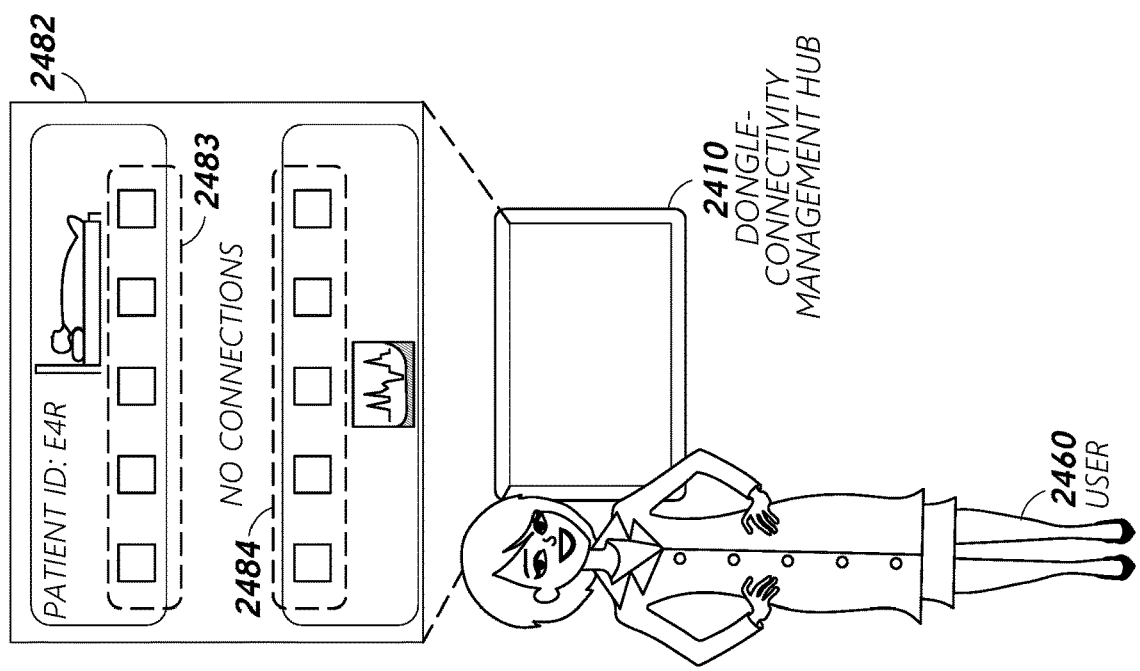
Figure 24:
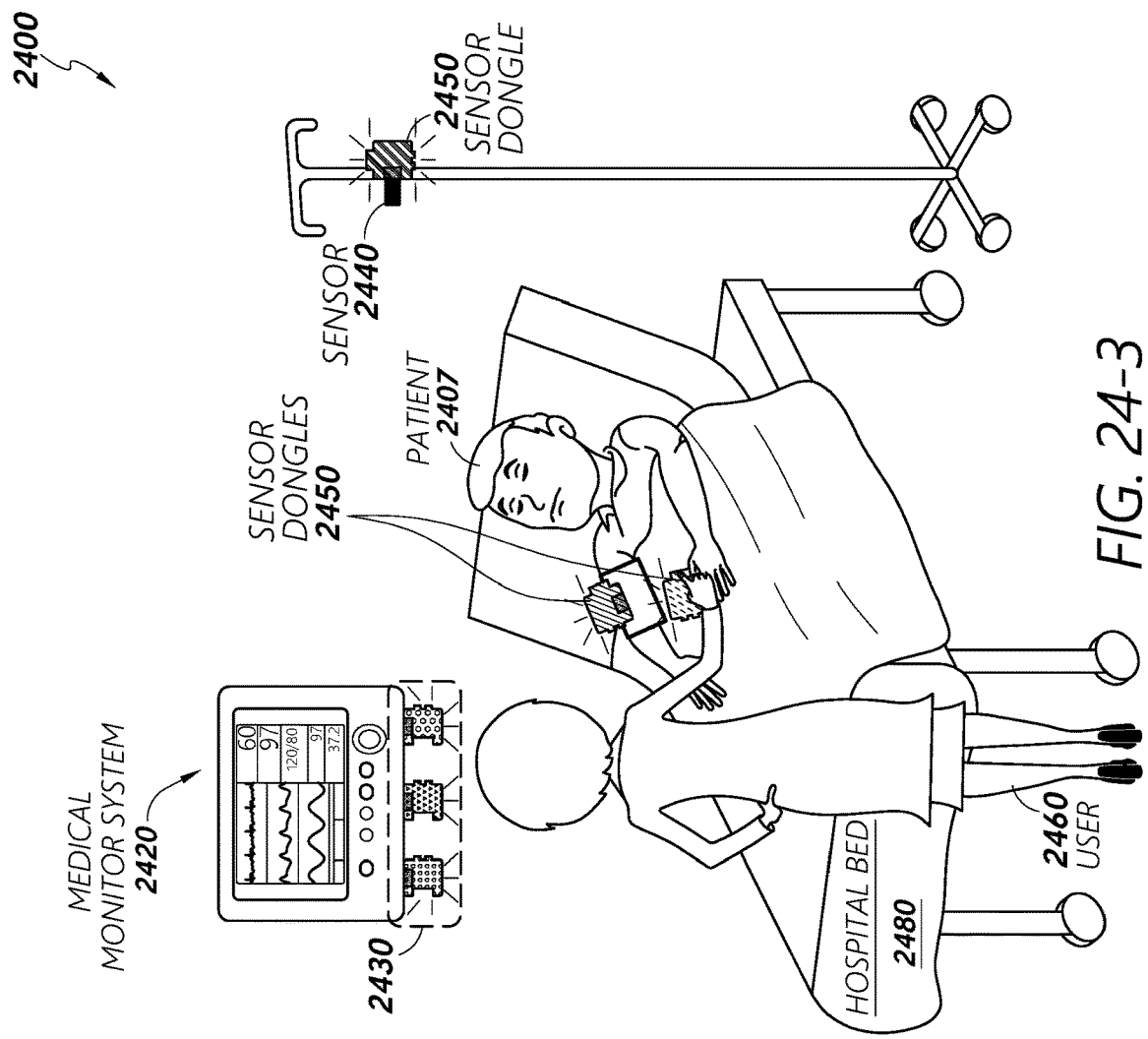
Figure 3:
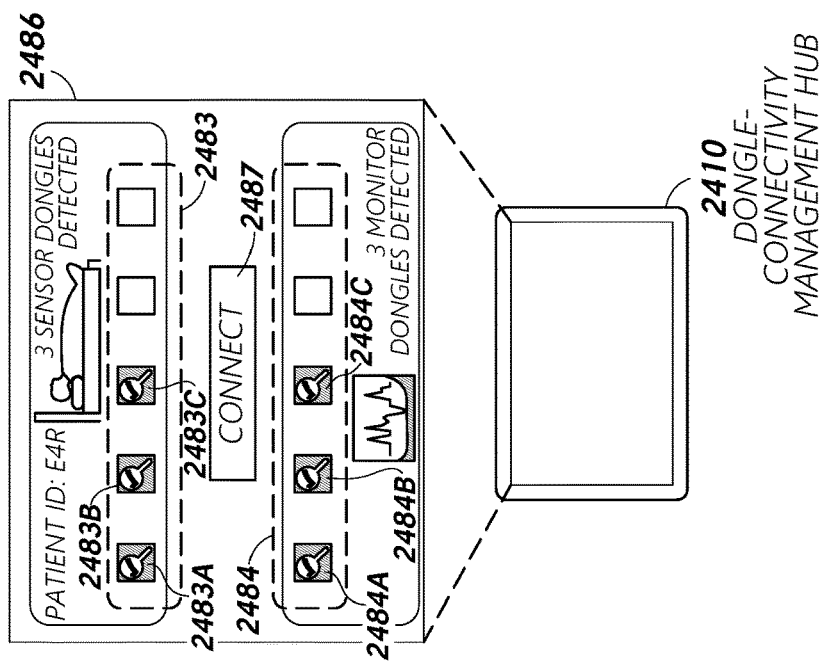
Figure 24:
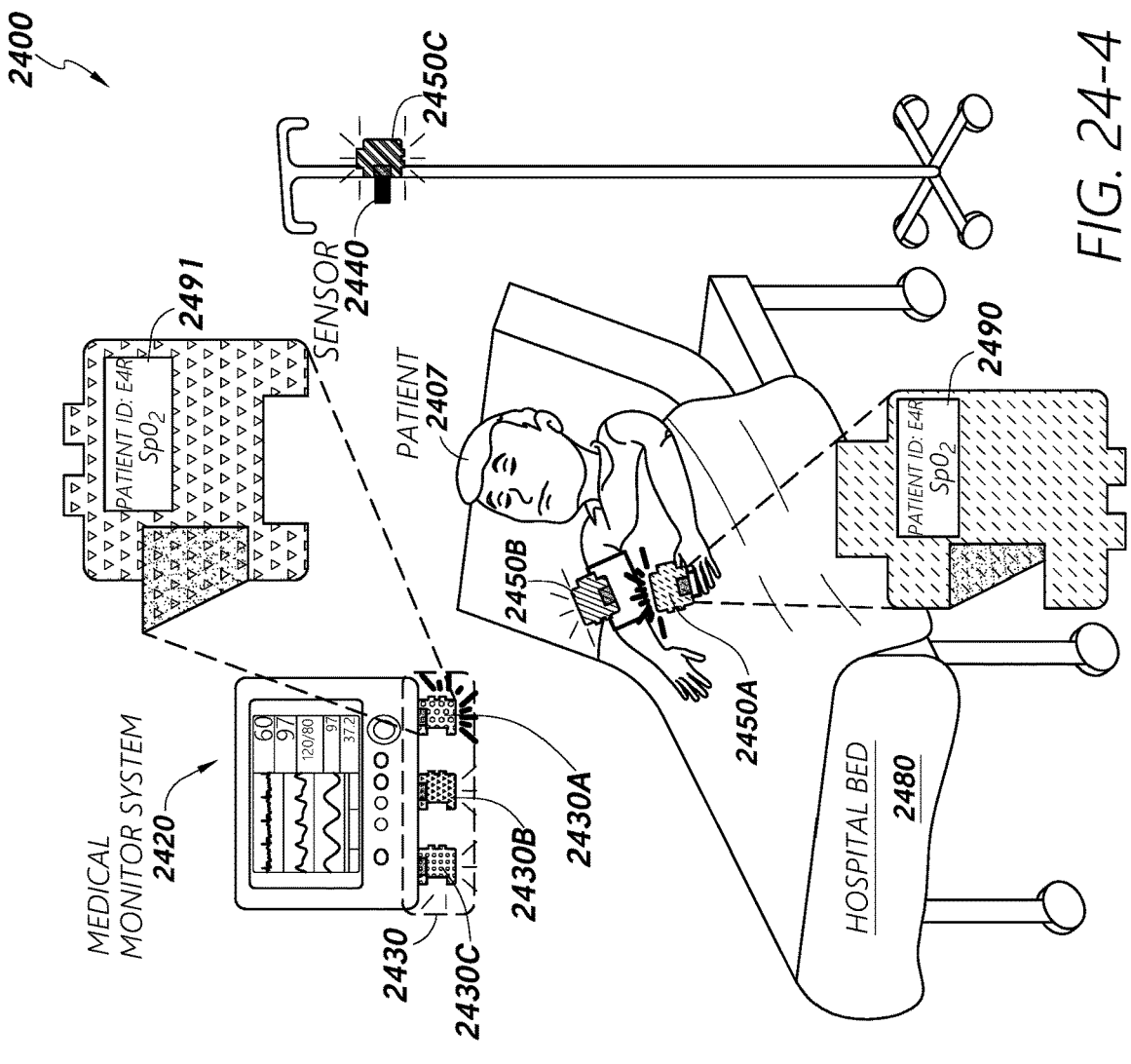
Figure 4:
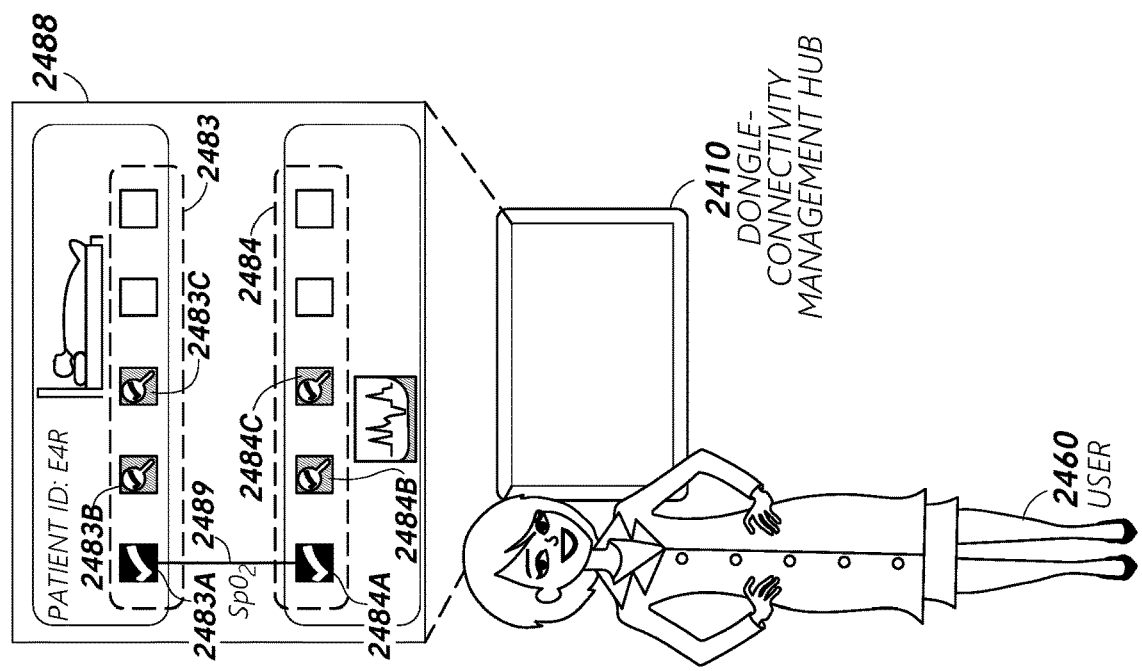
Figure 24:
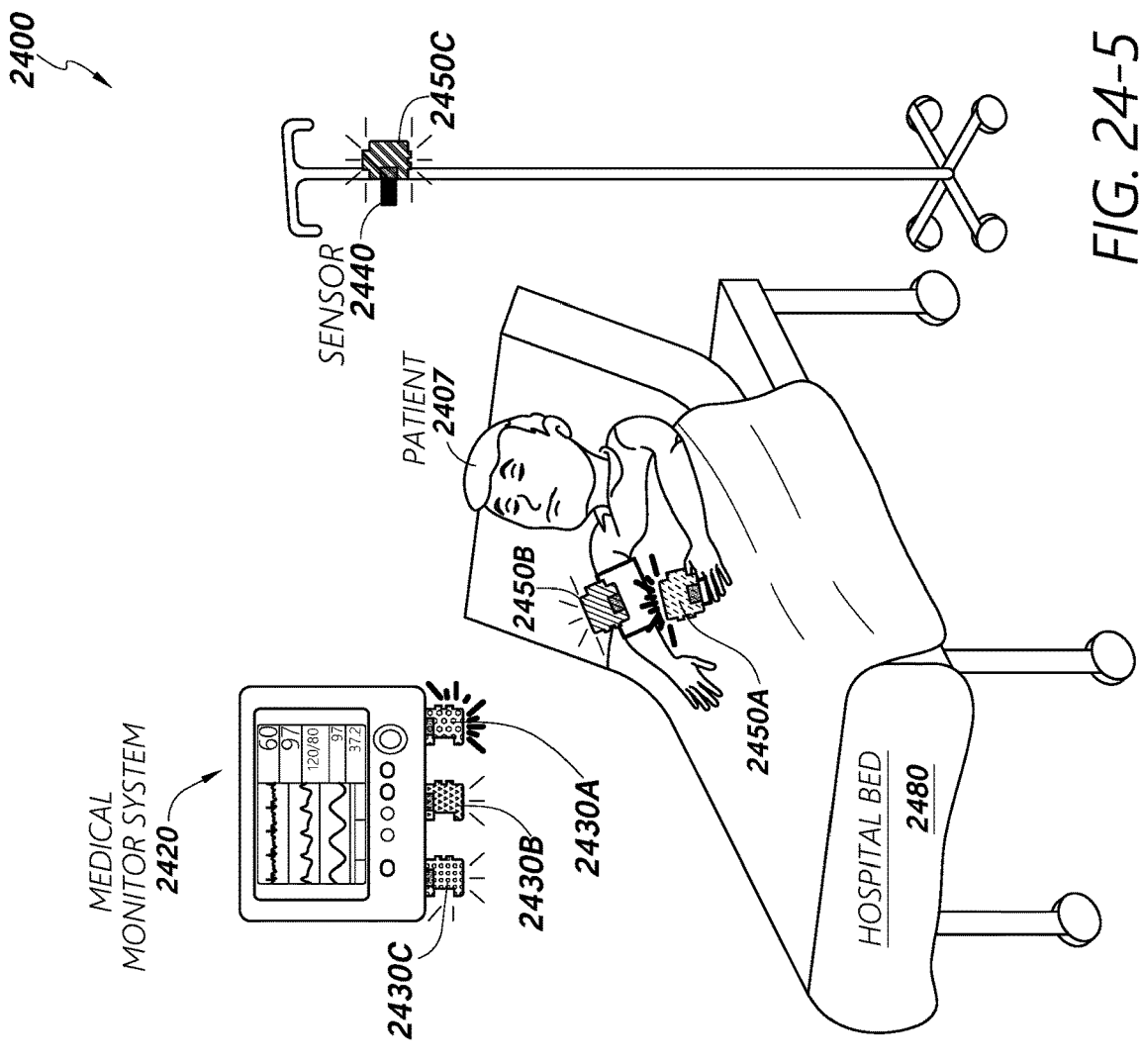
Figure 5:
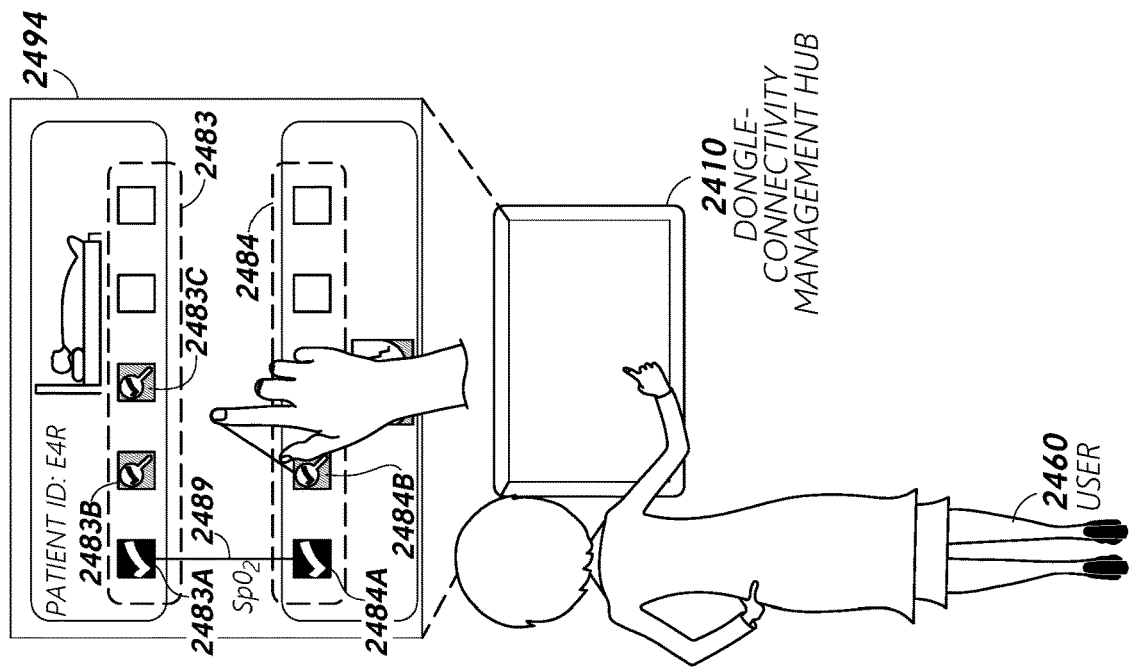
Figures 6, 24:
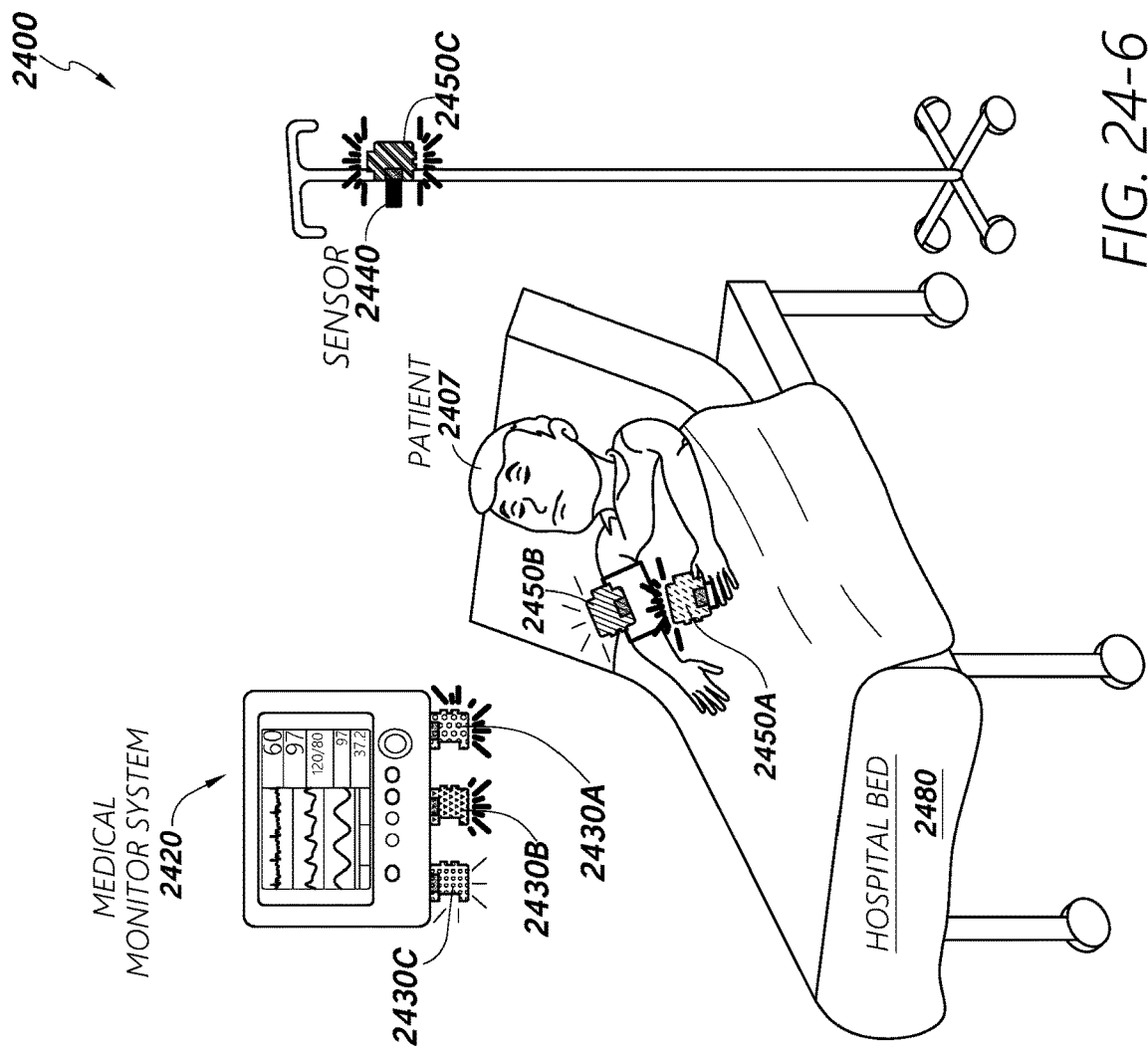
Figure 24:
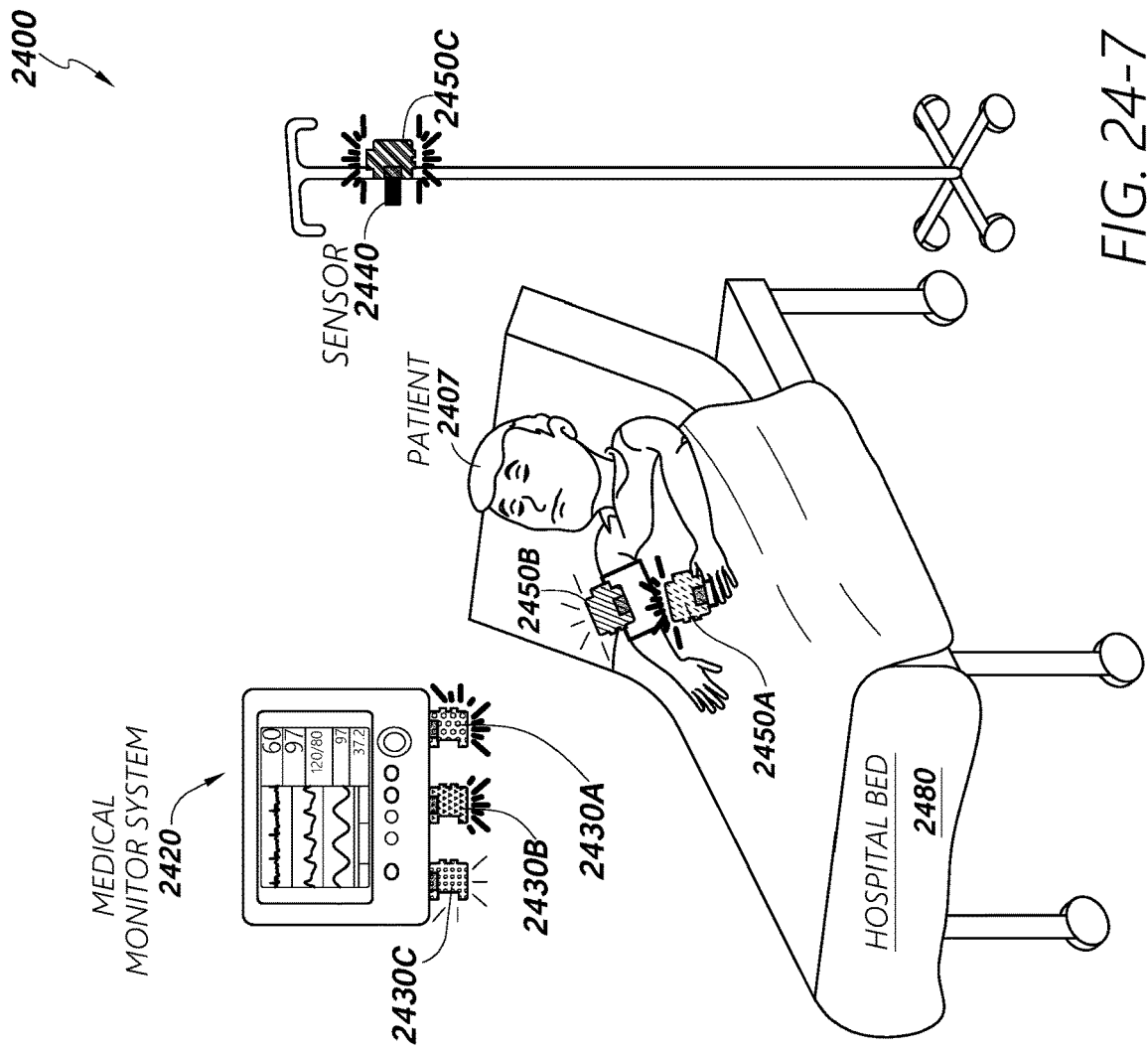
Figure 7:
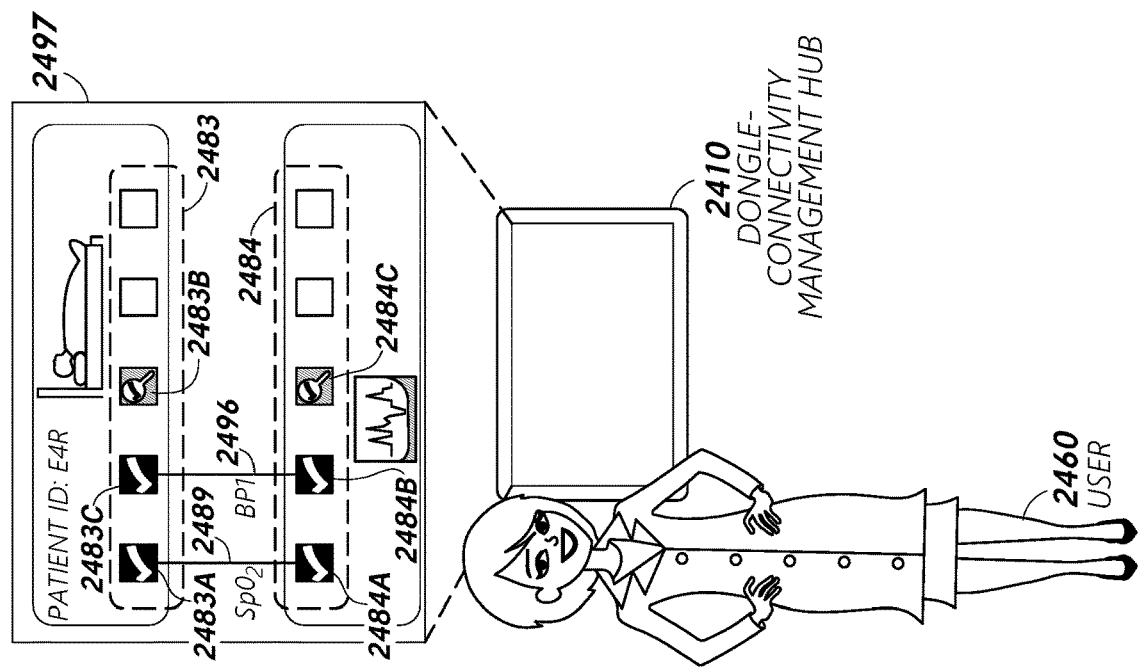
Figure 24:
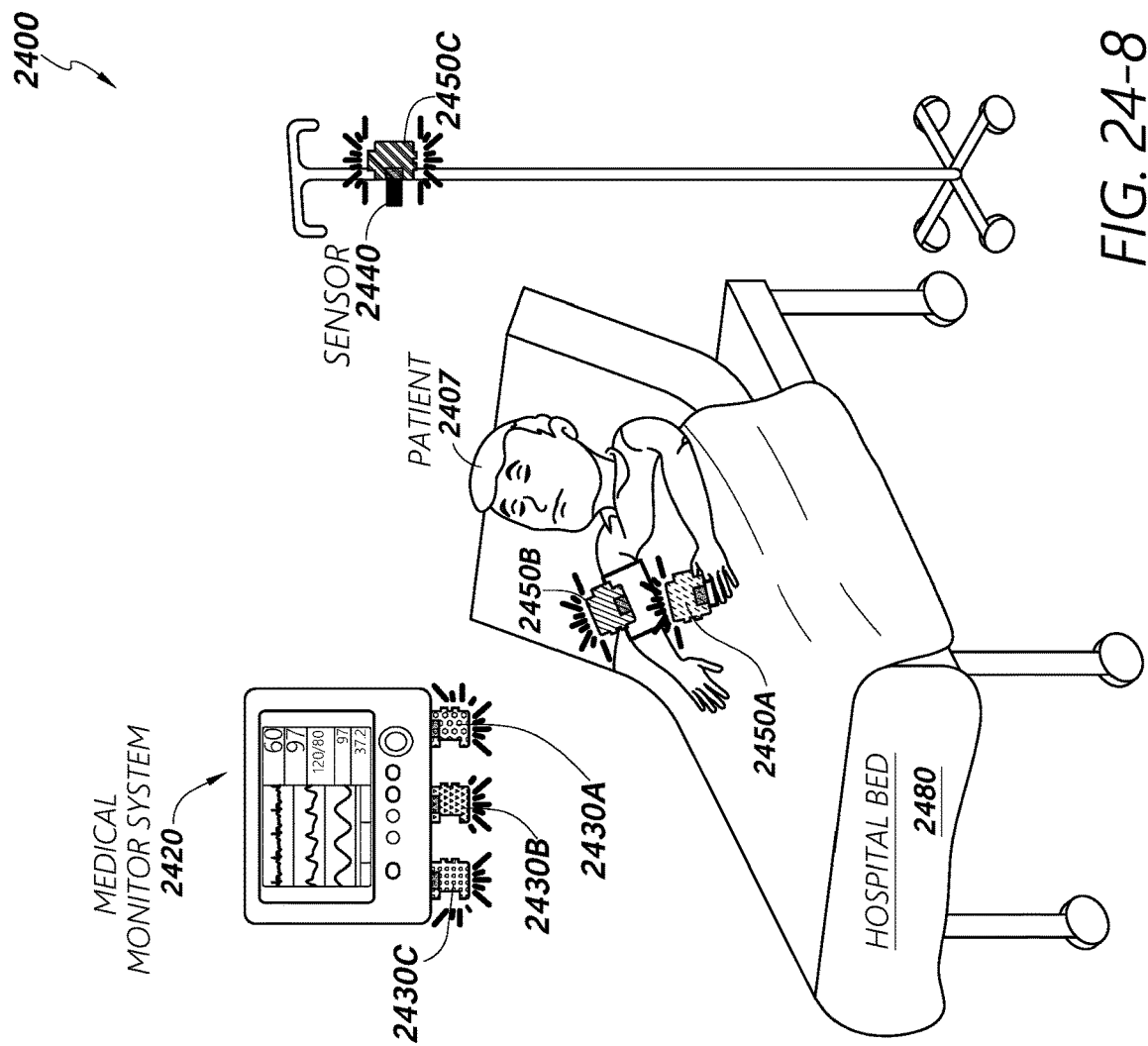
Figure 8:
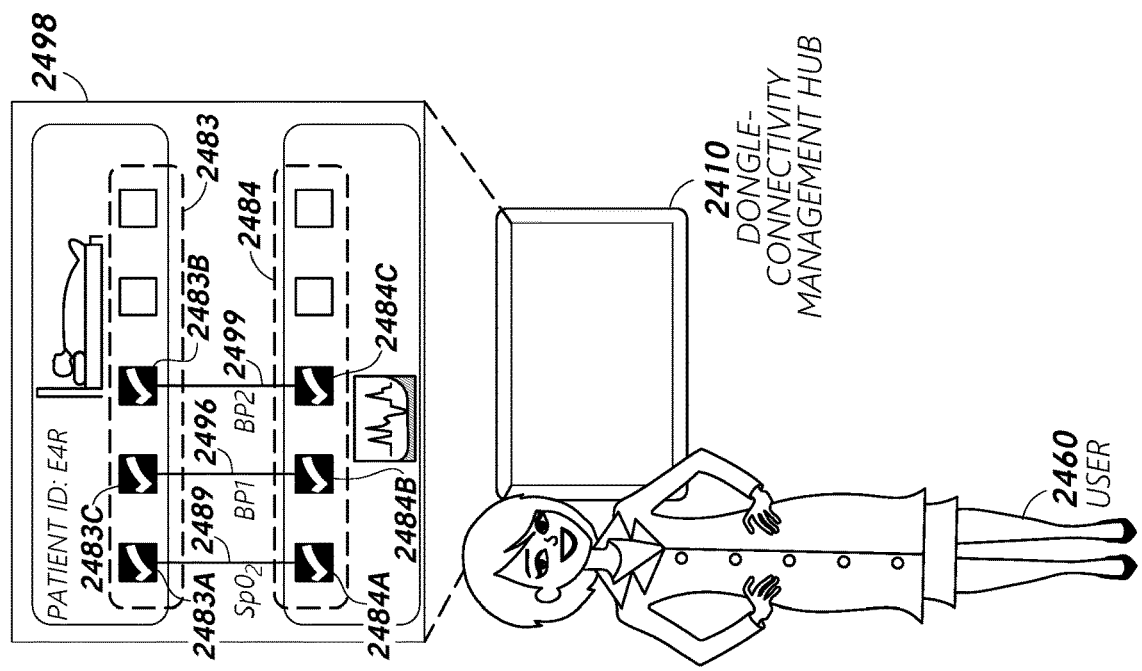
Figure 24:
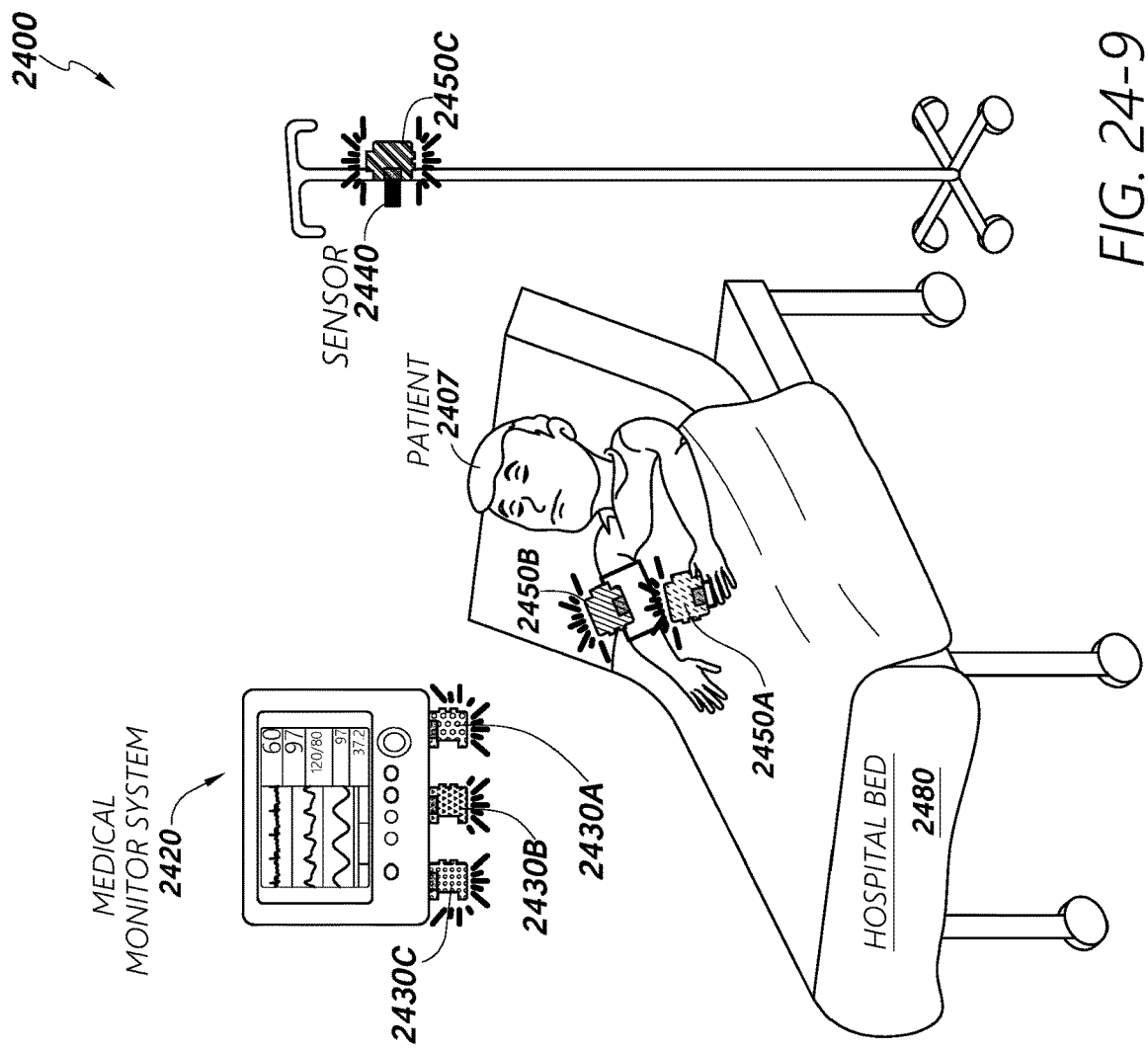
Figure 9:
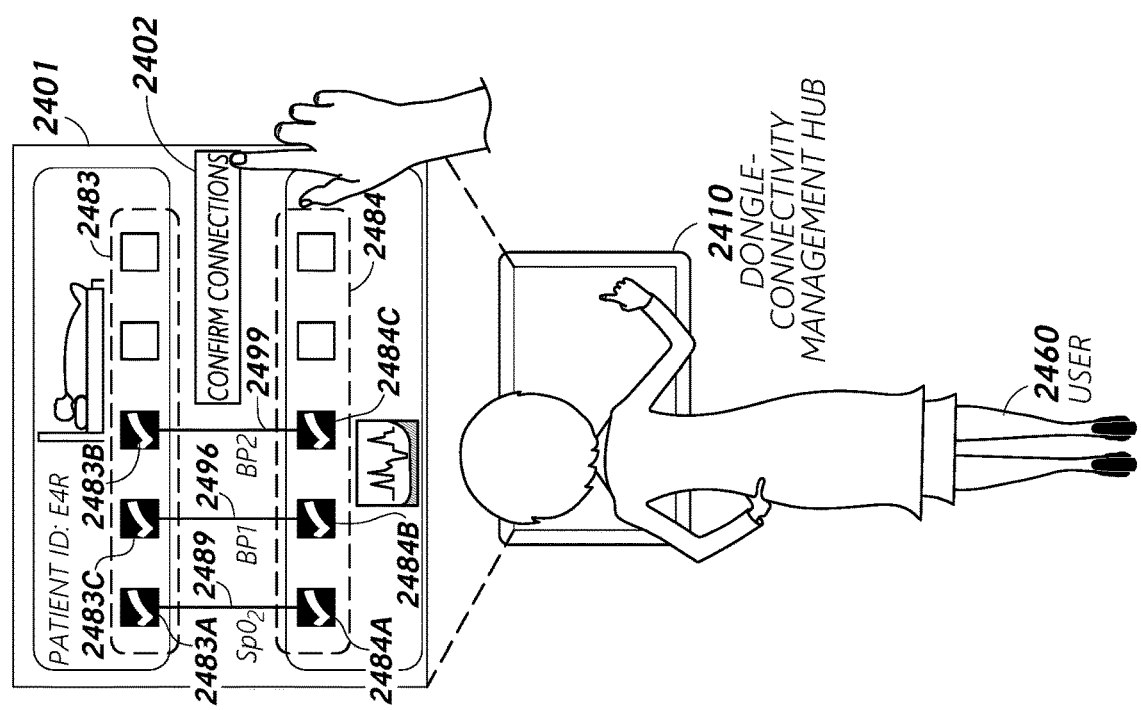

FIGS. 24-1 through 24-9 illustrate aspects of certain example process(es) of connecting various dongles in accordance with one or more embodiments of the present disclosure. Certain aspects of the relevant process(es) are illustrated and described in the context of a wireless sensor-monitor connectivity system 2400 implemented within a healthcare environment, such as a hospital room, operating room, or any other room or facility where a patient 2470 can receive medical care/treatment. The system 2400 can advantageously include one or more monitor dongles 2430, sensor dongles 2450 electrically connected to sensors 2440, and a dongle-connectivity management hub 2410 configured to facilitate connections between the monitor dongles 2430 and the sensor dongles 2450. As illustrated, the patient 2470 can be positioned on a hospital bed 2480 or other position/furniture and attached to the sensors 2440. The illustrated user 2460 can represent one or more of a doctor, a nurse, an administrator, or any other individual.

In the examples of FIGS. 24-1 through 24-9 (and/or other examples discussed herein), the user 2460 can operate the dongle-connectivity management hub 2410 to manage wireless connectivity of the monitor dongles 2430 and/or the sensor dongles 2450. For example, the system 2400 can allow the user 2460 to provide input and/or receive output via a user interface (UI) (e.g., graphical user interface (GUI)) presented on the dongle-connectivity management hub 2410 and/or one or more associated device(s). A user interface (as well as other user interfaces discussed herein) can include one or more user interface elements configured to provide output and/or receive input.

The terms "interface element," "user interface element," graphical user "interface element," "interface," "user interface," and "graphical user interface" are used herein according to their broad and ordinary meanings and may refer to the rendering of data (i.e., "interface data," "user interface data," or "graphical user interface data") on an electronic or other display device. "User interface" and "graphical user interface" can refer to the relevant interface data and/or to the rendering/representation of the interface data. For example, a user interface element can include/represent one or more windows configured to present information and/or additional user interface element(s) (e.g., a pop-up window or other window), one or more menus configured to provide list(s) of items that can be selected, one or more icons that present information in a graphical manner to represent item(s), one or more user-control mechanisms/features that are configured to be selected (e.g., a button, scroll bar, etc.), and so on. In some embodiments, a user can provide input via one or more user interface elements, such as by selecting a user interface element through a touchscreen, selecting a user interface element with a mouse/cursor or keyboard, selecting a user interface element using speech input, selecting a user interface element using a gesture, and so on.

In some embodiments, to initiate wireless connectivity, the user 2460 can use the dongle-connectivity management hub 2410 to open or access an application or other software and/or hardware that is configured to facilitate wireless connectivity management functionality for dongles. In response to such user initiation/engagement, the dongle-connectivity management hub 2410 can display/render a graphical user interface 2481 (e.g., rendering of user interface data) to allow for user input to be received by the dongle-connectivity management hub 2410 indicating/identifying a patient, as illustrated in FIG. 24-1. For example, the system 2400 may allow for the user 2460 to provide input through the dongle-connectivity management hub 2410, such as through text, touch, or speech input that may be received through user engagement/input in a field 2481A of the graphical user interface 2481. The input can include, for example, an identifier for a patient, such as a name or a number (e.g., patient identifying number, room number, or any other identifying information for the patient). By entering an identifier for a patient, the system 2400 can allow a user to associate one or more dongles and/or one or more sensors connected to the one or more dongles with the patient, as discussed in further detail below.

Although the example of FIG. 24-1 is discussed in the context of the user 2460 providing a patient identifier through the graphical user interface 2481, in some embodiments other process(es) can be implemented to identify a patient. For example, an image can be captured of at least a portion of the local environment and analyzed with image processing, such as facial recognition, to identify one or more patients. To illustrate, in accordance with certain use cases, one of the sensor dongles 2450 and/or the monitor dongles 2430 can be configured to capture an image and/or transmit the image wirelessly to the dongle-connectivity management hub 2410 or another device/system (e.g., one of the monitor dongles 2430, a remote computing device, etc.). The dongle-connectivity management hub 2410 or the other device/system can be configured to process the image using facial recognition techniques to identify an individual in the environment, such as the patient 2470 that has one or more of the sensors 2440 attached thereto.

In some embodiments, one or more of the sensor dongles 2450 and/or the monitor dongles 2430 may be oriented/pointed at (e.g., in the general direction of) the patients 2470, such that a field-of-view of a camera associated with a dongle includes at least a portion of the face of the patient 2470. A camera associated with one or more of the sensor dongles 2450 and/or the monitor dongles 2430 can be adjusted/calibrated by a user or otherwise to configure a field-of-view of the dongle as desired. In some embodiments, an image and/or other data processed by one or more components of the system 2400 can be subjected to security measures to ensure that the image and other data is maintained in a secure/confidential manner. For example, the image or other data can be encrypted when stored or transmitted, such as when sending the data from the sensor dongles 2450 to the dongle-connectivity management hub 2410 and/or the monitor dongles 2430 for processing. Such encryption can advantageously be of a nature to comply with relevant patient-confidentiality standards.

In response to identification of a patient, the dongle-connectivity management hub 2410 can be configured to display/render a graphical user interface 2482 to manage wireless connectivity of one or more of the sensor dongles 2450 and the monitor dongles 2430, as illustrated in FIG. 24-2. Although the graphical user interface 2482 is discussed in the context of being presented/displayed in response to identification of a patient, the graphical user interface 2482 can be presented/displayed at other times and/or in response to other triggering event(s). As shown, the graphical user interface 2482 can include certain visual representations 2483 (e.g., icons) representing the sensor dongles 2450 and visual representations 2484 representing the monitor dongles 2430. With respect to the state/environment shown in FIG. 24-2, the graphical user interface 2482 can also include visual representations indicating that there are presently no wireless couplings between the sensor dongles 2450 and the monitor dongles 2430, as illustrated by the example "no connections" text between the visual representations 2483 and 2484.

In some embodiments, to establish a wireless coupling, the user 2460 selects/engages with a connect button 2487 that is displayed via a graphical user interface 2486, as illustrated in FIG. 24-3. In response to such selection/engagement, the dongle-connectivity management hub 2410 may be configured to search for devices that are within a wireless communication range of each other or the hub 2410 and/or are otherwise detectable (e.g., associated with a detectable state). When a sensor/monitor dongle is detected, the dongle-connectivity management hub 2410 can be configured to present data/information via the graphical user interface 2486 indicating that the sensor/monitor dongle has been detected. In some embodiments, a sensor/monitor dongle can enter a detectable state when the user 2460 presses a connect button (not shown in FIG. 24-3; see FIGS. 7 and 10) on the sensor/monitor dongle. Additionally or alternatively, a sensor/monitor dongle can enter a detectable state in response to another event, such as receiving a signal from the dongle-connectivity management hub 2410 directing the dongle to wake-up from a sleep/low-power state or another state. In a detectable state, a sensor/monitor dongle can be configured to communicate with another device to inform the other device that the sensor/monitor dongle is present. Further, a sensor/monitor dongle can provide output indicating a detectable state, such as by outputting light, outputting light in a pattern (e.g., outputting a blinking or solid yellow light), outputting a sound (e.g., speech of "detectable," beeps in a pattern, etc.), and so on.

In the example of FIG. 24-3, the user 2460 presses a connect button on one or more (e.g., each) of the sensor dongles 2450 and/or the monitor dongles 2430, wherein, in response to such user interaction/engagement, one or more (e.g., each) of the sensor dongles 2450 and/or the monitor dongles 2430 provide output indicating a present dongle status (e.g., a detectable state/status has been entered), as represented by the illustrated lines emanating from the sensor dongles 2450 and the monitor dongles 2430 in FIG. 24-3. Moreover, in accordance with the example of FIG. 24-3, the dongle-connectivity management hub 2410 can be configured to detect each of the sensor dongles 2450 and the monitor dongles 2430 with the sensor dongles 2450 and the monitor dongles 2430 presently in respective detectable states. The dongle-connectivity management hub 2410 can be configured to provide output via the graphical user interface 2486 indicating such detection, as represented/illustrated by the icons/images 2483A-2483C and 2484A-2483C (which may include, in some embodiments, certain 'searching' and/or 'detected' icons and/or related text) and the text "3 sensor dongles detected" and "3 monitor dongles detected".

Upon detecting one or more of the sensor dongles 2450 and the monitor dongles 2430, the dongle-connectivity management hub 2410 can utilize software and/or hardware thereof to attempt to establish (e.g., at least partially automatically establish) one or more wireless couplings between one or more of the detected sensor dongles 2450 and respective ones of the monitor dongles 2430. In particular, the dongle-connectivity management hub 2410 can be configured to determine/identify a sensor dongle and a corresponding monitor dongle that are associated with one or more common/similar features (e.g., dongle types, connector types, related sensor types, etc.) and/or that have previously been coupled, and establish a wireless coupling (e.g., direct the dongle(s) to establish a wireless coupling) between such determined/identified sensor dongle and monitor dongle. For example, the dongle-connectivity management hub 2410 can be configured to establish a wireless coupling between a sensor dongle and a monitor dongle based at least in part on one or more of the following determinations: that the sensor dongle and the monitor dongle are associated with a common/similar type of sensor/connector (e.g., they have corresponding male/female connectors for the same connector type); that the sensor dongle and the monitor dongle were previously coupled; that the sensor dongle and the monitor dongle are within a certain distance/proximity; and so on. Various of the illustrated and/or described dongles can be configured to communicate wirelessly with the dongle-connectivity management hub 2410 to provide information (e.g., embodied in wireless data packets) indicating a type of the respective dongle, a type of a sensor physically, electrically, and/or communicatively connected to the respective dongle, and/or a type of connector associated with the respective dongle to facilitate such processing. According to some implementations/processes of establishing a wireless coupling, the dongle-connectivity management hub 2410 can send/transmit a wireless communication (e.g., one or more wireless signals) to a sensor dongle and/or a monitor dongle instructing the sensor dongle and/or the monitor dongle to communicate with each other when needed, such as to send sensor data obtained by a sensor to the medical monitor system 2420. Such dongle-to-dongle wireless communication may be facilitated by initiating a wireless handshake or other communication/pairing protocol.

The sensor dongles 2450 and monitor dongles 2430 can be sorted into either "auto-matched" pairs or "confirmation required" pairs. That is, sensor and monitor dongles can be communicatively coupled/associated automatically when matched dongles are detected. For example, color wheel or other visual-indicator-based user input on one or more of the matched dongles can be set by the user 2460 to identify the other or to identify a common color, shape, or other identifier associated with the other dongle, wherein the control circuitry of the hub 2410, sensor dongle 2450, and/or monitor dongle 2430 is configured to initiate wireless coupling of the dongles based on the user input that has previously been set with respect to one or both of the dongles.

In some embodiments, physical buttons or other user input features of either or both of the sensor dongles 2450 and monitor dongles 2430 can be engaged by the user to cause the dongles to be automatically associated with respective dongles when connection process is implemented. Furthermore, embodiments of the present disclosure can involve identifying conflicts among sensor and monitor dongles. Example conflicts can include a situation where a sensor dongle is in a condition for pairing (e.g., pairing input has been provided by the user 2460, the hub 2410 identifies the availability for pairing of the sensor dongle, and/or the sensor dongle is turned on or otherwise activated/initiated), but there is no available corresponding monitor dongle to connect to. As another example conflict, a monitor dongle can be in a condition for pairing wherein no available sensor dongle is found. As another example dongle connectivity conflict, two or more sensor (or monitor) dongles are available for coupling to monitor dongles, wherein the user or system have not provided/determined clarity with regard to what dongles are to be connected with, respectively. For example, where two blood pressure sensors are implemented, the connected sensor dongles may broadcast/transmit two separate pressure signals without clarity regarding which pressure-compatible monitor dongle should receive the respective pressure sensor signals. Dongle connection conflicts can be resolved automatically by control circuitry of the system based on certain parameter(s) and/or may be resolved through user input/confirmation. The user/clinician 2460 can turn color wheel(s) of the dongles 2483a and/or 2484a to certain position(s) on either of both of the dongles to confirm/establish the connection 2489. In some embodiments, the user 2460 pushes 'connect' buttons/inputs on the sensor dongles 2450 and/or monitor dongles 2430. The dongles can provide output in response, such as flashing lights or the like, indicating the available for connection state thereof. In response, the dongle-connectivity management hub can connect and/or label the available dongles, When a wireless coupling is established, the dongle-connectivity management hub 2410 can provide information indicating such wireless coupling. For example, if the sensor dongle 2450A and the monitor dongle 2430A are wirelessly coupled, the dongle-connectivity management hub 2410 can provide information via a graphical user interface 2488, as illustrated in FIG. 24-4, in accordance with certain use cases, wherein certain visual representations 2483A and 2484A (which correspond to the sensor dongle 2450A and the monitor dongle 2430A, respectively) each change to a check mark or other indicator/symbol and/or a visual representation of a link 2489 is created/displayed between the visual representations 2483A and 2484A. In some cases, the graphical user interface 2488 can indicate sensor and/or monitor dongle types. For example, according to some use cases, the interface 2488 can represent that the sensor dongle 2450A and the monitor dongle 2430A are associated with a pulse oximeter sensor. The dongle-connectivity management hub 2410 can also store data indicating that a wireless coupling is established between the sensor dongle 2450A and the monitor dongle 2430A. Furthermore, the dongle-connectivity management hub 2410 can manage, store, and/or present data indicating an association/relationship between the patient 2470 and the sensor dongle 2450A and/or the monitor dongle 2430A (e.g., associate/relate the sensor dongle 2450A and/or the monitor dongle 2430A with the patient identifier previously received).

In some embodiments, a sensor dongle and/or a monitor dongle can provide certain output when a wireless coupling is established between the sensor dongle and the monitor dongle. For example, a dongle can output certain colors, intensities, and/or types of light (e.g., output solid green light), certain patterns (e.g., outputting a blinking green light), certain sounds (e.g., audible speech of "connected," beeps in a pattern, etc.), and so on. Further, a dongle can provide notification(s), such as via a display, indicating/identifying a patient associated with the dongle, a type of sensor associated with the dongle, and/or a status of the dongle. In the example of FIG. 24-4, the sensor dongle 2450A has been wirelessly coupled to the monitor dongle 2430A and is associated with the patient 2470, as illustrated by the darker lines around the sensor dongle 2450A and the monitor dongle 2430A and information that is displayed via the displays 2490 and 2491 (e.g., the patient identifier and the type of sensor).

In some situations, the dongle-connectivity management hub 2410 may be unable to establish a wireless coupling between a sensor dongle and a monitor dongle. For example, the dongle-connectivity management hub 2410 may be unable to identify a common/similar feature between an available sensor dongle and an available monitor dongle. In such situations, the sensor dongle and the monitor dongle can remain in detectable states without being wirelessly coupled to another dongle, as illustrated in FIG. 24-4 with respect to the sensor dongles 2450B and 2450C (and the corresponding visual representations 2483B and 2483C) and the monitor dongles 2430B and 2430C (and the corresponding visual representations 2484B and 2484C), which each display and/or are represented by icons indicating searching/detected status/states.

In some implementations, when the dongle-connectivity management hub 2410 is unable to establish a wireless coupling, the user 2460 can provide input to establish a wireless coupling, as illustrated in FIG. 24-5. For example, the dongle-connectivity management hub 2410 can display a graphical user interface 2494 with the visual representations 2483 and 2484, indicators identifying/indicating dongles that are wirelessly connected, indicators identifying/indicating dongles that are detected but not yet wirelessly coupled, and/or indicators (as discussed in further detail below with reference to FIG. 30) indicating a type of dongle associated with the visual representations 2483 and/or 2484. In some implementations, the user 2460 can select a first visual representation, such as the visual representation 2484B for the monitor dongle 2430B, that is not yet wirelessly coupled to a sensor dongle, and draw/indicate a line or other connection/line to another visual representation in some manner (e.g., using touch screen, cursor, or other input mechanism), such as the visual representation 2483C that represents the sensor dongle 2450C that is not yet wirelessly coupled to a monitor dongle. The dongle-connectivity management hub 2410 can then, in at least partly in response to the indication by the user, establish/initiate a wireless coupling between the identified/relevant dongles, such as the monitor dongle 2430B and the sensor dongle 2450C, as illustrated in FIG. 24-6.

The monitor dongle 2430B and/or the sensor dongle 2450C can provide output indicating the establishment of the wireless coupling, as illustrated by the darker lines around the monitor dongle 2430B and the sensor dongle 2450C in FIG. 24-6. Further, the dongle-connectivity management hub 2410 can provide a graphical user interface 2495 that includes the visual representations 2483C and 2484B (which correspond to the sensor dongle 2450C and the monitor dongle 2430B, respectively) each changed to a check mark or other indicator and/or a representation of a link 2496 created between the visual representations 2483C and 2484B.

As illustrated in by the graphical user interface 2497 in FIG. 24-7, in some embodiments, the dongle-connectivity management hub 2410 can rearrange visual representations to line up visual representations that are associated with wireless couplings. For example, the graphical user interface 2497 can move/show the visual representation 2483C to the left so that the visual representation 2483C is lined up with the visual representation 2484B in a vertical (or horizontal in other implementations) direction, and/or move the visual representation 2483B to the right. Further, the graphical user interface 2497 can provide information indicating that the wireless coupling associated with the visual representations 2483C and 2484B are associated with a blood pressure (BP) sensor (e.g., text "BP1").

In some embodiments, the dongle-connectivity management hub 2410 can establish a wireless coupling between remaining/additional sensor dongle(s) and monitor dongle(s), as illustrated in FIG. 24-8. For example, according to an example use case in which the sensor dongle 2450B and the monitor dongle 2430C are the only remaining dongles that have not been wirelessly coupled, the dongle-connectivity management hub 2410 can be configured to establish a wireless coupling between the sensor dongle 2450B and the monitor dongle 2430C. In some implementations, the sensor dongle 2450B and/or the monitor dongle 2430C can provide output indicating the establishment of the wireless coupling, as illustrated by the darker radially-emanating lines around the sensor dongle 2450B and the monitor dongle 2430C. Further, the dongle-connectivity management hub 2410 can be configured to generate, provide, and/or display/present a graphical user interface 2498 (e.g., graphical user interface data) that includes representations 2483B and 2484C (which correspond to the sensor dongle 2450B and the monitor dongle 2430C, respectively) that are each changed to a check mark (or other visual indicator) and a link 2499 created between the visual representations 2483B and 2484C.

In some embodiments, when wireless couplings have been established between some or all (e.g., or one or more) of the sensor dongles 2450 and the monitor dongles 2430 that have been detected, the dongle-connectivity management hub 2410 can be configured to provide a graphical user interface 2401 to confirm and/or allow for confirmation of the one or more wireless couplings, as illustrated in FIG. 24-9. In particular, the graphical user interface 2401 can provide a confirmation button 2402 or other confirmation mechanism that, when selected, causes the sensor dongles 2450 and/or the monitor dongles 2430 to provide output confirming the wireless couplings. For example, the dongle-connectivity management hub 2410 can be configured to cause the sensor dongle 2450A and the monitor dongle 2430A associated with the link 2489 in the graphical user interface 2401 (e.g., dongles associated with a pulse oximeter sensor) to provide output confirming a wireless coupling between the dongles 2430A and 2450A (e.g., the sensor dongle 2450A can provide a flashing light (e.g., green light) or output a sound (e.g., beep) and/or the monitor dongle 2430A can provide a similar light and/or output sound). In some embodiments, the dongle-connectivity management hub 2410 can be configured to cause the sensor dongle 2450C and the monitor dongle 2430B associated with the link 2496 in the graphical user interface 2401 (e.g., BP1 sensor) to provide output confirming a wireless coupling between the dongles 2450C and 2430B (e.g., the sensor dongle 2450C can provide a flashing light (e.g., green light) or output a sound (e.g., beep) and then the monitor dongle 2430B can provide a flashing light (e.g., green light) or output a beep sound).

The dongle-connectivity management hub 2410 can further cause the sensor dongle 2450B and the monitor dongle 2430C associated with the link 2499 in the graphical user interface 2401 (e.g., BP2 sensor) to provide output confirming a wireless coupling between the dongles 2450B and 2430C (e.g., the sensor dongle 2450B can provide a flashing light (e.g., green light) or output a sound (e.g., beep) and then the monitor dongle 2430C can provide a flashing light (e.g., green light) or output a sound (e.g., beep)). In some embodiments, the dongle-connectivity management hub 2410 can be configured to cause a dongle to provide certain output at least in part by sending a communication to the dongle with a request to provide the desired output.

Although the example confirmation process of FIG. 24-9 is described and/or shown as being initiated in response to the user 2460 selecting the confirmation button 2402, the confirmation process can be initiated in a variety of manners in accordance with the present disclosure. In some embodiments, the confirmation process is initiated at least in part by the dongle-connectivity management hub 2410 and/or one or more of the dongles of the system automatically when all (or a predetermined number) of dongles that have been detected are wirelessly coupled. Further, although the confirmation process of FIG. 24-9 is discussed as providing confirmation output in a certain manners and orders, the confirmation output can be provided in any number of ways and/or any order (e.g., with different output lights, light patterns, sounds, etc. and/or in a different output order of devices).

Figure 25:
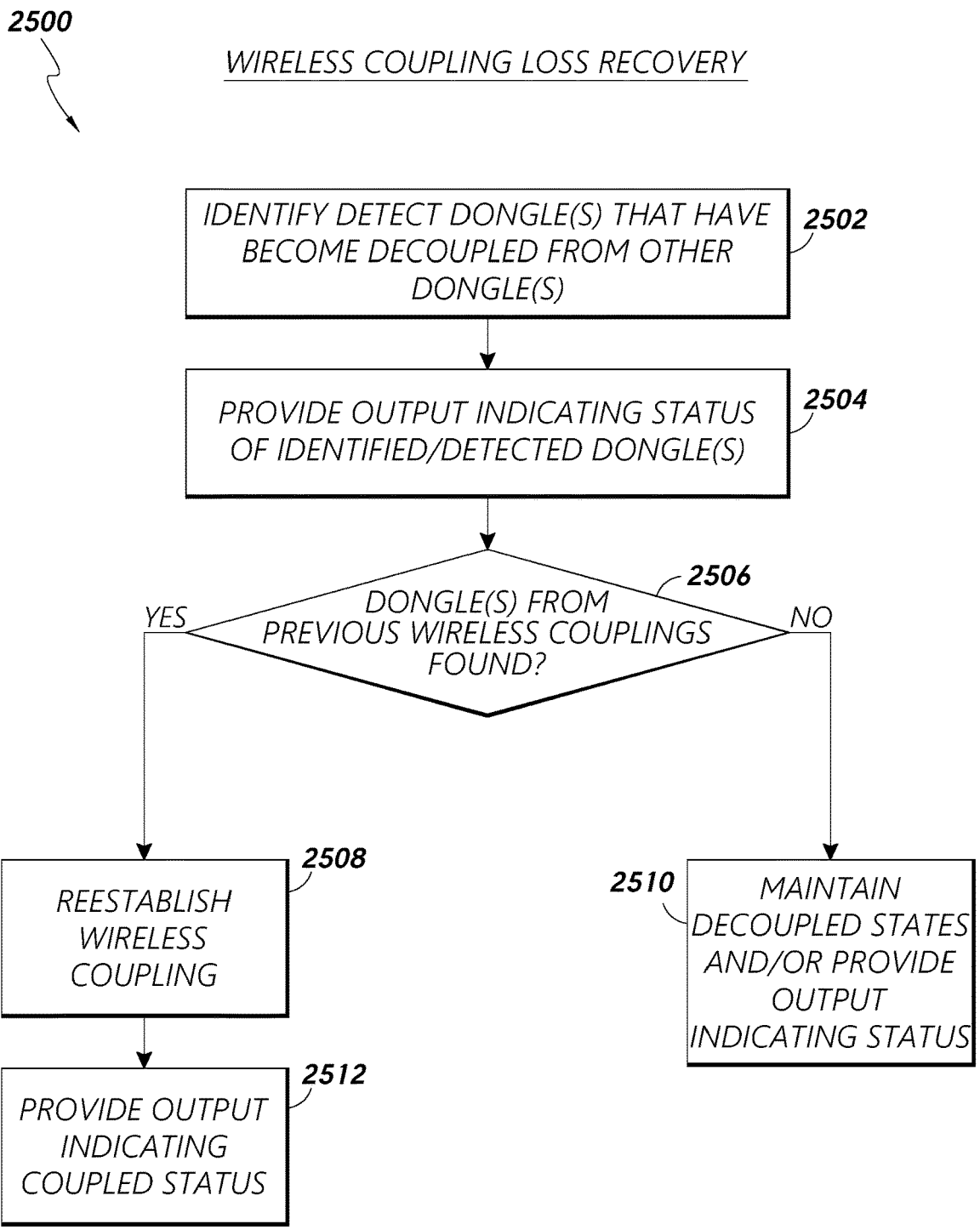
FIG. 25 is a flow diagram illustrating a process for attempting to reestablish one or more wireless couplings that have been lost between dongles in accordance with one or more embodiments.

FIG. 25 illustrates an example flow diagram of a process 2500 for attempting to reestablish one or more wireless couplings that have been lost between dongles in accordance with one or more embodiments of the present disclosure. The process 2500 can be performed by any of the systems and devices discussed herein, such as a dongle-connectivity management hub, a sensor dongle, a monitor dongle, and/or a medical monitor system.

At block 2502, the process 2500 involves identifying, detecting, or otherwise determining one or more dongles that have become decoupled from one or more other dongles within a healthcare environment. For example, a dongle-connectivity management hub can be configured to detect that one or more sensor dongles have decoupled from one or more monitor dongles (e.g., one or more wireless couplings have been lost). The dongle-connectivity management hub can be configured to maintain communication with the one or more sensor dongles and/or the one or more monitor dongles and receive information indicating the status and/or loss of a wireless coupling between such dongles.

At block 2504, the process 2500 can involve providing an output indicating a status of one or more dongles, such as a status output indicating a loss or absence of a previously-established wireless coupling of the one or more dongles. For example, a sensor dongle and/or a monitor dongle can output light, audio, or other indicator via one or more user I/O components to provide an indication of a status of the sensor dongle and/or the monitor dongle. The status can indicate that the sensor dongle and/or the monitor dongle have decoupled from each other and/or that one or both of the sensor dongle and/or the monitor dongle are searching for the other to reestablish a wireless coupling. Additionally or alternatively, a dongle-connectivity management hub can be configured to provide output via one or more user I/O components (e.g., an icon or other visual representation on a display) to indicate a status of a sensor dongle and/or a monitor dongle.

At block 2506, the process 2500 can involve determining whether one or more dongles from a previous wireless coupling are found. That is, with respect to a sensor dongle that was previously coupled to a particular monitor dongle, after such wireless coupling is lost, the process 2500 can involve searching (e.g., by a dongle-connectivity management hub) for one or both of the previously-coupled dongles. According to certain example use cases, a dongle-connectivity management hub can search for a first sensor/monitor dongle and a second sensor/monitor dongle that were previously wirelessly coupled but have decoupled from each other for various reasons. Further, in some embodiments, a first sensor/monitor dongle can search for a second sensor/monitor dongle that was previously wirelessly coupled to the first sensor/monitor dongle. If one or more dongles from a previous coupling are found in connection with the decision block 2506, the process 2500 can proceed to operation/block 2508 (i.e., the "YES" branch). Alternatively, if one or more dongles from a previous coupling are not found, the process 2500 can proceed to operation/block 2510 (i.e., the "NO" branch).

At block 2508, the process 2500 can involve reestablishing a wireless coupling. In some embodiments, a dongle-connectivity management hub can reestablish a wireless coupling between dongles that were previously wirelessly coupled but have become decoupled from each other. The dongle-connectivity management hub can send a communication to a sensor dongle and/or a monitor dongle to direct/initiate the reestablishment of a wireless coupling. Further, in some embodiments, a sensor/monitor dongle can communicate with another sensor/monitor dongle to reestablish a wireless coupling with the sensor/monitor dongle without involvement from the dongle-connectivity management hub.

At block 2512, the process 2500 can involve providing output indicating a coupled status. For example, a sensor dongle and/or a monitor dongle can output light, audio, or other indicator via one or more user I/O components to provide an indication of a coupled status. Additionally or alternatively, a dongle-connectivity management hub can provide output via one or more user I/O components (e.g., an icon or other visual representation on a display) to indicate a coupled status of a sensor dongle and/or a monitor dongle.

At block 2510, the process 2500 can involve maintaining and/or outputting output indicating a decoupled (e.g., disconnected) state/status. In some embodiments, if a first sensor/monitor dongle is unable to reestablish a wireless coupling with a second sensor/monitor dongle from a previously-established but subsequently-lost wireless coupling, the first sensor/monitor dongle and/or the second sensor/monitor dongle can maintain a decoupled state and/or provide output indicating a decoupled status. A sensor dongle and/or a monitor dongle can output light, audio, or other indicator via one or more user I/O components to provide an indication of a decoupled status. Further, in some embodiments, a dongle-connectivity management hub can provide output via a display or otherwise indicating a decoupled status of a sensor dongle and/or monitor dongle.

Figure 26:
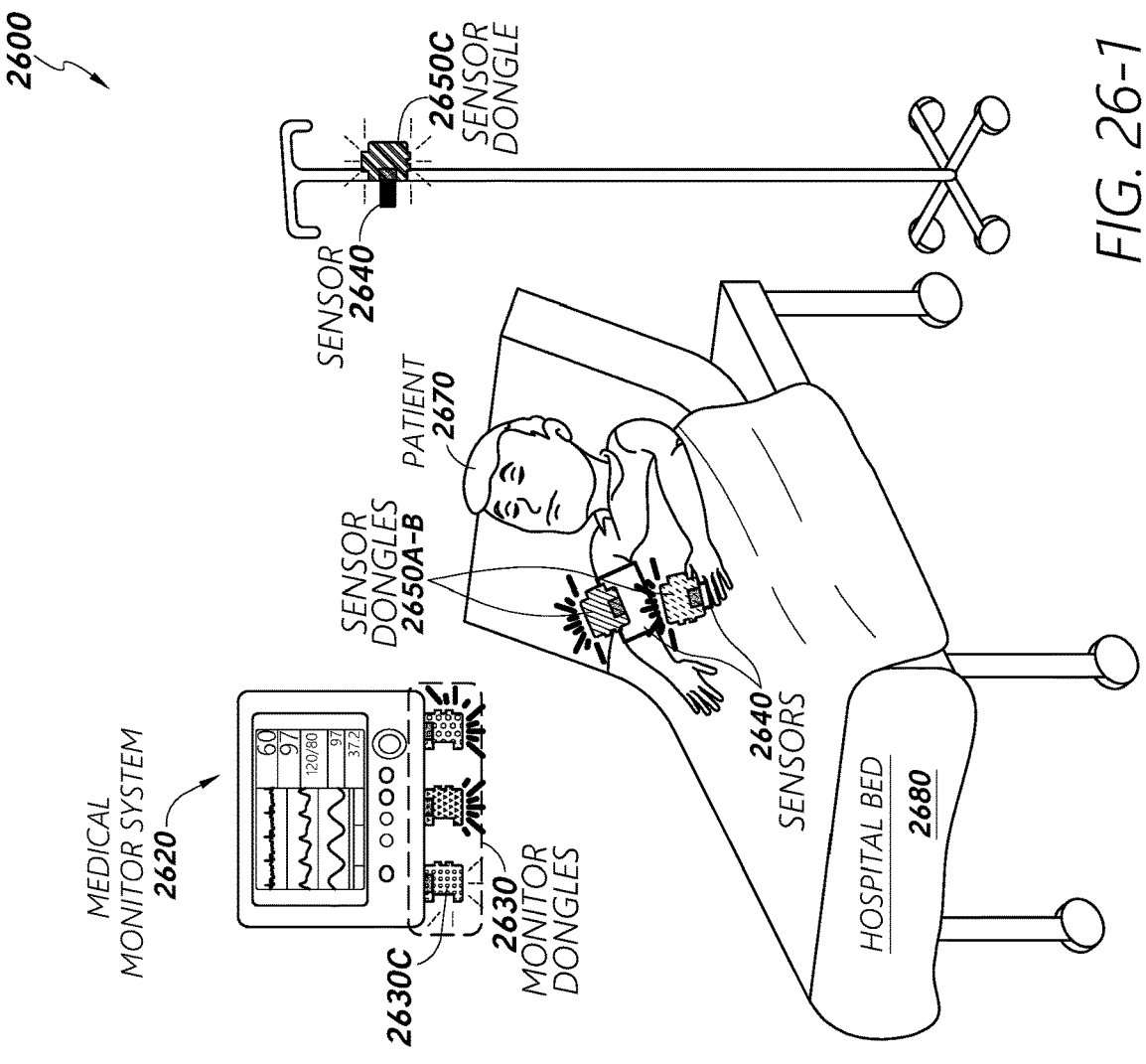
Figure 1:
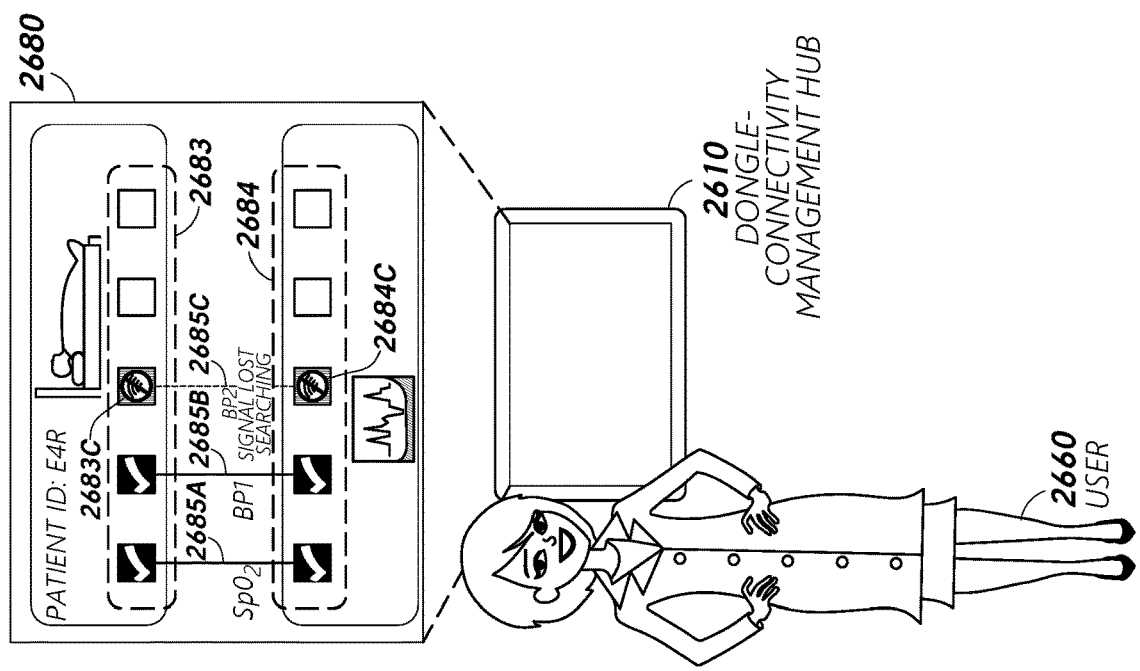
Figure 26:
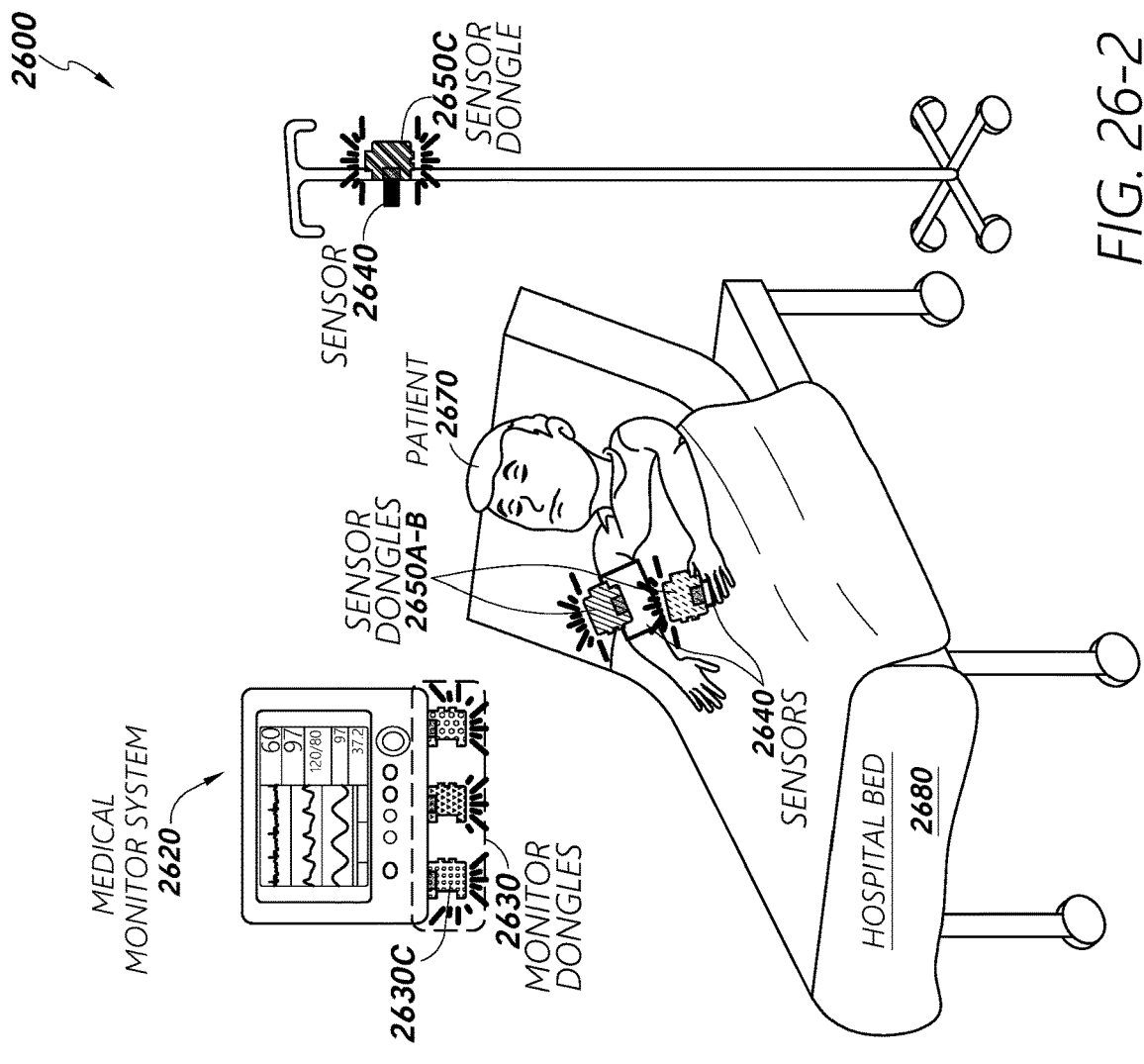
Figure 2:
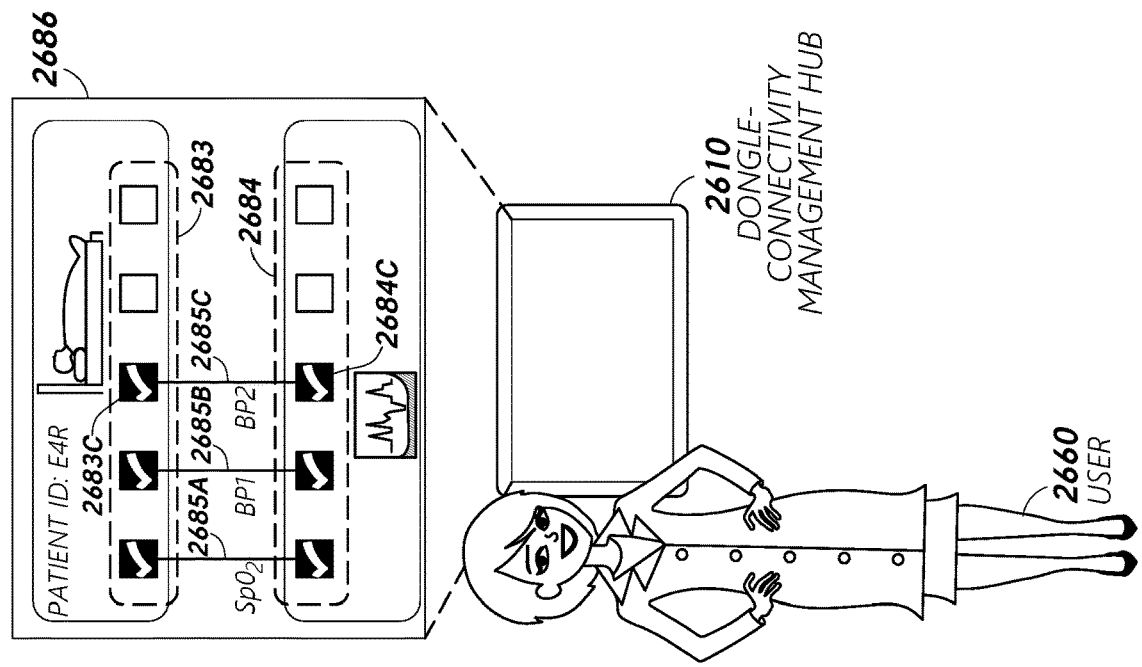
Figure 26:
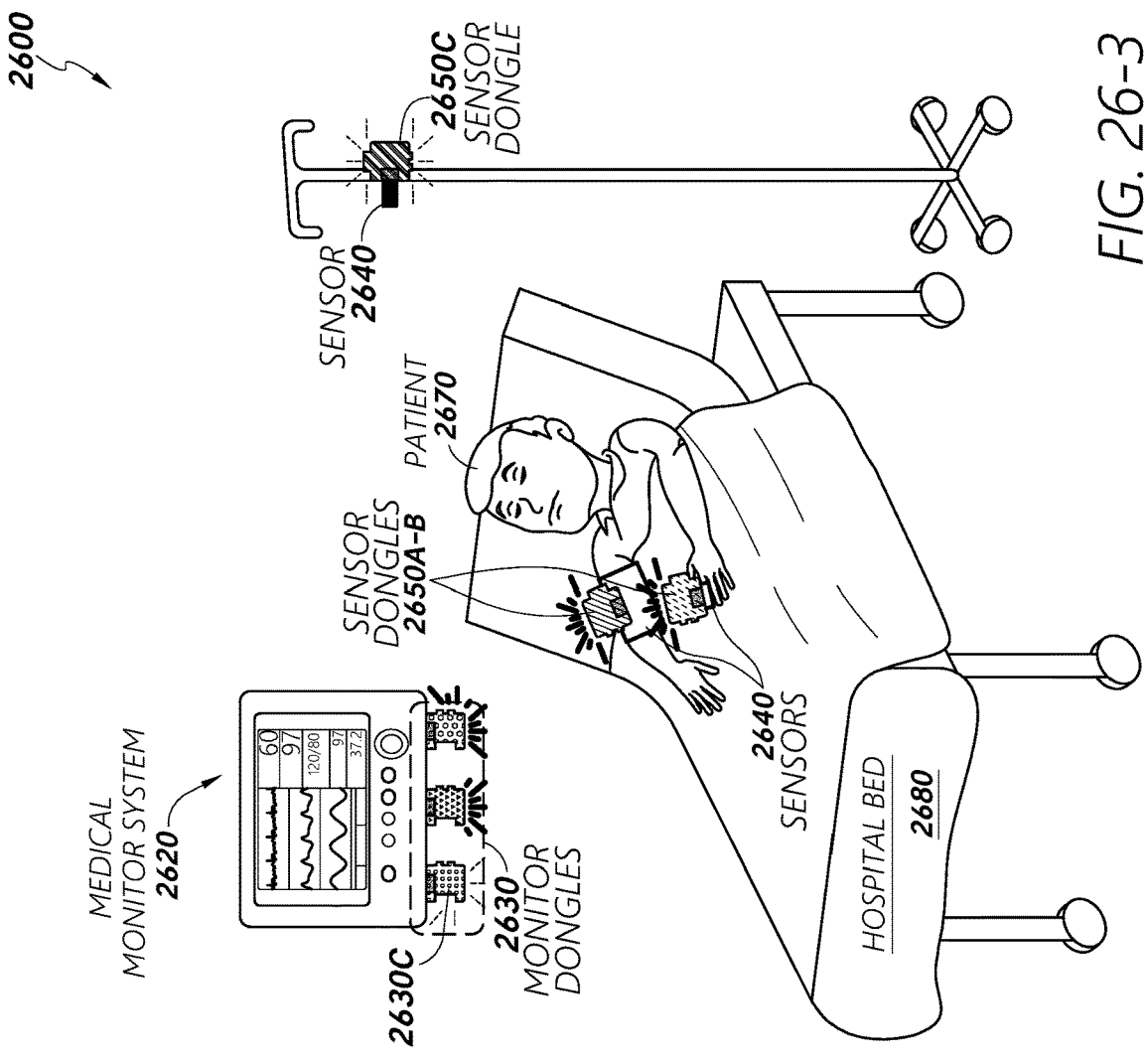
Figure 3:
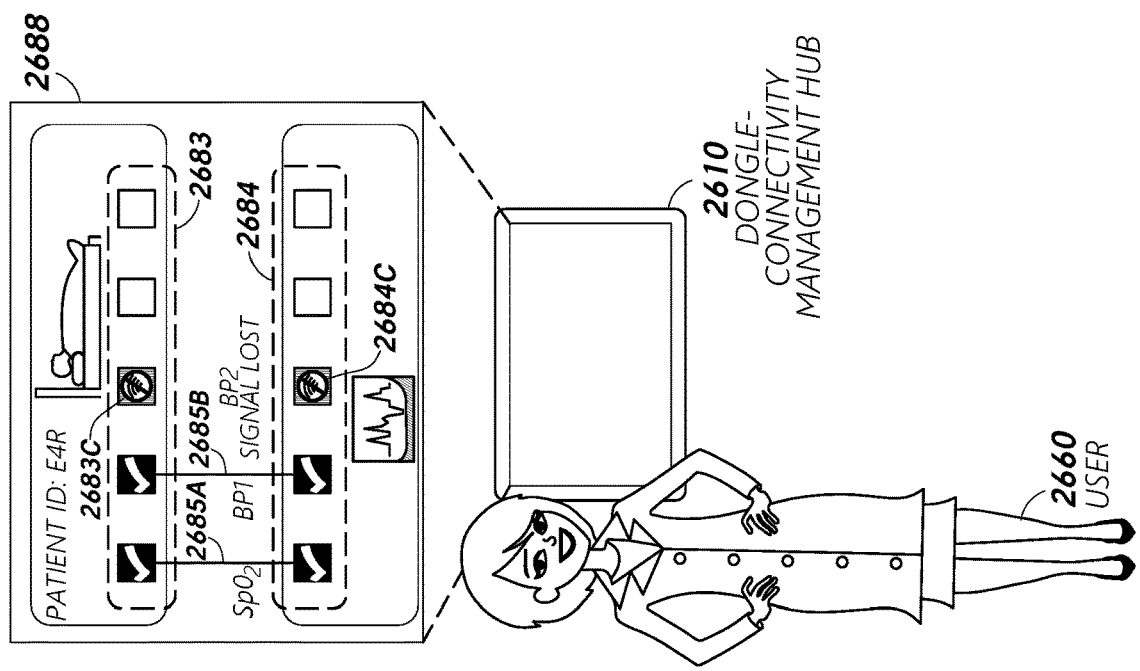

FIGS. 26-1 through 26-3 illustrate aspects of example processes of attempting to reestablish one or more wireless couplings that have been lost (e.g., unintentionally) between dongles in accordance with one or more embodiments. Dongles can lose a wireless coupling for a variety of reasons, such as an object or signal that obstructs a signal path between the dongles, wireless signal interference/corruption, operational error at one or more of the dongles (which can cause one or more of the dongles to restart in some cases), and so on. The process aspects of FIGS. 26-1 through 26-3 are generally illustrated in the context of a wireless sensor-monitor connectivity system 2600 implemented within a healthcare environment, such as a hospital room, operating room, or any other room or facility where a patient 2670 can receive medical care/treatment. In this example, the patient 2670 is positioned on a hospital bed 2680 and attached to sensors 2640 that are configured to obtain information about the health of the patient 2670. The system 2600 includes sensor dongles 2650 configured to physically and/or electrically connect to respective ones of the sensors 2640, monitor dongles 2630 configured to wirelessly couple to the sensor dongles 2650 and physically and/or electrically connect to respective connectors associated with the medical monitor system 2620, and a dongle-connectivity management hub 2610 configured to manage wireless connections/couplings between the monitor dongles 2630 and the sensor dongles 2650. The dongle-connectivity management hub 2610 can generate and/or provide a user interface UI 2680 to interface with a user 2660.

FIG. 26-1 illustrates an example where a sensor dongle 2650C loses connection with a monitor dongle 2630C. Upon losing the connection (e.g., a wireless coupling), either or both of the sensor dongle 2650C and the monitor dongle 2630C can be configured to enter a decoupled state, as illustrated by the dashed lines emanating from the sensor dongle 2650C and the monitor dongle 2630C. In a decoupled state, the sensor dongle 2650C and/or the monitor dongle 2630C can output light, audio, or another indicator via one or more user I/O components to provide an indication of the decoupled state (e.g., output a solid red light, a flashing red light, speech of "disconnected," information on a display, etc.). Further, the sensor dongle 2650C and/or the monitor dongle 2630C (with or without the assistance of the dongle-connectivity management hub 2610) can be configured to search for each other in an attempt to reestablish a wireless coupling in response to and/or based at least in part on the decoupling event. In some embodiments, the search can continue for a predetermined amount of time, such as a particular number of seconds, minutes, and so on.

In some implementations, the dongle-connectivity management hub 2610 can detect the decoupling of sensor and monitor dongles of interest and generate user interface data representing/indicating such decoupling and/or provide such representation/indication of the decoupling within the UI 2680 (e.g., on an electronic display presenting the UI 2680). In the illustrated example, the UI 2680 includes/displays visual representations 2683 (e.g., icons) representing/corresponding-to the sensor dongles 2650, visual representations 2684 representing/corresponding-to the monitor dongles 2630, and links 2685 representing/corresponding-to wireless couplings between the sensor dongles 2650 and the monitor dongles 2630 and/or respective statuses thereof. As shown, the link representation 2685C can includes a dashed line, wherein visual representations 2683C and 2684C include icons to illustrate that a wireless coupling has been lost between the sensor dongle 2650C (represented by the visual representation 2683C) and the monitor dongle 2630C (represented by the visual representation 2684C). However, a lost wireless coupling can be illustrated in other manners.

As noted above, in a decoupled state, the sensor dongle 2650C, the monitor dongle 2630C, and/or the dongle-connectivity management hub 2610 can attempt to reestablish a wireless coupling. If a wireless coupling is reestablished, the dongle-connectivity management hub 2610 can present a UI 2686 (e.g., on an electronic display associated with the dongle-connectivity management hub 2610) including an indication that the wireless coupling has been reestablished, as shown in FIG. 26-2. In particular, the UI 2686 can include/display a solid line to visually represent the link 2685C and/or checkmarks for the visual representations 2683C and 2684C to indicate that the wireless coupling between the sensor dongle 2650C and the monitor dongle 2630C has been reestablished. Further, the sensor dongle 2650C and/or the monitor dongle 2630C can provide output via one or more user I/O components indicating that a status has been changed to 'connected' (e.g., 'coupled').

Alternatively, if the sensor dongle 2650C and the monitor dongle 2630C are unable to reestablish a wireless coupling, the dongle-connectivity management hub 2610 can generate/present a UI 2688 including an indication that the sensor dongle 2650C and the monitor dongle 2630C remain in a decoupled state, as shown in FIG. 26-3. In particular, the UI 2688 can omit/remove any link between the visual representation 2683C and the visual representation 2684C and show the visual representations 2683C and 2684C with disconnected icons to indicate that the sensor dongle 2650C and the monitor dongle 2630C remain in a decoupled state and/or that the sensor dongle 2650C and the monitor dongle 2630C are not attempting to reestablish a wireless coupling. In some embodiments, the UI 2688 is displayed if a wireless coupling is not able to be established between the sensor dongle 2650C and the monitor dongle 2630C after attempting to do so for a predetermined amount of time, such as a number of seconds, minutes, and so on.

Figure 27:
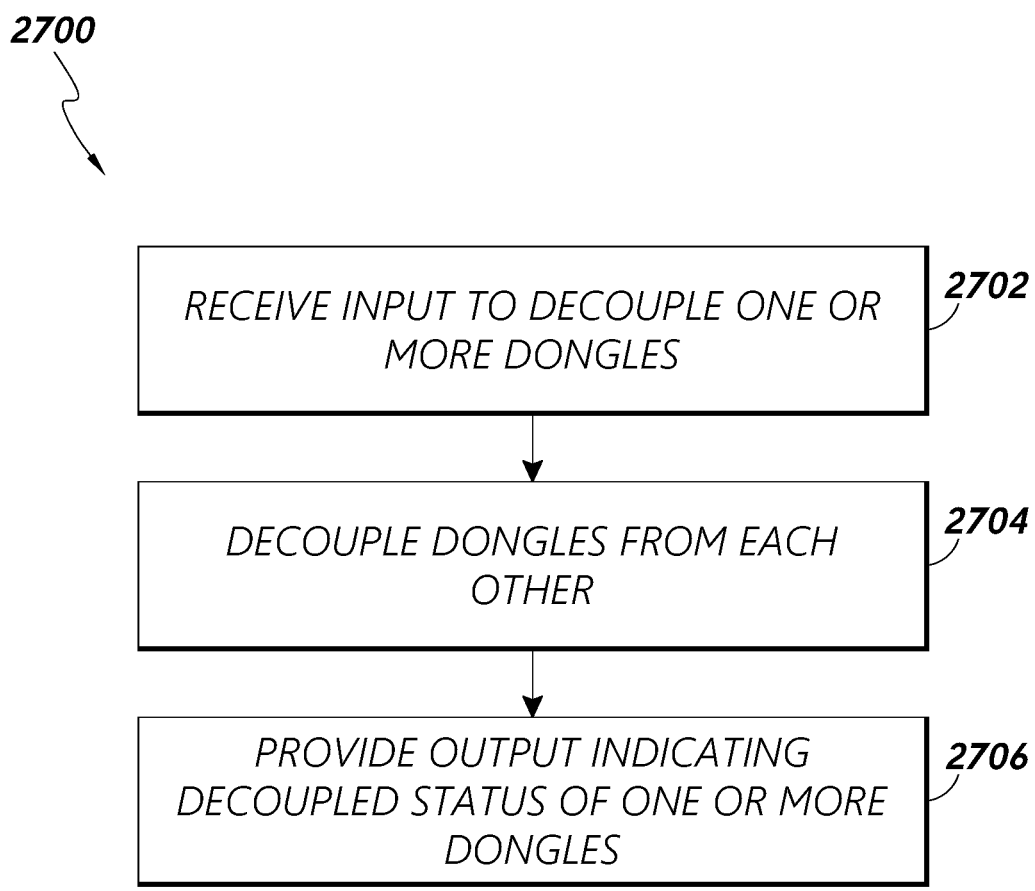
FIG. 27 is a flow diagram illustrating a process for decoupling one or more dongles in accordance with one or more embodiments of the present disclosure.

FIG. 27 illustrates an example flow diagram of a process 2700 for decoupling one or more dongles from communicating with each other in accordance with one or more embodiments of the present disclosure. The process 2700 can be performed by any of the devices discussed herein, such as a dongle-connectivity management hub, one or more sensor dongles, one or more monitor dongles, and/or a medical monitor system.

At block 2702, the process 2700 can involve receiving input indicating a desire or condition for decoupling one or more dongles. For example, in some embodiments, a user can select a disconnect button, or engage another type of user-input mechanism, on or associated with a sensor/monitor dongle to initiate/direct a decoupling of the sensor/monitor dongle from another sensor/monitor dongle. Further, in some embodiments, a user can interact with a dongle-connectivity management hub, such as by selecting/engaging a disconnect button/feature of or otherwise associated with a user interface, to thereby initiate a decoupling of a sensor/monitor dongle with another sensor/monitor dongle, at least under and/or subject to certain conditions (e.g., pre-conditions).

At block 2704, the process 2700 can involve decoupling the identified/indicated dongles from one another. For example, based on input received in connection with the operation associated with block 2702, a sensor/monitor dongle can disconnect (e.g., be disconnected) from a wireless coupling with another sensor/monitor dongle. In some embodiments, a dongle-connectivity management hub can communicate with one or more sensor/monitor dongles to facilitate the decoupling (e.g., request that a sensor/monitor dongle disconnect from an association with another sensor/monitor dongle).

At block 2706, the process 2700 can involve providing output indicating a 'decoupled' status of one or more of the dongles of interest described above in connection with operations associated with blocks 2702 and/or 2704 of the process 2700. For example, a sensor/monitor dongle that has recently become disconnected from a wireless coupling can output light, audio, and/or other indicator via one or more user I/O components to provide an indication of a decoupled status of the sensor dongle and/or the monitor dongle. Additionally or alternatively, a dongle-connectivity management hub can provide output via one or more user I/O components (e.g., an icon or other visual representation associated with a graphical user interface) to indicate a decoupled status of a sensor dongle and/or a monitor dongle that have disconnected from a wireless coupling.

FIG. 28 illustrates aspects relating certain example processes of decoupling one or more dongles from communicating with each other based on input received at a dongle in accordance with one or more embodiments. The processes associated with FIG. 28 are described and illustrated for convenience in the context of a wireless sensor-monitor connectivity system 2800 implemented within a healthcare environment, such as a hospital room, operating room, or any other room or facility where a patient 2870 can receive medical care/treatment. In the illustrated example, the patient 2870 is disposed on a hospital bed 2880 with one or more sensors 2840 configured to measure certain physiological parameters associated with the patient 2870 that can be utilized to obtain/derive information about the health of the patient 2870. The system 2800 includes sensor dongles 2850 configured to physically and/or electrically connect to respective ones of the sensors 2840, monitor dongles 2830 configured to wirelessly couple to the sensor dongles 2850 and/or to physically and/or electrically connect to respective connectors of and/or communicatively coupled to the medical monitor system 2820, and a dongle-connectivity management hub 2810 configured to manage connections between the monitor dongles 2830 and the sensor dongles 2850. The dongle-connectivity management hub 2810 can be configured to generate user interface data and/or provide/present a user interface (UI) 2881 to a user 2860.

In the example use case represented at least in part by the diagram of FIG. 28, the sensor dongle 2850C may be initially wirelessly coupled to the monitor dongle 2830C for communication therewith. In accordance with some use cases, the user 2860 may select/engage a disconnect button or other input mechanism or feature of or otherwise associated with the sensor dongle 2850C to initiate a decoupling (e.g., decoupling process) of the sensor dongle 2850C from the monitor dongle 2830C. In response to engagement with the disconnect button/feature of the sensor dongle 2850C, the sensor dongle 2850C can be configured to send a communication/signal(s) (e.g., wireless data transmission) to the monitor dongle 2830C and/or the dongle-connectivity management hub 2810 directing the same to decouple the sensor dongle 2850C from the monitor dongle 2830C. The sensor dongle 2850C and the monitor dongle 2830C may then become wirelessly decoupled/disconnected in some manner, as illustrated by the dashed lines around the sensor dongle 2850C and the monitor dongle 2830C. In a decoupled state, the sensor dongle 2850C and/or the monitor dongle 2830C can be configured to output light, audio, or another indicator via one or more user I/O components to provide an indication of the decoupled state (e.g., output a solid red light, a flashing red light, speech of "disconnected," information on a display, etc.). Although some examples are discussed herein in the context of the user 2860 pressing/engaging a disconnect button on the sensor dongle 2850C to initiate the decoupling, the user can, alternatively or additionally, utilize a disconnect button on the monitor dongle 2830C to initiate wireless decoupling.

In some embodiments, the dongle-connectivity management hub 2810 can be configured to provide output to indicate the decoupled state of the sensor dongle 2850C and/or the monitor dongle 2830C. For example, the dongle-connectivity management hub 2810 can present a UI 2881 that includes visual icons/representations 2883 and 2884 representing the sensor dongles 2850 and the monitor dongles 2830, with the visual representations 2883C and 2884C (representing the sensor dongle 2850C and the monitor dongle 2830C, respectively) being displayed with disconnection-related/indicating icons/imagery and/or without a visual link between the representations 2883C and 2884C. Although certain disconnection-type icons are illustrated in FIG. 28, in some embodiments other types of visual representations are presented/utilized. For example, the visual representations 2883C and 2884C can be presented with searching/detection-indicating icons to illustrate that the sensor dongle 2850C and the monitor dongle 2830C are disconnected but are still detected. Moreover, in some embodiments, the disconnection-type icons shown in FIG. 28 can change to searching/detection-type icons after an amount of time, such as a number of seconds, minutes, etc. In some embodiments where the sensor dongle 2850C and the monitor dongle 2830C have intentionally decoupled, and the visual representations 2883C and 2884C are displayed with searching/detected icons, the sensor dongle 2850C and/or the monitor dongle 2830C may not actually be searching for a new wireless coupling even though such icons are presented.

Figures 1, 29:
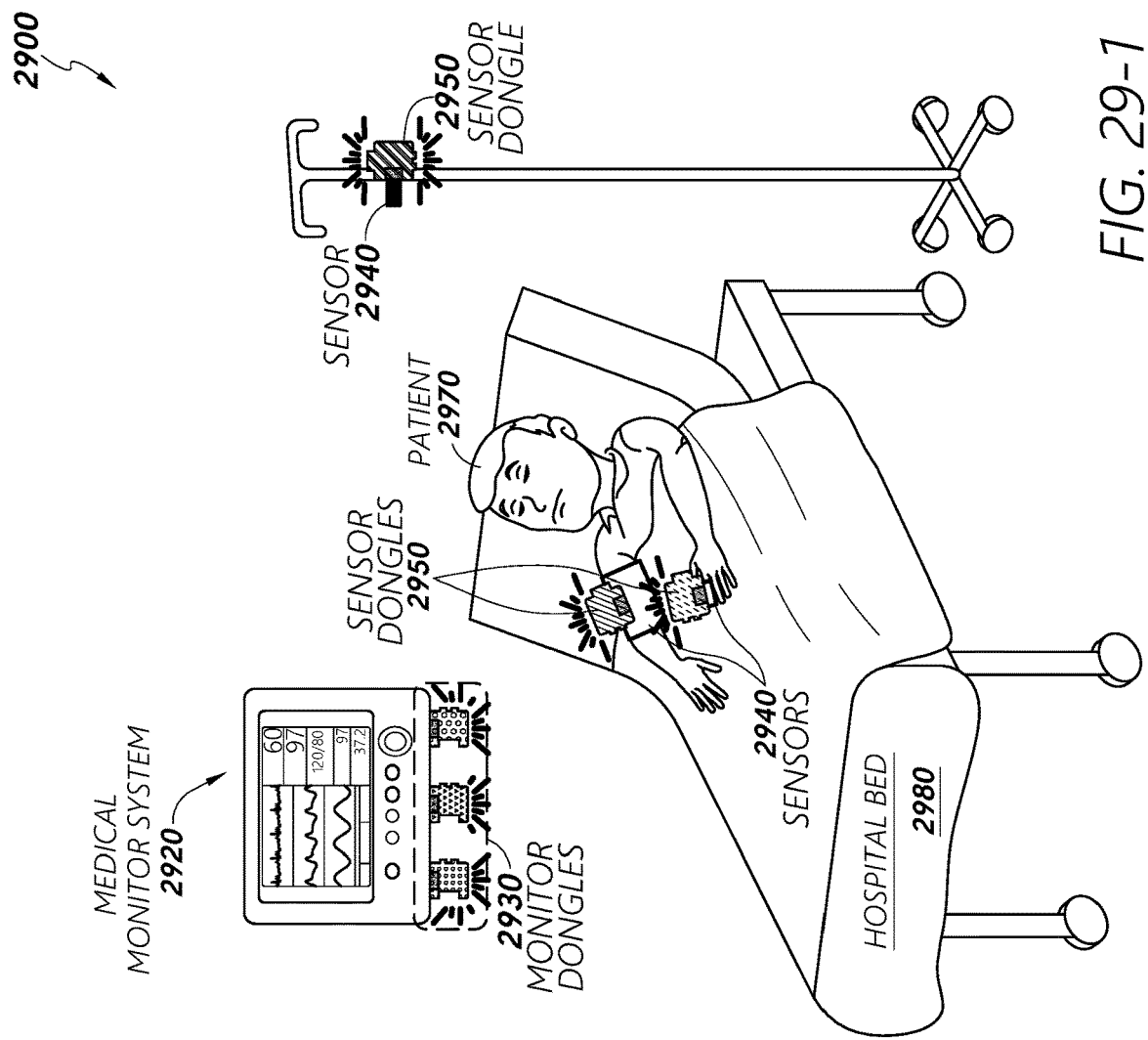
Figure 29:
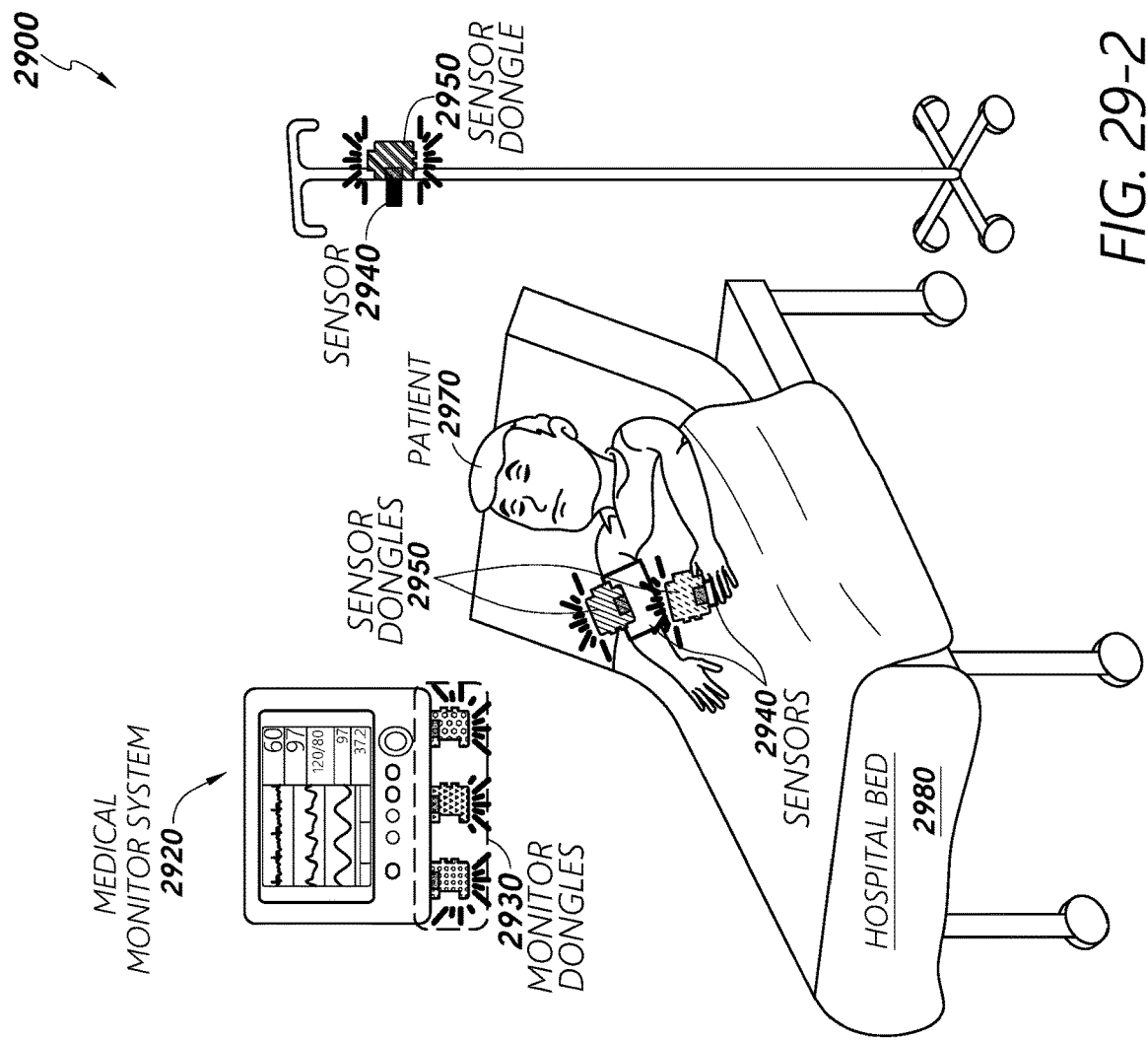
Figure 2:
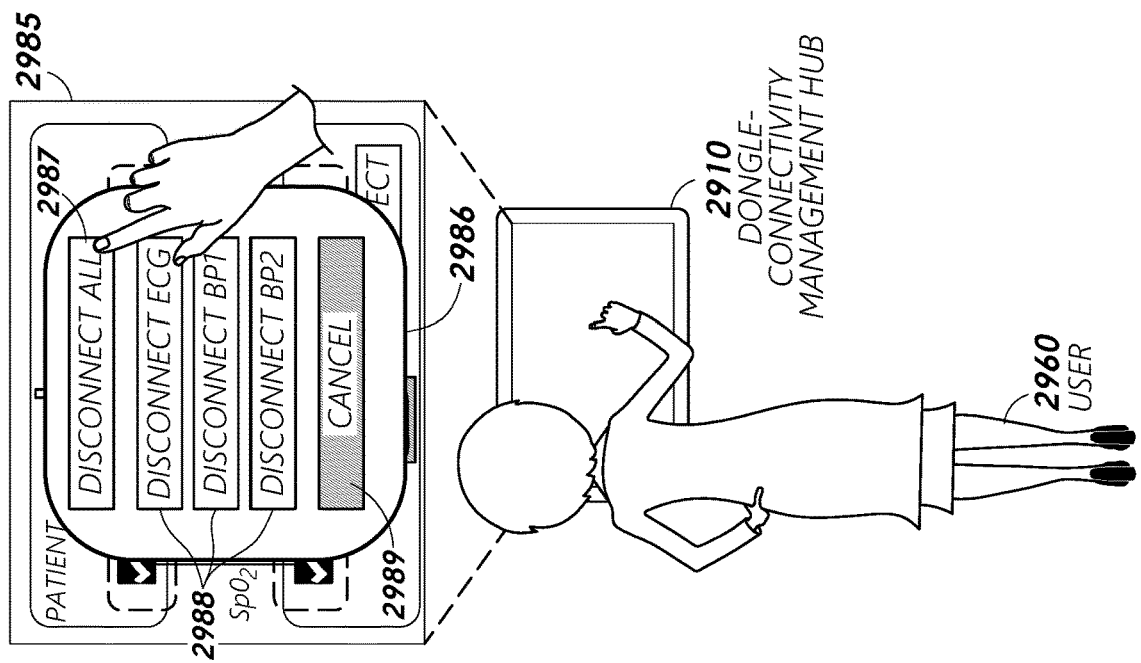
Figures 3, 29:
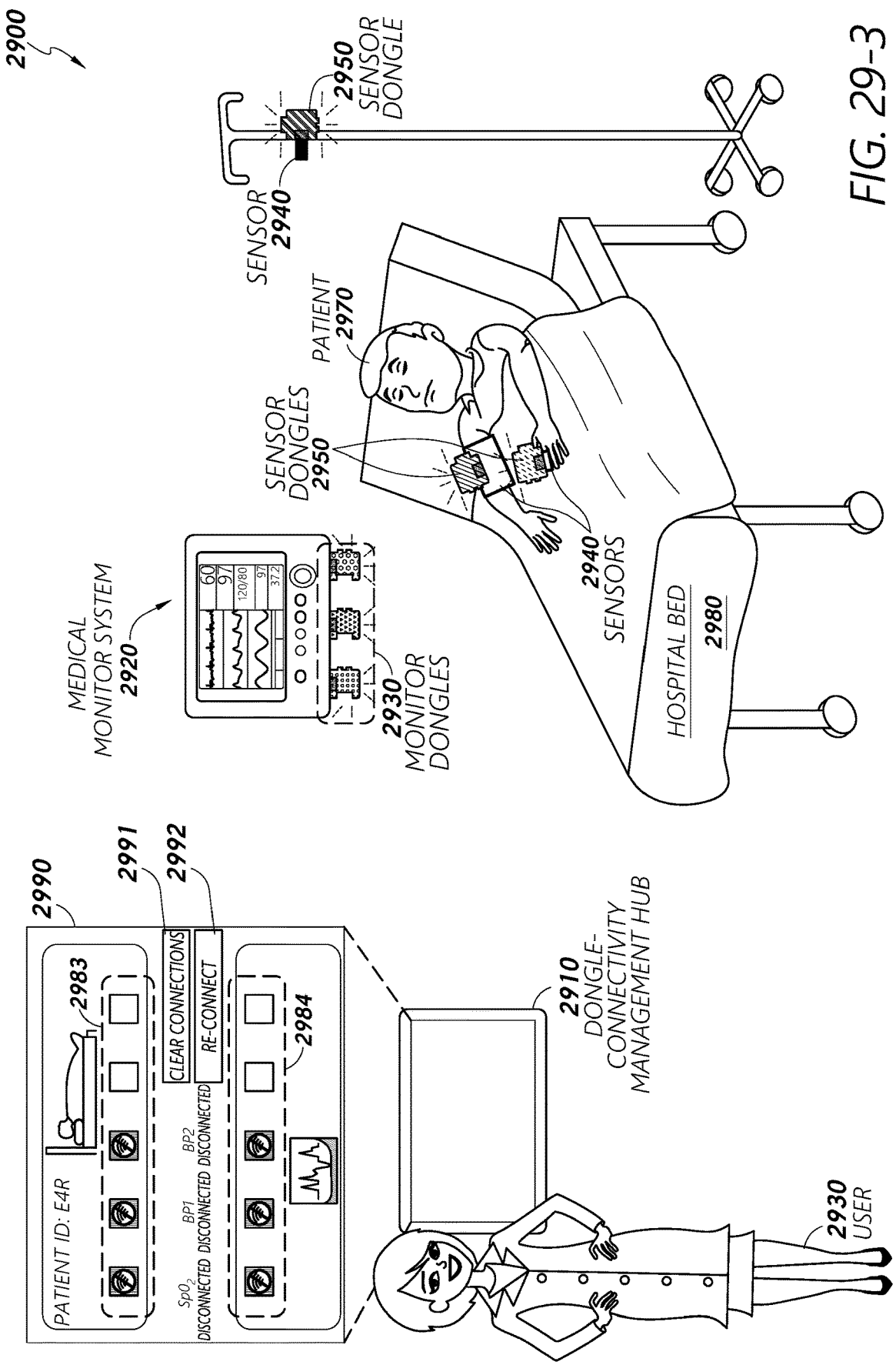

FIGS. 29-1 through 29-3 illustrate aspects of certain example process(es) for decoupling one or more dongles from wireless connectivity with each other based on input received at a dongle-connectivity management hub in accordance with one or more embodiments. The embodiments associated with FIGS. 29-1 through 29-3 are generally described and illustrated, for simplicity, in the context of a wireless sensor-monitor connectivity system 2900 implemented within a healthcare environment, such as a hospital room, operating room, or any other room or facility where a patient 2970 can receive medical care/treatment. In the illustrated examples, the patient 2970 is disposed on a hospital bed 2980 with one or more sensors 2940 configured to measure certain physiological parameters associated with the patient 2870 that can be utilized to obtain/derive information about the health of the patient 2970. The system 2900 includes sensor dongles 2950 configured to physically and/or electrically connect to respective ones of the sensors 2940, monitor dongles 2930 configured to wirelessly couple to the sensor dongles 2950 and/or to physically and/or electrically connect to respective connectors of and/or communicatively coupled to the medical monitor system 2920, and a dongle-connectivity management hub 2910 configured to manage connections between the monitor dongles 2930 and the sensor dongles 2950. The dongle-connectivity management hub 2910 can be configured to generate user interface data and/or provide/present a user interface (UI) 2981 to a user 2960.

According to certain use cases relating to the diagram of FIG. 29-1, one or more of the sensor dongles 2950 may be initially wirelessly coupled to respective ones of the monitor dongles 2930, respectively, as illustrated by the solid lines emanating from the sensor dongles 2950 and the monitor dongles 2930. Further, a user interface (UI) 2981 can be displayed using the dongle-connectivity management hub 2910, wherein the UI 2981 includes certain visual representations 2983 and 2984 and visual links between the various icons/representations to illustrate/represent wireless couplings between the sensor dongles 2950 and the monitor dongles 2930. In this example, the user 2960 initiates one or more decouplings of the sensor dongles 2950 to the monitor dongles 2930 by pressing/engaging a disconnect button or other mechanism/feature 2982 provided via the UI 2981. The dongle-connectivity management hub 2910 can be configured present a UI 2985 (e.g., on an electronic display device) in response to pressing/engaging the disconnect button 2982, as shown in FIG. 29-2.

The UI 2985 shown in FIG. 29-2 can include a pop-up window 2986, or similar type of interface, with options to disconnect all dongles or to individually disconnect dongles. In particular, the UI 2985 can include a button 2987 that, when pressed/selected, initiates a disconnect of all the sensor dongles 2950 from the monitor dongles 2930. Additionally or alternatively, the UI 2985 can include one or more buttons 2988 that, when selected, initiate a disconnect of a respective one of the sensor dongles 2950 (or sensor/ monitor dongle pair) from one of the monitor dongles 2930, and/or a cancel button 2989 that, when selected, closes-out the pop-up window 2986. In the example of FIG. 29-2, the user 2960 selects the button 2987 to disconnect all of the sensor dongles 2950 and the monitor dongles 2930. In response, the dongle-connectivity management hub 2910 may decouple the sensor dongles 2950 from the monitor dongles 2930 by updating information stored on the dongle-connectivity management hub 2910 or elsewhere, such as in a cloud resource, to indicate that the sensor dongles 2950 and the monitor dongles 2930 are no longer wirelessly coupled to each other. Further, the dongle-connectivity management hub 2910 can be configured to send/transmit a communication to each of the sensor dongles 2950 and/or the monitor dongles 2930 to instruct/direct the sensor dongles 2950 and/or the monitor dongles 2930 to cease communication with each other.

The sensor dongles 2950 and/or the monitor dongles 2930 can decouple from each other and/or provide output indicating a disconnected status, as illustrated by the dotted lines emanating from the sensor dongles 2950 and the monitor dongles 2930 in FIG. 29-3. In some embodiments, the dongle-connectivity management hub 2910 can also send/transmit communications to the medical monitor system 2920 indicating that the sensor dongles 2950 have decoupled from the monitor dongles 2930.

Moreover, in response to selecting the button 2987, the dongle-connectivity management hub 2910 can present a UI 2990 that shows a disconnected status of the sensor dongles 2950 and the monitor dongles 2930, as also illustrated in FIG. 29-3. In particular, the UI screen 2990 shows the visual representations 2983 and 2984 with disconnected icons to show that the wireless couplings between the sensor dongles 2950 and the monitor dongles 2930 have been disconnected. In some embodiments, the dongle-connectivity management hub 2910 can maintain, at least for a period of time, information indicating dongle pairings (e.g., which sensor dongle was wirelessly coupled to which monitor dongle). If, for example, one or more of the previous dongle pairings are desired, the user 2960 can select a reconnect button 2992 to reestablish the previous wireless couplings between the sensor dongles 2950 and the monitor dongles 2930. However, if desired, in some implementations, the user 2960 can clear the information indicating the previous dongle pairings (e.g., delete the information) by selecting a clear connections button 2991. If the clear connections button 2991 is selected, the dongle-connectivity management hub 2910 can update the visual representations 2983 and 2984 to a searching/detected status to indicate that the sensor dongles 2950 and/or the monitor dongles 2930 have been detected by the dongle-connectivity management hub 2910 but are not yet wirelessly coupled to each other.

In some embodiments, the sensor dongles 2950 and/or the monitor dongles 2930 can be disconnected while transporting the patient 2970 from one room to another. If the clear connections button 2991 is not selected, the dongle-connectivity management hub 2910 can maintain information indicating previous dongle pairings. For example, if the patient 2970 returns to the same room with the medical monitor system 2920 or if the monitor dongles 2930 are moved to a new room where the patient 2970 is relocated and connected to a new medical monitor system, the dongle-connectivity management hub 2910 can reestablish the wireless couplings between the sensor dongles 2950 and the monitor dongles 2930 in response to a user selecting the reconnect button 2992.

Additional User Interfaces Features

Figure 30:
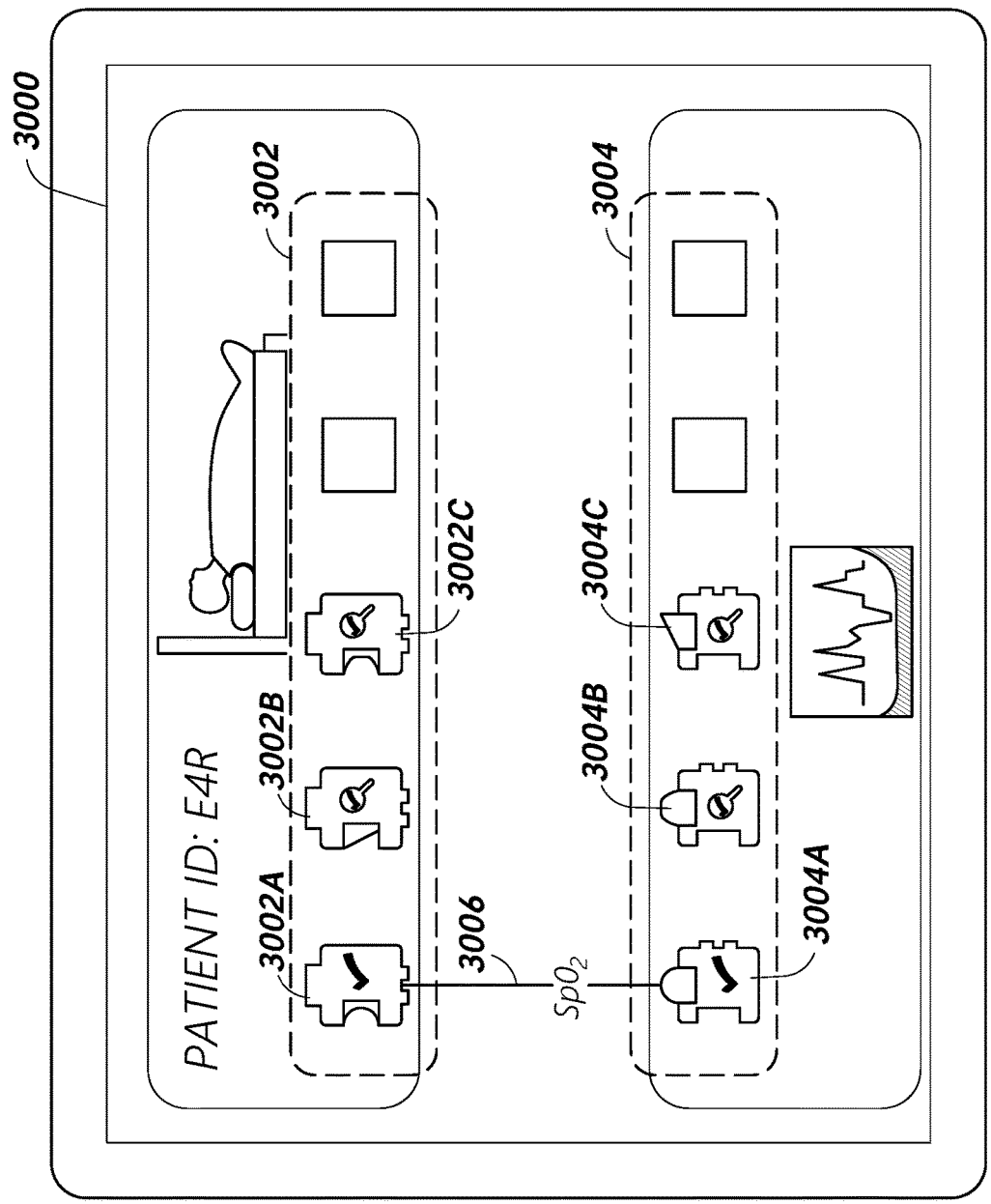
FIG. 30 illustrates a dongle-connectivity user interface in accordance with one or more embodiments.

FIG. 30 illustrates an example user interface 3000 that includes visual representations 3002 and 3004 with visual indications representing the types of dongles associated with the visual representations in accordance with one or more embodiments. The user interface 3000 can be presented using any of the dongle-connectivity management hubs discussed herein and/or any other device, such as a medical monitor system, a user device, and so on. In examples, the visual representations 3002 can represent sensor dongles that have been detected by a dongle-connectivity management hub (not illustrated), whereas the visual representations 3004 can represent monitor dongles that have been detected by the dongle-connectivity management hub. In some embodiments, as shown, a wireless coupling can be established between a sensor dongle associated with the visual representation 3002A and a monitor dongle associated with the visual representation 3004A, as represented by the checkmarks on the visual representations 3002A and 3004A and a visual link 3006 between the representations 3002A and 3004A.

In the example of FIG. 30, the visual representations 3002 and 3004 have shapes that represent the types of associated dongles. For example, the visual representations 3002 can be shaped similar to shapes of the associated sensor dongles and the visual representations 3004 can be shaped similar to shapes of the associated monitor dongles. A connector portion on each of the visual representations 3002 and 3004 can have a shape that indicates a type of the associated dongle. For example, the connector portion of the visual representations 3002A has a semi-circle female shape indicating that the associated sensor dongle has a sensor connector that is configured to connect to a particular type of sensor (e.g., a pulse oximetry device). Similarly, the connector portion of the icon 3004A has a semi-circle male shape indicating that the associated monitor dongle has a monitor connector that is configured to connect to a particular type of monitor port (e.g., pulse oximetry port on a medical monitor system).

In some embodiments, a dongle can provide information to a dongle-connectivity management hub that indicates a type of the dongle, wherein the dongle-connectivity management hub can use such information to present a shape of the visual representations 3002 and 3004. For example, a dongle can send information indicating a particular type of connector on the dongle, a particular type of sensor or port with which the dongle is configured connected, and so on. Although the visual representations 3002 and 3004 are illustrated with particular shapes to indicate the types of associated dongles, other indicators can be used, such as by displaying an icon on a visual representation that indicates a type of dongle/sensor (which can indicate a brand of a sensor), displaying a visual representation in a particular color/fill pattern/shading, or displaying the visual representation in another manner.

In some embodiments, displaying a shape for a visual representation allows a user to more easily match dongles to establish wireless couplings between the dongles. For example, if a dongle-connectivity management hub has automatically established a wireless coupling between dongles associated with the visual representations 3002A and 3004A, and the dongles associated with the visual representations 3002B-3002C and 3004B-3004C remain waiting to be wirelessly coupled (e.g., wireless couplings were not able to be automatically established), a user (not illustrated) can view the shapes of the visual representations 3002B-3002C and 3004B-3004C to more easily determined which dongles to wirelessly couple. For instance, a user can view that the connector portions of the visual representation 3002B and the visual representation 3004C are associated with a triangle shape (indicating that corresponding dongles are associated with a blood pressure cuff and/or a particular brand, for example) and can draw or indicate a line/link between the visual representation 3002B and the visual representation 3004C to cause a wireless coupling to be established between the dongles. The user can therefore provide input associating respective icons of a monitor dongle and a sensor dongle on an electronic display or other input device to initiate establishment of a wireless coupling/association between such dongles. Further, in some embodiments, displaying a shape for a visual representation allows a user to more easily confirm a wireless coupling that is established. For example, a user can confirm that the dongles associated with the visual representations 3002A and 3004A (which are linked together), are appropriately coupled, since the visual representations 3002A and 3004A are associated with a semi-circle shape at a connector portion of the visual representations 3002A and 3004A.

Patient Transport Connectivity

Figure 31:
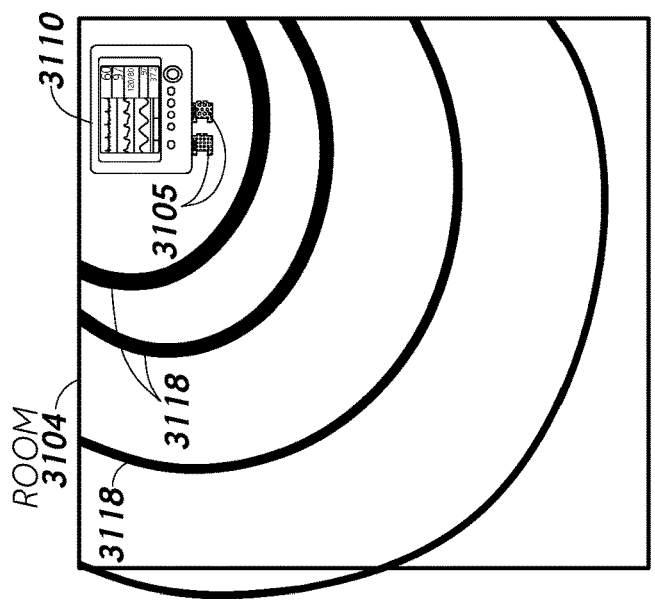
Figure 1:
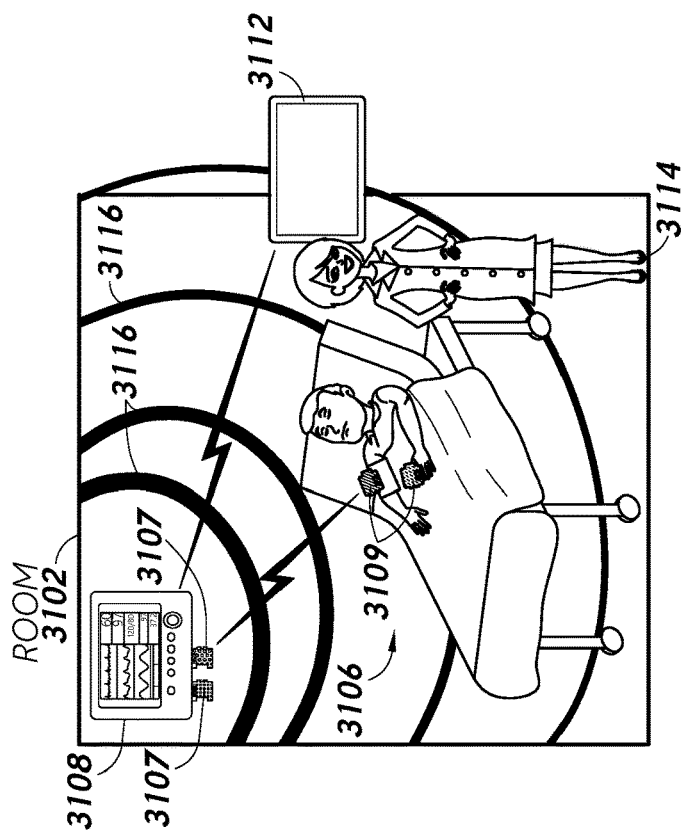
Figures 2, 31:
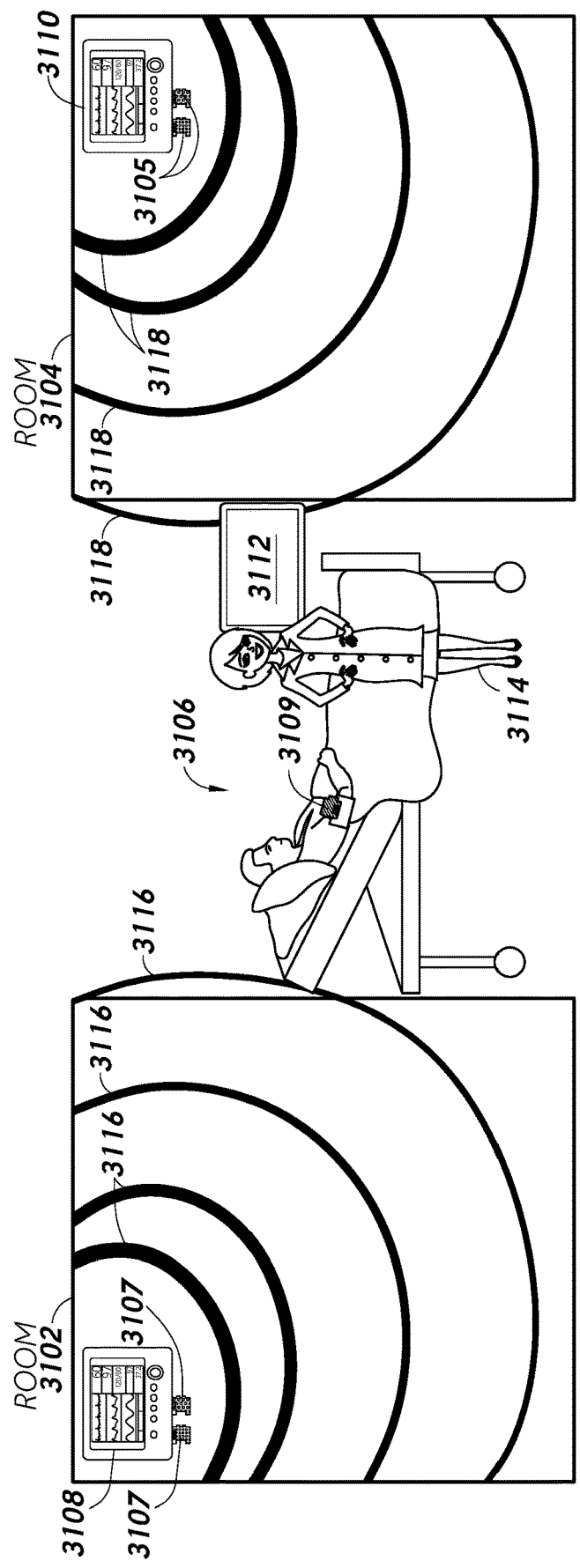
Figure 31:
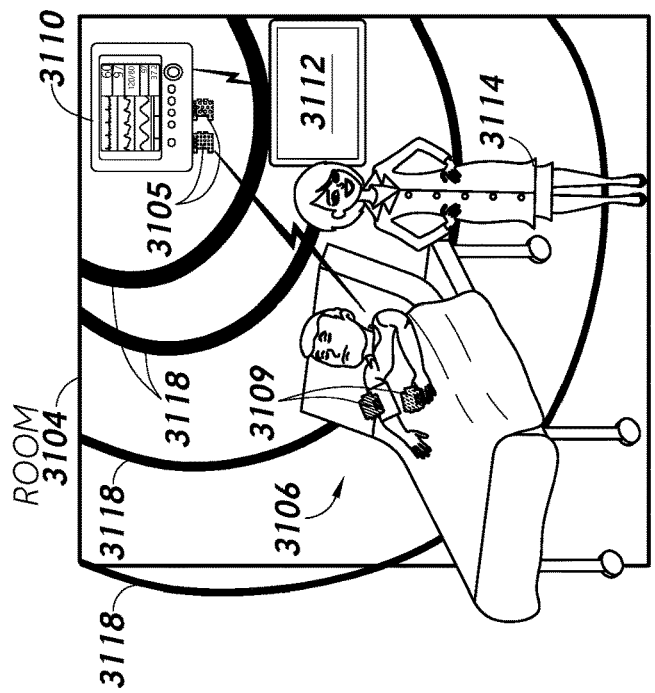
Figure 3:
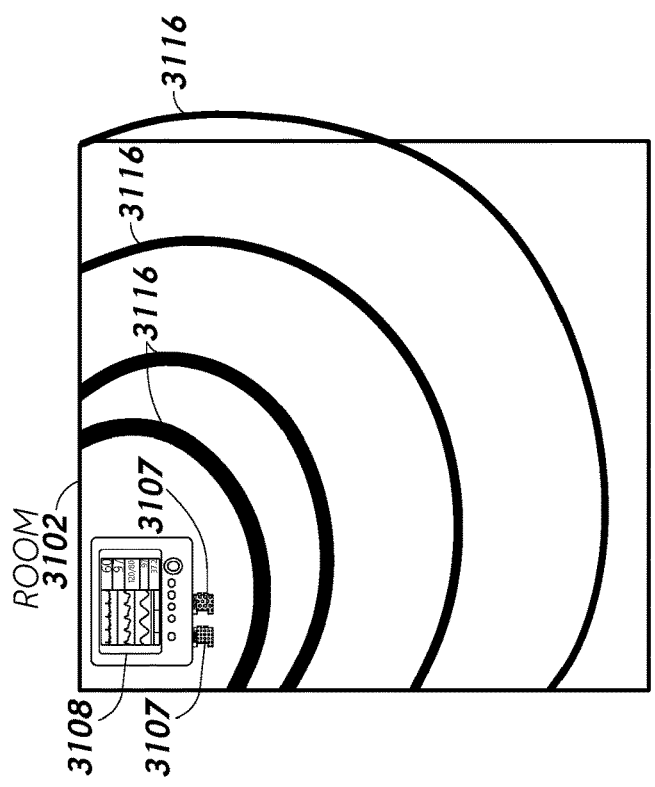

FIGS. 31-1 through 31-3 illustrate aspects of example patient-transport systems and processes in which patient-monitoring functionality is transferred from a medical monitor system to a dongle-connectivity management hub and/or a sensor dongle during mobilization of a patient in accordance with one or more embodiments of the present disclosure. In some implementations, as shown in FIG. 31-1, sensors are attached to, or otherwise configured/disposed to measure certain physiological parameter(s) of, a patient 3106, wherein the sensors are physically and/or electrically connected to respective sensor dongles.

As illustrated in FIG. 31-1, the patient 3106 may initially be located in a room 3102, wherein sensor dongles 3109 are wirelessly coupled to respective monitor dongles 3107. The monitor dongles 3107 are physically and electrically connected to a medical monitor system 3108 and/or connector(s) associated therewith to monitor health of the patient 3106. That is, the medical monitor system 3108 may initially perform patient-monitoring functionality to monitor one or more parameters associated with the health of the patient 3106. Although areas 3102 and 3104 are described herein as rooms, it should be understood that such features of FIGS. 31-1 through 31-3 may be any physical area or space, structure, or location, whether or not partitioned in any manner. For example, the areas 3102 and 3104 may represent different areas of a single room, hall, or other at least partially enclosed space.

When an event occurs, such as the patient 3106 being removed from the room 3102, or simply moved out of an effective wireless range of the monitor dongle(s) 3107 and/or monitor system 3108, the patient-monitoring functionality can be transferred to a dongle-connectivity management hub 3112 and/or one or more of the sensor dongles attached to the patient 3106 at least partially in response to such event. The dongle-connectivity management hub 3112 and/or one or more of the sensor dongles 3109 can then implement certain patient-monitoring functionality while the patient 3106 is being transported, such as from the room 3102 to a room 3104, as illustrated in FIG. 31-2. When another event occurs, such as the patient 3106 entering the room 3104, and/or coming into wireless communication range 3118 of monitor dongle(s) 3105 and/or a monitor system 3110 associated with the second room or area 3104, the patient-monitoring functionality can be transferred to the medical monitor system 3110 located in the room/area 3104, as illustrated in FIG. 31-3.

In some embodiments, a user 3114 can interface with the dongle-connectivity management hub 3112 to facilitate a transfer of patient-monitoring functionality. For example, the dongle-connectivity management hub 3112 can provide an interface (e.g., a transfer interface) with one or more interface elements that allow the user 3114 to initiate a transfer of patient-monitoring functionality to another device, such as may be implemented in anticipation of the patient 3106 being transported from the room 3102. The management hub 3112 may further provide a mechanism to designate a device to implement the patient-monitoring functionality during patient transport. The management hub 3112 may further provide a mechanism to transfer the patient-monitoring functionality to a local device when the patient 3106 has been transported to the room 3104, and so on. In some examples, the user 3114 can designate the dongle-connectivity management hub 3112 and/or one or more of the sensor dongles 3109 to implement the patient-monitoring functionality during patient transport. Further, in some examples, the dongle-connectivity management hub 3112 can automatically designate a device to implement the patient-monitoring functionality during patient transport. Additionally or alternatively, the dongle-connectivity management hub 3112 can provide a user interface with one or more disconnect buttons, such as that shown in the context of FIG. 29-2, that allows the user 3114 to disconnect one or more sensor/monitor dongles, which can initiate a transfer of patient-monitoring functionality. For example, in response to selecting a disconnect button, the dongle-connectivity management hub 3112 can present a button that can be selected to initiate a transfer of patient-monitoring functionality.

Further, in some embodiments, the user 3114 can interface with one or more of the sensor dongles 3109 configured for the patient 3106 and/or one or more of the monitor dongles 3107 to facilitate a transfer of patient-monitoring functionality. For example, if the patient 3106 is located in the room 3102 and the user 3114 selects a patient-transport button on a sensor/monitor dongle, the sensor/monitor dongle can begin to buffer sensor-related data locally (e.g., on one or more data storage devices thereof) and/or send/transmit sensor-related data to the dongle-connectivity management hub 3112 to allow the hub 3112 to implement certain patient-monitoring functionality. In some examples, if the user 3114 presses a patient-transfer button (or engages another type of I/O feature in a relevant manner) on a sensor dongle attached to the patient 3106 (or a monitor dongle connected to the medical monitor system 3108), all of the sensor dongles attached to the patient 3106 (or a predetermined number of sensor dongles) can begin to buffer sensor-related data locally and/or send the sensor-related data to the dongle-connectivity management hub 3112. Additionally or alternatively, the medical monitor system 3110 can be configured to assume at least some aspects of the patient-monitoring functionality when the patient 3106 enters the room 3104 and/or the user 3114 selects a patient transport button on the monitor dongle associated with the medical monitor system 3110 and/or a patient transport button on one or more of the sensors associated with the patient 3106.

Further, in some embodiments, patient-monitoring functionality can be transferred when one or more sensor dongles decouple from one or more monitor dongles and/or the one or more sensor dongles establish wireless couplings with the one or more monitor dongles (e.g., at least partially in response to occurrence of such event(s)). For example, the dongle-connectivity management hub 3112, a sensor dongle, and/or a monitor dongle can determine that a predetermined number (or all) of wireless couplings have been disconnected and/or disconnected within a predetermined amount of time, such as when the patient 3106 is transported out of the room/area 3102. In some embodiments, the dongle-connectivity management hub 3112 and/or a sensor dongle can take over patient-monitoring functionality. To illustrate, if all of the sensor dongles 3109 associated with the patient 3106 lose connectivity signal fidelity to some degree with corresponding respective monitor dongles (e.g., the signal strength drops below a threshold) within the same period of time, such as a number of seconds, the dongle-connectivity management hub 3112 can be configured to assume certain patient-monitoring functionality at least partially based on such determination. Additionally or alternatively, the medical monitor system 3110 may be configured to assume certain patient-monitoring functionality at least partially in response to a determination by the dongle-connectivity management hub 3112, a sensor dongle, and/or a monitor dongle that a predetermined number (or all) of wireless couplings have been established and/or established within a predetermined amount of time.

A wireless coupling between a sensor dongle associated with the patient 3106 and a monitor dongle connected to the medical monitor system 3110 can be established in any of the manners discussed herein, such as the user 3112 selecting a connect button on a dongle and/or the dongle-connectivity management hub 3112, a sensor dongle and a monitor dongle automatically establishing a wireless coupling when within communication range due to the sensor dongle and the monitor dongle having been previously wirelessly coupled, and so on.

In some embodiments, patient-monitoring functionality is transferred to and/or from a device when the patient 3109 is outside a particular proximity to the medical monitor system 3108 and/or within a particular proximity to the medical monitor system 3110. For example, the dongle-connectivity management hub 3112 can receive data from one or more of the sensor dongles associated with the patient 3106 and/or the monitor dongles connected to the medical monitor system 3108, such as acceleration data generated by an accelerometer on a dongle indicating an acceleration, magnetism data generated by a magnetometer on a dongle indicating a direction, strength, and/or relative change of a magnetic field, orientation/angular-velocity data generated by a gyroscope on a dongle indicating orientation and/or angular velocity, geolocation data generated by a satellite-based navigation system (e.g., Global Positioning System (GPS)) indicating a geolocation of the dongle, signal strength data generated by a dongle to indicate a signal strength with another dongle, and so on. The dongle-connectivity management hub 3112 or another device can analyze the data to determine that one or more of the sensor dongles associated with the patient 3106 have moved outside a predetermined distance to the medical monitor system 3108. In some implementations, the dongle-connectivity management hub 3112 and/or a sensor dongle can assume certain patient-monitoring functionality.

Additionally or alternatively, the medical monitor system 3110 can assume certain patient monitoring functionality when it is determined, based on an analysis of data, that the patient 3106 is within a predetermined distance of the medical monitor system 3110. In the example of FIG. 31-1, lines 3116 represent signal strength or connectivity range of the monitor dongles 3107 connected to the medical monitor system 3108 and lines 3118 represent signal strength or connectivity range of the monitor dongles connected to the medical monitor system 3110. In examples, a medical monitor system that implements patient-monitoring functionality can be a medical monitor system that is closest to the patient 3106 and/or associated with a relatively strong signal strength to the sensor dongles 3109 attached to the patient 3106.

As noted above, in some embodiments, the dongle-connectivity management hub 3112 can be configured to perform certain patient-monitoring functionality during a patient transport. For example, the dongle-connectivity management hub 3112 can assume or take over certain communication and/or management functionality from the medical monitor system 3108 when the patient 3106 leaves the room 3102 so that the sensor dongles 3109 communicate with the dongle-connectivity management hub 3112 instead of with the monitor dongles 3107 connected to the medical monitor system 3108. That is, the sensor dongles 3109 can be configured to send sensor-related data to just the dongle-connectivity management hub 3112 in a transport mode. The dongle-connectivity management hub 3112 can be configured to process the sensor-related data and/or provide output regarding one or more parameters relating to the health of the patient 3106, similar to certain medical monitor systems.

As referenced above, in some embodiments, a sensor dongle in accordance with aspects of the present disclosure can be configured to implement patient-monitoring functionality during a patient transport. For example, a specific sensor dongle associated with the patient 3106 can be designated to perform certain patient-monitoring functionality and/or connectivity-management functionality that is generally performed by a dongle-connectivity management hub (e.g., the sensor dongle can act as a connectivity management hub) in accordance with some embodiments of the present disclosure. For instance, a sensor dongle can be configured to receive sensor-related data from one or more other sensor dongles and maintain (e.g., store) the sensor-related data locally until the patient 3106 arrives at the room/space 3104. Additionally or alternatively, a sensor dongle can assume certain connectivity-management functionality to manage wireless couplings between sensor dongles and monitor dongles at least in part, which may allow the system to function substantially without the dongle-connectivity management hub 3112. Moreover, in some embodiments, the sensor dongles 3109 associated with the patient 3106 can be configured to individually buffer (e.g., temporarily store) sensor-related data in local data storage without sending the sensor-related data to another dongle and/or the dongle-connectivity management hub 3108 (or in addition to sending the sensor-related data to the dongle-connectivity management hub 3108, in some cases) in a transport mode of operation. For example, each of the sensor dongles 3109 can be configured to individually store sensor data locally in response to the patient 3116 leaving the room/area 3102 and/or individually provide the sensor data to the medical monitor system 3110 in response to the patient entering the room/area 3104.

By transferring at least certain aspects of necessary or desirable patient-monitoring functionality during a patient transport, the patient-transport techniques and processes/mechanisms discussed herein can advantageously reduce cumbersomeness and/or improve ease of use compared to certain other patient-transport solutions. For example, patient-monitoring functionality can be transferred to and/or from a dongle-connectivity management hub and/or a sensor dongle without using a separate transport medical monitor system, which is implemented in some patient-transport solutions. In particular, some patient-transport solutions can require a user to disconnect sensors from a first medical monitor system, connect the sensors to a separate transport medical monitor system, and then re-connect the sensors to a new medical monitor system at a new location after the patient has been transported to the new location in order to maintain substantially continuous monitoring during transport. Such patient-transport solutions can be undesirably time-consuming, which can adversely affect the medical care/treatment provided to the patient, such as in cases where a patient is suffering from a critical medical condition needs to be urgently transported to another room or facility. The patient-transport techniques and processes/mechanisms discussed above can at least partially alleviate or avoid/prevent such drawbacks that may be associated with some patient-transport solutions.

Multi-Patient Connectivity Management

Figure 32:
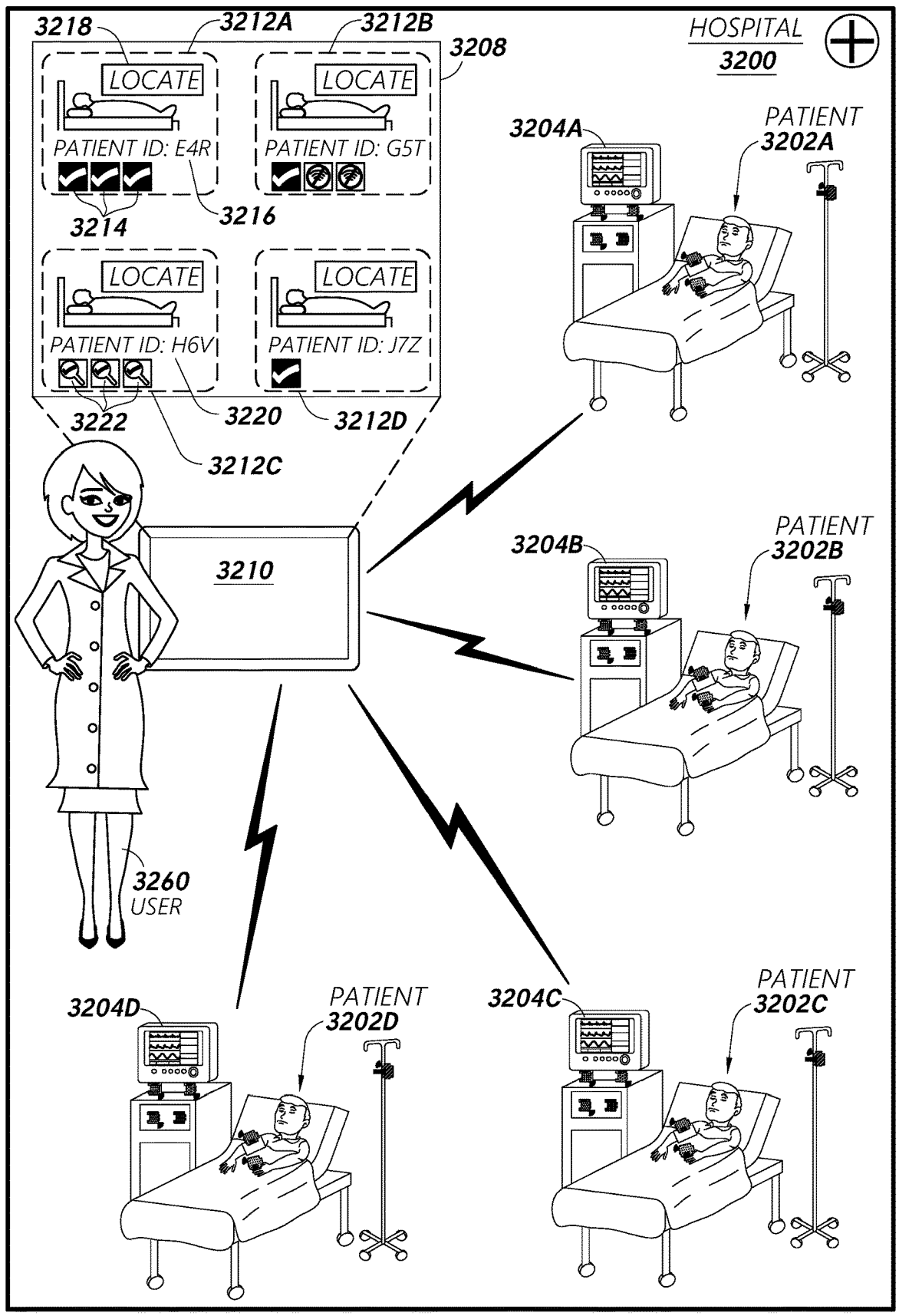
FIG. 32 illustrates example multi-patient patient-monitoring systems, devices, and processes in according with one or more embodiments.

FIG. 32 illustrates example multi-patient patient-monitoring systems, devices, and processes in according with one or more embodiments of the present disclosure. In particular, the systems, devices, and processes relating to FIG. 32 and the associated descriptive text herein can relate to a dongle-connectivity management hub 3210 that is configured to provide certain functionality for managing devices associated with multiple patients 3202 in accordance with one or more embodiments. In some implementations, the dongle-connectivity management hub 3210 is implemented at least in part in a hospital environment 3200 and is configured to communicate with multiple medical monitor systems 3204 and/or dongles associated with respective ones of the multiple patients 3202.

The patients 3202 can be located in different rooms, the same room, or a combination thereof. In some embodiments, the dongle-connectivity management hub 3210 is used to establish and/or manage wireless couplings between monitor dongles and respective sensor dongles associated with each of the patients 3202. In some embodiments, one or more other dongle-connectivity management hubs and/or medical monitor systems 3204 are used to establish and/or manage wireless couplings, wherein the central dongle-connectivity management hub 3210 is used to collectively manage such wireless couplings. As shown, the dongle-connectivity management hub 3210 can be configured to generate user interface (UI) data including data regarding the dongles that are associated with the patients 3202 and/or present a user interface 3208 embodying/representing such data at least in part in some manner. The dongle-connectivity management hub 3210 can generate/present the UI 3208 based at least in part on one or more of data maintained at the dongle-connectivity management hub 3210, data received from dongles associated with the patients 3202, data received from the medical monitor systems 3204, data stored in at a remote-computing device (e.g., a cloud computing resource), and so on.

The UI 3208 can include various sections 3212 presenting various information to facilitate management of the devices associated with the patients 3202. For example, the section 3212A may be associated with the patient 3202A and may provide a patient identifier 3216 that identifies the patient 3202A in some manner. The section 3212A can additionally or alternatively provide status indicator icons 3214 indicating statuses of wireless couplings between sensor dongles and monitor dongles associated with the patient 3202A, such as 'searching/detected,' 'wirelessly coupled,' 'wirelessly decoupled/signal lost,' 'not receiving sensor data' with respect to a sensor/sensor dongle, and/or other status types.

Each of the status indicators icons 3214 can indicate a status of a wireless coupling, a status of an individual sensor dongle, and/or a status of an individual monitor dongle. For example, a first status indicator icon can indicate that a first sensor dongle and a first monitor dongle are wirelessly coupled (e.g., a checkmark), a second status indicator icon can indicate that a second sensor dongle and a second monitor dongle are detected and have previously been wirelessly coupled (e.g., circle with diagonal cross through), and a third status indicator icon can indicate that a third sensor dongle and a third monitor dongle were wirelessly coupled but have lost connection (e.g., wireless signals with a diagonal cross through it). Although FIG. 32 illustrates three status indicator icons in the section 3212A to indicate statuses of three wireless couplings, and that the three wireless couplings are established, the section 3212 could alternatively display a status indicator icon for each dongle associated or detected (e.g., display six status indicator icons for three wireless couplings).

As further shown in FIG. 32, the section 3212A can present a locate button 3218 to assist in locating the patient 3202A and/or confirming a wireless coupling of a sensor dongle and a monitor dongle associated with the patient 3202A. In some embodiments, in response to a user 3260 selecting the locate button 3218, one or more dongles associated with the patient 3202A can be configured to provide output (e.g., visual, audible, etc.) to assist the user 3260 in locating the patient 3202A. Further, in some embodiments, in response to the user 3260 selecting the locate button 3218, one or more sensor dongles and/or monitor dongles associated with the patient 3202A can provide output in an organized/sequential manner to confirm one or more wireless couplings. For example, if the patient 3202A is associated with three wireless couplings/pairings between sensor dongles and monitor dongles, and the locate button 3218 is selected, a first sensor dongle and a first monitor dongle that are wirelessly coupled can provide output first (e.g., simultaneously or one after the other dongle), a second sensor dongle and a second monitor dongle that are wirelessly coupled can provide output second (e.g., simultaneously or one after the other dongle), and a third sensor dongle and a third monitor dongle that are wirelessly coupled can provide output last (e.g., simultaneously or one after the other dongle). This can allow the user 3260 to confirm wireless couplings between sensor and monitor dongles that are associated with the patient 3202A.

In some embodiments, each dongle or type of dongle can provide a unique type of output (e.g., different sounds, lights, etc. for different dongles). Further, in some embodiments, one or more dongles associated with a patient can periodically or sporadically provide output to confirm that the one or more dongles are wirelessly coupled and/or associated with the patient. Although a locate button is discussed in FIG. 32 as being used to locate a patient and/or confirm a wireless coupling in a multi-patient management context, a locate button can be used in other contexts, such as a single-patient management situation where a user interface is displayed for a single patient.

In some embodiments, one or more of the sections 3212 are selectable to present additional information to manage one or more dongles associated with a patient. For example, the user 3260 can select a patient identifier 3220 and/or one of the status indicator icons 3222 within the section 3212C and view more detailed information regarding dongles associated with the patient 3202C, such as an interface similar to the UI 2486 provided in FIG. 24-3 or any other interface. In some embodiments, the user 3260 can, if desired, manually establish wireless couplings between dongles that are not yet coupled, such as by providing touch input via the dongle-connectivity management hub 3210 to connect a sensor dongle with a monitor dongle as discussed in various embodiments herein. The dongle-connectivity management hub 3210 can also provide a variety of other user interfaces to facilitate management of one or more dongles associated with the patient 3202C, such as in response to selection user input within the section 3212C.

Wireless Connectivity Using a Service Provider

Figure 33:
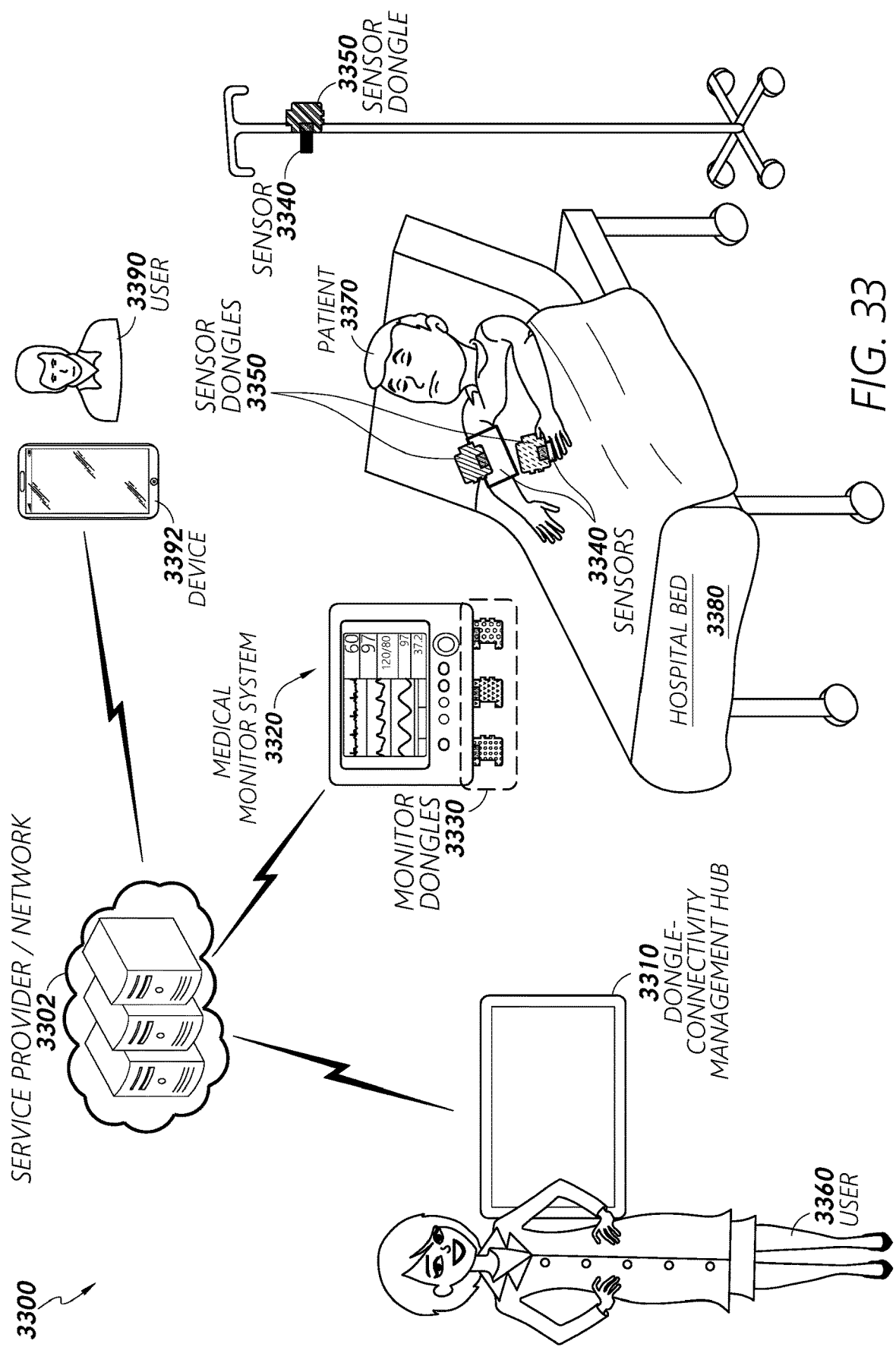
FIG. 33 illustrates an example system that includes a service provider configured to provide functionality to manage various devices associated with a patient over a local or wide area network in accordance with one or more embodiments.

FIG. 33 illustrates an example system 3300 that includes a service provider 3302 configured to provide functionality to manage various devices associated with a patient over a local or wide area network in accordance with one or more embodiments of the present disclosure. In particular, the service provider 3302 can be configured to communicate with a device 3392, a dongle-connectivity management hub 3310, a medical monitor system 3320, one or more monitor dongles 3330 connected to the medical monitor system 3320, and/or one or more sensor dongles 3350 connected to one or more sensors 3340 over, for example, a communication network (e.g., the internet). It should be understood that the service provider 3302 may perform the various communications disclosed herein through a wide (or local) area network connection, whether or not such network connection is explicitly stated or shown. For example, any of the communications described herein between two or more of the device 3392, the medical monitor system 3320, the monitor dongles 3330, the sensor dongles 3350, and/or the dongle-connectivity management hub 3310 may be communications over a network (e.g., wide or local area network, such as the internet). Furthermore, one or more of the various components, devices, systems, or features of the system 3300 of FIG. 33 may be located remotely (e.g., in another room, building, area, city, state, or country) with respect to one or more of the other components, devices, systems, or features of the system 3300.

The service provider 3302 may be a server device or system configured to communicate with one or more components of the system 3300 using any type of communication protocol (e.g., HTTP or other network protocol). As illustrated, the one or more sensors 3340 can be attached or otherwise associated with a patient 3370 located on a hospital bed 3380. For ease of discussion, the dongle-connectivity management hub 3310, the medical monitor system 3320, the one or more monitor dongles 3330, and/or the one or more sensor dongles 3350 can collectively be referred to as a "wireless connectivity system."

In some embodiments, the service provider 3302 can act as an intermediary between the device 3392 and any of the devices of the wireless connectively system. For example, the service provider 3302 can receive information from the medical monitor system 3320 (e.g., over a communication network) regarding a health of the patient 3370 (e.g., health parameters), information regarding a status of the one or more monitor dongles 3330 and/or the one or more sensor dongles 3350 (e.g., connectivity status information, battery status information, etc.), information regarding the one or more sensors 3340 (e.g., sensor data, battery status information, etc.), and so on. The service provider 3302 can send the information or data based on the information to the device 3392 (e.g., over a communication network) for output to a user 3390. The device 3392 can provide any information and/or functionality that might typically be provided and/or performed by the medical monitor system 3320 and/or the dongle-connectivity management hub 3310 (e.g., over a communication network). In some embodiments, the service provider 3302 can provide software and/or firmware updates (e.g., over a communication network) to the one or more sensor dongles 3350, the one or more monitor dongles 3330, the dongle-connectivity management hub 3310, and/or the medical monitor system 3320.

In some embodiments, the service provider 3302 can process information received from any of the devices of the wireless connectivity system and provide a notification to the device 3392 based on the processed information. For example, the service provider 3302 can receive battery status information from a dongle, estimate a time when the battery life will be below a threshold based on current battery usage and/or previous battery usage, and provide the estimated time to the device 3392. In some embodiments, the service provider 3302 can provide a notification to alert the device 3392 of a particular event, such as a decoupling of a sensor dongle from a monitor dongle, a low battery on a dongle, a health parameter reaching a critical threshold, and so on. Such notifications can allow the user 3390 and/or other entities/devices of the system 3300 to take certain action in response thereto, such as by resetting a dongle, notifying a medical individual that is located in proximity to the patient 3372 address a critical situation, and so on.

In some embodiments, the service provider 3302 can process information across a variety of types of dongles and/or sensors to provide metric data, a notification, or other information. For example, the service provider 3302 can receive information from many sensor dongles over time and process the information to determine an average battery life of a dongle/sensor, an average battery life of a particular type of dongle/sensor, a device life of a dongle/sensor, an average device life of a particular type of dongle/sensor, and so on. In some implementations, the service provider 3302 can be configured to estimate a time when battery life of a particular sensor dongle will be below a threshold based on a history of previous battery life of sensor dongles of a same type, an average battery life for the particular sensor dongle, and so on. The service provider 3302 can provide a notification to the device 3392 indicating the estimated time and/or provide a notification at an appropriate time before the battery life reaches below the threshold.

The service provider 3302 can be implemented as one or more computing devices, such as one or more servers, one or more desktop computers, one or more laptops computers, or any other type of device configured to process data. The one or more computing devices can be configured in a cluster, data center, cloud computing environment, or a combination thereof. In some embodiments, the one or more computing devices of the service provider 3302 are implemented as a remote computing resource that is located remotely to the dongle-connectivity management hub 3310, the medical monitor system 3320, the one or more monitor dongles 3330, the one or more sensor dongles 3350, and/or the device 3392. In some embodiments, the one or more computing devices of the service provider 3302 are implemented as local resources that are located locally at the dongle-connectivity management hub 3310, the medical monitor system 3320, the one or more monitor dongles 3330, the one or more sensor dongles 3350, and/or the device 3392. The service provider 3302 can include various control circuitry, data storage, and one or more network interfaces. The control circuitry may include one or more processors, such as one or more central processing units (CPUs), one or more microprocessors, one or more graphics processing units (GPUs), one or more digital signal processors (DSPs), etc. Alternatively, or additionally, the control circuitry may include one or more application specific integrated circuits (ASIC), one or more field-programmable gate arrays (FPGAs), one or more program-specific standard products (ASSPs), one or more complex programmable logic devices (CPLDs), and/or the like.

Data Flow Systems

Figure 34:
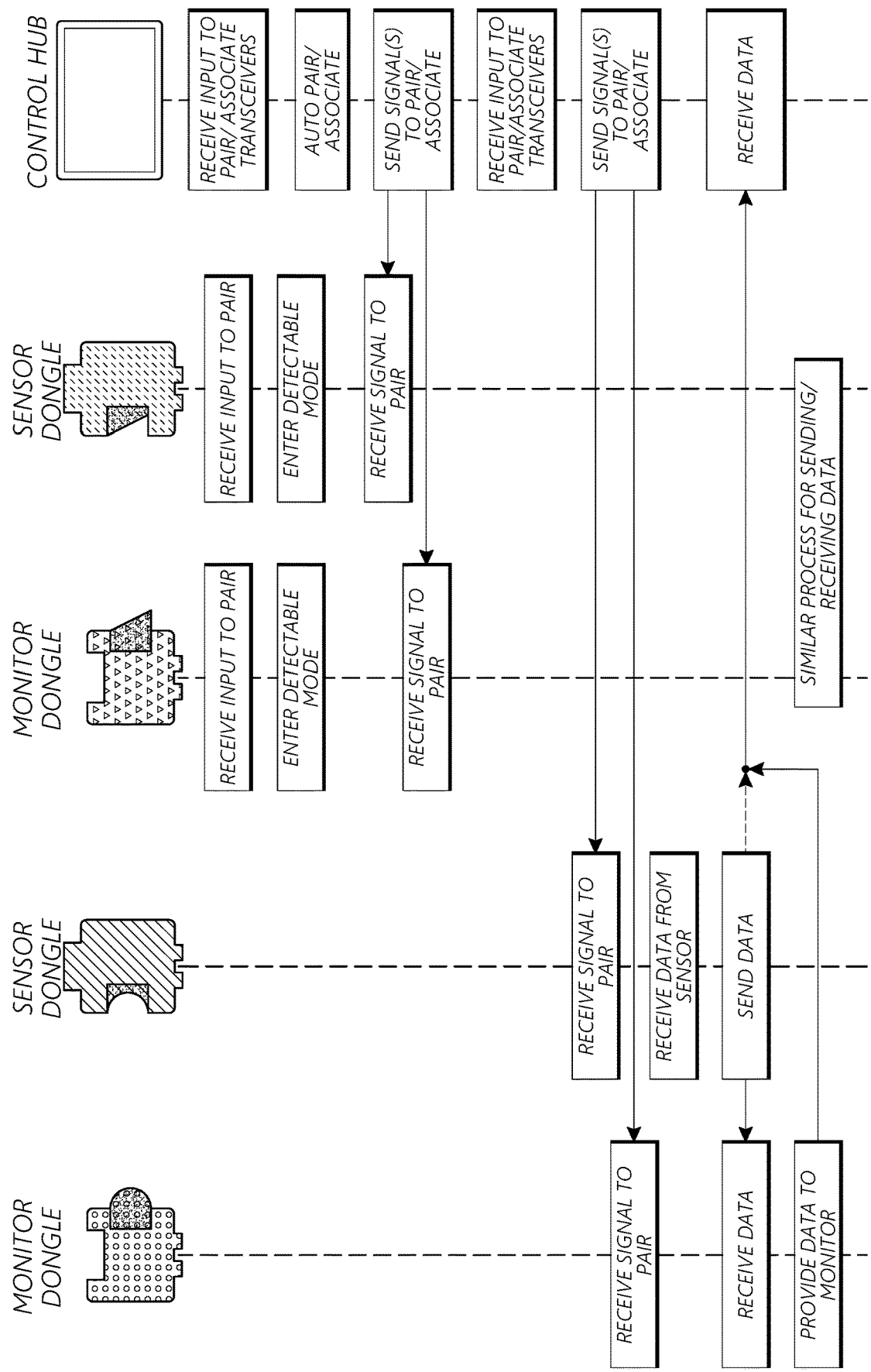
FIG. 34 is a data flow diagram showing certain data transmissions between components of a wireless connectivity management system in accordance with one or more embodiments.

FIG. 34 is a data flow diagram showing certain data transmissions between components of a wireless connectivity management system in accordance with one or more embodiments of the present disclosure. In some embodiments, vertical positioning of certain blocks in the diagram of FIG. 34 may represent relative temporal occurrence of operation(s) associated with such blocks. However, it should be understood that vertical positioning does not represent temporal characteristics in some embodiments. In examples, the illustrated control hub is also referred to as a "dongle-connectivity management hub."

ADDITIONAL FEATURES AND EMBODIMENTS

The above description of embodiments of the disclosure is not intended to be exhaustive or to limit the disclosure to the precise form disclosed above. While specific embodiments, and examples, are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

Certain terms of location are used herein with respect to the various disclosed embodiments. Although certain spatially relative terms, such as "outer," "inner," "upper," "lower," "below," "above," "vertical," "horizontal," "top," "bottom," and similar terms are used herein to describe a spatial relationship of one device/element or anatomical structure relative to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited. In some contexts, description of an operation or event as occurring or being performed "based on," or "based at least in part on," a stated event or condition can be interpreted as being triggered by or performed in response to the stated event or condition.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

Unless the context clearly requires otherwise, throughout the description and the claims, the terms "comprise," "comprising," "have," "having," "include," "including," and the like are to be construed in an open and inclusive sense, as opposed to a closed, exclusive, or exhaustive sense; that is to say, in the sense of "including, but not limited to."

The word "coupled" can refer to two or more elements that may be physically, mechanically, electrically, and/or wirelessly connected or otherwise associated, whether directly or indirectly (e.g., via one or more intermediate elements, components, and/or devices). Additionally, the words "herein," "above," "below," and words of similar import, when used in this application, shall refer to this application as a whole, including any disclosure incorporated by reference, and not to any particular portions of the present disclosure. Where the context permits, words in present disclosure using the singular or plural number may also include the plural or singular number, respectively.

The word "or" in reference to a list of two or more items, that word covers all of the following interpretations of the word: any of the items in the list, all of the items in the list, and any combination of the items in the list. Furthermore, as used herein, the term "and/or" used between elements (e.g., between the last two of a list of elements) means any one or more of the referenced/related elements. For example, the phrase "A, B, and/or C" means "A," "B," "C," "A and B," "A and C," "B and C," or "A, B, and C."

As may be used herein, the terms "substantially" and "approximately" provides an industry-accepted tolerance for its corresponding term and/or relativity between items. For some industries, an industry-accepted tolerance is less than one percent, while for other industries, the industry-accepted tolerance may be 10 percent or more. Other examples of industry-accepted tolerances range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the terms "processing circuitry," "processing circuit," "processor," "processing module," and/or "processing unit" may refer to a single processing device or a plurality of processing devices. Such a processing device may comprise a chip, die (e.g., semiconductor die including one or more active and/or passive devices and/or connectivity circuitry), microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be remotely located (e.g., cloud computing via indirect coupling via a local area network and/or a wide area network). Further note that if the processing module, module, processing circuit, processing circuitry and/or processing unit implements one or more of its functions via a hardware and/or software state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same, related, or unrelated reference numbers. The relevant features, elements, functions, operations, modules, etc. may be the same or similar functions or may be unrelated.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid-state memory, a hard drive memory, cloud memory, thumb drive, server memory, computing device memory, and/or other physical medium for storing digital information.

What is claimed is:

1. A wireless-connectivity system comprising:
   a plurality of sensor dongles, each of the plurality of sensor dongles configured to be physically and electrically coupled to a connector of a respective sensor device, the plurality of sensor dongles including a first sensor dongle configured to be physically and electrically coupled to a connector of a first sensor device;
   a plurality of monitor dongles, each of the plurality of monitor dongles configured to be physically and electrically coupled to a respective monitor port of a medical monitor system; and
   dongle-connectivity management hub circuitry configured to:
      selectively cause a first wireless coupling to be established between the first sensor dongle and a first one of the plurality of monitor dongles, thereby facilitating transmission of data between the first sensor dongle and the first one of the plurality of monitor dongles;
      terminate the first wireless coupling between the first sensor dongle and the first one of the plurality of monitor dongles; and
      selectively cause a second wireless coupling to be established between the first sensor dongle and a second one of the plurality of monitor dongles, thereby facilitating transmission of data between the first sensor dongle and the second one of the plurality of monitor dongles;
      receive user input initiating a patient transport mode of the first sensor dongle; and
      initiate the patient transport mode, wherein the dongle-connectivity management hub circuitry is configured to, in the transport mode:
      instruct the first sensor dongle to terminate the second wireless coupling between the first sensor dongle and the second one of the plurality of monitor dongles;
      instruct the first sensor dongle to send sensor data wirelessly to the dongle-connectivity management hub circuitry rather than to a monitor dongle; and
      display physiological parameter data based on the sensor data on an electronic display of a mobile computing device.

2. The system of claim 1, wherein the first sensor device is configured to measure one or more physiological parameters of a patient.

3. The system of claim 1, wherein said selectively causing the first wireless coupling to be established includes sending a signal to one or more of the first sensor dongle and the first one of the plurality of monitor dongles, the signal instructing the one or more of the first sensor dongle and the first one of the plurality of monitor dongles to establish the first wireless coupling.

4. The system of claim 1, wherein the connector of the first sensor device is associated with a distal end of a cable coupled to a sensor housing of the first sensor device.

5. The system of claim 1, wherein the connector of the first sensor device has a form that is configured to mate with a monitor port of the medical monitor system that is coupled to the first one of the plurality of monitor dongles and is not configured to mate with a monitor port of the medical monitor system that is coupled to the second one of the plurality of monitor dongles.

6. The system of claim 1, wherein the first sensor dongle has a sensor connector that is configured to receive the connector of the first sensor device.

7. The system of claim 1, wherein a monitor connector of the first one of the plurality of monitor dongles has a same type of form as the connector of the first sensor device.

8. The system of claim 1, wherein the dongle-connectivity management hub circuitry is a component of the medical monitor system.

9. The system of claim 1, wherein:
   the connector of the first sensor device and a monitor connector of the first one of the plurality of monitor dongles are male connectors; and
   a sensor connector of the first sensor dongle and monitor ports of the medical monitor system are female connectors.

10. The system of claim 1, further comprising an electronic display communicatively coupled to the dongle-connectivity management hub circuitry, wherein the dongle-connectivity management hub circuitry is further configured to generate user interface data representing the first wireless coupling and the second wireless coupling.

11. The system of claim 10, wherein the dongle-connectivity management hub circuitry is further configured to receive user input using the electronic display, wherein said causing the first wireless coupling to be established is performed in response to the user input.

12. The system of claim 10, wherein:
   the user interface data includes representations of each of the plurality of sensor dongles and each of the plurality of monitor dongles; and
   the representations of the plurality of sensor dongles and the plurality of monitor dongles have shape characteristics that indicate a type of the respective dongles.

13. The system of claim 1, wherein the dongle-connectivity management hub circuitry is further configured to:
   determine that the first sensor dongle has moved outside a connection range of the first one of the plurality of monitor dongles; and
   in response to said determination, receive sensor-based data from the first sensor dongle over a wireless connection with the first sensor dongle.

14. The system of claim 1, wherein the dongle-connectivity management hub circuitry is embodied in a mobile computing device that is separate from the plurality of sensor dongles, the plurality of monitor dongles, and the medical monitor system.

15. The system of claim 14, wherein the mobile computing device is one of the group consisting of a smartphone, a tablet computer, and a laptop computer.

16. The system of claim 1, wherein the first sensor dongle is configured to be physically mated to the first one of the plurality of monitor dongles by a coupling that is separate from a sensor connector of the first sensor dongle over which the first sensor dongle is configured to be physically and electrically coupled to the connector of the first sensor device.

17. The system of claim 16, wherein the first sensor dongle and the first one of the plurality of monitor dongles are configured to transmit power between the first sensor dongle and the first one of the plurality of monitor dongles over the coupling.

18. A wireless-connectivity system comprising:
- a plurality of sensor dongles, each of the plurality of sensor dongles configured to be physically and electrically coupled to a connector of a respective sensor device;
- a plurality of monitor dongles, each of the plurality of monitor dongles configured to be physically and electrically coupled to a respective monitor port of a medical monitor system; and
- a computing device that is separate from, and not physically coupled to, the plurality of sensor dongles and the plurality of monitor dongles, the computing device comprising dongle-connectivity management hub circuitry configured to:
  - render a user interface on an electronic display of the computing device, the user interface including icons representing each of the plurality of sensor dongles and each of the plurality of monitor dongles;
  - receive first user input using the electronic display, the first user input selecting a connect button rendered as part of the user interface;
  - in response to the first user input, initiate a search for sensor dongles of the plurality of sensor dongles that are in wireless communication range of at least one of the plurality of monitor dongles;
  - identify a first sensor dongle of the plurality of sensor dongles as being in communication range of a first monitor dongle and a second monitor dongle of the plurality of monitor dongles;
  - receive second user input using the electronic display, the second user input selecting the first sensor dongle and the first monitor dongle at least in part by touch-contacting icons representing the first sensor dongle and the first monitor dongle;
  - in response to the second user input, cause a first wireless coupling to be established between the first sensor dongle and the first monitor dongle, thereby facilitating transmission of data between the first sensor dongle and the first monitor dongle;
  - receive second user input using the electronic display, the second user input selecting the first sensor dongle and a second monitor dongle of the plurality of monitor dongles at least in part by touch-contacting the icon representing the first sensor dongle and an icon representing the second monitor dongle; and
  - in response to the second user input, cause a second wireless coupling to be established between the first sensor dongle and the second monitor dongle, thereby facilitating transmission of data between the first sensor dongle and the second monitor dongle.

19. The system of claim 18, wherein the dongle-connectivity management hub circuitry is further configured to, in response to the second user input, terminate the first wireless coupling.

20. The system of claim 18, wherein the dongle-connectivity management hub circuitry is further configured to:
- receive third user input comprising a patient identifier;
- in response to the second user input and the third user input, associate the first sensor dongle and the second monitor dongle with the patient.

* * * * *